(12) United States Patent
Eggers et al.

(10) Patent No.: US 6,471,659 B2
(45) Date of Patent: Oct. 29, 2002

(54) MINIMALLY INVASIVE INTACT RECOVERY OF TISSUE

(75) Inventors: Philip E. Eggers, Dublin, OH (US); Andrew R. Eggers, Ostrander, OH (US); Eric A. Eggers, Columbus, OH (US); John Kociecki, Powell, OH (US)

(73) Assignee: Neothermia Corporation, Natick, MA (US)

( * ) Notice: Subject to any disclaimer, the term of this patent is extended or adjusted under 35 U.S.C. 154(b) by 0 days.

(21) Appl. No.: 09/904,396

(22) Filed: Jul. 12, 2001

(65) Prior Publication Data

US 2002/0019596 A1 Feb. 14, 2002

Related U.S. Application Data

(63) Continuation-in-part of application No. 09/472,673, filed on Dec. 27, 1999, now Pat. No. 6,277,083.

(51) Int. Cl.[7] .................................................. A61B 5/00
(52) U.S. Cl. ...................................................... 600/564
(58) Field of Search ............................... 600/564–567; 606/45–50

(56) References Cited

U.S. PATENT DOCUMENTS

| | | |
|---|---|---|
| 3,910,279 A | 10/1975 | Okada |
| 3,955,578 A | 5/1976 | Chamness |
| 4,611,594 A | 9/1986 | Grayhack |
| 4,638,802 A | 1/1987 | Okada |
| 4,997,435 A | 3/1991 | Demeter |
| 5,026,371 A | 6/1991 | Rydell et al. |
| 5,064,428 A | 11/1991 | Cope |
| 5,078,716 A | 1/1992 | Doll |
| 5,083,570 A | 1/1992 | Mosby |
| 5,111,828 A | 5/1992 | Kornberg |
| 5,183,464 A | 2/1993 | Dubrul |

(List continued on next page.)

FOREIGN PATENT DOCUMENTS

| | | |
|---|---|---|
| DE | 195 28 440 A1 | 2/1997 |
| EP | 0 829 232 A3 | 3/1998 |
| EP | 0 829 232 A2 | 3/1998 |
| EP | 0 841 036 A1 | 5/1998 |
| FR | 2275226 | 1/1976 |
| GB | 2311468 A | 1/1997 |
| NL | 1004723 | 8/1998 |
| SE | 8206417-1 | 7/1984 |
| SU | 1235497 A1 | 6/1986 |
| SU | 1355266 A1 | 11/1987 |

(List continued on next page.)

OTHER PUBLICATIONS

Atkins, H. *The Treatment of Breast Cancer*. Baltimore: University Park Press. 1974. 58–59.

Cardenosa, G. *Breast Imaging Companion*. Philadelphia: Lippincott–Raven Publishers. 1997. 308–310, 386–387, 391, 395–396.

(List continued on next page.)

*Primary Examiner*—Max Hindenburg
(74) *Attorney, Agent, or Firm*—Mueller and Smith,LPA

(57) ABSTRACT

System, method and apparatus for carrying out the recovery of an intact volume of tissue wherein a delivery cannula distal end is positioned in confronting adjacency with the volume of tissue to be recovered. A capture component formed of a plurality of metal leafs is deployed from the distal end of the delivery cannula. The tips of these leafs carry a pursing cable assembly which is electrically excited to electrosurgically cut around and circumscribe the tissue volume. These pursing cables are tensioned to complete the envelopment of the tissue volumes by drawing the leaf tips together. Drive to the capture component ultimately is developed from an electric motor and electrosurgical cutting current is supplied initially at a boost voltage level and thereafter at a lower normal cutting voltage level.

170 Claims, 58 Drawing Sheets

U.S. PATENT DOCUMENTS

| | | |
|---|---|---|
| 5,192,286 A | 3/1993 | Phan |
| 5,197,484 A | 3/1993 | Kornberg |
| 5,217,458 A | 6/1993 | Parins |
| 5,275,611 A | 1/1994 | Behl |
| 5,279,539 A | 1/1994 | Bohan et al. |
| 5,300,070 A | 4/1994 | Gentelia |
| 5,312,360 A | 5/1994 | Behl |
| 5,324,288 A | 6/1994 | Billings |
| 5,336,227 A | 8/1994 | Nakao |
| 5,353,804 A | 10/1994 | Kornberg |
| 5,370,647 A | 12/1994 | Graber |
| 5,397,320 A | 3/1995 | Essig |
| 5,415,656 A | 5/1995 | Tihon |
| 5,417,687 A | 5/1995 | Nardella |
| 5,417,697 A | 5/1995 | Wilk |
| 5,423,809 A | 6/1995 | Klicek |
| 5,423,830 A | 6/1995 | Schneebaum |
| 5,431,676 A | 7/1995 | Dubrul |
| 5,437,665 A | 8/1995 | Munro |
| 5,445,142 A | 8/1995 | Hassler |
| 5,454,790 A | 10/1995 | Dubrul |
| 5,465,731 A | 11/1995 | Bell |
| 5,486,182 A | 1/1996 | Nakao |
| 5,499,989 A | 3/1996 | LaBash |
| 5,514,153 A | 5/1996 | Bonutti |
| 5,599,348 A | 2/1997 | Gentelia |
| 5,626,578 A | 5/1997 | Tihon |
| 5,630,822 A | 5/1997 | Hermann |
| 5,643,282 A | 7/1997 | Kieturakis |
| 5,647,372 A | 7/1997 | Tovey |
| 5,658,279 A | 8/1997 | Nardella |
| 5,674,184 A | 10/1997 | Hassler |
| 5,709,697 A | 1/1998 | Ratcliff |
| 5,741,271 A | 4/1998 | Nakao |
| 5,746,740 A | 5/1998 | Nicholas |
| 5,749,870 A | 5/1998 | Gloth et al. |
| 5,749,889 A | 5/1998 | Bacich |
| 5,759,187 A | 6/1998 | Nakao |
| 5,779,715 A | 7/1998 | Tu |
| 5,782,840 A | 7/1998 | Nakao |
| 5,794,626 A | 8/1998 | Kieturakis |
| 5,795,308 A | 8/1998 | Russin |
| 5,797,907 A | 8/1998 | Clement |
| 5,807,276 A | 9/1998 | Russin |
| 5,810,806 A | 9/1998 | Ritchart |
| 5,814,052 A | 9/1998 | Nakao |
| 5,824,002 A | 10/1998 | Gentelia |
| 5,846,248 A | 12/1998 | Chu |
| 5,848,978 A | 12/1998 | Cecchi |
| 5,857,982 A | 1/1999 | Millman |
| 5,882,316 A | 3/1999 | Chu |
| 5,904,679 A | 5/1999 | Clayman |
| 5,913,857 A | 6/1999 | Ritchart |
| 5,925,044 A | 7/1999 | Hofmann |
| 5,928,163 A | 7/1999 | Roberts |
| 5,957,923 A | 9/1999 | Hahnen |
| 5,968,056 A | 10/1999 | Chu |
| 5,980,515 A | 11/1999 | Tu |
| 5,997,547 A | 12/1999 | Nakao |
| 6,013,086 A | 1/2000 | Ouchi |
| 6,019,720 A | 2/2000 | Bito |
| 6,019,758 A | 2/2000 | Slater |
| 6,022,362 A | 2/2000 | Lee |
| 6,027,508 A | 2/2000 | Ren |
| 6,030,365 A | 2/2000 | Laufer |
| 6,030,403 A | 2/2000 | Long |
| 6,033,402 A | 3/2000 | Tu |
| 6,036,698 A | 3/2000 | Fawzi |
| 6,036,708 A | 3/2000 | Sciver |
| 6,136,014 A | 10/2000 | Sirimanne |
| 6,156,035 A | 12/2000 | Songer |
| 6,176,834 B1 | 1/2001 | Chu |
| 6,261,241 B1 | 7/2001 | Burbank |

FOREIGN PATENT DOCUMENTS

| | | |
|---|---|---|
| WO | WO 95/02370 | 1/1995 |
| WO | WO 95/02371 | 1/1995 |
| WO | WO 97/42991 | 11/1997 |
| WO | WO 97/43958 | 11/1997 |
| WO | WO 98/06448 | 2/1998 |
| WO | WO 98/08441 | 3/1998 |
| WO | WO 99/04704 | 2/1999 |
| WO | WO 99/39648 | 8/1999 |
| WO | WO99/44506 | 9/1999 |
| WO | WO99/52441 | 10/1999 |
| WO | WO 99/53851 | 10/1999 |
| WO | WO 00/33743 | 6/2000 |
| WO | WO 00/78221 A1 | 12/2000 |
| WO | WO 00/78224 A2 | 12/2000 |
| WO | WO 01/05320 A1 | 1/2001 |

OTHER PUBLICATIONS

Chung, Y., et al. "Generation and Observation of Radio Frequency Thermal Lesion Ablation for Interventional Magnetic Resonance Imaging." *Invest Radiol* 1997. 32:466–474.

D'Angelo, P. C., et al. "Stereotactic Excisional Breast Biopsies Utilizing the Advanced Breast Biopsy Instrumentation System." *Am J Surg*. 1997. 174: 297–302.

Daniel, B.L., et al. "Breast Lesion Localization, A Freehand, Interactive MR Imaging–Guided Technique." *Radiology* 1998. 207: 455–463.

Ferzli, G.S., et al. "Advanced Breast Biopsy Instrumentation: A Critique." *J. Am Coll Surg* 1997. 185: 145–151.

Fornage, B.D. "Guided Needle Biopsy of Nonpalpable Breasr Masses." *Mastology–Breast Diseases*. Eds. A.S.S. Figueira Fo., et al. Amsterdam: Elsevier, 1995. 96–107.

Fornage, B.D. "Percutaneous Needle Biopsy of the Breast." *Mastology–Breast Diseases*. Eds. A.S.S. Figueira Fo., et al. Amsterdam: Elsevier, 1995. 90–95.

Gorczyca, D.P., et al. "Wire Localization of Breast Lesions Before Biopsy: Use of an MR–Compatible Device in Phantoms and Cadavers." *AJR* 1995. 165: 835–838.

Harris, J.R., et al. "Cancer of the Breast." *Cancer: Principles and Practices of Oncology, Fourth Edition*. Eds. DeVita, et al. Philadelphia: J.B. Lippincott Co., 1993. 1264–1285.

Hendrick, R.E., et al. "Principles of Stereotactic Mammography and Quality Assurance." *Percutaneous Breast Biopsy*. Eds. Parker, et al. New York: Raven Press, 1993. 49–59.

Heywang–Kobrunner, S.H, et al. "New methods for Minimally Invasive Clarification of Uncertain Mammographic and MR Tomographic Results." *Zentralbl. Chir*. 1998. 123 (Supp 5): 66–69.

Jellins, J. "Current Concepts in Breast Ultrasound: Developments in Technology and Quality Assurance." *Mastology–Breast Diseases*. . . Eds. A.S.S. Figueira Fo., et al. Amsterdam: Elsevier, 1995. 79–83.

Jobe, W.E. "Historical Perspectives." *Percutaneous Breast Biopsy*. Eds. Parker, et al. New York: Raven Press, 1993. 1–5.

Kahn, T., et al. "In Vivo MRI Thermometry Using a Phase–Sensitive Sequence: Preliminary Experience During MRI–Guided Laser–Induced Interstitial Thermotherapy of Brain Tumors." *JMRI* 1998. 8: 160–164.

Kelley, W.E., et al. "Advanced Breast Biopsy Instumentation." *J Am Coll Surg* 1997. 604–605.

Kuhl, C.K, et al. "Interventional Breast MR Imaging: Clinical Use of a Stereotactic Localization and Biopsy Device." *Radiology* 1997. 204: 667–675.

Matthews, B.D. "Initial Experience with the Advanced Breast Biopsy Instrumentation System." *Am J Surg*. 1999. 177: 97–101.

Parker, S.H. "The Advanced Breast Biopsy Instrumentation: Another Trojan Hourse?" AJR 1998. 171: 51–53.

Parker, S.H. "Needle Selection." *Percutaneous Breast Biopsy*. Eds. Parker, et al. New York: Raven Press, 1993. 7–14.

Parker, S.H. "Stereotactic Large–Core Breast Biopsy." *Percutaneous Breast Biopsy*. Eds. Parker, et al. New York: Raven Press, 1993. 61–79.

Rosen, P.P. *Rosen's Breast Pathology*. Philadelphia: Lippincott–Raven Publishers, 1997. 837–858.

Stavros, A.T, et al. "An Introduction to Breast Ultrasound." *Percutaneous Breast Biopsy*. Eds. Parker, et al. New York: Raven Press, 1993. 95–109.

Truell, J.E., et al. "The Pathologist's Perspective." *Percutaneous Breast Biopsy*. Eds. Parker, et al. New York: Raven Press, 1993. 15–23.

Vogl, T.J., et al. "Magnetic Resonance Imaging—Guided Abdominal Interventional Radiology: Laser–Induced Thermotherapy of Liver Metastases." *Endoscopy* 1997. 29: 577–583.

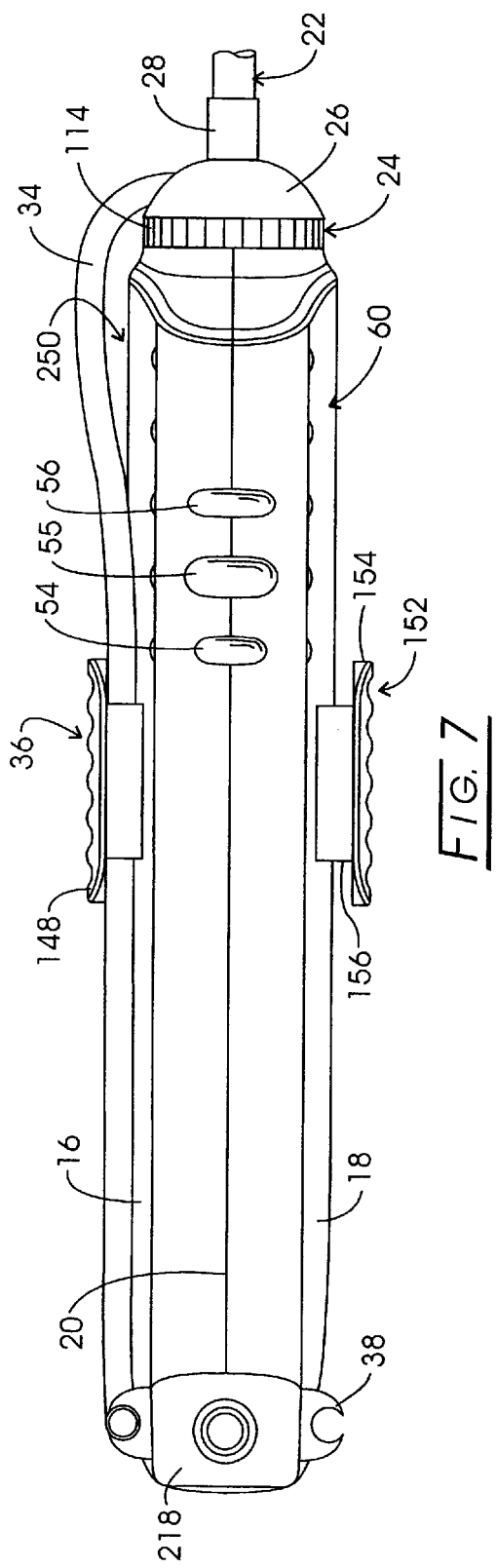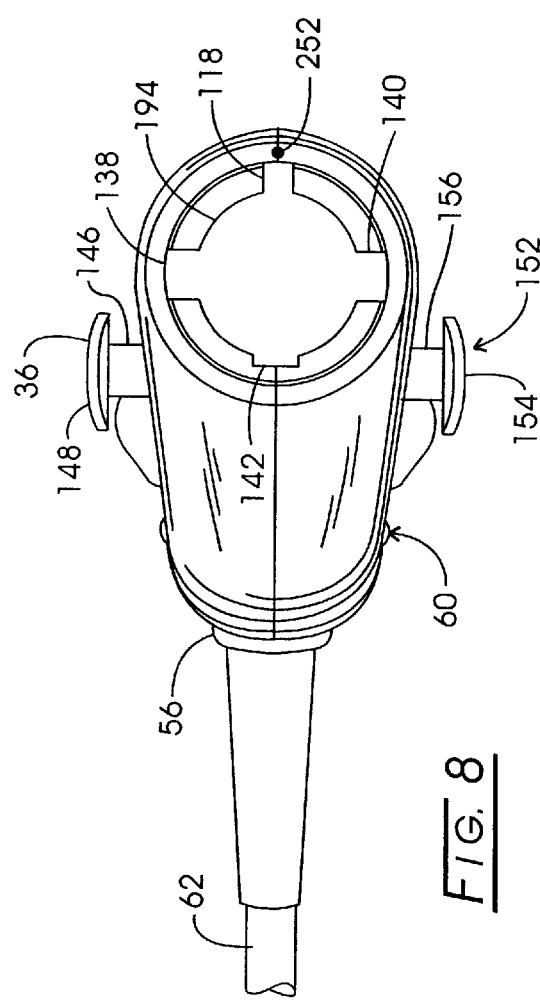

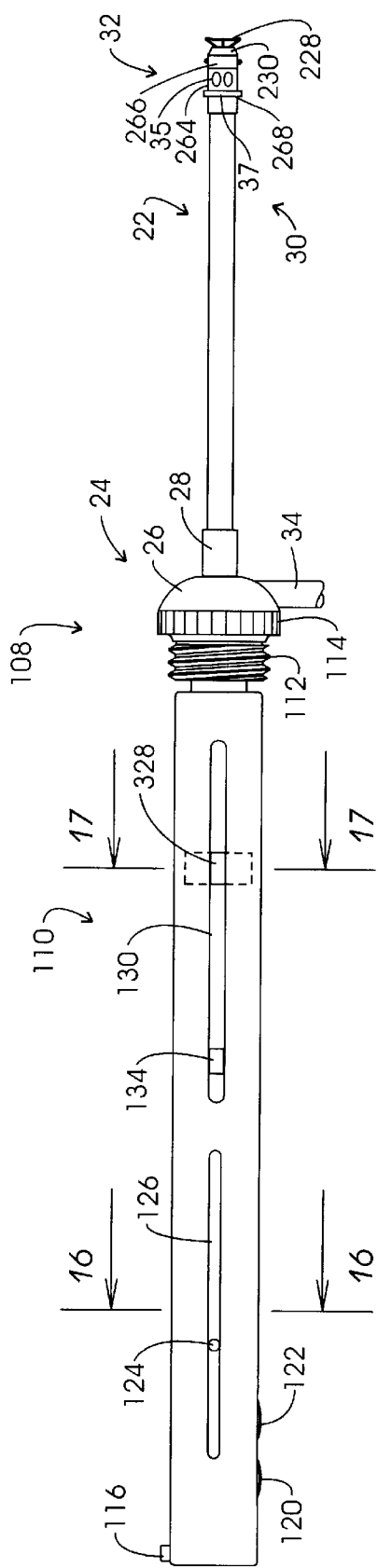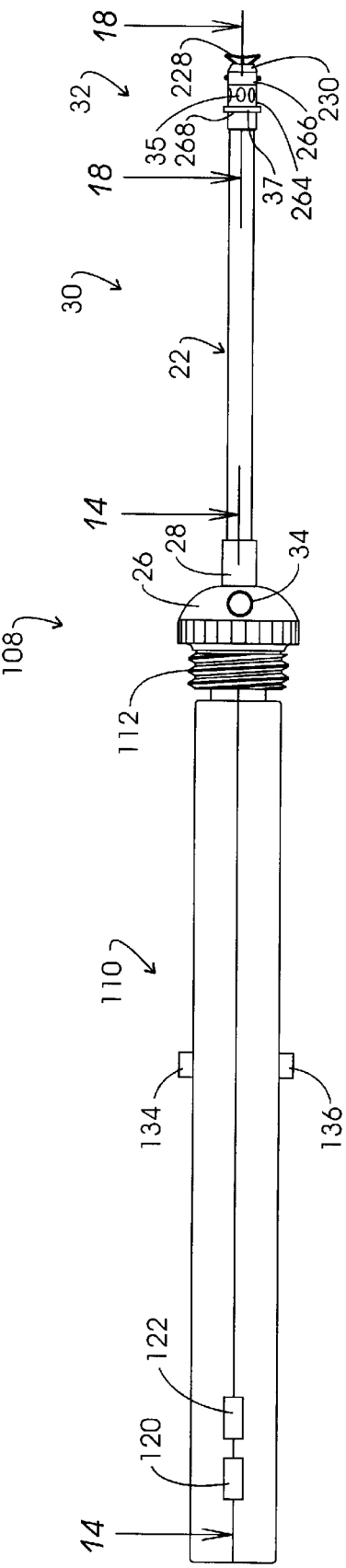

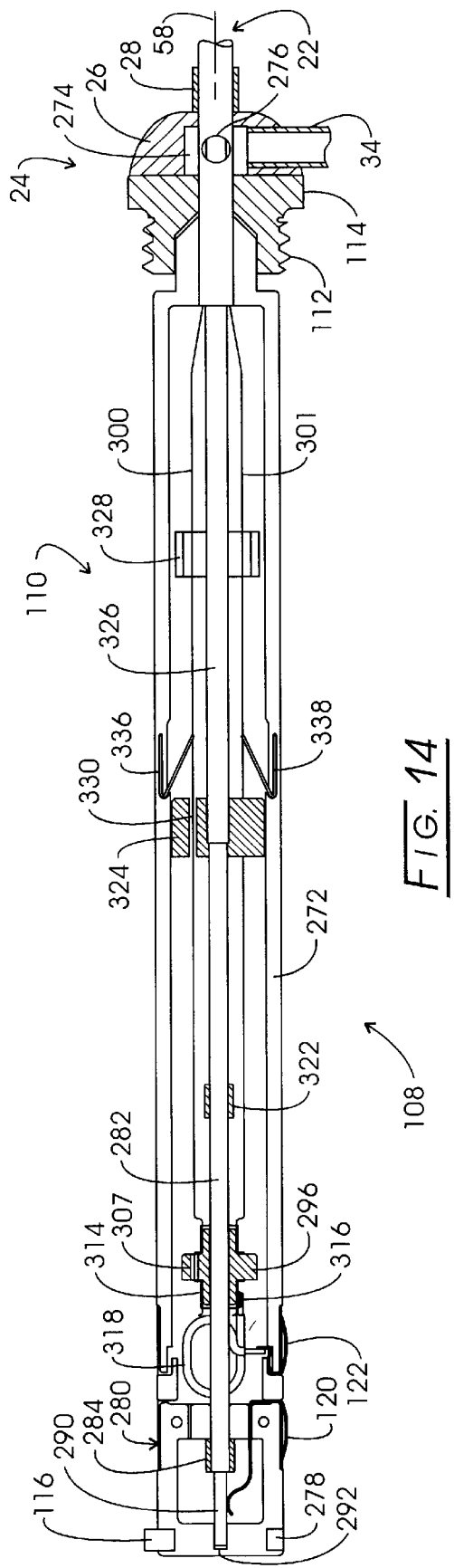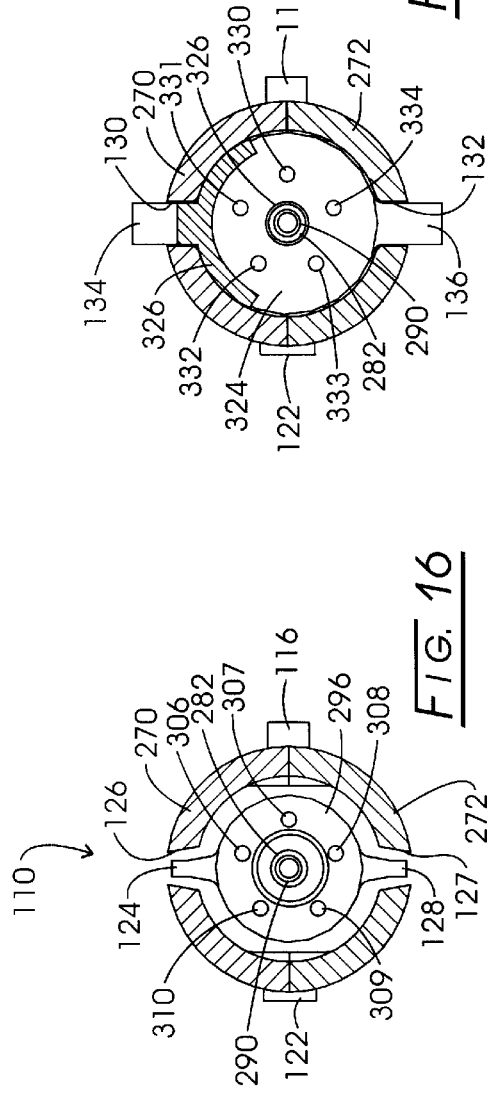

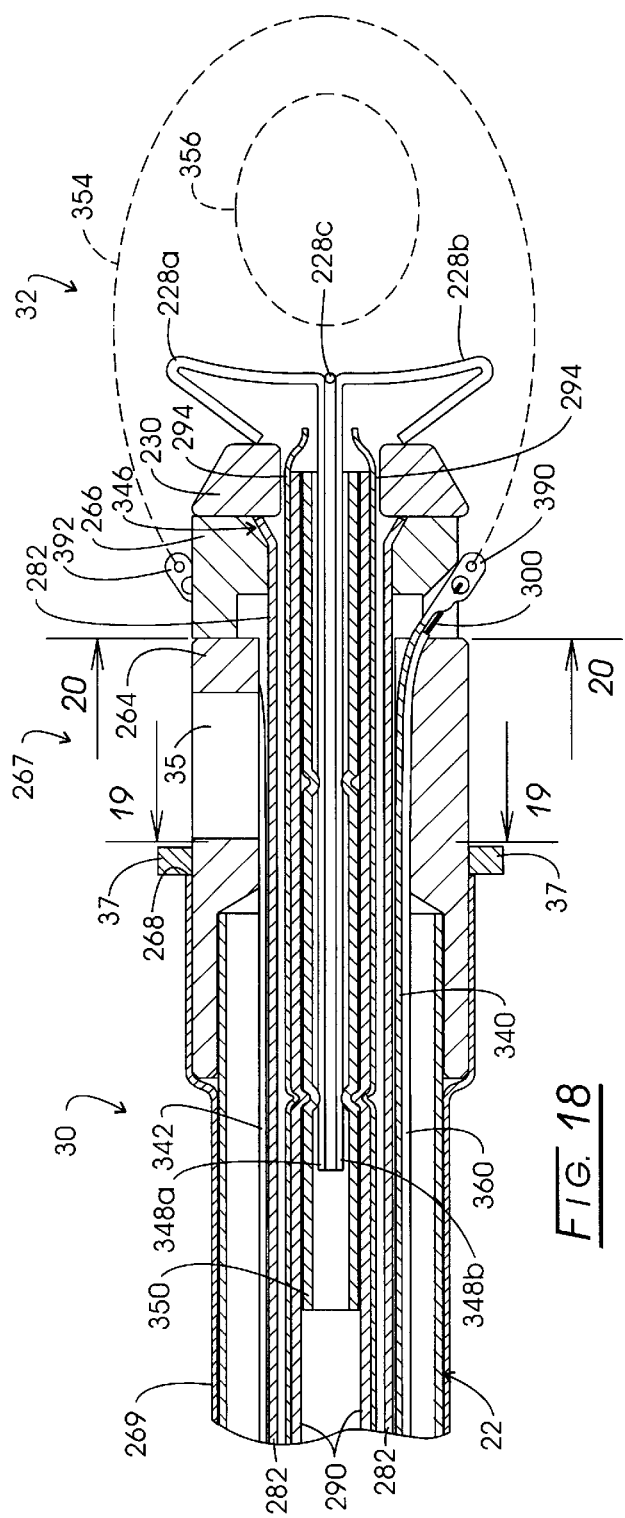
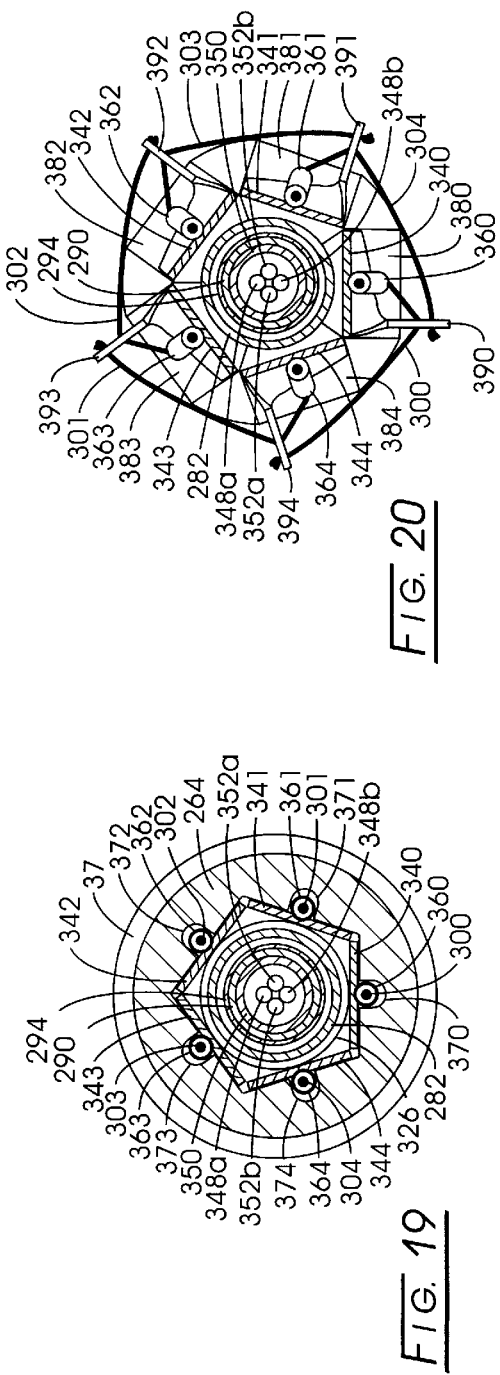
FIG. 18
FIG. 20
FIG. 19

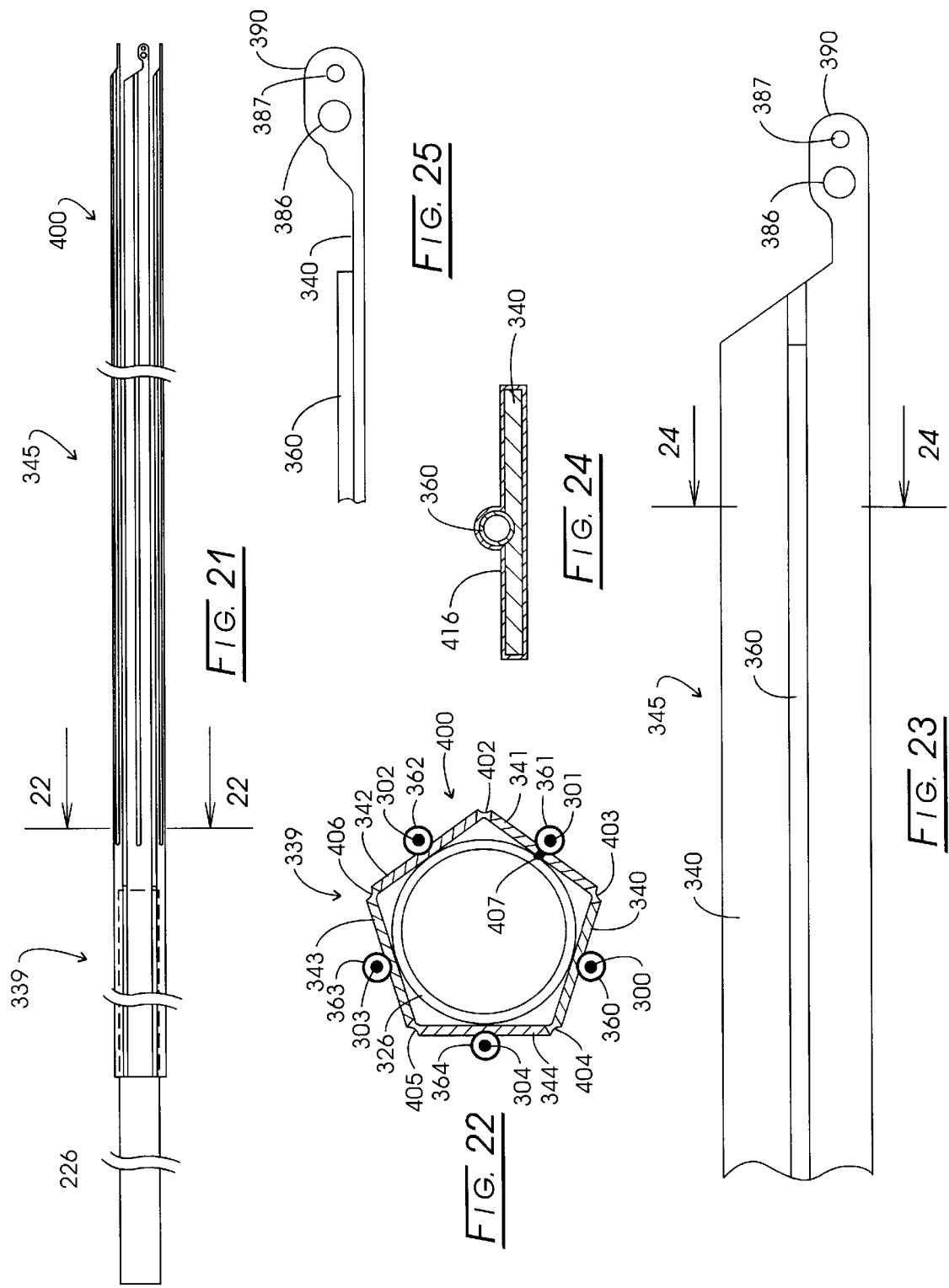

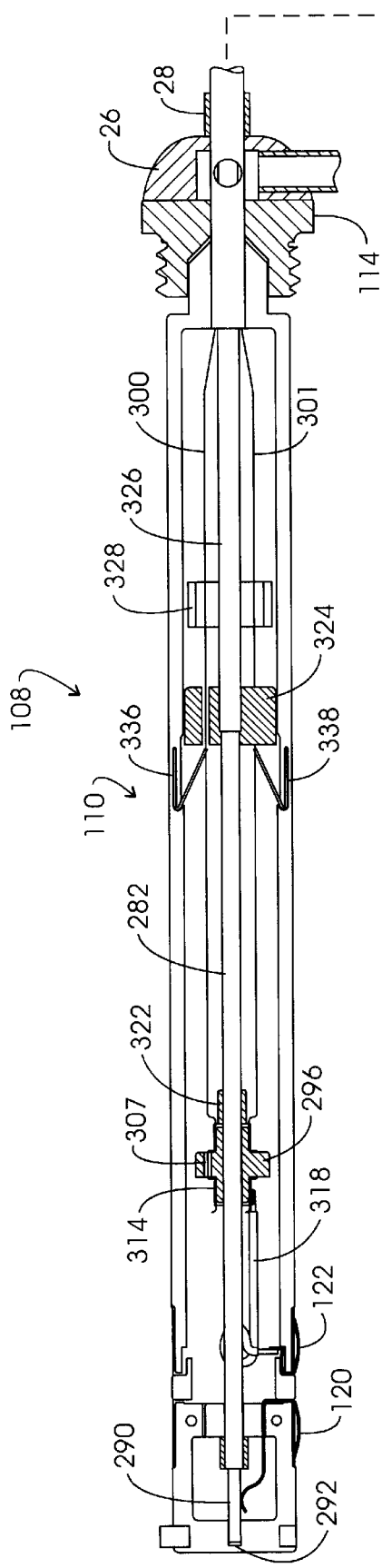
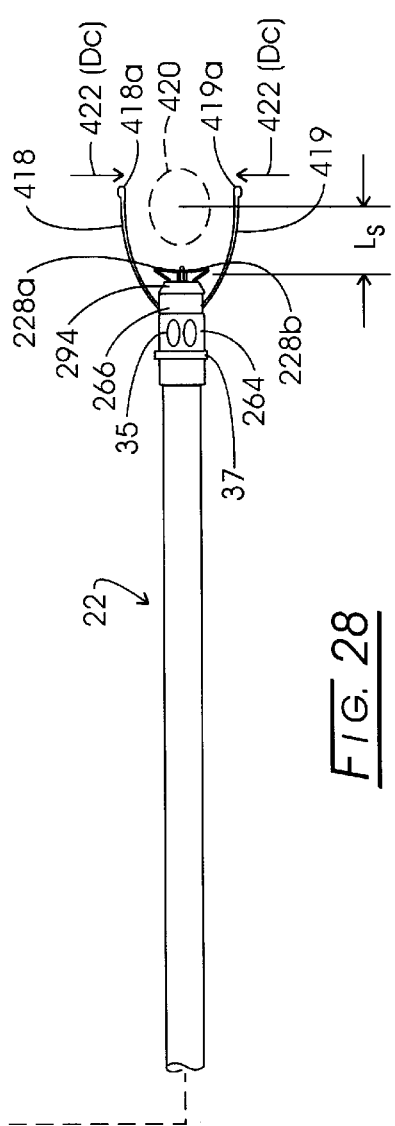
FIG. 28

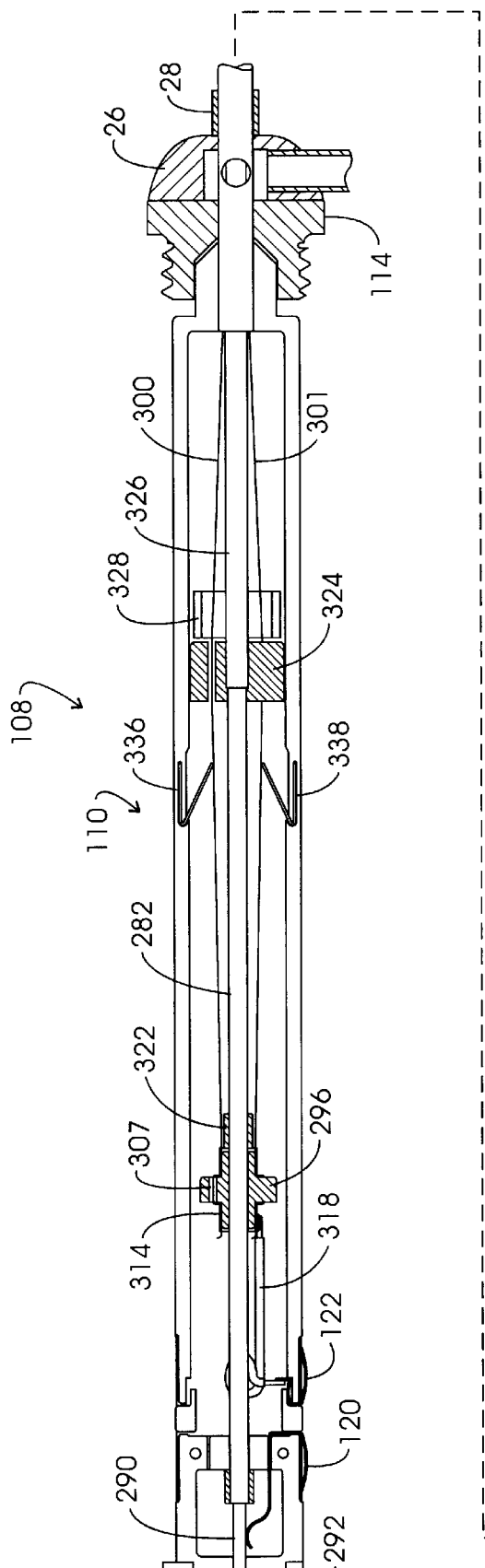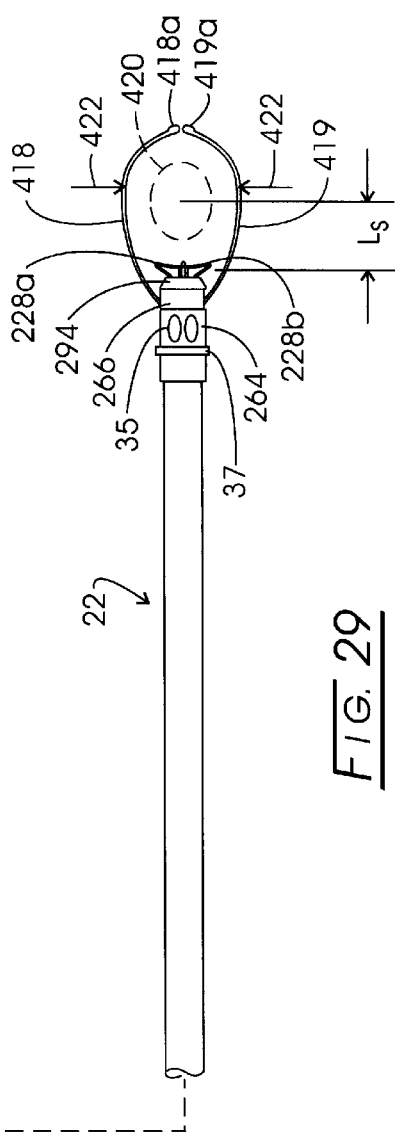
FIG. 29

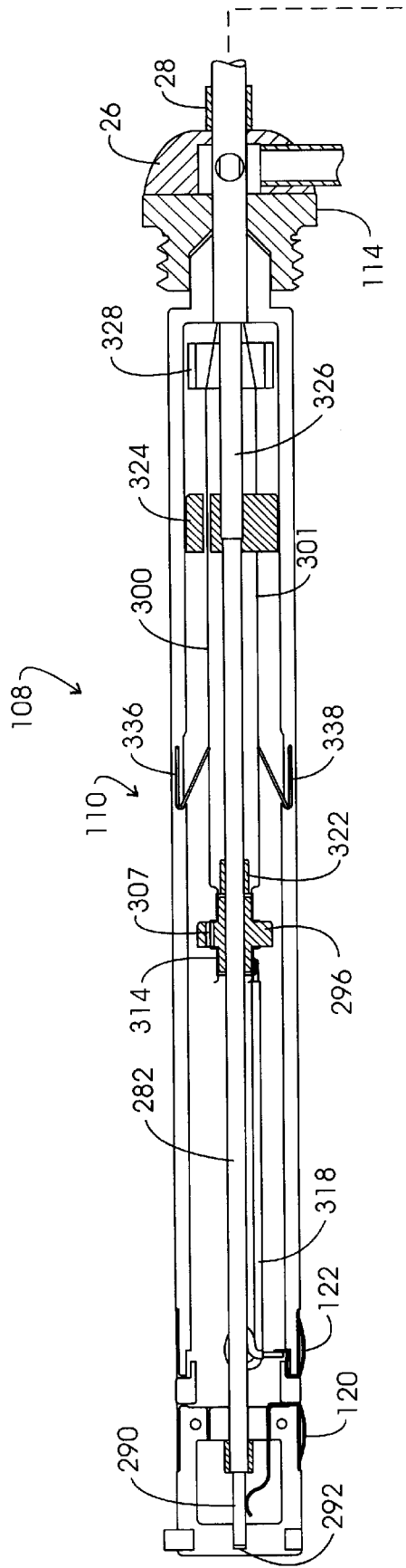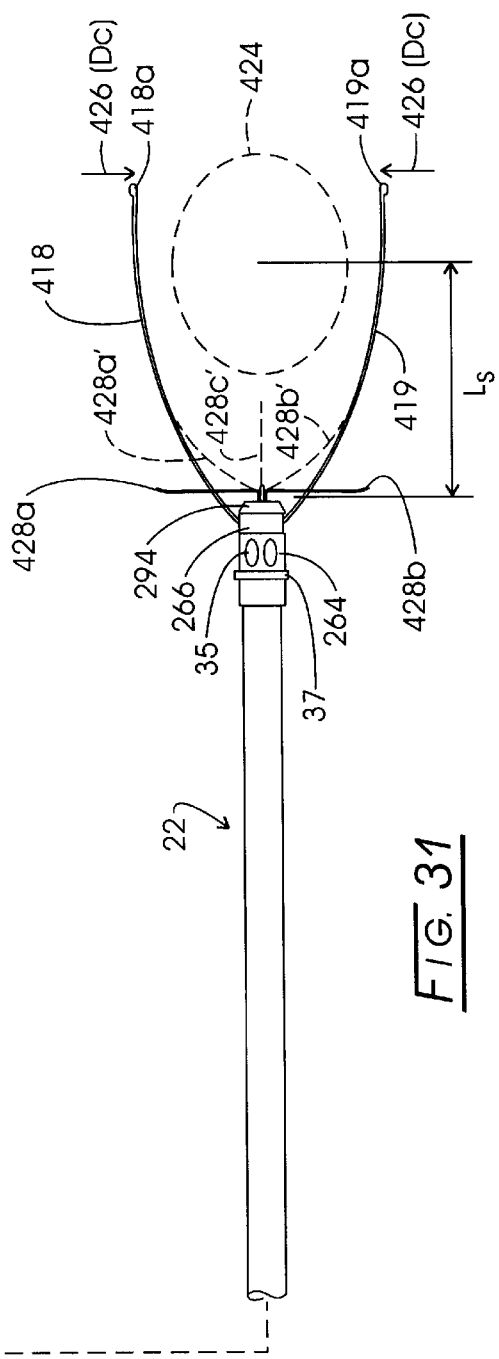
FIG. 31

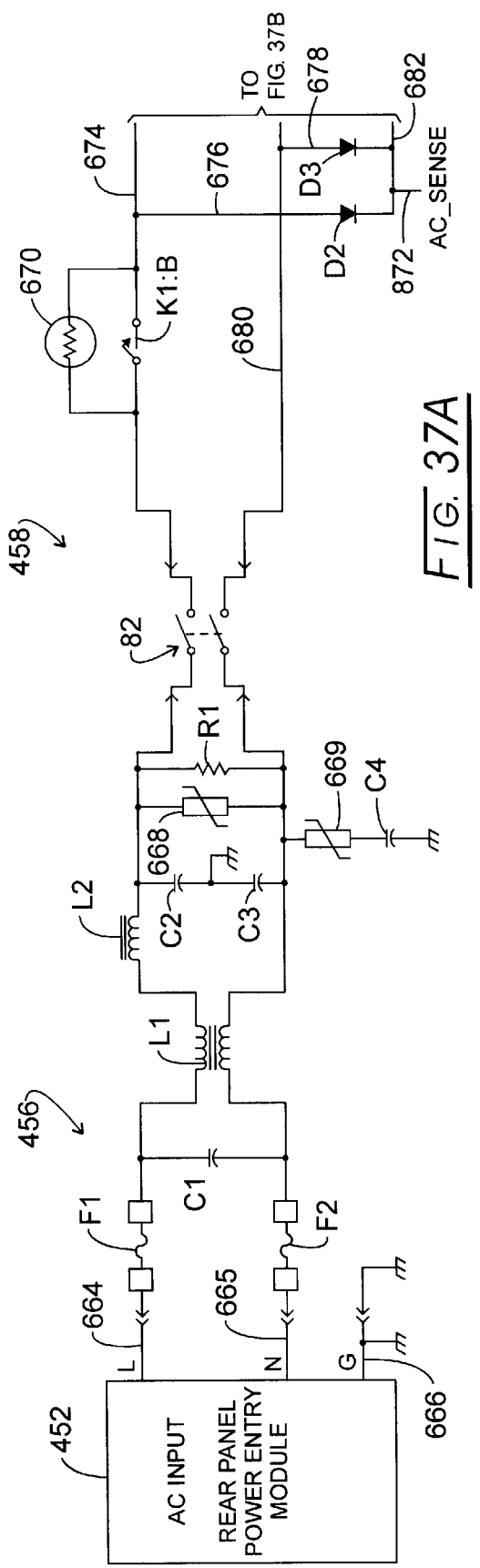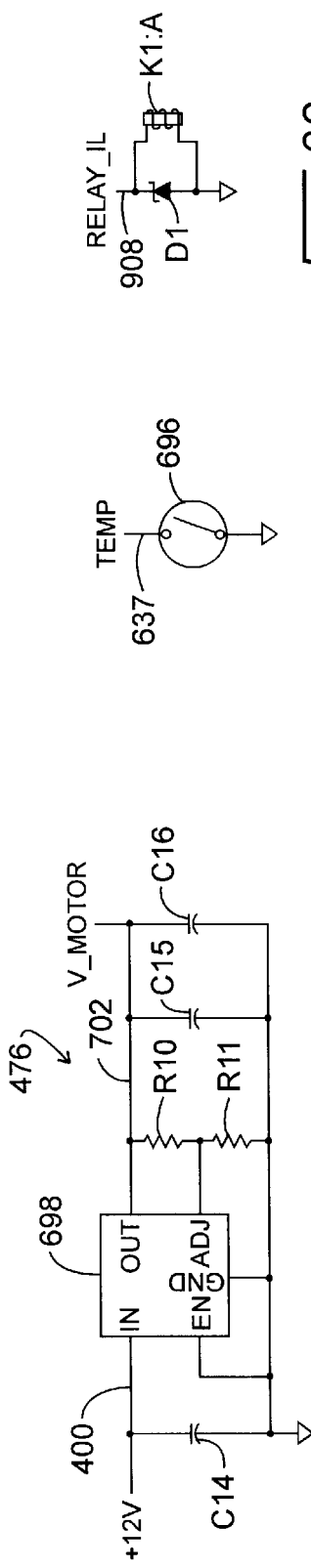

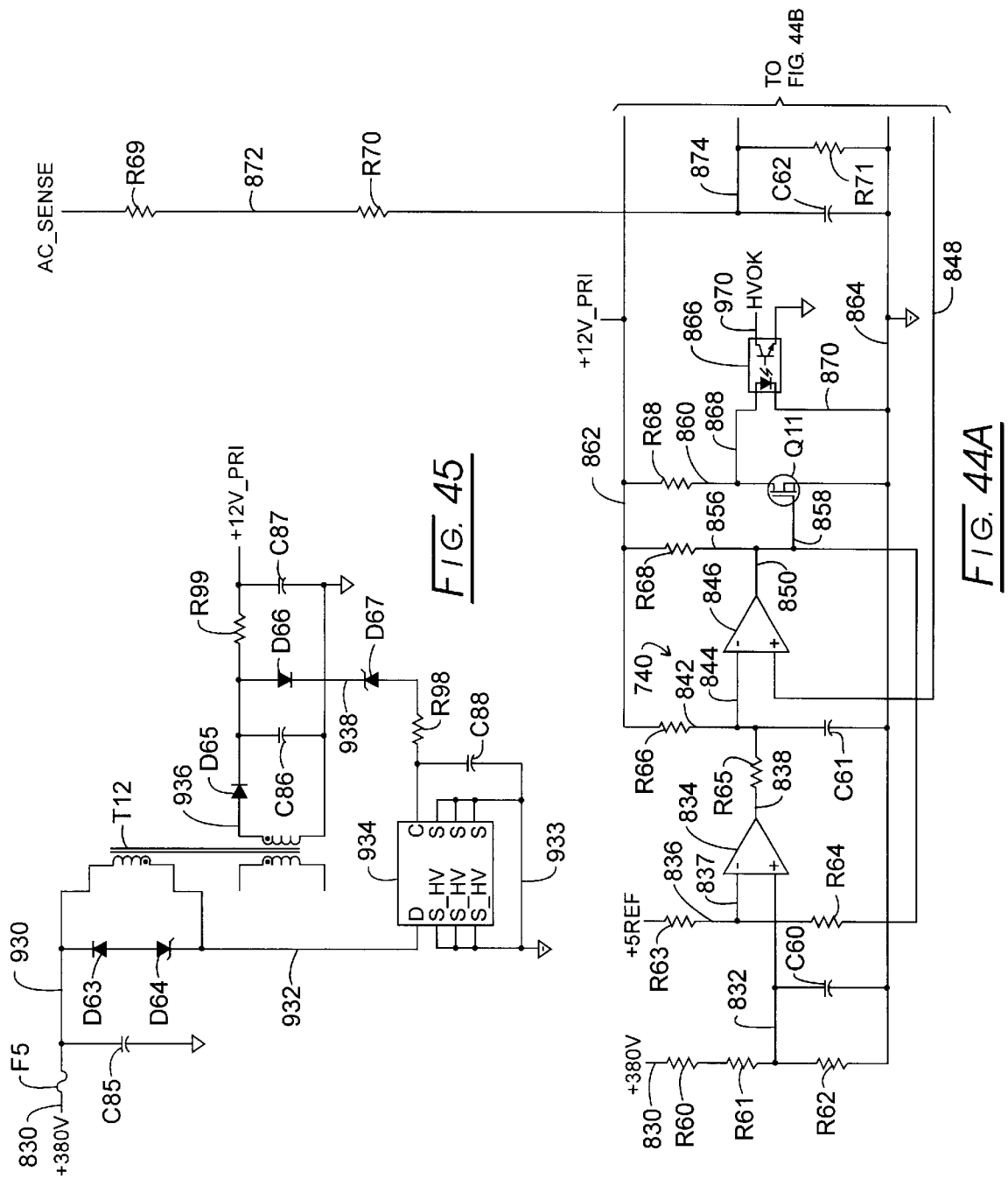

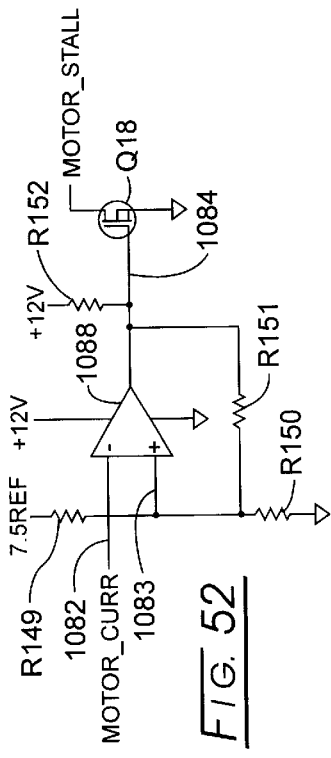
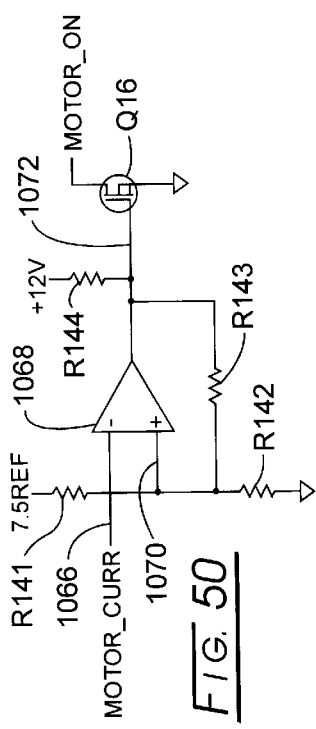
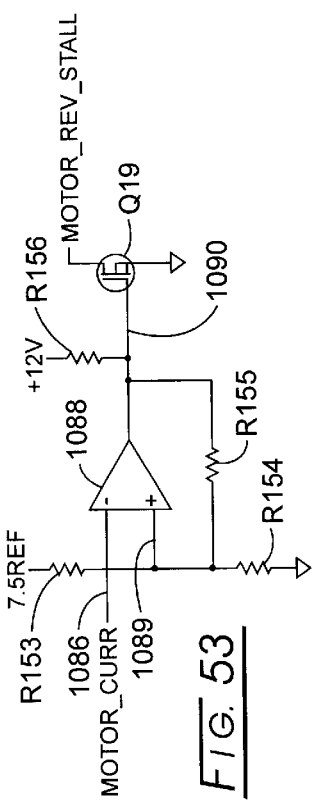
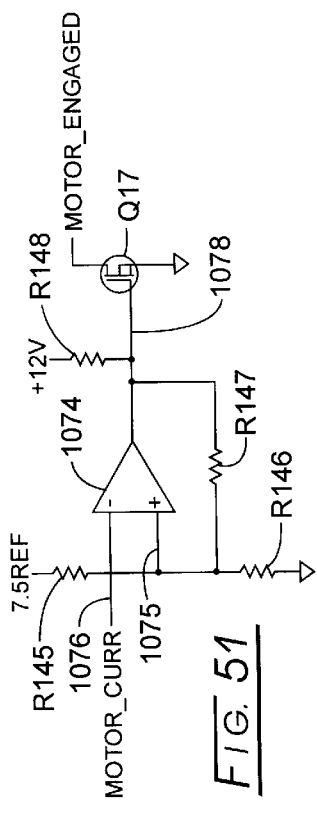
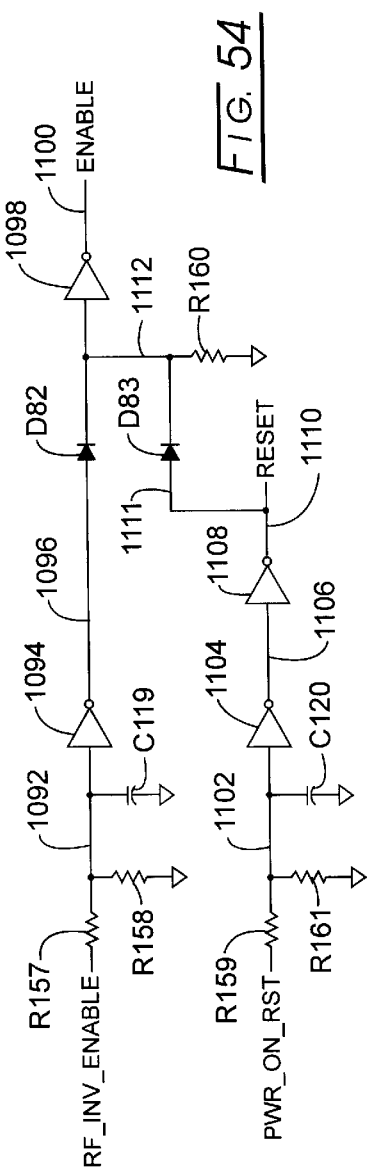

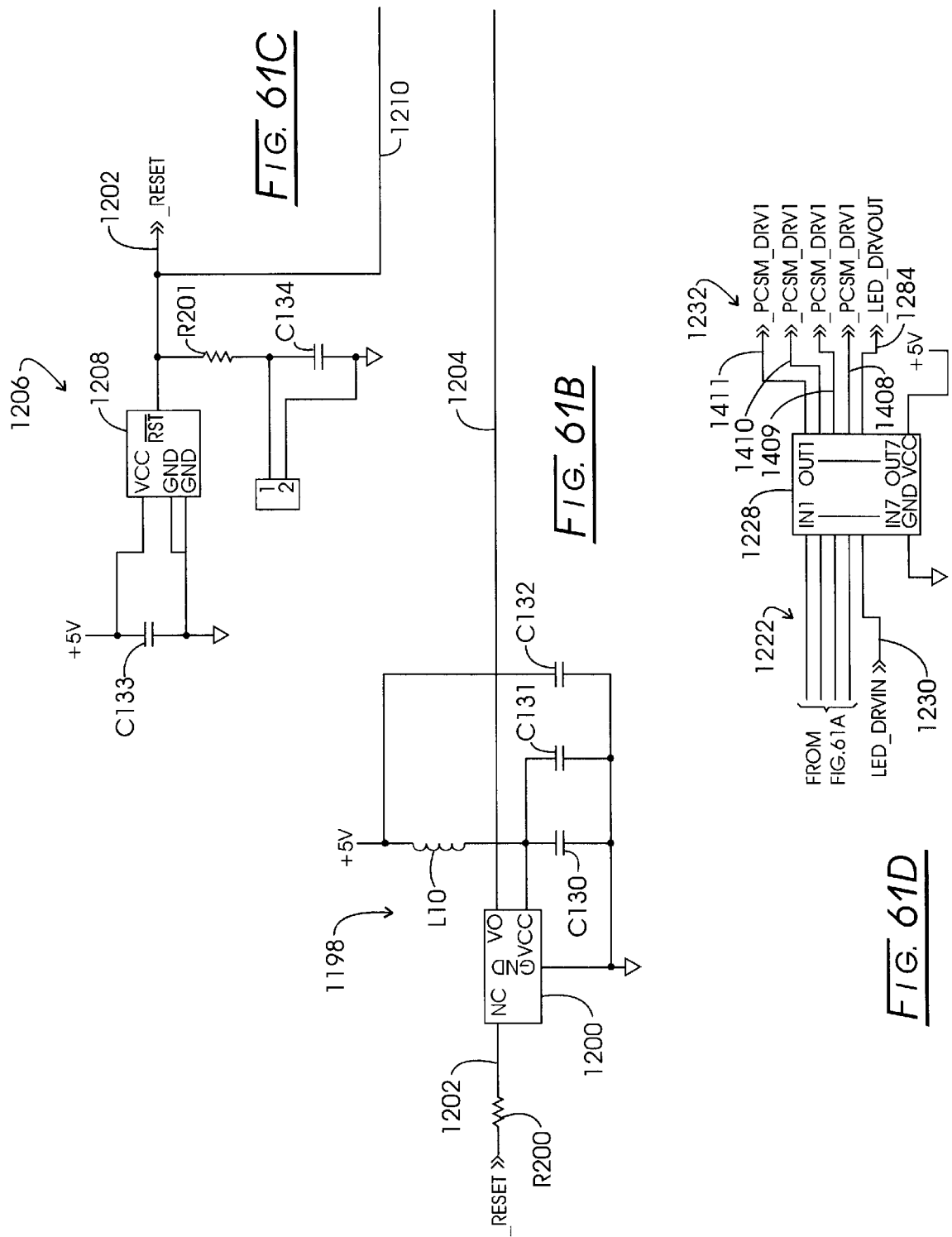

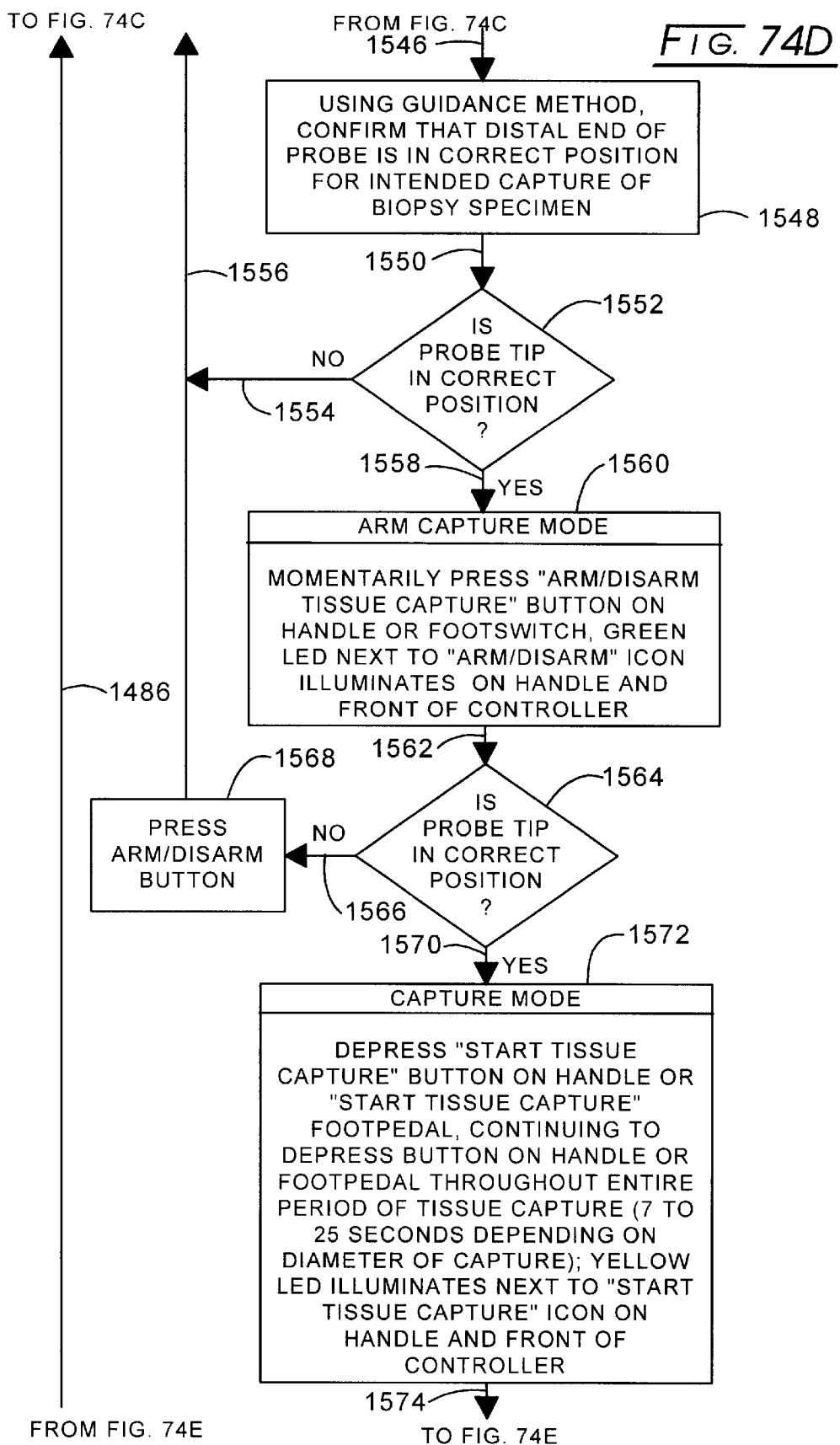

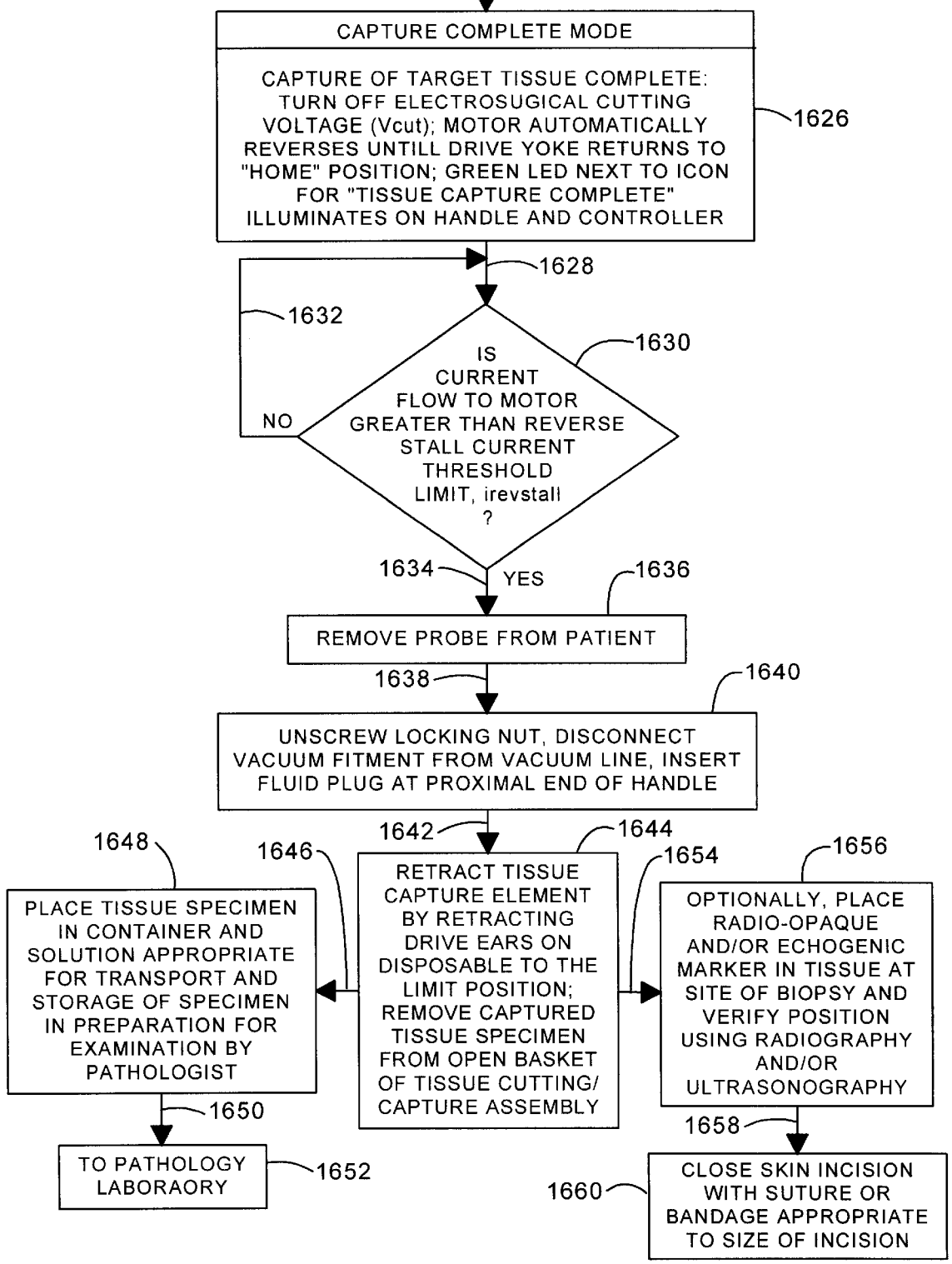

MINIMALLY INVASIVE INTACT RECOVERY OF TISSUE

CROSS-REFERENCE TO RELATED APPLICATIONS

This application is a Continuation-In-Part of United States application for patent Ser. No. 09/472,673 entitled: "Minimally Invasive Intact Recovery of Tissue", filed Dec. 27, 1999 by Eggers, et al., now U.S. Pat. No. 6,277,083.

STATEMENT REGARDING FEDERALLY SPONSORED RESEARCH

Not applicable.

BACKGROUND OF THE INVENTION

It is estimated that one out of eight women will face breast cancer at some point during her lifetime, and for women age 40–55, breast cancer is the leading cause of death. While methods for detecting and treating breast cancer initially were crude and unsophisticated, advanced instrumentation and procedures now are available which provide more positive outcomes for patients.

In the 1800s the only treatment for breast cancer was removal of the entire breast. Given that the sole method of detection and diagnosis was palpation, treatment was only directed when the breast tumor was well advanced. Modified radical mastectomies are still performed today for patients with invasive cancer, such a procedure involving the removal of the entire breast and some or all of the axillary lymph nodes. Radical or modified radical mastectomies involve serious trauma for the patient during surgery with the severest cosmetic results after surgery.

Another surgical option upon the discovery of malignant tumor is what is referred to as breast conserving surgery, which also is referred to as lumpectomy, tumorectomy, segmental mastectomy and local excision. Meant to address the cosmetic concerns associated with removal of the breast, only the primary tumor and a margin of surrounding normal breast tissue is removed. Determining the proper amount of tissue to be removed involves balancing the need to take sufficient tissue to prevent recurrence with the desire to take as little tissue as possible to preserve the best cosmetic appearance. A more limited nodal dissection now is performed with the primary purpose being staging rather than therapy. While an improvement over radical mastectomy, breast-conserving surgery still involves the removal of large sections of breast tissue. Risks associated with such surgery include wound infection, seroma formation, mild shoulder dysfunction, loss of sensation in the distribution of the intercostobrachial nerve, and edema of the breast and arm. For more information on invasive tumor therapy, see:

(1) Harris, Jay R., et al. "Cancer of the Breast." *Cancer: Principles and Practices of Oncology, Fourth Edition.* Eds. DeVita, et al. Philadelphia: J.B. Lippincott Co., 1993. 1264–1285.

(2) Jobe, William E. "Historical Perspectives." *Percutaneous Breast Biopsy.* Eds. Parker, et al. New York: Raven Press, 1993. 1–5.

Mastectomies and breast-conserving surgeries generally are procedures utilized for invasive tumor. Advances in tumor detection, however, have radically changed the course of diagnosis and treatment for a tumor. With the advent of imaging devices, such as the mammogram, suspect tumor may be located when it is of relatively small size. Today, tumor detection generally involves both a mammogram and a physical examination, which takes into account a number of risk factors including family history and prior occurrences. Technical improvements in mammogram imaging include better visualization of the breast parenchyma with less exposure to radiation, improvements in film quality and processing, improved techniques for imaging, better guidelines for the diagnosis of cancer and greater availability of well-trained mammographers. With these advancements in imaging technology, a suspect tumor may be detected which is 5 mm or smaller. More recently substantial progress has been witnessed in the technical disciplines of magnetic resonance imaging (MRI) and ultrasound imagining. With these advances, the location of a lesion is observable as diagnosticlanalytic or therapeutic procedures are carried out.

In the past, because a tumor normally was not discovered until it had reached an advanced stage, the issue of whether a tumor was malignant or benign did not need to be addressed. With the ability to locate smaller areas of suspect tumor, this issue becomes of critical importance, particularly in light of the fact that only 20% of small, non-invasive tumors are malignant. Tumors identified as being benign may be left in situ with no excision required, whereas action must be taken to excise suspect tissue confirmed to be malignant. In view of the value of classifying a tumor as malignant or benign, breast biopsy has become a much-utilized technique with over 1 million biopsies being performed annually in the United States. A biopsy procedure involves the two step process of first locating the tumor then removing part or all of the suspect tissue for examination to establish precise diagnosis.

One biopsy option available upon detection of a suspect tumor is an open surgical biopsy or excisional biopsy. Prior to surgery, a radiologist, using mammography, inserts a wire into the breast to locate the tumor site. Later during surgery, the surgeon makes an incision in the breast and removes a large section of breast tissue, including the suspect tissue and a margin of healthy tissue surrounding the tumor. As with other similar procedures, such as those described above, open surgery may result in high levels of blood loss, scarring at the location of the incision and permanent disfigurement, due to the removal of relatively large amounts of tissue. Because of the critical prognostic significance of tumor size, the greatest advantage of the excisional biopsy is that the entire area of the suspect tumor is removed. After being removed and measured, the specimen is split by a pathologist in a plane that should bisect a tumor if present, then the margin between tumor and healthy tissue is examined. Microscopic location of carcinoma near the margin provides information for future prognosis. Thus the pathology laboratory is oriented to the morphological aspect of analysis, i.e. the forms and structures of involved tissue.

For information on pathology of breast biopsy tissue, see:

(3) Rosen, Paul Peter. Rosen's Breast Pathology. Philadelphia: Lippincott-Raven Publishers, 1997. 837–858.

Other less invasive options are available which avoid the disadvantages associated with open surgery. One such non-invasive option is that of needle biopsy, which may be either fine needle aspiration or large core. Fine needle aspiration (FNA) is an office procedure in which a fine needle, for example of 21 to 23 gauge, having one of a number of tip configurations, such as the Chiba, Franzeen or Turner, is inserted into the breast and guided to the tumor site by mammography or stereotactic imaging. A vacuum is created and the needle moved up and down along the tumor to assure that it collects targeted cellular material. Generally, three or more passes will be made to assure the collection of a sufficient sample. Then, the needle and the tissue sample are withdrawn from the breast.

The resulting specimen is subject to a cytologic assay, as opposed to the above-noted morphological approach. In this regard, cell structure and related aspects are studied. The resultant analysis has been used to improve or customize the selection of chemotherapeutic agents with respect to a particular patient.

While a fine needle aspiration biopsy has the advantages of being a relatively simple and inexpensive office procedure, there are some drawbacks associated with its use. With fine needle aspiration, there is a risk of false-negative results, which most often occurs in cases involving extremely fibrotic tumor. In addition, after the procedure has been performed there may be insufficient specimen material for diagnosis. Finally, with fine needle aspiration alone the entire area of suspect tissue is not removed. Rather, fragmented portions of tissue are withdrawn which do not allow for the same type of pathological investigation as the tissue removed during an open surgery biopsy.

This limitation also is observed with respect to large core needle biopsies. For a large core needle biopsy, a 14 to 18 gauge needle is inserted in the breast having an inner trocar with a sample notch at the distal end and an outer cutting cannula. Similar to a fine needle aspiration, tissue is drawn through the needle by vacuum suction. These needles have been combined with biopsy guns to provide automated insertion that makes the procedure shorter and partially eliminates location mistakes caused by human error. Once inserted, multiple contiguous tissue samples may be taken at a time.

Samples taken during large core needle biopsies may be anywhere from friable and fragmented to large pieces 20 to 30 mm long. These samples may provide some histological data, unlike fine needle aspiration samples, however, they still do not provide the pathological information available with an open surgical biopsy specimen. Further, as with any mechanical cutting device, excessive bleeding may result during and following the procedure. Needle biopsy procedures are discussed in:

(4) Parker, Steve H. "Needle Selection" and "Stereotactic Large-Core Breast Biopsy." *Percutaneous Breast Biopsy*. Eds. Parker, et al. New York: Raven Press, 1993. 7–14 and 61–79.

A device which is somewhere between a needle biopsy and open surgery is referred to as the Advanced Breast Biopsy Instrumentation (ABBI). With the ABBI procedure, the practitioner, guided by stereotactic imaging, removes a core tissue sample of 5 mm to 20 mm in diameter. While the ABBI has the advantage of providing a large tissue sample, similar to that obtained from an open surgical biopsy, the cylindrical tissue sample is taken from the subcutaneous tissue to an area beyond the suspect tumor. For tumors embedded more deeply within the breast, the amount of tissue removed is considerable. In addition, while less expensive than open surgical biopsy, the ABBI has proven expensive compared to other biopsy techniques, and it has been noted that the patient selection for the ABBI is limited by the size and location of the tumor, as well as by the presence of very dense parenchyma around the tumor. For discussion on the ABBI, see:

(5) Parker, Steve H. "The Advanced Breast Biopsy Instrumentation: Another Trojan Hourse?" Am. J.
Radiology 1998; 171: 51–53.

(6) D'Angelo, Philip C., et al. "Stereotactic Excisional Breast Biopsies Utilizing the Advanced Breast Biopsy Instrumentation System." Am J Surg. 1997; 174: 297–302.

(7) Ferzli, George S., et al. "Advanced Breast Biopsy Instrumentation: A Critique." J Am Coll Surg 1997; 185: 145–151.

Another biopsy device has been referred to as the Mammotome and the Minimally Invasive Breast Biopsy (MIBB). These devices carry out a vacuum-assisted core biopsy wherein fragments of suspect tissue are removed with a 11 to 14 gauge needle. While being less invasive, the Mammotome and MIBB yields only a fragmentary specimen for pathological study. These devices therefore are consistent with other breast biopsy devices in that the degree of invasiveness of the procedure necessarily is counterbalanced against the need for obtaining a tissue sample whose size and margins are commensurate with pathology requirements for diagnosis and treatment.

In a co-pending application for United States patent entitled "Minimally Invasive Intact Recovery of Tissue", Ser. No. 09/472,673, filed Dec. 27, 1999 by Eggers, et al, an instrument for removing a targeted tissue volume in a minimally invasive manner is described. That instrument includes a tubular delivery cannula of minimum outer diameter, the tip of which is positioned in confronting adjacency with a tissue volume to be removed. Following such positioning, the electrosurgically excited leading edge of a capture component is extended forwardly from the instrument tip to enlarge while electrosurgically cutting and surrounding or encapsulating a tissue volume, severing it from adjacent healthy tissue. Following such capture, the instrument and encaptured tissue volume are removed through an incision of electively limited extent.

BRIEF SUMMARY OF THE INVENTION

The present invention is addressed to apparatus, system and method for retrieving a tissue volume in intact form utilizing surgical instrumentation which is minimally invasive. This instrumentation includes a tubular delivery cannula of minimum outer diameter, the tip or distal end of which is positioned in confronting adjacency with the target tumor or tissue volume to be removed. Such positioning is facilitated through the utilization of a forwardly disposed precursor electrosurgical electrode assembly. Located within the interior channel of this delivery cannula is a capture component configured with a plurality of relatively elongate leafs mutually interconnected at their base to define a polygonal cross-sectional configuration. Each of the leafs terminates forwardly with a transversely bent, eyelet containing tip. Slidably extending through each eyelet is an electrically conductive pursing cable of a pursing cable assembly which is then attached to another leaf tip and extends rearwardly through a small, flexible guide tube attached to the leaf for connection with the cable terminator component of a drive assembly. The drive assembly is driven forwardly by a motor, translation assembly and abuttably engaged transfer assembly to actuate the capture component. This actuation is carried out by electrosurgically exciting the pursing cable assembly to establish a cutting leading edge. Then, the leafs, carrying the excited cable assembly, are driven at an attack angle mutually outwardly through a guidance assembly to an extent that the cutting leading edge reaches an effective maximum diameter extending about the tissue volume. At this juncture, the cable terminator encounters a stop member and the leaf tips are drawn mutually inwardly to define a curvilinear profile to close the leading edge about the tissue volume as their forward movement continues. These pursing cables, now under stress and constrained within the guide tubes at the outer surfaces of the leafs, contribute to the structural stability of the resultant tissue specimen containment structure. Adjustment of the number of leafs associated with a given cable establishes the rates of containment closure as well as the degree or extent of curvature of the noted curvilinear profile. Following capture, the instrument is removed from adjacent tissue with the retained tissue specimen.

By employing this noted cable terminator and stop member construction, the diameter of the delivery cannula can be maintained at a constant minimum value, while the instrument enjoys the capability of providing an important range of capture component leading edge maximum effective diameters. The relatively straightforward structuring of the delivery cannula, capture component and drive assembly permits their fabrication as a discrete disposable component, removably insertable within a hand maneuvered housing.

Practitioner control over the instrument principally is provided from either three button-type switches mounted upon its housing assembly or from a three pedal footswitch. A remotely located electrosurgical generator and control assembly is coupled by cable with the housing assembly and footswitch. In carrying out the retrieval procedure, following preliminary self checks for proper electrode and instrument connections and transfer assembly positioning, either a position switch on the housing or the footswitch is actuated by the practitioner. This energizes a forwardly disposed precursor electrode from the electrosurgical generator, initially at a boost voltage level for a short boost interval, then at a lower, normal cutting voltage level as the forward region of the delivery cannula is positioned in confronting adjacency with the involved tissue volume. The switch utilized then is released to terminate this positioning mode of the procedure.

The delivery cannula being thus positioned, the practitioner momentarily depresses an arm capture switch button on the housing assembly to cause the control assembly to enter an arm capture mode which disables the housing mounted position switch. Next, the practitioner depresses either the capture switch or capture footswitch which now performs a capture function. Upon depressing and continuing to depress a capture switch mounted upon the housing assembly or the capture footswitch, the control assembly enters a capture mode. At the commencement of this capture mode, motor performance initially is tested, whereupon the motor is de-energized as electrosurgical current at the boost voltage level is applied to the capture component cables for a short boost interval. Following this boost interval, current at a lower, normal cutting voltage level is asserted from the electrosurgical generator in conjunction with activation of the motor drive and the leafs commence to be deployed from the guidance assembly. During the ensuing actuation of the capture component under motor drive, the load characteristics of the motor are monitored for both motor performance and for detecting the completion of capture. In the latter regard, a forward stall condition is detected to determine capture completion commencing a capture complete mode. In this capture complete mode, motor rotational direction is reversed to cause a return of the transfer assembly to its original or home position, thus releasing the drive assembly of the disposable component from engagement. The delivery cannula with captured tissue specimen is removed from the incision and the disposable component of the instrument is removed from the housing assembly. When so removed, the practitioner may manually retract the drive component to a position causing the capture component leafs and associated pursing cable assembly to assume an open cup formation permitting facile access to the recovered specimen.

If, during the capture mode, the practitioner wishes to halt the procedure, the capture switch or capture footswitch is released to cause the control assembly to enter a pause mode. In this pause mode the motor is de-energized and electrosurgical cutting current to the capture component cable assembly is terminated. Return to capture mode performance is carried out by the practitioner by again depressing the handle mounted capture switch or capture footswitch.

The remotely disposed electrosurgical generator is configured with an input treatment network which responds to a conventional power input to derive an interim direct current (d. c.) voltage output of relatively higher value, for example, 380 volts. This input treatment preferably includes both EMI filtering as well as power factor correction. In general, a boost converter network is employed in conjunction with this power factor correction. The interim d. c. voltage then is applied to a 100 kilohertz inverter which provides a rectangular waveform output, the peak-to-peak voltage amplitude of which is developed by an inverter control network which performs in a resonant transition phase shift mode to achieve soft switching and quite accurate control of the noted voltage amplitude. This amplitude controlled output then is directed through an isolation transformer to rectification and filtering to evolve a d.c. link voltage, the amplitude of which is used as a control for the voltage amplitude of the ultimately derived electrosurgical boost and normal cutting voltage levels. In this regard, the d. c. link voltage input is directed to the input of a resonant tank circuit for deriving a sinusoidal output at a stable electrosurgical frequency which is directed to the primary side of a high voltage transformer. From the secondary side of that high voltage transformer, an output stage directs electrosurgical energy to the precursor electrodes and, alternately, to the capture component cable assembly. To provide control over the assertion of electrosurgical energy, the system employs a relay disconnect function within the d. c. link voltage circuit path.

The housing assembly also incorporates a manually graspable stabilizer grip which is removably connectable at either side of the instrument to accommodate both right handed and left handed practitioners. Further, the grip is adjustable longitudinally to accommodate for the size of the hand of the practitioner to facilitate reaching the three button switches mounted upon the housing assembly.

Other objects of the invention, will in part, be obvious and will, in part, appear hereinafter. The invention, accordingly, comprises the method, system and apparatus possessing the construction, combination of elements, arrangement of parts and steps which are exemplified in the following detailed description. For a fuller understanding of the nature and objects of the invention, reference should be made to the following detailed description taken in connection with the accompanying drawings.

BRIEF DESCRIPTION OF THE DRAWINGS

FIG. 7 is a bottom view of the instrument shown in FIG. 1;

FIG. 8 is a front view of the reusable housing shown in FIG. 2;

FIG. 12 is side view of the disposable component of the instrument as shown in FIG. 2;

FIG. 13 is a bottom view of the disposable component of FIG. 12;

FIG. 14 is a sectional view taken through the plane 14—14 shown in FIG. 13;

FIG. 16 is a sectional view taken through the plane 16—16 shown in FIG. 12;

FIG. 17 is a sectional view taken through the plane 17—17 shown in FIG. 12;

FIG. 18 is a sectional view taken through the plane 18—18 shown in FIG. 13;

FIG. 19 is a sectional view taken through the plane 19—19 shown in FIG. 18;

FIG. 20 is a sectional view taken through the plane 20—20 shown in FIG. 18;

FIG. 21 is a top view of a leaf assembly employed with the disposable component shown in FIG. 2;

FIG. 22 is a general sectional view of a capture component leaf assembly and drive rod;

FIG. 23 is a partial plan view of a leaf employed with the structure shown in FIG. 21 as it appears prior to the bending of its tip portion;

FIG. 24 is a sectional view taken through the plane 24—24 shown in FIG. 23;

FIG. 25 is a partial view of the leaf shown in FIG. 23 with its tip bent into an operative orientation;

FIG. 28 is a partial sectional view of the disposable component of the instrument shown in FIG. 1 schematically showing a deployment of capture component leafs to a maximum diametric extent;

FIG. 29 is a partial sectional view of the instrument of FIG. 28 schematically showing the orientation of the capture component leafs at the completion of capture of a tissue volume;

FIG. 31 is a partial sectional view of the instrument shown in FIG. 1 with the capture component leafs schematically depicted at a maximum diametric extent orientation for use with a larger tissue volume sample;

FIGS. 37A and 37B combine as labeled thereon to provide a schematic circuit diagram showing the EMI filter, front panel switch, and PFC boost converter components shown in block form in FIG. 34;

FIG. 38 is an electrical schematic diagram showing a relay solenoid component employed with contacts shown in FIG. 37A;

FIG. 39 is an electrical schematic diagram of a temperature responsive component employed with the console shown in FIG. 1;

FIG. 40 is an electrical schematic diagram of a power supply dedicated to provide input power to a motor contained in the reusable housing of the instrument as shown in FIG. 4;

FIGS. 44A and 44B combine as labeled thereon to provide an electrical schematic diagram of a link voltage evaluation circuit and a controller for a power factor correction boost converter with associated enablement circuitry;

FIG. 45 is an electrical schematic diagram of a primary side power supply;

FIG. 50 is an electrical circuit schematic diagram of a motor current monitoring circuit;

FIG. 51 is an electrical schematic diagram of a motor monitoring electrical circuit;

FIG. 52 is an electrical schematic diagram of a motor monitoring electrical circuit;

FIG. 53 is an electrical schematic diagram of a motor monitoring electrical circuit;

FIG. 54 is an electrical schematic diagram showing a derivation of reset and enable signals;

FIGS. 61A–61E combine as labeled thereon to describe a programmable logic device based circuit with associated output buffering and filtering;

FIGS. 74A–74G combine as labeled thereon to provide a flow chart describing the methodology of the invention.

DETAILED DESCRIPTION OF THE INVENTION

A predominate characteristic of the invention resides in the employment of a capture component in conjunction with a delivery cannula, This capture component is configured with a forward portion which extends to a forwardly disposed cutting leading edge which is electrosurgically excited to provide for electrosurgical cutting. Targeted tumor or tissue along with adjacent healthy tissue is circumscribed or encapsulated by this capture component through the utilization of a pursing cable assembly which both provides the noted electrosurgical cutting and constricts the leading edge to, in effect, encapsulate the incised tissue volume. The capture component is implemented with five elongate flexible metal leafs the tips of which are formed with eyelets for receiving cables of the noted pursing cable assembly. By selecting a component orientation establishing where a pursing or constricting action commences, the maximum leading edge periphery for capture may be elected and, typically, may range, for example, from about a 10 mm to about a 40 mm effective diametric extent. Initial positioning of the delivery cannula tip in confronting adjacency with a tissue volume is facilitated through the utilization of a precursor electrosurgical electrode assembly located at the tip. Following appropriate positioning of the tip, a motorized drive is enabled to actuate the capture component thus providing an optimized rate of movement of the leading edge positioned electrosurgical cutting cables about the target tissue. A desirable feature of the system of the invention resides in the incorporation of the delivery cannula and cable implemented capture component with a disposable support housing. That disposable component is mounted with reusable motorized drive and control components. The term "cannula" as used herein is intended to refer to any elongate surgical delivery structure, rigid or flexible, having a capability for deploying electrosurgical components.

Figure 1:
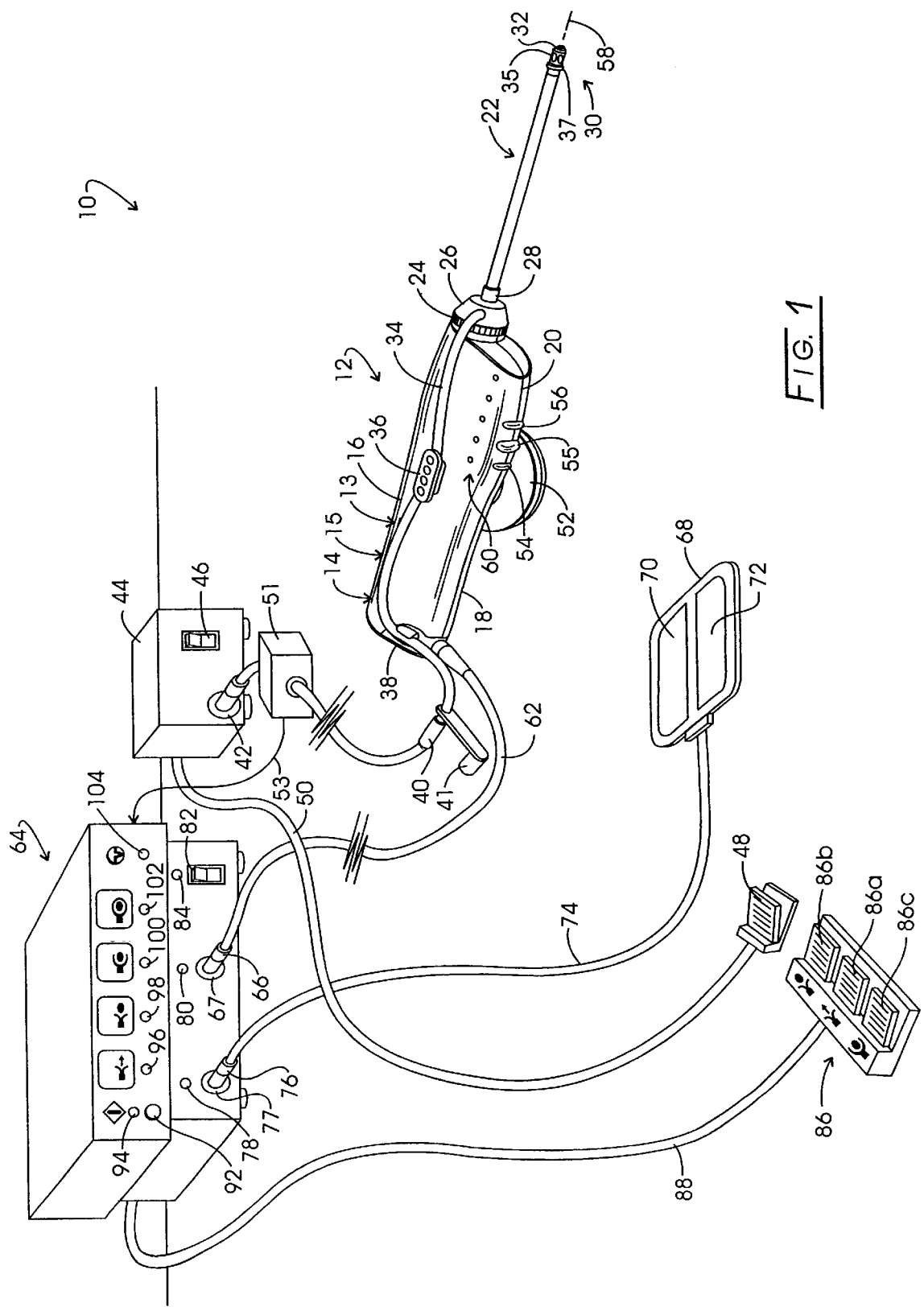
FIG. 1 is a perspective view of the system of the invention showing a hand held instrument, control console, return electrode, footswitches and a vacuum system component.

Referring to FIG. 1, a system according to the invention is represented in general at 10. System 10 includes a tissue retrieval instrument or apparatus represented generally at 12 which includes a polymeric housing assembly represented generally at 14. Housing assembly 14 comprises a re-useable housing 15 and a disposable support housing (seen at 108 in FIG. 2). Housing 15 is formed of two identically molded components shown as housing right side 16 and a housing left side 18. Sides 16 and 18 extend mutually outwardly from a medial plane represented at a joint line 20. An elongate delivery cannula represented at 22 is shown supported from the forward portion of the housing assembly 14 which extends along a longitudinal axis 58. A distal end of the delivery cannula extends through a rotatable threaded connector 24 as well as a freely rotatable suction manifold 26 which is retained in position by a collar 28. The forward region of the cannula 22, as represented at 30 extends to a distal end or tip 32. A flexible suction conduit providing a body fluid, smoke and steam evacuation function is shown at 34 extending from the manifold 26 beneath a grip connector 36 through a guide 38 and connector 40 to the input 42 of the housing or console of a vacuum system 44. System 44 may be activated by a console mounted switch 46 or from a foot pedal switch represented at 48 having an electrical cable connection with the system 44 as represented at 50. Smoke, steam evacuation from the distal end 32 is called for to avoid thermal injury to tissue due to a migration of steam back along the exterior surface of delivery cannula 22. A plug 41 is provided to close connector 40 and control any fluid movement within conduit 34 at the termination of a procedure.

Grip connectors are positioned on both the right and left housing sides 16 and 18, that at side 16 being revealed at 36. These connectors are utilized to support a hand engaged stabilizer grip, for example, the annulus-shaped grip represented at 52 which is shown coupled to the left housing side 18 for use by a right handed practitioner. Positioned at the forward portion of housing assembly 14 and accessible from the stabilizer grip 52 are three button switches 54–56 which will be seen to function respectively as an arm/disarm switch; an energize position switch; and a start tissue capture switch. Immediately above the switches 54–56 on both the right hand housing side 16 and left hand housing side 18 are linear arrays of indicator lights one such array being represented generally at 60 in connection with right housing side 16. The arrays as at 60 are implemented with light emitting diodes (LEDs) and provide visual cues which, from front to rear provide a start/reset cue as a green light; a tissue capture complete cue provided as a green light; a start tissue capture cue (above switch 56) provided as a yellow light; an energize/position cue (above switch 55) provided as a yellow light; and an arm/disarm tissue capture cue (above switch 54) provided as a green light. Energization and control is provided to the instrument 12 via a multi-strand cable 62 (i.e., a 10 foot or 3 meter cable) which connects with a control assembly and electrosurgical generator console or controller represented generally at 64. Connection is shown through a multi-lead connector 66 at the end of cable 62 which is coupled to a housing connector 67.

The electrosurgical components of the apparatus 12 perform in monopolar fashion. Alternatively, a return electrode could be positioned on the surface of cannula 22 near its distal end in place of the illustrated use of a return electrode pad attached to skin of patient. For the former arrangement, a conventional large, dispersive return electrode assembly as at 68 is positioned adjacent the skin surface of the patient. Assembly 68 is configured having two electrode components 70 and 72 which are connected via cable 74 and connector 76 to a console 64 connector 77. At the time of attachment with an initially powered (switch 82) console 64, a patient circuit safety monitor circuit (PCSM) carries out a self test. Upon subsequent start/reset actuation (switch 92) a fault test with respect to the two electrode components 70 and 72 of the assembly 68 is performed. In the event the latter test fails, then both visual and aural pulsation warning cues are activated and the procedure is halted. The visual cue is implemented with a red LED 78 located above the connector 76. Proper connection of the cable 62 and connector 66 with the console 64 connector 67 is indicated by an illuminated green LED 80 positioned above connector 67. This connection test is carried out by directing current to a coding resistor (i.e., 10 kOhms) within housing assembly 14. Thus, the controller checks to confirm that the coding resistor is present in the handle to confirm that the handle is properly connected to the controller receptable which is connector 67. To the right of connector 67 is an on/off power input switch 82. When switch 82 is in an on orientation, a green LED 84 is energized. A second three-pedal footswitch 86 is coupled via a cable 88 to the rear panel of the console 64. Pedal 86a of this footswitch functions during an initial portion of the procedure utilizing instrument 12 to alternately activate a precursor electrosurgical cutting electrode assembly located at the distal end 32 of delivery cannula 22. Footswitch 86 also performs with respective pedals 86b and 86c to alternatively enter the arm/disarm mode and to activate the capture electrode during a capture procedure, the practitioner being required to depress either footswitch 86c or fingerswitch 55 throughout that procedure in order to enable the capture activity to proceed. Release of either footswitch 86c or fingerswitch 56 during the capture procedure will cause the system to enter a pause mode. It may be observed that the energize/position, arm/disarm and start tissue capture switch functions of respective switches 55, 54 and 56 are emulated at three-pedal switch 86 as shown respectively at 86a–86c.

Visual cuing corresponding with that at housing assembly 14 also is provided at the console 64. In this regard, a start/reset switch 92 is operationally associated with an LED 94 which illuminates in a green color upon actuation of that switch. A yellow position mode visual cue representing an energization of the noted precursor electrode is shown at 96. This LED provides a yellow output during the electrosurgical advancement of the delivery cannula tip 32 into confronting adjacency with a targeted tissue volume. Next, a green arm capture mode visual cue is provided by an LED 98 to represent an arming of the tissue capture feature of instrument 12. Once the arm/disarm button is depressed, the energize/position fingerswitch 55 or footswitch 86a is no longer activatable. However, the practitioner may return to the position mode by again depressing arm/disarm fingerswith 54 or footswitch 86b followed by an actuation of fingerswitch 55 or footswitch 86a. A yellow capture mode visual cue is provided by an LED 100 to represent the start of and carrying out of a tissue capture procedure and upon completion of such capture, a green capture complete mode visual cue is provided by a green LED 102. Finally, the pause mode condition is represented by a green LED, provided at 104. Aural cues are provided by a speaker located at the rear of console 6A. in general, a continuous tone is provided wherever electrosurgical cutting is taking place. A pulsed tone occurs in the event of a return electrode 68 fault. Because of the above-noted opportunity for steam migration, it is preferred that system 10 provide an assurance that the vacuum system as represented at housing or console 44 be actuated. Preferably, the control assembly of console 64 functions to permit commencement of the procedure only upon a turning on of system 44. Such a monitoring of system 44 is accomplished with a vacuum actuated switch shown at block 51 attached within conduit 34. The monitoring output to console 64 is represented at arrow 53.

Figure 2:
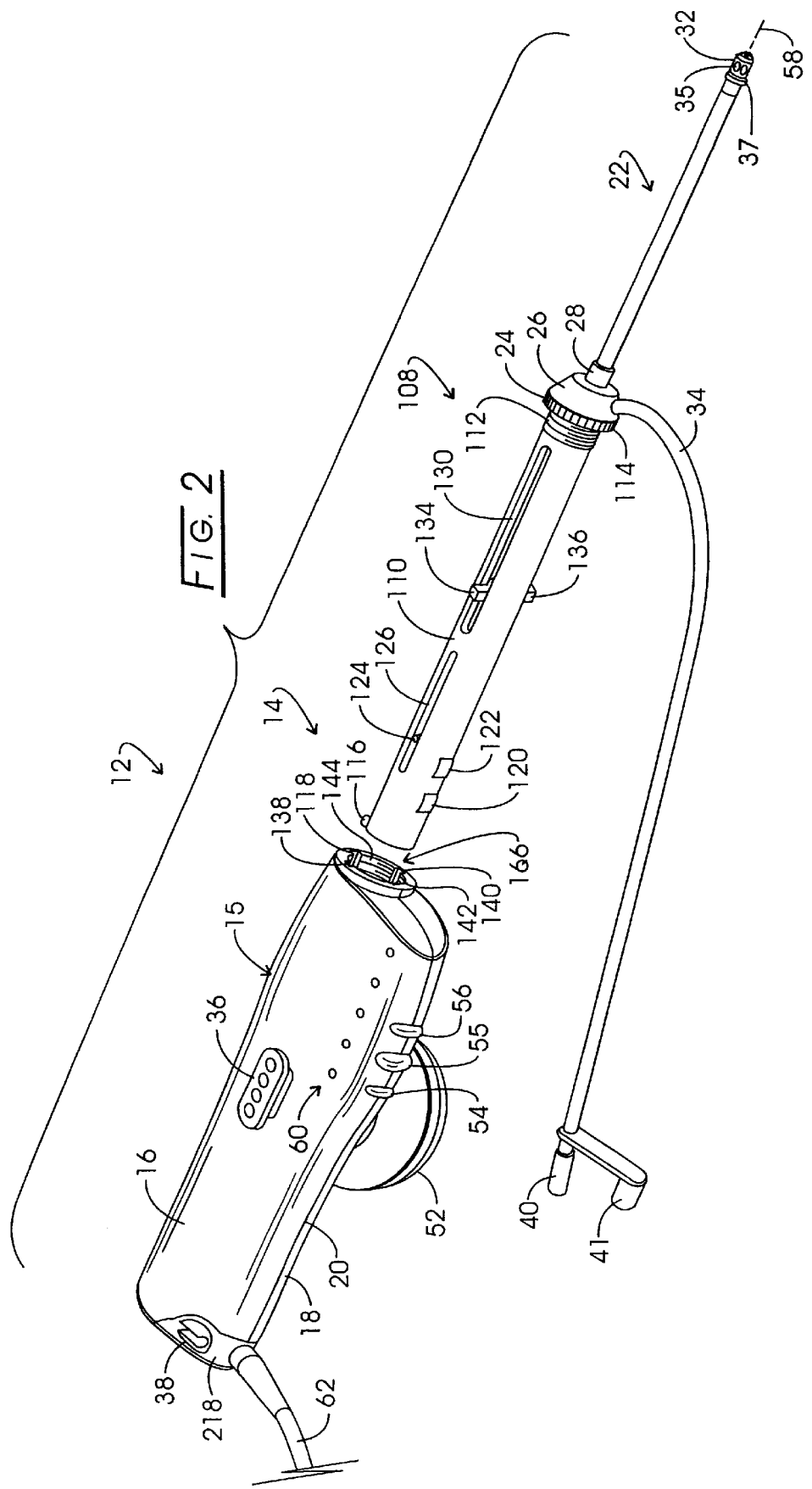
FIG. 2 is a perspective view of the instrument shown in FIG. 1 with a disposable component being shown removed from a reusable housing.

Referring to FIG. 2, the disposable component indicated generally at 108, of the instrument 12 is revealed in an orientation prior to insertion within the reusable, motor containing housing 15. In the figure, delivery cannula 22 is seen extending forwardly from a cylindrically shaped disposable support housing 110. The forward region of support housing 110 supports the rotatable connector 24. In this regard, it may be observed that the connector 24 is configured with external threads 112 which are fixed for rotation with a knurled flange 114. At the rearward end of support housing 110 there is located an upstanding indexing pin 116 which, during installation of the disposable assembly, is slidably received within an upwardly disposed slot 118 extending internally along an elongate receiving cavity 166 within housing 15.

Positioned opposite indexing pin 116 on support housing 110 are two spaced apart electrical contacts 120 and 122 which are oriented to make wiping contact with corresponding electrical terminals disposed within housing 15 upon insertion of support housing 110 within the receiving cavity 166. Contacts 120 and 122 selectively receive electrosurgical cutting current applied respectively to the precursor electrode at tip 32 and the pursing cables associated with the capture component. Those cables extend from the capture component to a cable terminator component having guidance tabs or ears one of which is revealed at 124 slidably mounted within an elongate stabilizer slot 126 arranged in parallel with axis 58. A corresponding guidance tab and slot combination is found in the opposite side of the support housing 110. Located forwardly of the slots as at 126 are two additional elongate drive slots one of which is shown at 130 similarly arranged in parallel with axis 58. The outwardly extending ears or guide tabs of a drive assembly drive member extend from these slots and are seen at 134 and 136. These ears or tabs 134 and 136 support rearwardly disposed driven surfaces which are used to impart forward movement to the drive assembly functioning, in turn, to deploy the capture component from delivery cannula 22. When the support housing 110 is installed within the receiving cavity or region 166 of housing 15 shown generally at 166, these ears or tabs 134 and 136 pass through oppositely disposed notches shown respectively at 138 and 140 provided at the forward portion of housing 15. Similarly, a notch 142 is located forwardly within reusable housing 15 to permit passage of the electrical terminals 120 and 122. Note, that the forward portion of reusable housing 15 also is provided with internally disposed threads 144 at the entrance of its receiving cavity or region 166. The axis of that receiving region is coincident with instrument axis 58. The figure also reveals that the axis of cannula 22 is coincident with instrument axis 58. Accordingly, when the support housing 110 is inserted within the receiving cavity of housing 15, the knurled flange 114 of connector 24 is rotated to provide threaded engagement between threaded surface 112 and internal threads 144.

Figure 3:
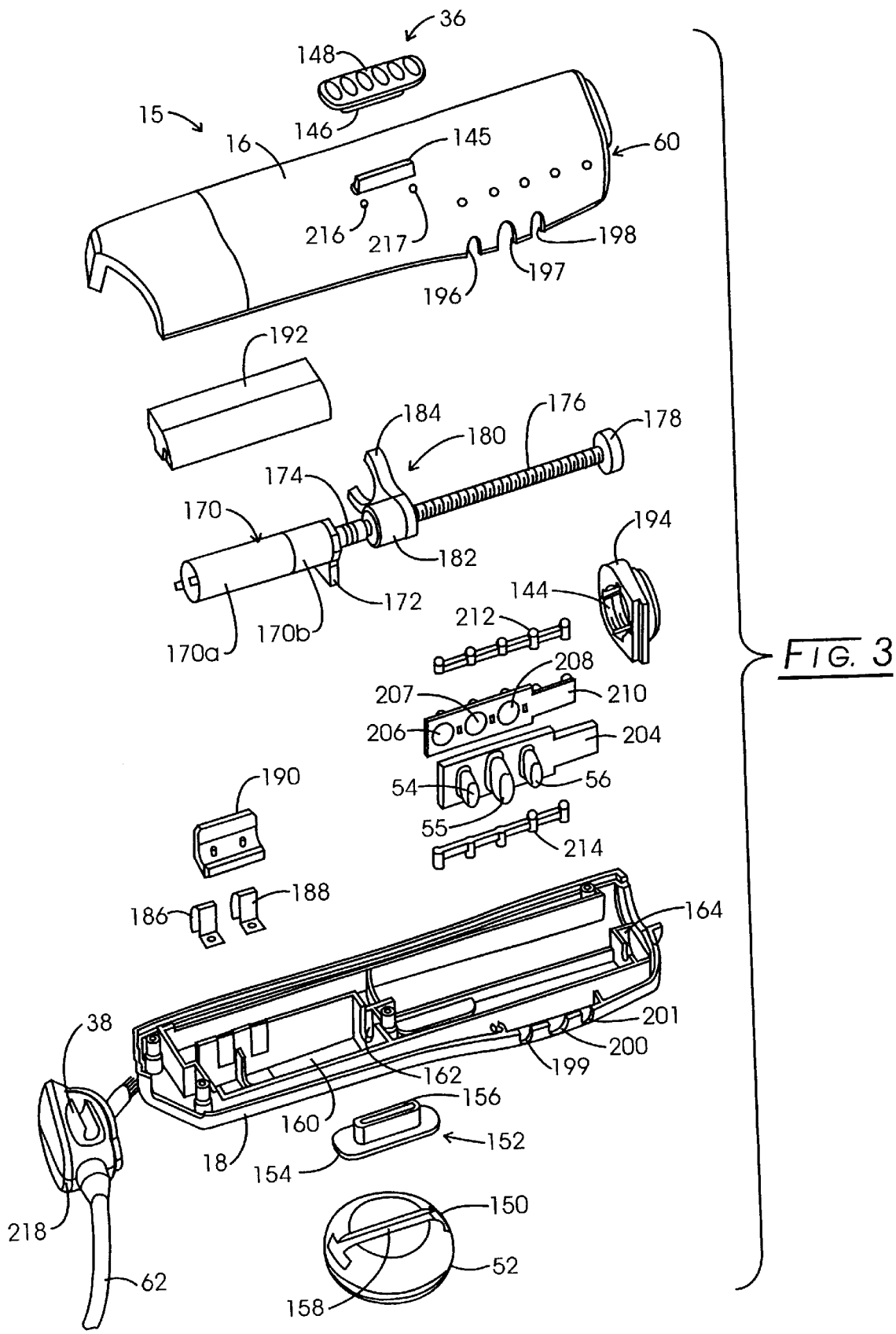
FIG. 3 is an exploded view of the reusable housing shown in FIG. 2.

Referring to FIG. 3, the assembly of the reusable components of the apparatus 12 is revealed in exploded fashion. In the figure, the exterior surface of the right side 16 of housing 15 is revealed and the corresponding interior of left housing left side 18 is revealed. These two sides are symmetrical and identical. Side 16 is shown as being formed with a rectangular opening 145 into which the pier portion 146 of connector 36 is attached. Fixed to the upper side of this pier 146 is an elongate platform 148 in which indentations are formed for positioning engagement with a threaded component 158 of the stabilizer grip as at 52. The underside of that grip 52 appears in the figure. That underside is formed with an inverted, T-shaped slot 150 which is configured to ride over the platform 148. In this regard, a connector 152 which is attached to the right housing side 18 is revealed in adjacency therewith. This connector also is formed with an elongate platform 154 which is fixed to a pier 156, in turn fixed to side 18 opposite connector 36. As apparent from the figure, the stabilizer grip 52 may be slid forwardly or rearwardly to accommodate the hand size of the user. Each of the housing sides 16 and 18 is formed with one half of a motor mount chamber as shown, for example, at 160 in connection with housing side 18. Positioned just forwardly of the chamber 160 are bulkheads defining a seal chamber 162. A forward region of each housing side is configured with one half of a thrust bearing chamber as represented at 164 in connection with housing side 18.

Positioned within the motor mount chamber as at 160 is a motor and planetary gear train assembly represented generally at 170 which incorporates a motor component 170*a* in combination with a planetary gear assembly 170*b*. Assembly 170 is relatively loosely positioned within chamber 160 to the extent that it has a freedom of movement with the exception of rotational movement. In this regard, a torque stop component 172 prohibiting overall motor assembly rotation is coupled to the forward or output end of the assembly 170. That output is connected through a stainless steel flexible bellows-shaped coupler 174 extending through a flexible fluid seal to connection with a translation component 176 implemented with the threaded elongate rod of a ball screw mechanism arranged in parallel with the longitudinal axis 58 of the apparatus 12. This bellows 174 provides a torsionally rigid, but axially flexible coupling reducing the vagaries of elongate mechanical-rotational force transmission. Bellows couplers as at 174 are marketed under a model designation SC-3 by Servometer Corp. of Cedar Grove N.J. Alternatively, other flexible coupling components may be used for this purpose including u-joint coupling, couplings with elastomeric members, three-piece "spider" couplings, disc couplings and helical beam couplings (e.g., See "Flexible Shaft Couplings", MacMaster-Carr Supply Company, Cleveland, Ohio).

Rotatably driven from the motor assembly 170 through the bellows coupler 174, the translation component is attached to a thrust bearing 178. Bearing 178, in turn, is mounted and secured within the thrust bearing chamber 164. With this arrangement, a freedom of movement is provided for the entire assembly rearwardly of the thrust bearing 178 including motor assembly 170, coupling 174 and translation component 176 permitting the motor assembly 170 to be mounted in self aligning confinement within the housing 14. Thus, binding or like phenomena are avoided in connection with the motor drive actuator system. The translation component 176 is threadably engaged with a transfer assembly represented generally at 180 which comprises a ball screw or nut component 182 and a generally Y-shaped yoke 184 which is configured to extend to a position spaced from but aligned for driven engagement with the tabs or ears 134 and 136 (FIG. 2) when the support housing 110 initially is inserted in the receiving cavity 166. Mounted upon an upper wall portion of the motor mount chamber 160 are two electrical contacts 186 and 188 which are retained in place by a polymeric contact clamp 190 and which function to supply electrosurgical cutting current to the two contact surfaces 120 and 122 (FIG. 2) located on the disposable support housing 110. Motor assembly 170 is protected from the high voltage conditions extant at the terminals 186 and 188 by a motor cover 192. FIG. 3 also reveals a polymeric forwardly disposed header 194 which is internally threaded as at 144 to provide threaded connection with the connector 24 located upon the noted disposable housing 110.

Openings are provided in each of the housing sides 16 and 18 to receive flexible polymeric switch buttons. These notch-like openings are revealed at 196–198 in connection with side 16 and at 199–201 in connection with housing side 118. Extending through the notch-like openings 196–201 are flexible molded switch buttons formed with assembly 204. These switch buttons as at 54–56 cooperate with switch components shown respectively at 206–208 formed within one side of a printed circuit board 210. The opposite side of circuit board 210 supports five light emitting diodes (not shown) which, in turn, provide the earlier described visual cues through oppositely disposed molded light pipe assemblies 212 and 214. The lenses of these assemblies extend through corresponding linearly arrayed openings. For example, the lenses of the light pipe array 212 extend through the openings identified at array 60 for right housing side 16. A similar arrangement is provided with respect to left housing side 18 and light pipe array 214. Two outwardly protruding dimples as at 216 and 217 are molded in the housing in adjacency with the connectors as at 36 and 152. These dimples facilitate the positioning of the flexible conduit 34 extending from the suction manifold 26 under a connector platform. Finally, FIG. 3 shows an input assembly for the cable 62. This is a molded plastic component which functions to introduce fourteen leads into the housing 14. The component, shown at 218 is over-molded with a flexible plastic to provide stress relief for the cable 62.

Figure 4:
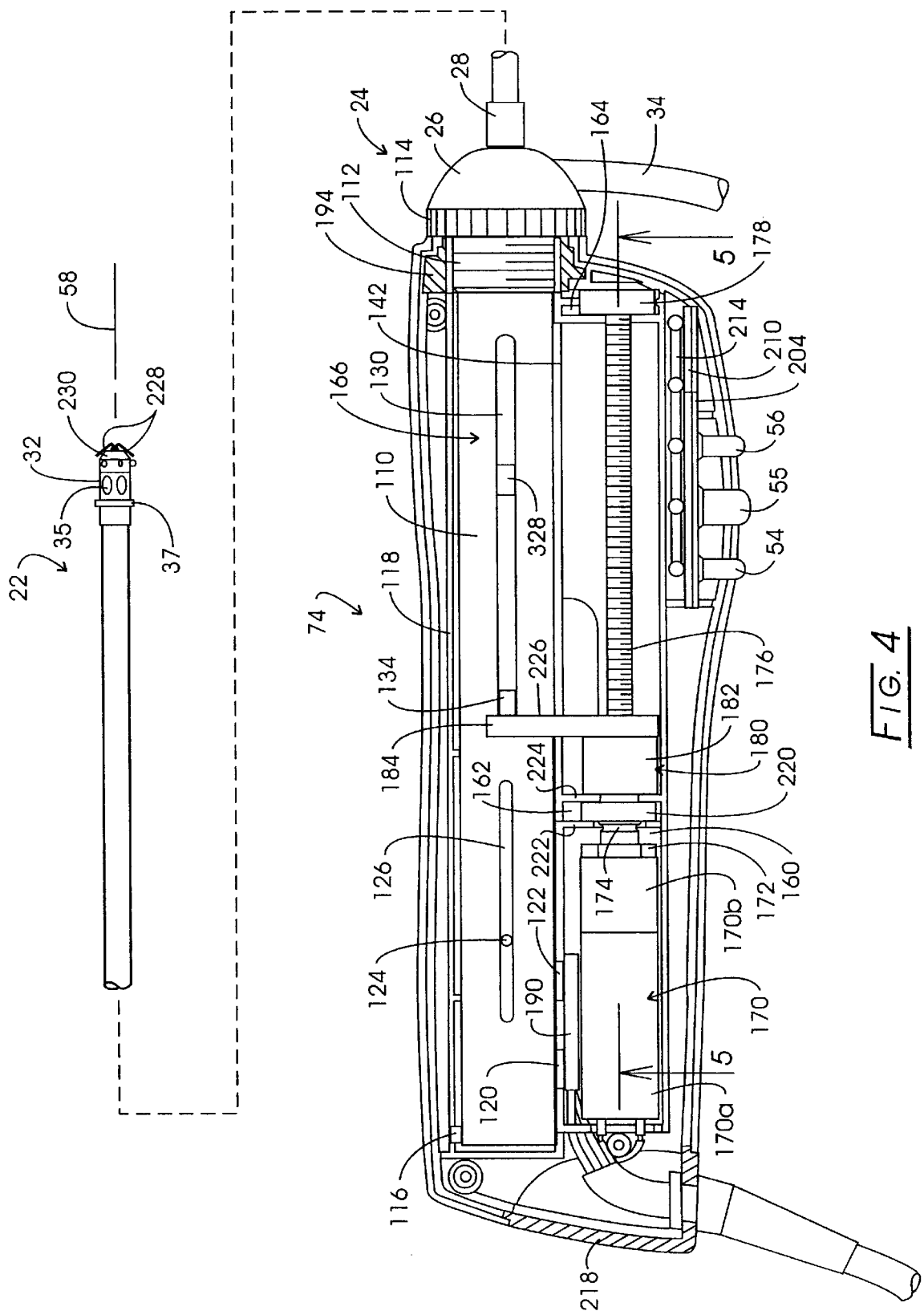
FIG. 4 is a partial sectional view of the instrument shown in FIG. 1 with portions broken away.

Referring to FIG. 4, a sectional view is presented illustrating the operative association of the motor drive features with the disposable support housing 110 contained components. In the figure, the motor assembly 170 is seen to be located within motor mount chamber 160. As noted above, in that chamber 160, the assembly 170 is permitted some self-aligning movement but is restrained from rotational movement by the torque stop component 172. The output from the planetary gear assembly 170b is coupled to the driven input side of coupler 174 which is seen to extend through a taurus-shaped fluid seal 220 located within the seal chamber 162 defined by oppositely disposed and spaced apart bulkheads 222 and 224. Note that the flexible seal does not constrain the coupler 174 and permits the noted self-alignment of the motor assembly 170 with respect to the elongate threaded translation component 176. That component is seen extending to the thrust bearing 178. Bearing 178 provides support against all of the driving forces imposed from the motor assembly 170 as it drives the transfer assembly 180 from the translation component 176. The figure reveals that the driving surfaces 226 of the Y-shaped yoke 184 engage the tabs or ears as at 134 to urge a drive component forwardly as is described in connection with FIG. 6.

FIG. 4 also reveals some details of the tip 32 of delivery cannula 22. That tip 32 is depicted as it is utilized for relatively smaller tissue volumes, for example, encompassed within a diametric extent of about 10 mm. The tip incorporates four precursor electrode components arranged in a cross shape or symmetrically about longitudinal axis 58. Two of the electrosurgical cutting portions of the precursor electrodes are revealed at 228 located just forwardly of a truncated cone-shaped ceramic(alumina) protective tip 230. Tip 230 functions to provide an arc-resistant or arc isolating tip portion preventing its' breakdown. Located at distal end 32 are five smoke/steam collection or suction intake ports as are represented at 35. Just behind these ports 35 is a blocking rib or ring 37 which functions to block any migration of steam or smoke along the outer surface of delivery cannula 22. The edges of ports 35 are positioned about 0.2 inch from ceramic tip 230 and have a diameter of about 0.08 inch. Rib or ring 37 may be about 0.050 inch wide and about 0.050 inch radially high.

Figure 5:
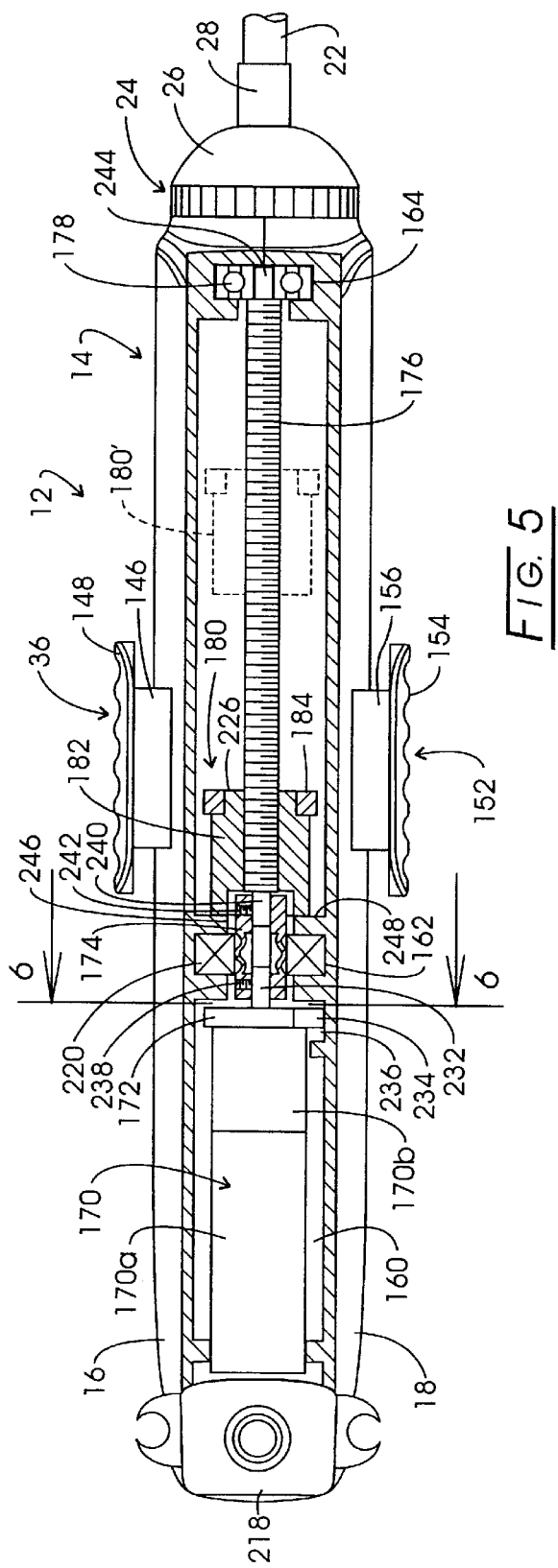
FIG. 5 is a sectional view taken through the plane 5—5 shown in FIG. 4.
Figure 6:
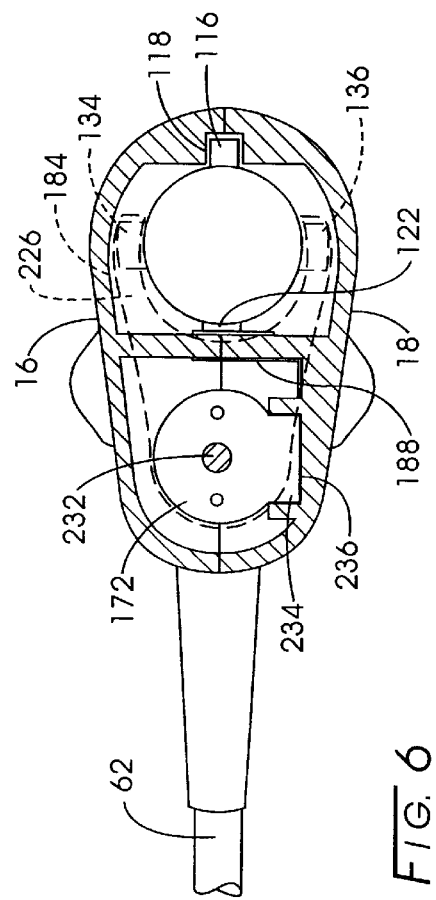
FIG. 6 is a sectional view taken through the plane 6—6 shown in FIG. 5.

The actuator and transfer assemblies which are mounted within the housing 15 are more clearly depicted in connection with FIGS. 5 and 6. Looking to those figures, the motor assembly 170 is seen to be comprised of a d.c. motor 170a having a 3.2 watt assigned power rating marketed under the catalog designation 118686 by Maxon, Precision Motors Inc., of Burlingame, Calif. This motor 170a is combined with planetary gear head 170b exhibiting a 29:1 reduction and marketed under the catalog designation 118185 by Maxon Precision Motors Inc. (supra). The output shaft of the gear head 170b is shown at 232 and is seen to extend through the torque stop component 172. That component 172 is seen in FIG. 6 to be bolted to the forward casing of the gear head assembly 170b and is configured with a rectangular tab portion 234 which engages a slot 236 within housing 15 side 18. Motor assembly output drive shaft 232 is fixed by a setscrew 238 into driving relationship with one side of the cylindrical bellows coupler 174, which is surmounted in turn by the flexible fluid seal 162. The opposite side of the bellows coupler 174 is connected to the necked-down shaft 240 of the threaded elongate translation component 176. Fixed connection with component 176 is provided by another setscrew 242 extending within bellows coupler 174. The opposite end or forward end of the threaded translation component 176 as at necked-down shaft portion 244 is fixed to the thrust bearing 178 and is rotatable therein. Nut component 182 of transfer assembly 180 is shown threadably engaged with the translation component 176 and FIG. 6 reveals that the yoke thereof at 184 extends upwardly such that it can engage the driven surfaces of the tabs or ears extending outwardly from a drive member located within the support housing 110 of the disposable component 108 of the system. Note that the nut component 182 of transfer assembly 180 is configured with a rearwardly disposed inwardly extending chamber resembling a counter-bore and shown at 246. This chamber 246 permits the nut component 182 to pass over a portion of the coupler 174 and seat against a bulkhead surface 248 formed within the housing 14. When so seated against the bulkhead 248 surface, the transfer assembly 180 is considered to be in a "home" position, i.e., the most fully retracted position where it may, for example, accept the next new biopsy probe. During operation of the instrument 12, the translation component 176 is rotated to drive the transfer assembly 180 forwardly to effect a motorized driving of the capture component of the instrument through a drive assembly. Such a forward movement is represented in FIG. 5 in phantom at 180'. In general, the motor assembly 170 drives the transfer assembly 180 forwardly until a motor stall condition (i.e., defined as current flow in the motor exceeding 60 mAmps) is encountered which represents a completion of pursing activity or tissue volume capture. A control assembly associated with instrument 12 then recognizes the stall to carry out a motor reversal, returning the transfer assembly 180 to the noted home position which is recognized by a reverse stall characteristic at the motor 170a.

Figure 9:
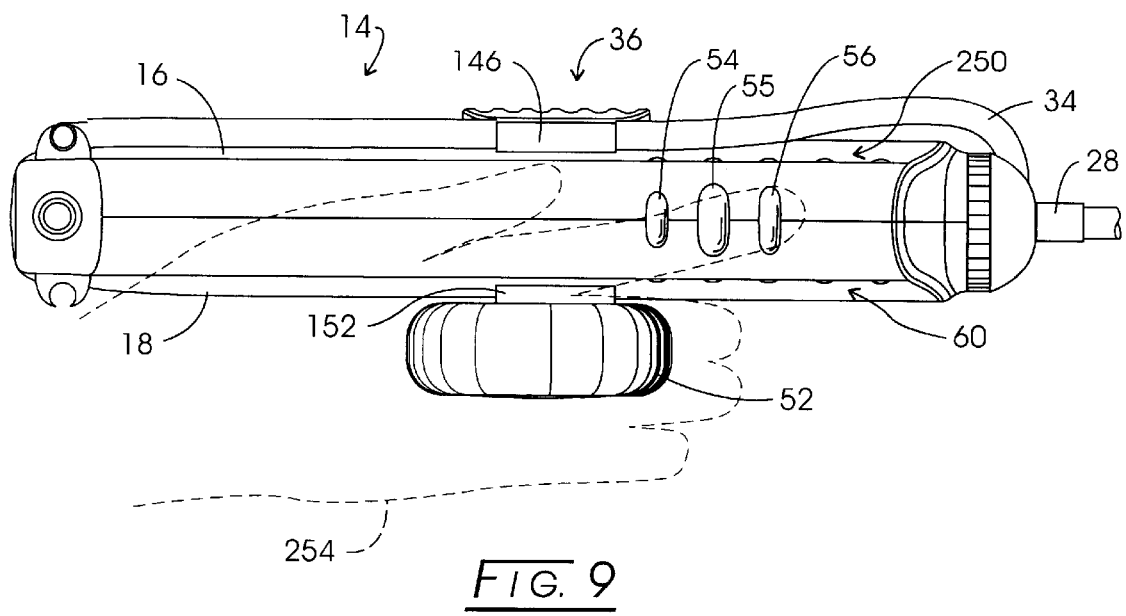
FIG. 9 is a bottom view of the instrument shown in FIG. 1 adjusted for utilization by a practitioner with a larger right hand.
Figure 10:
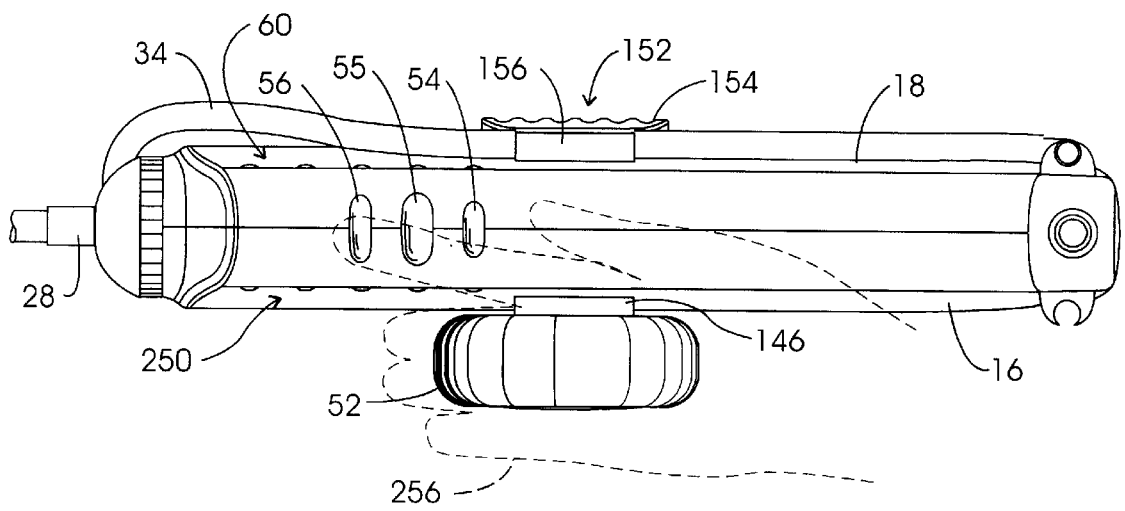
FIG. 10 is a bottom view of the instrument of FIG. 9 shown adjusted for accommodating a small left hand of a practitioner.

Because the instrument 12 will be used by practitioners who are both right handed and left handed, the components forming it are made symmetrical as evidenced by FIGS. 7 and 8. Looking to those figures, it may be observed that actuator switches 54–56 are centered between housing 14 halves 16 and 18 and that the light pipe structures extending from printed circuit board 210 (FIG. 3) mounted light emitting diodes extend to the bottom of each housing half to provide LED implemented visual cue arrays as represented by array 60 and by array 250. Assurance of a proper insertion of the disposable support housing 110 and its associated delivery cannula 22 is provided by the noted indexing pin 116 and elongate slot 118. To assure proper alignment, a red dot is positioned on the former component as well as above the aligning slot as shown at 252 in FIG. 8. FIG. 9 shows an orientation of the stabilizer grip 52 for use by a right handed practitioner having a relatively larger hand structure as represented in phantom at 254. For this arrangement, the stabilizer grip 52 is positioned somewhat rearwardly on connector 152. FIG. 10, on the other hand, shows a more forward orientation of the stabilizer grip 52 for a left handed practitioner with a relatively smaller hand as represented in phantom at 256.

Figure 11:
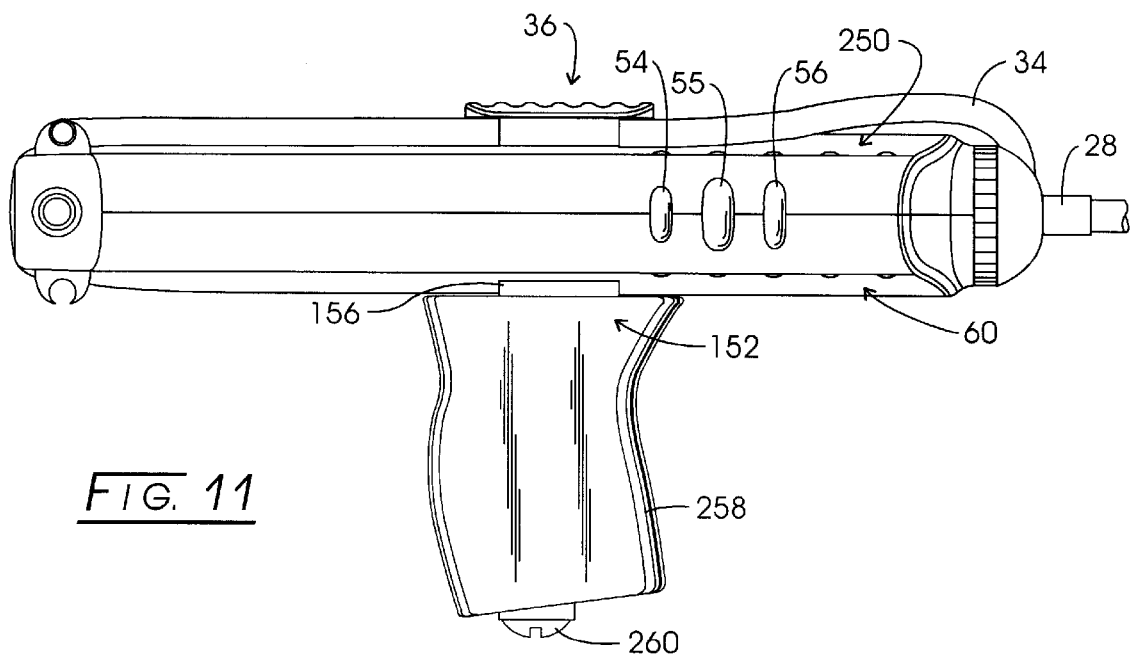
FIG. 11 is a bottom view of the instrument of FIG. 1 showing a pistol grip form of support.

As revealed in FIG. 11, the grip connectors as at 36 and 152 also can be utilized in conjunction with pistol grip style stabilizers. In this regard, a pistol grip is shown in FIG. 11 at 258 having a slot (not shown) engaging the platform 154 extending over pedestal 156. Grip 258 is retained in position by a bolt 260 which engages the indentations within platform 154 (FIG. 7).

The disposable or replaceable component 108 with support housing 110 and delivery cannula 22 is illustrated in detail in connection with FIGS. 12 and 13. Support housing 110 is formed of two identically molded housing halves which are joined together and additionally interconnected with the delivery cannula 22, threaded connector 24, and the smoke/steam exhausting suction manifold 26 which is connected with suction tube 34. The embodiment of these figures shows the distal tip 32 at the forward region 30 of the delivery cannula 22 to incorporate a pair of polymeric tip components 264 and 266, the latter component providing a ramp structure for the leafs of a capture component retained within the forward region 30. Two of the four components of a forwardly extending precursor electrode are shown in these figures in the manner as described in connection with FIG. 4. In general, the freely rotatable suction manifold 26 is retained in position over the cannula 22 by collar 28 and the entire rod-like delivery cannula 22 is covered with an electrically insulative shrink wrap 269 (FIG. 18) which terminates at a union represented at line 268.

Referring to FIG. 14, a sectional view of the support housing 110 is revealed showing its formation from two identical moldings 270 and 272. Note that moldings 270 and 272 are retained together at their forward portions by connector 24 which, additionally, supports the delivery cannula 22. Cannula 22 is seen to be a hollow tube and extends through an evacuation chamber 274 formed within freely rotatable manifold 26. It further may be observed that the delivery cannula 22 is formed with a hole or aperture 276 such that vacuum can be communicated from the tubing 34 into the chamber 274 and thence along delivery cannula 22 toward its tip or distal portion 32. At the opposite end of the molding components 270 and 272, the earlier-described indexing pin 116 is adhesively attached within a molded slot, the corresponding open slot in component 272 being seen at 278.

Extending from a rearward bulkhead represented generally at 280 and defined by molded components of support housing 110 moldings 270 and 272, there is provided an elongate support tube 282. Tube 282 is formed of stainless steel and is anchored at the rearward side of the bulkhead 280 by a plastic collar 284 adhesively bonded thereto. Support tube 282 extends symmetrically along longitudinal axis 58 to be outwardly flared for engagement with forward tip component 266 (FIG. 12).

Figure 15:
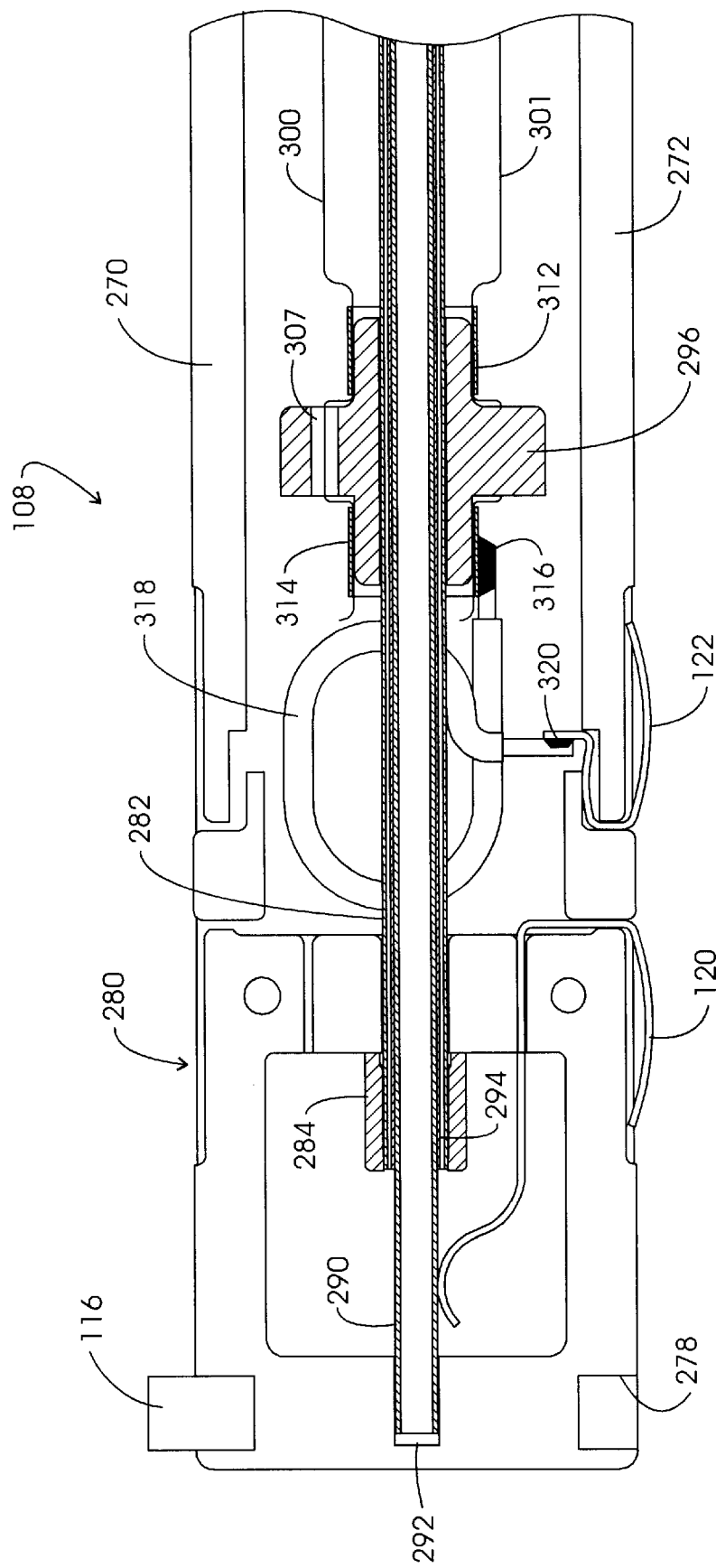
FIG. 15 is an enlarged partial sectional view taken at the rearward portion of the disposable component shown in FIG. 14.

Looking additionally to the enlarged representation of FIG. 15, it may be observed that, extending through the interior of the support tube 282, is a stainless steel precursor electrode tube 290 the rear tip of which extends along axis 58 into engagement with the paired molding components 270 and 272 at cavity 292. That portion of the precursor electrode rod 290 which extends rearwardly from support tube 282 is configured with an electrically conductive surface which receives electrosurgical precursor electrode current through resiliently biased terminal component 120. The remainder of the precursor electrode tube 290, as it extends within support tube 282, is covered with an electrically insulating shrink wrap seen in FIG. 15 at 294. It may be recalled that the terminal 120 lower disposed wiping surface engages corresponding contacts distributing electrosurgical cutting current in the vicinity of cable clamp 190 as described in connection with FIGS. 3 and 4. This component 190 also serves as an electrically insulating barrier to isolate electrical contacts (at high RF voltage) from motor assembly 170.

Five, nineteen-strand, braided stainless steel cables extend from their connection with the capture component of the instrument located at forward region 30 to a polymeric cable terminator component which is slidably mounted over the support tube 282 and moveable thereon in parallel with the longitudinal axis 58 of the instrument. Two of the braided pursing cables are stylistically represented in the drawing at 300 and 301. However, all five of these cables extend to and are connected with the cable terminator component 296. Looking additionally to the sectional view at FIG. 16, the terminator component 296 is seen to be formed with five longitudinally disposed and radially spaced channels 306–310 into each of which one of the cables as at 300–301 extend. In this regard, cable 300 is seen extending through channel 307. All five cables are retained or fixed to the terminator component 296 by two stainless steel collars. In this regard, a forward stainless steel collar or ferrule 312 is press-fitted over the five cables following a point-in-time of fabrication wherein they have been positioned through the channels 306–310 and retained in uniform, balanced tension from their engagement with the forwardly disposed capture component assembly. Uniform tensioning of the five cables is essential to a symmetrical pursing action and symmetrical cage structuring of the capture component at its forwardmost location. With appropriate tensioning, both the electrically conductive collar 312 and a rearwardly disposed electrically conductive stainless steel ferrule or collar 314 are rigidly press-fitted or attached over the five cables. Collar 314 additionally functions to apply electrosurgical cutting power or current simultaneously to all five of the cables and, accordingly, it is nickel plated and then gold plated (by way of example, 5 micro inch and 20 micro inch, respectively) such that electrosurgical cutting current may be applied to it through a solder union 316 connecting the collar 314 with a braded multi-strand and highly flexible insulated copper cable 318. Cable 318, in turn, is soldered (or welded) to the forward electrical terminal assembly 122 at a solder union seen in FIG. 15 at 320. As in the case of terminal 120, terminal 122 also engages a current delivery terminal within the housing or reusable housing component 15.

FIG. 16 further reveals the presence of two guidance components or ears extending outwardly from the cable terminator component 296. These ears or guidance components are shown at 124 and 128 within respective slots 126 and 127. With the arrangement, as the five cables are electrically excited with electrosurgical cutting current they are drawn in tension forwardly in the sense of the instrument to, in turn, pull the cable terminator component 296 in attachment with cable 318 in slidable fashion forwardly over the support tube 282. This sliding movement under the drive of cable tension continues until the cable terminator component 296 encounters and engages a cable stop 322 which, as seen in FIG. 14 is fixed to the support tube or rod 282 at a location which is selected to establish the maximum diametric extent of opening and overall length of the containment structure or cage generated by the capture component. This is the only adjustment or election required for developing a variation in such diametric extent and length dimensioning. For example, that diametric extent will range from about 10 mm to about 40 mm. As the cable terminator component 296 engages stop 322, the five cables continue to be stressed in tension to an extent causing the pursing activity of the electrically excited cables at the leading edge of this capture component.

Returning now to the drive assembly under which the five cables are drawn in tension, FIG. 14 reveals a drive assembly which incorporates a drive member 324 which is connected to an elongate drive tube or drive rod 326. Drive tube 326 is slidably mounted over support tube 282 and extends forwardly through the delivery cannula 22 into welded engagement with a pentagonally cross-sectionally configured leaf assembly of the capture component at forward region 30. The five pursing cables 300–304 pass through this drive member 324. FIG. 17 reveals five channels for slidably passing the five pursing cables rearwardly to their attachment at cable terminator component 296. Note that cable 300 is shown stylistically extending through channel 330 in FIG. 14. Drive component 334 is configured having two oppositely outwardly extending ears or driven engagement portions which are actuated forwardly by the motor assembly 170 drive imparted to the yoke 184 (FIG. 3). These ears or tabs as shown at 134 and 136 slide in alignment within corresponding respective drive slots 130 and 132 formed within the support housing 110. As the drive component 324 and attached drive tube 326 are driven forwardly in parallel with the axis 58, the leafs of the capture component commence to emerge from the forward region of the 30 of the device and drive component 324 will pass across either one or possibly two oppositely disposed resilient latches of a latch assembly as seen at 336 and 338. As a consequence of passing over and beyond resilient latches 336 and 338, the drive component and associated drive tube or rod 326 cannot be manually retracted rearwardly further than the forward portion of latches 336 and 338. This will be seen to provide a manually retractable arrangement for the drive member wherein the capture component can be adjusted to open only to a limited extent making an open cup-shaped access to the biological sample available from stable containment and easily off-loaded.

A drive safety stop mechanism or member 328 is fixed to the support housing to limit the forward movement of drive member 324 beyond a location representing a full pursing or contracting of the capture component for the elected maximum diametric extent of capture. Such unwanted movement may occur, for example, with a failure of cable stop 322 to hold forward movement of cable terminator component 296. For normal operation, the drive member 324 ultimately will reach a location in spaced adjacency with safety stop member 328.

Referring to FIG. 18, the forward region 30 and tip 32 of the delivery cannula 22 are revealed in sectional detail. In the figure, the delivery cannula 22 is seen extending forwardly to the earlier-described polymeric (e.g., polyetherimide) tip component 264. Delivery cannula 22 is electrically insulated with a 5 mil thick polyolefin shrink tube 269 extending to the earlier-noted border 268 at component 264. Next inboard from the internal surface of the delivery cannula 22 are five capture component leafs in a pentagonal configuration, two of which are seen in FIG. 18 at 340 and 342. Extending next inwardly inboard is the earlier-described support tube 282 which is seen to extend to tip 32 and is flared at region 346 in addition to being adhesively coupled to the tip component 266. This flaring is found to be helpful in permitting the support tube to overcome the rather substantial forwardly directed forces occurring during the forward deployment of the capture component leafs and cables. Extending inside the support tube 282 is the earlier-described precursor electrode tube 290 which, in turn, for the instant diametric capture embodiment, supports a precursor electrode assembly which comprises four precursor electrodes extending forwardly of the ceramic cap 230, three of which are revealed at 228a–228c. The precursor electrodes are mounted as a subassembly of four stainless steel electrode wires having a generally elongate L-shape, including an elongate shank region or shaft, two of which are shown in conjunction with electrodes 228a and 228b at 348a and 348b. Four such electrode assemblies are crimped inside of tube 350 and that tube 350, in turn, is crimped within the forward portion of the precursor electrode tube 290. It has been found that the utilization of four cutting surfaces for the electrodes, arranged in quadrature, provides preferable instrument positioning results. Such an arrangement of confronting electrode surfaces is revealed, for example, in FIGS. 25 and 26. Sections of the shank regions of these precursor electrodes are seen in FIGS. 19 and 20 at 348a, 348b, 352a and 352b. In general, the severing portions of the precursor electrodes will be extending normally to the longitudinal axis of the instrument and will be configured to directly confront the tissue being severed during the insertion or placement of the instrument in a confronting relationship to the involved tissue volume. The dimensional extent of the confronting severing portions of these precursor electrodes is selected to provide an effective length less than the corresponding maximum diametric extent developed by the capture component. In FIG. 18, that extent may be observed at stylized dashed locus of movement line 354. In deploying the capture component, the forward or leading edge thereof containing the noted cables will cut a path somewhat similar to that shown at dashed line 354, reaching the capture component predetermined maximum peripheral diametric extent at that point in the deployment when pursing commences as the cable terminator 296 engages the cable stop member 322 as described in conjunction with the FIG. 14. By assigning one cable for each of the leafs that are utilized with the capture component, it has been found that an almost hemispherical curvilinear path of enveloping closure will be defined as represented by the forward portion of dashed line 354 encapsulating a tissue volume including a target tissue volume represented symbolically at dashed line 356.

FIG. 18 further illustrates the smoke-steam evacuation ports 35 which communicate in vacuum association with an evacuation channel established initially as a gap between the outer surface of leafs 300–304 and the internal surface of tip component 264. The channel then extends rearwardly as a gap adjacent to internal surface of delivery cannula 22 to the suction manifold 26 (FIG. 2).

FIG. 19 reveals a section through the polymeric tip component 264. That component functions as a confinement or alignment sleeve for each of the five leafs 340–344. The figure further reveals that a cable guide is provided as an elongate flexible polyamide cable guide tube extending longitudinally along the center at the outside surface of each leaf. These guide tubes for leafs 340–344 are represented respectively at 360–364. Note that each of these tubes 360–364 is slidably located within a receiving chamber shown respectively at 370–374 which extends within the alignment sleeve 264. FIG. 19 further reveals that the leaf structure of pentagonal cross sectional configuration is connected, for example, by laser welding to the end of the drive tube 326 (FIG. 14).

Sleeve 264 directs each of the five leafs of the capture component into slidable engagement with a designated ramp located somewhat rearwardly within the tip component 266. Thus, sleeve 264 and tip component 266 cooperate to provide a guidance assembly represented generally at 267. Each of the leafs is configured with a perpendicularly oriented tip carrying two eyelets, a larger inner one slidably receiving an associated cable and a smaller opening or aperture for receiving and securing the knotted end of a cable. The five ramps established by the tip component 266 are revealed in FIG. 20 at 380–384 providing exit guidance for respective leafs 340–344 as they are urged forwardly by the drive tube 326. In general, ramps 380–384 provide an angle of attack for the individual leafs of about 45° with respect to the longitudinal axis of the instrument. The normally oriented, dual eyelet containing tips of leafs 340–344 are shown in FIG. 20 respectively at 390–394. Note that cable 300 emerges from guide tube 360, passes slidably through the inward eyelet of leaf tip 390 and is secured to the outer eyelet of tip 394. In similar fashion, pursing cable 301 emerges from guide tube 364 to slide through the inner eyelet of tip 394 and thence to be secured to the outer eyelet of tip 393. Cable 302 extends from guide tube 363 to slidably pass through the inward eyelet of tip 393 and thence is secured to the outward eyelet of leaf tip 392. Cable 303 emerges from guide tube 362 to slidably pass through the inward eyelet of leaf tip 392 and thence is secured to leaf tip 391. Finally, cable 304 emerges from guide tube 361, whereupon it slidably passes through the inward eyelet of leaf tip 391 and is secured to the outer eyelet of tip 390. As noted above, the assigning of one cable for each leaf in the manner thus disclosed provides a highly desirable rapid hemispherical closure of the capture component in the manner illustrated by the forward portion of the stylized locus of movement outlined at dashed line 354.

While appearing somewhat complex at first observation, the pentagonally associated leafs, associated cables, and polymeric guide tubes or conduits of the capture component are fabricable at costs commensurate with the disposable nature of the component 108 with support housing and associated delivery cannula. For the capture component to perform, it must emerge from the guidance assembly 267 alignment sleeve 264 and an associated tip 266 ramp unconstrained until it reaches that condition wherein the cable associated with it moves no further. At that juncture, the leaf leading edges commence to define a closing or pursing hemispherical locus of movement. Individual leafs are somewhat diminutive, being chemically milled from stainless steel with a widthwise extent selected to impart a lateral stability as well as flexibility during their outward movement. With such select structuring any warping away from the desired hemispherical pursing activity is avoided. This pursing activity forms a generally curvilinear cage periphery which may be defined within planes parallel with the longitudinal axis of the instrument. Stability with respect to the somewhat transverse forces involved during the retraction or pursing action of the cables also is achieved with the selection of leaf thickness and width, consideration also being given to requisite leaf flexibility.

For the instant leaf embodiment, a stainless steel implemented sequence of five leafs having a thickness of about 0.003 inch to about 0.005 inch and a widthwise extent of about 0.080 inch is utilized. Construction of this pentagonal embodiment of the assembly of leafs is illustrated in connection with FIGS. 21–25. To form the leaf structure represented generally at 400, the stainless steel material (ss 304) is chemically milled to define each of the leafs 340–344 within flat stainless steel stock. In this regard, both the central trough or retainer groove to which the polyamide tubing is connected as well as five longitudinal bend lines are chemically milled. Looking to FIGS. 21 and 22, the base portions 339 of leafs 340–344 are seen to have been bent and positioned about drive tube 324, such bending having taken place at the milled bend lines 402–406. To define a polygonal tube structure base. The tube structure is completed with a butt or lap form of weld located rearwardly of a trough or groove, for example, at location 407. This assemblage is then laser spot or tack welded along the inside center regions rearwardly of each leaf 340–344. Points of tangency between drive tube 324 and the leaf inside surfaces at which such tack welding takes place with respect to the pentagonal structure rearward of leafs 340–344 are represented at respective positions 410–414.

After to the bending and welding procedure forming the pentagonal structure of FIG. 21, the cable guides or polyamide tubes are attached to the forward portions 345 of the leafs as seen at 360–364 in FIG. 22. Tube 360 is shown in FIG. 23 in connection with blade 340. At this juncture of fabrication, the dual eyelet containing tip 390 of blade 340 has not been bent into a perpendicular orientation. Note that each tip as at 390 has an inwardly disposed pursing eyelet as at 386 and an outwardly disposed connection aperture 387 of lesser diametric extent. Polyamide tube 360 initially is adhesively attached to the chemically milled trough or groove formed along the middle of one side of each of the blades as at 340. Then, as revealed at the sectional view at FIG. 24, tube 360 is bonded to leaf 340 within the chemically milled groove utilizing an electrically insulating coating material and process which achieves bonding and provides requisite electrical insulation, and still permits necessary flexing of the blade. The coating, which has a thickness of about 0.001 inch, is shown in FIG. 24 at 416. Coating 416 is a vapor-phase-polymerized conformal coating marketed under the trade designation "Parylene". Parylene is the generic name for members of a polymer series. The basic member of the series, called Parylene C, is poly-para-xylene, a completely linear, highly crystalline material. Such coatings are available from Paryiene coating service companies such as Specialty Coating Systems, of Indianapolis Indiana. For the instant purpose, this coating will have a thickness ranging from about 0.0002 inch to about 0.003 inch and, preferably, about 0.00075 inch to 0.00125 inch. A significantly desirable bonding is achieved with this approach. These guide tubes are quite small, having, for example, an outside diameter of about 0.020 inch and a wall thickness of about 0.0015 inch. The pursing cables extending within the guide tubes have a diameter within a range of about 0.002 inch to about 0.020 inch and preferably of about 0.005 inch. The guide tubes may be formed of other materials, for example, a metal. When so fashioned the tubes may be formed or cut, for instance, in spiral fashion or the like to promote flexibility. The electrically insulative coating applied to the leafs and guide tubes may, for instance, be provided as a vitreous or polymeric material. As another step in the formation of the capture component assembly 400, the tips of the leafs are bent to a perpendicular or normal orientation with respect to their widthwise extent. This is illustrated in conjunction with leaf 340 and tip 390 in FIG. 25.

Of course, the Parylene coating as at 416 electrically insulates each of the capture component leafs such that the cutting action at the leading edge of the capture component is essentially only through the five stainless steel pursing cables. Cables 300–304 remain electrically insulated as they extend through the insulatively coated and adhered polyamide tubes shown in FIG. 22 respectively at 360–364.

Figure 26:
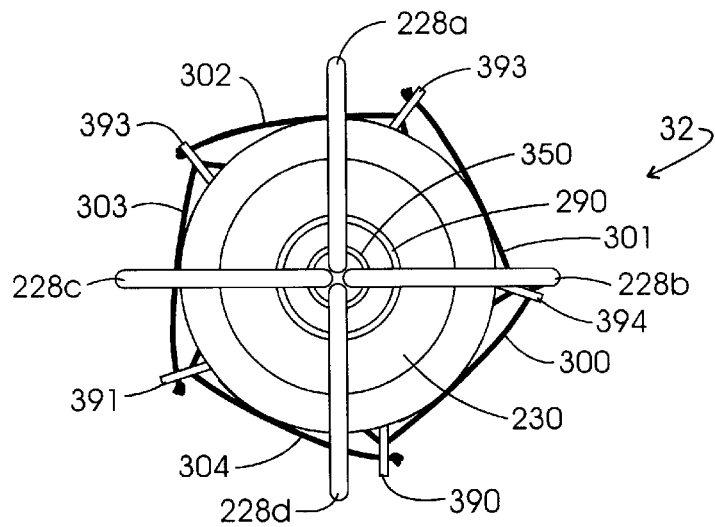
FIG. 26 is a front view of the forward portion of the instrument shown in FIG. 1 with components oriented prior to deployment of capture component leafs.
Figure 27:
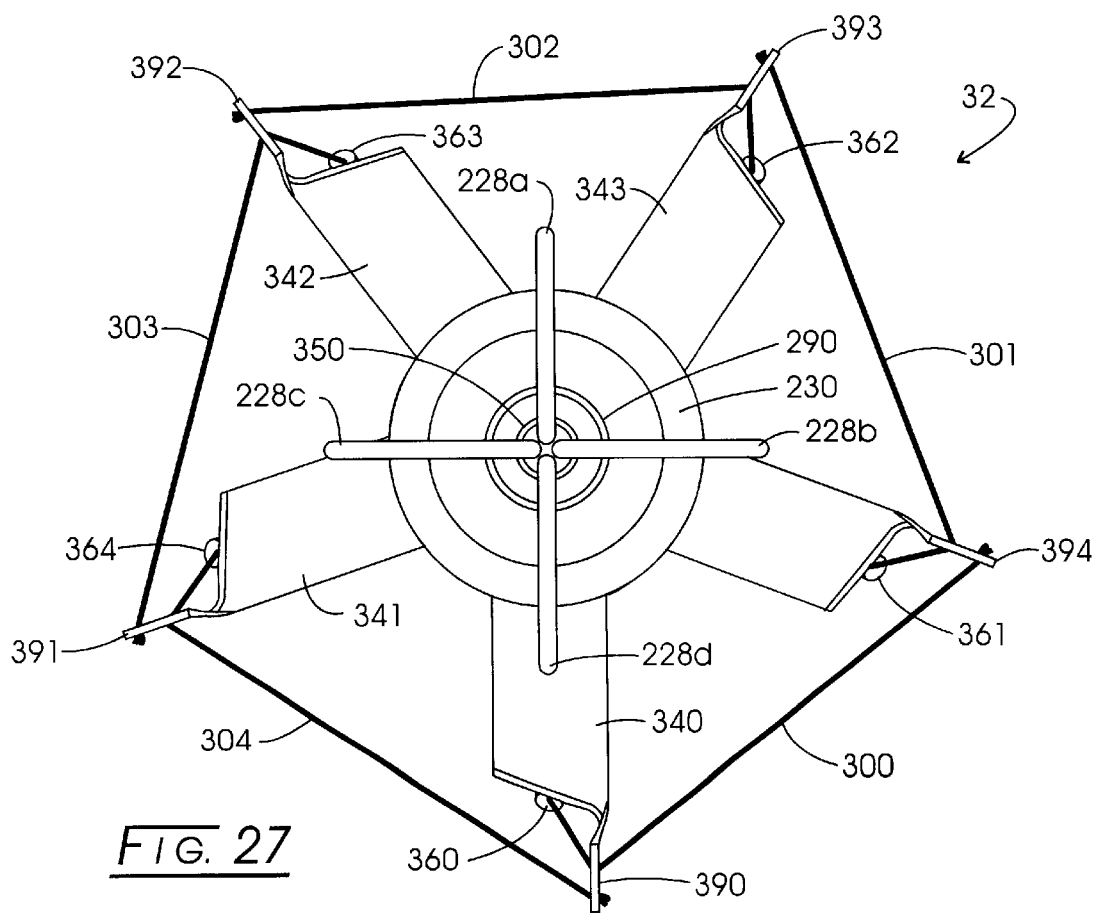
FIG. 27 is a front view of the forward portion of the instrument of FIG. 1 showing the orientation of components as the leafs of its capture component are being deployed.

FIGS. 26 and 27 present front views of the delivery cannula 22 tip region 32, illustrating in particular the orientation of the precursor electrodes, as well as the leafs and cables in a retracted state in FIG. 26 and as the leafs and cables emerge in FIG. 27. As the leafs are being deployed, the pursing cables 300–304 are receiving electrosurgical cutting current. In FIG. 26, the forward cutting portions of the precursor electrode pair 228a and 228b are shown and arranged perpendicularly thereto in quadrature are the corresponding forward cutting surfaces of electrode 228c and 228d. In the figure, the five leaf tips 390–394 are visible in connection with portions of the pursing cables 300–304. For the orientation shown, the precursor electrodes 228a–228d will have been excited while the instrument 12 is maneuvered into an orientation wherein the tip 32 is in a confronting relationship with the targeted tissue volume. The precursor electrode structure then is deactivated and the capture component is deployed in conjunction with the excitation of pursing cables 300–304 with electrosurgical cutting current. Note that these pursing cables 300–304 are "playing out" along the leaf tips 390–394 and the effective diametric extent of the assembly is expanding to circumscribe the targeted tissue volume to be removed.

In general, the precursor electrodes 228a–228d will have a tissue cutting and confronting length of about 6.5 to 7.0 mm for employment with a maximum effective capture diameter for the capture component of 10 mm. Similarly, where that effective diameter expands to 20 mm, the expanse of the precursor electrodes or their lengthwise confronting extent will be about 10 mm. As the diametric expanse of the capture component and the length of the precursor electrodes increases the electrosurgically excited pursing cables will necessarily physically contact the open-circuited flexible precursor electrodes and reenergize them as they are urged into alignment with the capture component leafs. This temporary re-energization of the longer precursor electrodes is found to be beneficial as the electrodes retract or bend into larger tissue samples being captured.

For applications of system 10 wherein magnetic resonance image guidance is employed for tip positioning, the precursor electrodes, capture component leafs, pursing cables and the delivery cannula may be formed of non-ferromagnetic materials such as titanium or nitinol.

Referring to FIG. 28, the partial sectional view presented in connection with FIG. 14 is reproduced, however, the drive member 324 is shown to have been advanced to a location wherein the cables 300–304 will have drawn the cable terminator component 296 just into adjacency with the cable stop 322. Stop 322, for the instant demonstration, is located to establish an embodiment providing for a capture component effective maximum diametric extent, for example, of about 10 mm. Note additionally that the multi-strand flexible copper cable 318 has been drawn forwardly by virtue of its connection with the cable terminator component 296. For the illustrated orientation of components 296 and 322, the leafs and associated cables of the capture component will be at an extended location just prior to the commencement of a pursing action carried out by a tensioning of the pursing cables. For clarity, two oppositely disposed symbolic leaf structures are shown in the drawing at 418 and 419 to illustrate the effective maximum diametric extent as the capture component commences to purse about a tissue volume represented in phantom at 420. This effective maximum diametric extent as thus symbolically represented, is identified by the dimension indicating arrows 422 along with the effective maximum capture diameter symbol: Dc. Also, the longitudinal distance between the forward surface of ceramic tip 294 and the center of the tissue volume 420 is labeled as: $L_s$ This distance, $L_s$, also corresponds with the position of extension of the capture component leafs at which cable tensioning for the pursing maneuver commences. The distance is that selected by the practitioner for the initial positioning of the delivery cannula tip 32 using the precursor electrodes. In general, the distance, $L_s$, is selected as about 0.6 $D_c$. It further may be observed that the drive component has been driven under the influence of the motor assembly 170 forwardly of the resilient one-way latches 336 and 338.

Referring to FIG. 29, the components described in connection with FIG. 28 again are reproduced, however, the drive member 324 and associated drive tube 326 are shown to have been driven further forwardly. Cable terminator component 296 has remained in abutting engagement with cable stop 322. This has caused a tensioning of the five cables 300–304 and a pursing encapsulation of the target tissue 420 as represented by the symbolic leaf structures 418 and 419. The illustrated cables 300 and 301 are symbolically represented as being under stress or tight and, while the maximum effective diametric extent represented by the dimensioning arrows 422 and the label, $D_c$, remain substantially constant, the capture assembly has, indeed, "captured" or encapsulated the targeted tissue volume 420 along with an amount of surrounding healthy tissue. Note that the pursing ends of the leaf structures as represented at 418a and 419a have been tied together by an array of five cables under tension extending back to the cable terminator component 296. In effect, a structural containment arch-form is evoked defining a forward curvilinear cross section resembling that of a hemisphere. This provides for protection for the tissue sample as delivery cannula 22, which is of relatively small diameter and noninvasive, is withdrawn with a stretching of tissue adjacent the capture component or containment structure but with structural protection of the encapsulated tissue volume. Thus, a noninvasive nature of the retrieval is achieved without physical impairment even though a relatively larger tissue sample is removed.

Figure 30:
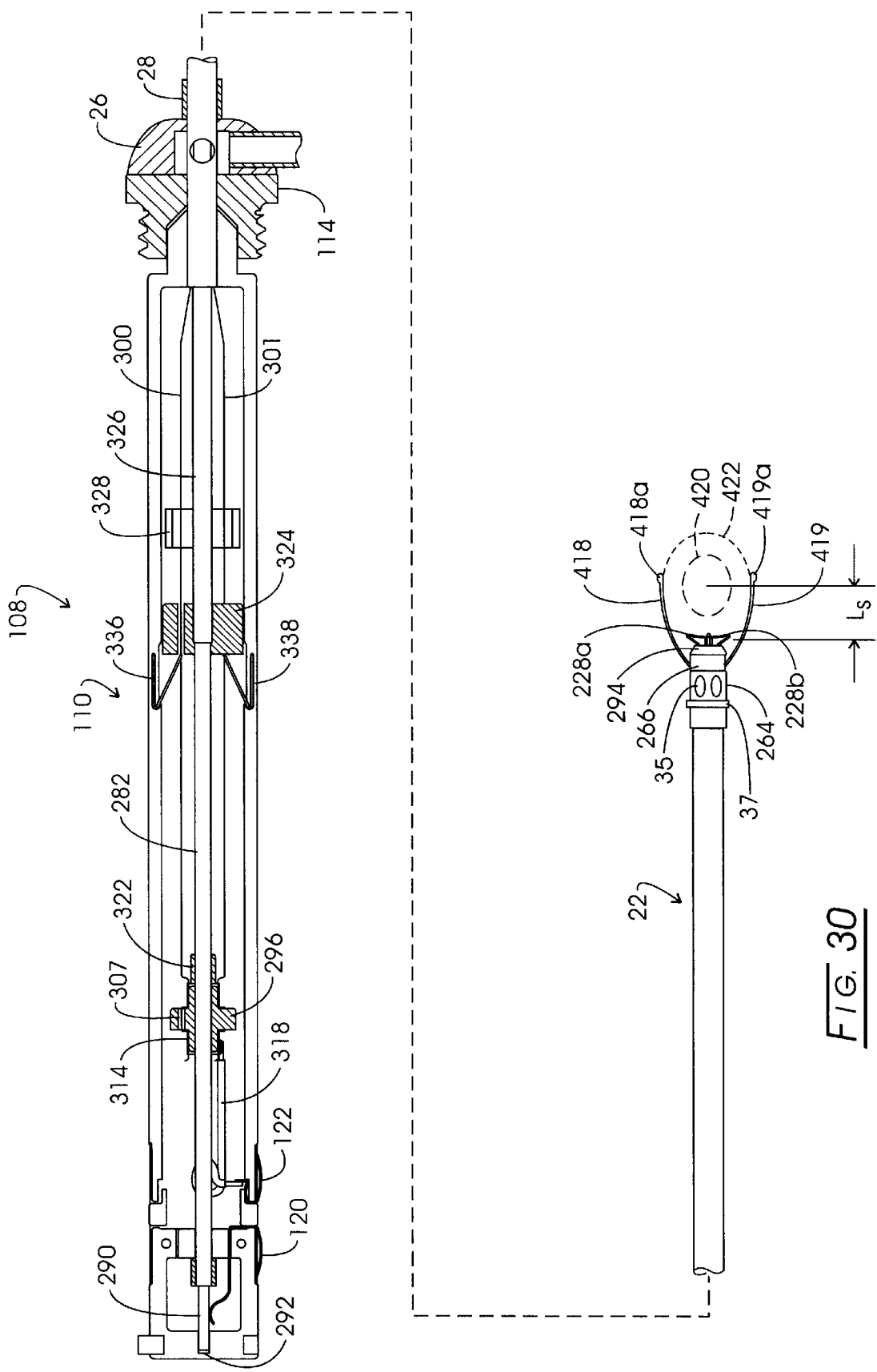
FIG. 30 is a partial sectional view of the instrument of FIG. 29 schematically showing an orientation wherein capture component leafs have been retracted manually for tissue sample access.

Returning momentarily to FIG. 4, when the five cables 300–304 have been stressed at the level associated with a fully carried-out pursing as described in connection with FIG. 29, the control over motor assembly 170 recognizes a resultant forward stall condition and reverses the motor drive assembly output, and consequently, the output of the translation component 176, to return the transfer assembly 180 to its "home" position as described in connection with FIG. 5. However, ears 134 and 136 extending outwardly from the drive member 324 now have been released at their forward position from engagement with the yoke component 184. (See FIG. 6). Accordingly, when the disposable components 108 of the instrument 12, including the support housing 110 and delivery cannula 22 have been removed from the reusable housing 14 with the tissue volume retained within the capture component as shown in FIG. 29, the practitioner may then manually return the drive component to a position against latches 336 and 338. Referring to FIG. 30, this arrangement is illustrated. Drive member 324 and coupled drive tube 326 have been manually moved rearwardly until the member 324 engages the inwardly extending components of the resilient latches 336 and 338. This manual retraction of drive member 324 by the practitioner has, in turn, retracted the five leaf structures as represented symbolically at 418 and 419 such that their tips, as shown respectively at 418a and 419a, have returned rearwardly to define an open ended tissue sample cup for access to and/or transporting the targeted volume of tissue 420 and surrounding healthy tissue represented in phantom at 422 for pathology investigation. For this orientation of the components, the cables as represented at 300 and 301 again are symbolically represented as being un-tensioned.

A salient feature of the invention resides in a structuring of the capture component and associated actuating system in a manner wherein the effective maximum tissue circumscribing diametric extent can be varied with the expedient of merely moving the cable stop component 322 to different locations along the longitudinal axis of the instrument. It may be recalled that the collar-shaped cable stop component 322 is mounted upon support tube 282. This alteration of capture component diametric extent is illustrated in connection with FIGS. 31 and 32 in association with a target tissue volume shown in phantom at 424. Comparing FIG. 31, for example, with FIG. 28, note that the cable stop member 322 now is positioned forwardly toward the latching components 336 and 338. The cable terminator component 296 is represented as having been drawn by cables 300–304 (here shown symbolically at 300 and 301) to adjacency with stop member 322. Drive member 324 and associated drive tube 326 have been moved forwardly with respect to their corresponding position shown in FIG. 28. Thus, the leafs are moved mutually outwardly to a greater extent. The result is an enlarged capture diameter. Symbolic leafs 418 and 419 are represented in FIG. 31 as having been expressed to develop an effective diametric extent, as defined at their respective tips 418a and 419a, surmounting the target tissue volume 424. This effective diametric extent is symbolically represented by the arrow pair 426 and symbol, $D_c$. For this embodiment achieving a capture diametric extent of greater value, an expanded precursor electrode assemblage is called for to the extent that the captured or encapsulated tissue volume may be readily removed. In general, the lengthwise extent of each of the wire components of the precursor electrodes will be less than the effective maximum diametric extent of the capture component as it is expressed to the commencement of cable pursing activity as represented in FIG. 31. As before, four precursor electrode components are employed, two of which are shown in solid line fashion at 428a and 428b. These precursor electrodes 428a and 428b are coplanar and arranged normally to a corresponding pair of such electrodes. With the arrangement shown, following the positioning of the tip of the delivery cannula 22 in confronting adjacency with the target tissue volume 424, electrosurgical cutting current is terminated at all precursor electrodes including those at 428a and 428b, the cutting drive circuit, in effect, being open circuited at a high voltage output stage 520 shown in FIG. 34. However, when the pursing cables commence to emerge from delivery cannula 22 at the tip component 266 in conjunction with capture component leaf movement, they will encounter the somewhat flexible electrode wires of the precursor electrodes, as shown for example at 428a and 428b and re-excite them with electrosurgical cutting current. These electrodes then will be bent forwardly into the tissue sample volume as they are so re-excited to assume the orientations shown in phantom, for example, at 428a', 428b' and 428c'. In the latter case, the precursor electrode 428c' is, as noted, perpendicular to or normal to the electrodes 428a and 428b. A fourth such electrode (not shown) coplanar with electrode 428c' will be flexed similarly from the opposite side of the capturing region by the pursing cables. As the pursing cables continue to move forwardly under electrosurgical cutting current excitement, contact and electrical conduction with the precursor electrodes is terminated and the latter electrodes are permitted to flex rearwardly to their original orientations in planes through the longitudinal axis of the instrument. Thus, these precursor electrodes will be permitted to return through the tissue cutting paths evoked with their re-energization by the pursing cables.

Figure 33:
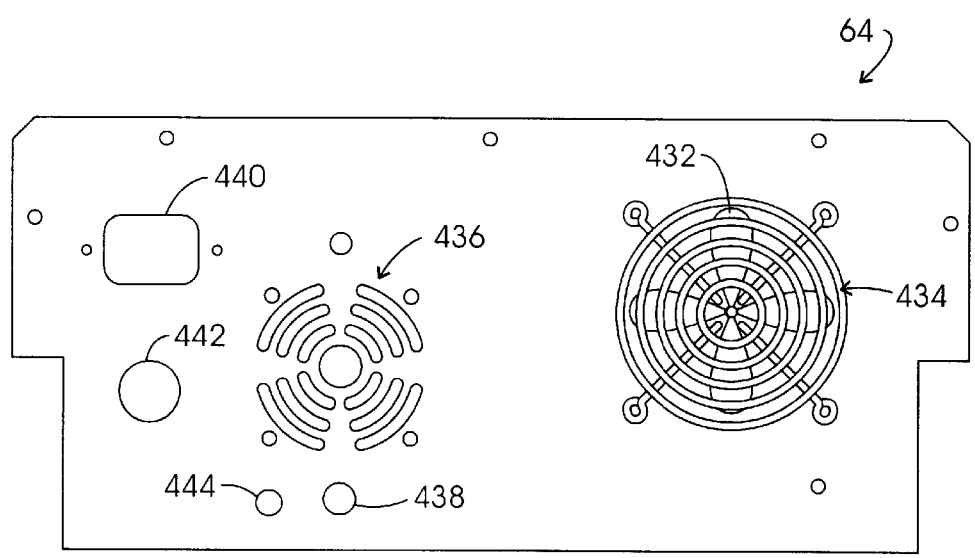
FIG. 33 is a plan view of the rear cover of the console shown in FIG. 1.
Figure 32:
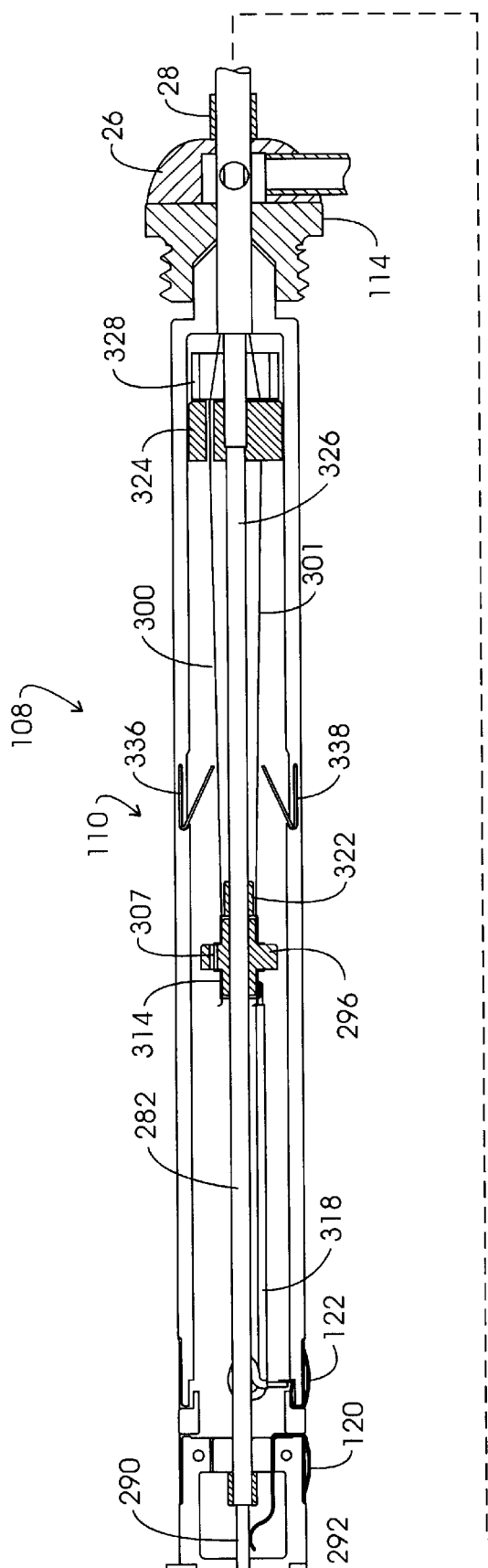
FIG. 32 is a partial sectional view of the instrument of FIG. 31 schematically showing the orientation of capture component leafs in an orientation of full capture.

Referring to FIG. 32, the orientation of the components of component 108 of instrument 12 are revealed as the drive component 324 and associated drive tube 326 have been forwardly driven along the support tube 282 while the cable terminator 296 has remained in stationary contact with cable stop 322. Accordingly, these symbolically depicted cables 300 and 301 are represented as being tight or under stress induced by the pursing action carried out by the drive member 324 subsequent to its orientation as shown in FIG. 30. Note that the tip portions 418a and 419a of the symbolically depicted leafs 418 and 419 have been drawn together by the pursing action of the cables 300–304 and thus, a hemispheric, dome-like configuration has been evoked having the forward curvature shown. A comparison of this curvature with that represented in FIG. 29 shows them to be quite similar in terms of degree of curvature, a phenomenon evoked by virtue of the utilization of a pursing cable in association with each of the leafs of the capture component. This association has been described, for example in connection with FIGS. 26 and 27 above. FIG. 32 also reveals that the precursor electrodes as at 428a and 428b have resiliently returned to an orientation normal to the longitudinal axis of the instrument 12. With this arrangement, the volume of targeted tissue 424 as well as an amount of surrounding healthy tissue 430 may be withdrawn while being protected by the structural integrity now extant at the capture component pursed together leafs which are retained in compression by the pursing cables, a state wherein they contribute to the formation of a structurally rigid containment structure cage. Referring to FIG. 33 (below FIG. 11) the rear panel of the console 64 is revealed. That rear panel supports a cooling fan represented symbolically at 432 positioned behind a grill 434. The speaker which generates aural cues representing electrosurgical cutting activity or a return electrode fault is positioned behind a grill represented generally at 436. A volume control knob performing in conjunction with a potentiometer is represented at 438 beneath the grill 436. A.c. line input is provided at a receptacle 440. A multi-channel footswitch input connector is provided at 442 and a suction system interlock connector is shown at 444 (see arrow 53 in FIG. 1).

Figure 34:
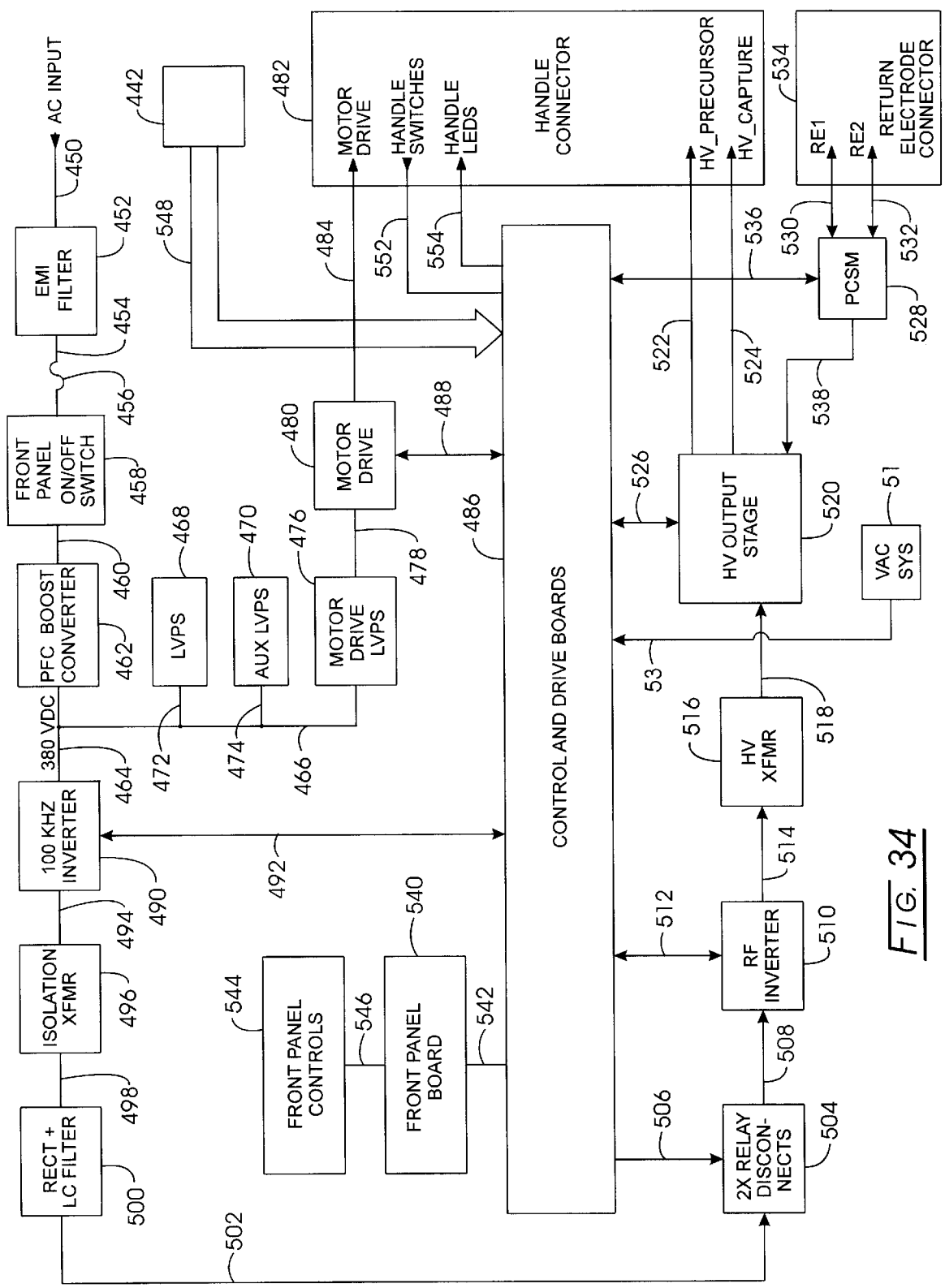
FIG. 34 is a block schematic diagram of the electrosurgical generation and control features of the system of the invention.

Referring to FIG. 34, a generalized block diagrammatic representation of the electrosurgical generation features, control assembly with motor controls, switching and the like is presented. In general, the electrosurgical inputs to the pursing cables 300–304 and to the precursor electrodes of the instrument are provided at an operating frequency of about 350 KHz. However the operating frequency may be selected to be in the range from about 250 KHz to about 100 MHz. For bipolar or quasi-bipolar instrument modalities as described in the above-noted application for U.S. patent, Ser. No. 09/472,673, now U.S. Pat. No. 6,277,083 where the return electrode is located on the shaft or delivery cannula of the disposable component just proximal to the distal end or tip, the operating frequency may be as low as about 100 KHz. Different capture component maximum diametric values and associated lengthwise capture dimensions are based solely on the location of the cable stop 322 (FIG. 14). With that configuration motor assembly 170 may perform in conjunction with a control which detects forward and rearward stall conditions as well as other load characteristic conditions which will represent fault states. In the figure, a conventional A.C. line input is represented at line 450 as extending to an electromagnetic interference (EMI) filter represented at block 452. As represented at line 454 and symbol 456, the filtered output then is passed through a fuse and into the front panel power on/off switch function represented at block 458. This switching function was described in connection with FIG. 1 at 82. Switch function 458 passes the filtered input to a power factor correcting boost converter as represented at line 460 and block 462. Converter 462 rectifies the A.C. input to it to a d.c. current and boosts the d.c. voltage level to a regulated 380 volts d.c. while also creating a sinusoidal input current waveform which matches the sinusoidal input voltage waveform. This provides for a high power factor to reduce line current harmonics. Converter 462 provides an interim voltage as a 380 volt d.c. bus as represented at lines 464 and 466. The provision of the power factor correction feature at block 462 derives a variety of beneficial attributes. Less current is drawn as compared to conventional electrosurgical generators and the device may be employed universally with power utilities on a worldwide basis. Of additional importance, converter 462 derives a pre-regulated interim voltage at line 464 which permits an optimization of a next following link inverter in the electrosurgical generator function. Line 466 functions to provide a d.c. input to a primary and an auxiliary low voltage power supply (LVPS) as represented respectively at blocks 468 and 470 in conjunction with lines 472 and 474. Redundant low voltage power supplies are employed in view of the criticality of the control system associated with the instrument 12. In this regard, a failure of a low voltage power supply otherwise occurring without such redundancy could result in shutting down the entire control system at a point-in-time during critical intervals in the procedure at hand.

The regulated 380 volts d.c. at lines 464 and 466 also is directed to a low voltage power supply represented at block 476 which functions to provide a very specific motor voltage to the motor drive circuitry as represented at line 478 and block 480. Control over the motor voltage, for example, at a level of around 10 volts is important, inasmuch as it is that voltage level which provides the proper rate of forward travel of the leafs and cable components of the capture component. In this regard, the deployment of the leafs and electrosurgically excited cables is measured in terms of millimeters per second. Should the drive imparted be too rapid, the excited cables will push against tissue and not cut properly which may result in a false capture stall based response on the part of the control system. Because the control system operates the motor drive 480 on a basis of detecting, for example, forward stall currents to determine the completion of a pursing activity, accommodation is made for anomalies in the motor drive caused by binding phenomena or the like wherein a forward stall would be detected by the control system before the capture component had been properly actuated. Because the rate of advance of the leafs and associated pursing cables is carefully controlled, it is known, for instance, that any stall condition detected before a certain initial test interval of time commencing with an initial motor activation would represent a drive malfunction. Instrument 12 or "handle connector" 67 is represented in the instant figure at block 482 which is shown communicating motor drive inputs as represented by arrow 484 coupled with the motor drive function at block 480. Control to the motor drive represented at block 480 additionally is provided from a control arrangement which includes control and drive circuit boards as represented at block 486 and dual arrow 488. In general, extension or deployment of the capture component is within a rate range of about 1 millimeter per second to about ten millimeters per second, and preferably between about 2.5 millimeters per second and about 4 millimeters per second.

Returning to line 464, the regulated 380 volts d.c. output of the converter 462 is introduced to a 100 KHz link inverter represented at block 490 which additionally is shown to be under the control of the control and drive circuit board function of block 486 as represented at dual arrow 492. That control is called upon to effect a constant voltage regulation of the electrosurgical output energy, accommodating the negative dynamic impedance of a cutting arc while achieving an arc-sustaining, non-oscillatory performance. The a.c. (squarewave form) output of inverter 490 is presented, as represented at line 494 to one side of an isolation transformer represented at block 496. Transformer 496 provides an output, as represented at line 498 which is rectified and filtered as represented at block 500 to develop a d.c. link voltage at line 502 having value of about 100 volts. The amplitude of the link voltage at line 502 is very well controlled and functions to modulate the amplitude of the output of the system. Line 502 is directed to two relay disconnects as represented at block 504. These relay disconnects are controlled from the control and drive circuit boards 486 as represented by arrow 506. The d.c. link voltage then, as represented at arrow 508 is directed to an RF inverter as represented at block 510. Inverter 510 operates in controlled relationship with the control and drive circuit boards represented at block 486 as indicated by arrow 512. It may be noted that by positioning the relay disconnects 504 ahead of the RF inverter 510, in case of a fault or other anomaly, input to the RF inverter 510 itself can be disconnected. Inverter 510 is of a conventional resonant or tank circuit variety which is tuned to a particular frequency. Its output peak-to-peak voltage amplitude is controlled by the amplitude of the d.c. link voltage. Thus, while the output voltage amplitude is controlled to remain constant, its frequency also will remain consistent.

The output of inverter 510 is directed, as represented by line 514 and block 516 to one side of a high voltage transformer which steps its amplitude up to about 800 to about 1000 volts peak-to-peak for normal (non-boost) cutting purposes from a 100 volt d.c. link voltage level. This output of the transformer stage 516 at line 518 is an arc generating electrosurgical cutting output which is, in effect, steered by series relays at a high voltage output stage, represented at block 520, to either the precursor electrode input as represented at arrow 522 or to the capture component cables as represented at arrow 524. Control over the stage represented by block 520 is indicated by arrow 526.

The control system also performs in conjunction with a patient circuit safety monitor (PCSM) which is represented at block 528. As discussed in connection with return electrode 68 in FIG. 1, the present system operates in monopolar fashion and utilizes a dual component dispersive pad as a return electrode. These two return electrode components were described at 70 and 72 in FIG. 1. As represented at dual arrows 530 and 532 directed respectively to the R and R leads of the return electrode connector, a small high frequency current can be directed from one pad as at 70 along the patient to the other as at 72 (FIG. 1) to verify the tissue resistance between those pads. For the instant illustration, the connector earlier described at 77 is shown as block 534. Control for this monitoring procedure is represented at dual arrow 536 and the output of the test at block 528 is represented at arrow 538. The PCSM circuit 528 will apply about a ten volt signal at 50 KHz to the two return electrode pads and verify proper resistance. Only upon such verification will the system permit the practitioner to continue the procedure by going into a ready mode. If the PCSM test is not met or passed, the system will not proceed and both visible and audible pulsed alarms are produced.

Also associated with the control and drive circuit boards represented at block 486 is a front panel circuit board as represented at block 540 and arrow 542. That front panel circuit board performs in conjunction with the front panel controls described in connection with FIG. 1 as represented at block 544 and arrow 546.

The footswitch connector earlier described in conjunction with FIG. 33 at 442 is identified in the instant figure at a block carrying that numeration. A three pair lead input from this footswitch connector is symbolically represented by bus arrow 548. Inputs from the button switches 54–56 of instrument 12 are represented at arrow 552, while outputs to the LED arrays as at 60 are represented at arrow 554. Finally, vacuum switch 51 is represented by a block with that same identifying numeration along with earlier described arrow 53 extending to block 486. Arrow 53 represents a two lead input.

With the circuit arrangement thus described, a primary circuit is developed between the A.C. input at line 450 and the isolation transformer 496. From the output of isolation transformer 496, providing the noted D. C. link voltage, a secondary, lower voltage circuit is evolved. That secondary circuit extends to the high voltage transformer represented at block 516. From that circuit location, a high voltage circuit obtains with the system which develops the noted electrosurgical cutting outputs. These three different circuit regions are incorporated with different isolation barriers of the system. In this regard, some components fall within a safety extra low voltage circuit regime (SELV) while all other circuits are completely isolated from potential contact. For medical devices which are going to be attached to a patient, concerns become more stringent for assuring that no current will flow from one device, for example, to another associated with the patient.

Figure 35:
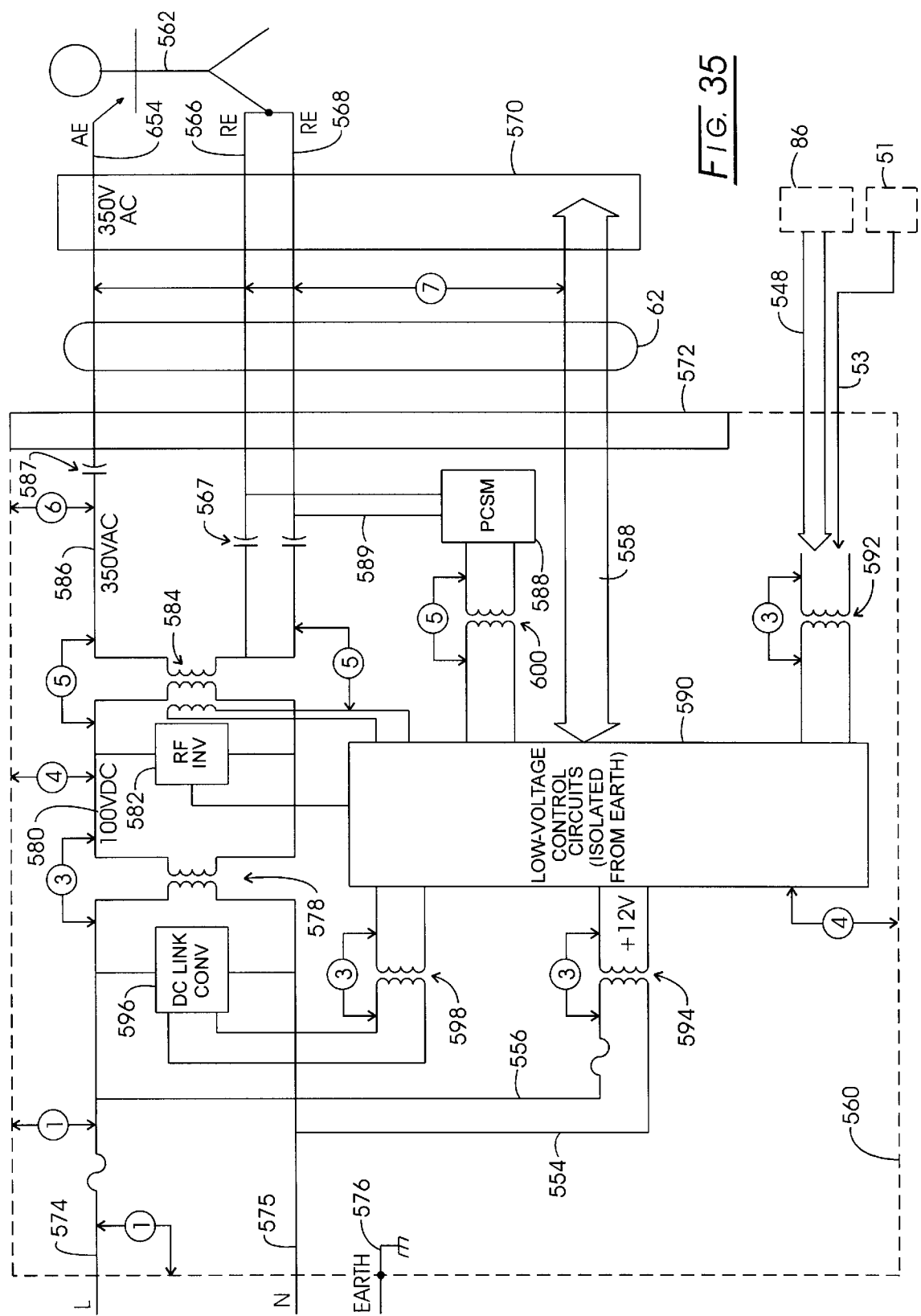
FIG. 35 is an insulation diagram for the control system shown in FIG. 34.

Referring to FIG. 35, an isolation and insulation diagram is presented which may be associated with the system diagram of FIG. 34. In FIG. 35, encircled insulation codes 1 through 7 are located. These codes correspond respectively with the insulation types: BI, BOP, RI, RI, BI, RI, and OP. These insulation types are further identifiable as follows:

"OP"—operational insulation;
"BOP"—basic insulation between parts of opposite polarity;
"BI"—basic insulation providing the first level of protection against electric shock;
"RI"—reinforced insulation.

Looking to FIG. 35, dashed boundary 560 represents the conductive enclosure of console 64. A patient is symbolically represented at 562 who will be contacted by the active electrode (AE) as represented at arrow 564 and return electrodes (RE) as represented at lines 566 and 568. The nonconductive handle of the instrument 12 is represented at block 570 and the cable and connector cover as represented at 62 again is identified with that numeration. A nonconductive front panel of the console 64 is represented at block 572.

A. C. input to the control system is represented by line, neutral and earth lines shown respectively at lines 574–576. This commences the earlier noted primary circuitry. Note that insulation code 1 extends between line 574 and the chassis 500. Next, the primary circuit extends to a transformer function represented symbolically at 578 and carrying a boundary code 3 which is a high voltage insulation boundary. Then a transition to about a 100 volt d.c. link voltage represented at line 580 occurs with an isolation boundary code 4. The system then extends through the RF inverter represented at block 582 to a high voltage transforming function represented generally at 584 with an isolation barrier code 5. This transforming function 584 develops the high voltage output as represented at line 586 in conjunction with an isolation code 6. Note that return lines 566 and 568 extend through coupling capacitors shown, generally at 567 to the output of transforming function 584. Next the system extends through blocking capacitors 587, front panel 572, cable 62 to instrument 12 with active electrode 564 and thence to the patient 562. The return electrodes as represented at lines 566 and 568 are seen associated with the PCSM circuit now shown at block 588 which is further isolated at insulation barrier 5 before having operational association with the low voltage control circuits represented at block 590. These low voltage control circuits as at 590 are shown insulated with respect to the chassis 560 at code 4. Certain inputs to and outputs from this low voltage control are represented at bidirectional arrow 558 extending across front panel 572, cable assembly 62 and instrument housing assembly 570. Footswitch function 86 is shown isolated from circuits 590 at transforming function 592 in conjunction with code 3 insulation. Bus arrow 548 is reproduced extending to function 592. Similarly, vacuum switch 51 is identified by a dashed block along with arrow 53 which extends to transforming function 592. The +12 volt d.c. input to the circuits 590 as represented at lines 554 and 556 are isolated as represented at transforming function 594 which is associated with code 3 insulation. The d.c. link converter function represented at block 596 is isolated from the low voltage control circuits 536 as represented by transforming function 598 in conjunction with insulation code 3. PCSM function 588 is coupled with return lines 566 and 568 via line pair 589 and is isolated by transforming function 600 from the low voltage control circuits, that isolating function being associated with an insulation code 5. Note additionally that code 7 insulation is associated at the interface between the cable assembly 62 and instrument 12 as represented at block 510.

Figure 36A:
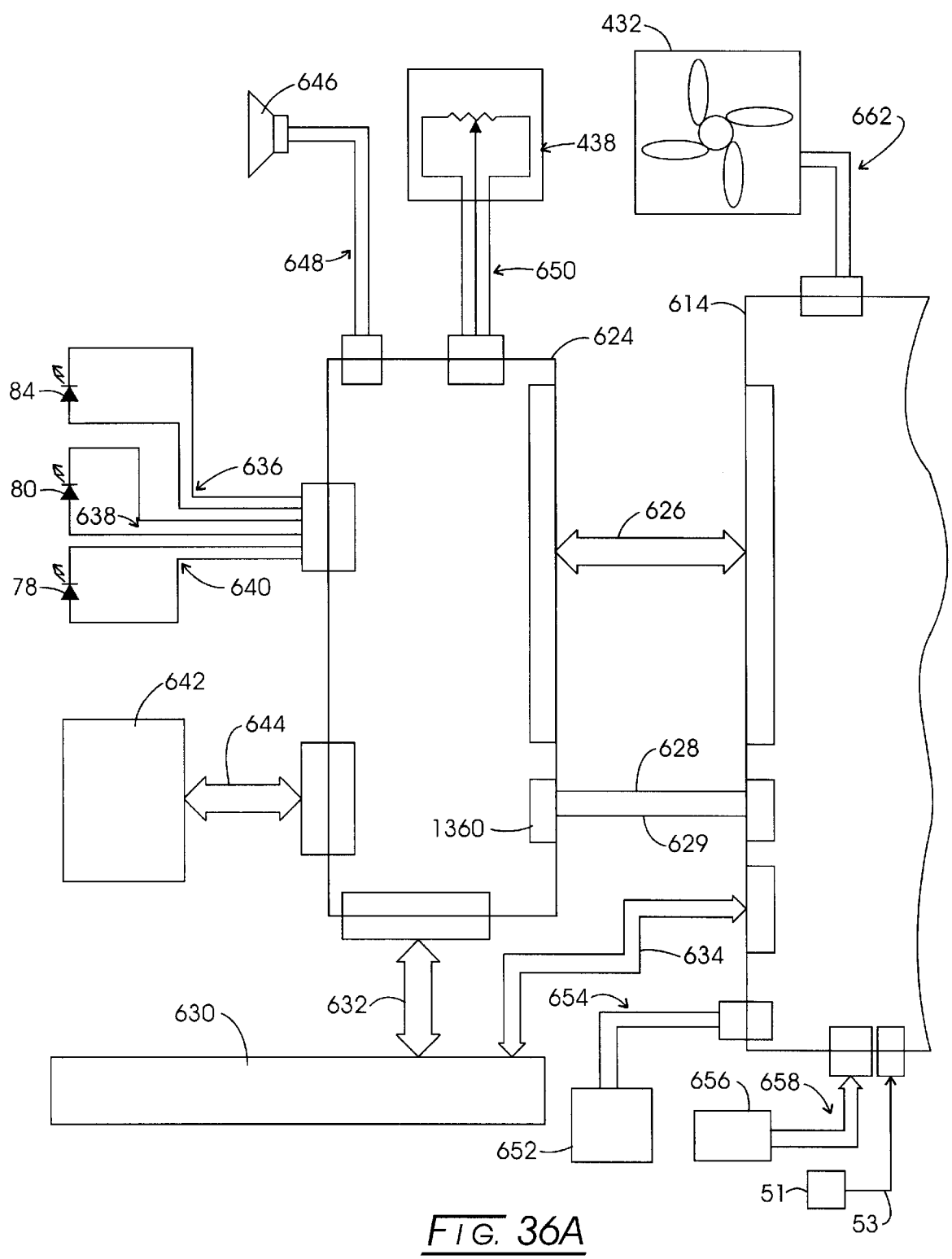
FIGS. 36A and 36B combine as labeled thereon to describe the interconnections of the printed circuit boards mounted with the console shown in FIG. 1 and associated peripheral components.
Figure 36B:
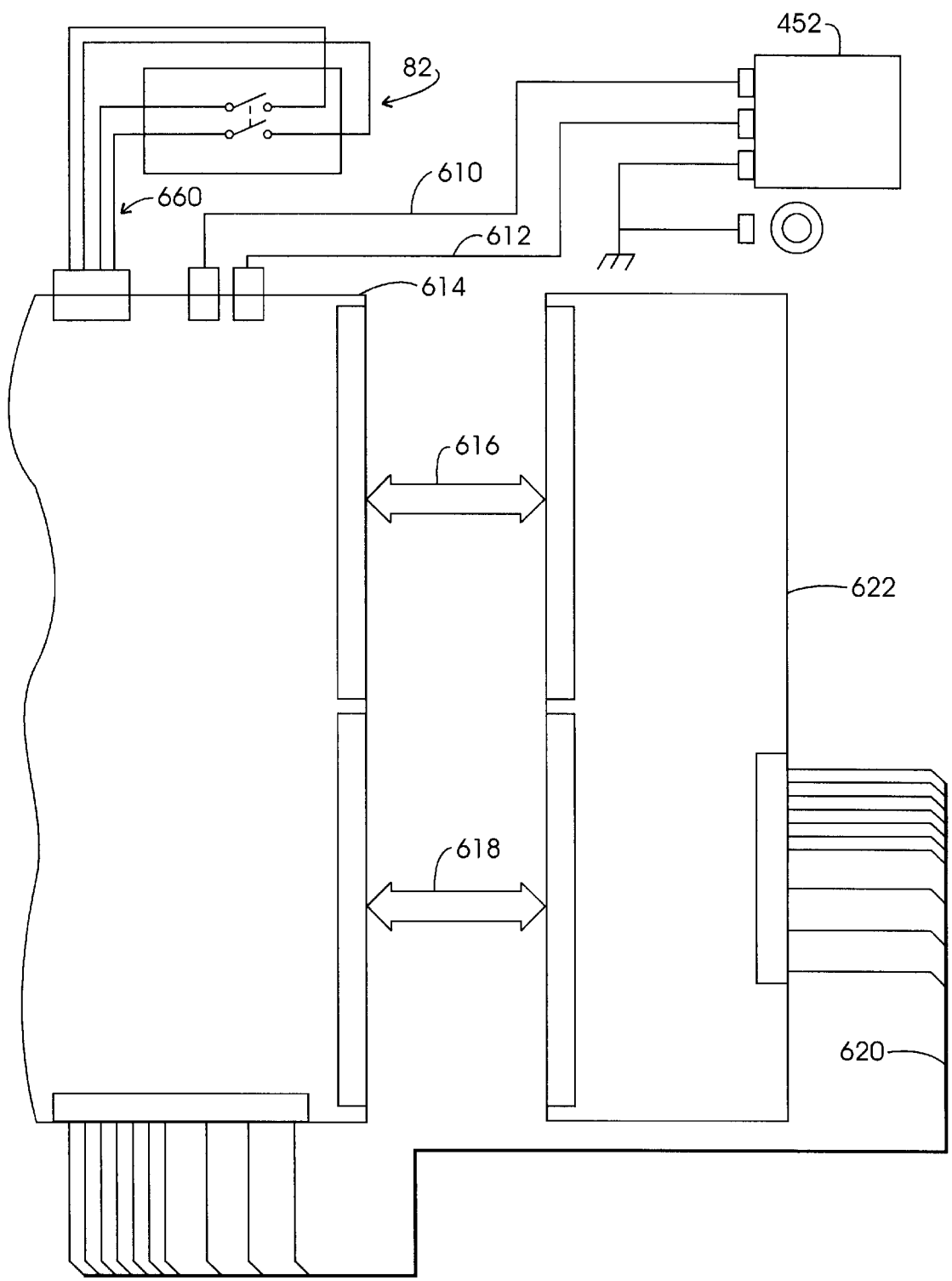

Referring to FIGS. 36A and 36B, the system association of a main power circuit board, daughter circuit boards, the instrument, and peripheral components is revealed. These figures should be considered in the manner labeled thereon. The earlier described EMI filter module reappears with the same numeration at block 452 in FIG. 36B in conjunction with line and neutral inputs 610 and 612 extending to the motherboard or power circuit board represented at 614. Power board 614 is shown to be operably associated by bus symbols 616, 618, and 620 with a "drive" printed circuit board represented at 622. Drive circuit board 622 carries components for the earlier-described power converters, for example, carrying out power factor correction, boost converting, D.C. link converting, the RF converter and low voltage power supplies.

FIG. 36A reveals another daughter circuit board referred to as a "control board" at 624. Control circuit board 624 incorporates components controlling the commencement and termination of events at drive board 622 and providing an interface with both the instrument 12 and the front panel of console 64. Logic for sequencing events in the system is developed with a programmable logic device (PLD) mounted with this control circuit board 624. General interfacing between the power circuit board 614 and this control circuit board 624 is represented at arrow 626 and the return electrode signal lines 628 and 629. The handle (housing assembly 14) connector earlier described at 69 is represented at block 630. An association of the handle connector 630 with the control circuit board is represented at arrow 632. That association includes the signaling employed with all housing assembly 14 mounted LEDs and switches. Handle connector 630 also receives motor control and electrosurgical cutting inputs from the power circuit board 614 as represented at arrow 634.

Illuminating control to the power on LED 84 shown at FIG. 1 is provided from line pair 636. Similarly, illuminating control over the green "handle" connector 67 LED 80 is provided from line pair 638. Finally, the illuminating control over the red LED 78 corresponding with a fault status at dispersive electrode 68 is provided at line pair 640 from control circuit board 624. In general, where the PCSM test as described at block 528 at FIG. 34 fails, the red LED 78 is pulse illuminated along with a pulsed aural alarm along with the imposition of a system shutdown. The handle LED 80 is illuminated if an initial interlock or connector test utilizing a small coding resistor within the instrument 12 shows a proper connection.

A front panel daughter board is represented at block 642 which is associated with the control board 624 as represented by arrow 644. In general, control is asserted as represented at arrow 644 to carry out a control over the LEDs at the upper region of console 64, including the indicator LEDs 94, 96, 98, 100, 102 and 104. Also, control over the start switch 92 is provided from this line grouping 644.

Upwardly disposed in the figure is a speaker 646 which is controlled from the control board 624 via line pairs 648. Volume control with respect to the speaker 646 is provided by a potentiometer earlier described at 438. Control from this potentiometer is developed at three line array 650 extending to control circuit board 624.

Returning to the power circuit board 614 components, the connector or harness associated with the return of dispersive electrode 68 is represented at block 652. Its association with the power circuit board is represented at line pair 654. Similarly, the wire harness or connector from the principal footswitch 86 is represented at block 656. The six lead inputs from the footswitch 86 to the power circuit board 614 are represented at bus 658. Similarly, the vacuum switch is represented at block 51 in conjunction with two lead arrow 53.

Front panel switch 82 is represented in FIG. 36B with the same numeration. The switch 82 is operatively associated with components of the power circuit board 614 through a four line array 660. Finally, fan 432 is represented by the same numeration in operative association with the power circuit board 614 through paired control lines 662.

Figure 37B:
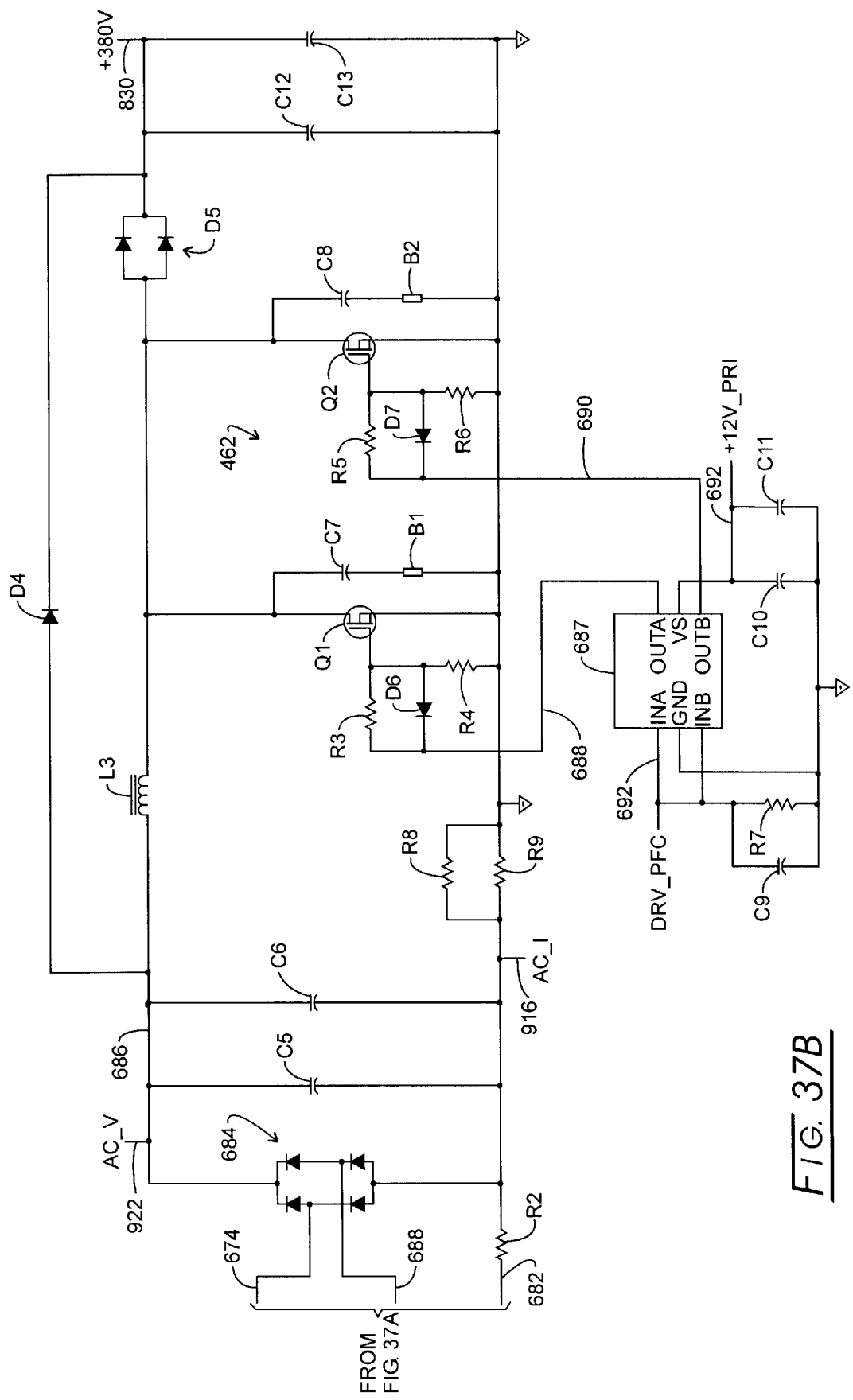

The discussion now turns to the functions and components associated with power circuit board 614. These components are described in connection with FIGS. 37A, 37B –43A, 43B, and 43C to follow. FIGS. 37A and 37B should be considered in the manner labeled thereon. Looking to FIG. 37A, line input is provided to the earlier described EMI filter 452 which is reproduced in the present figure. Referred to as a "rear panel power entry module", the device 452 may be provided as a line filter with A.C. inlet type 5110.1033.3 marketed by Schurter, Inc. of 79343 Endigen, GE. The filtered output from device 452 is present at line, neutral and ground lines shown respectively at 664–666. Lines 664 and 665 are directed to fuses f1 and f2, as well as to components providing additional EMI filtering. Those components include capacitors C1–C2, a dual inductor form of device L1, inductor L2 and a discharge resistor R1. Further protection is provided by varistors 668, 669 and capacitor. The filtered A. C. input then extends across the front panel power switch represented at 82 which, as described in connection with FIG. 36B, is accessed from a harness. In-rush current occasioned by the presence of relatively larger hold-up capacitors in the system is controlled by a negative temperature coefficient thermistor 670 extending across the contact K1:B of a relay K1 within line 674. Looking momentarily to FIG. 38, the solenoid actuating components of that relay K1 are revealed at :A. This solenoid actuator performs in conjunction with a RELAY_IL control input at line 908. Any inductive spikes occasioned by solenoid control are controlled by diode D1.

Returning to FIG. 37A, diode extending within line 676 from line 674 and diode D3 extending within line 678 from line 680 function to derive a rectified AC_SENSE signal in conjunction with a resistor R2 within line 682 and seen in FIG. 37B. The AC_SENSE signal at line 872 is utilized to derive an indication to the control that the input is of high enough voltage amplitude to operate the system.

FIG. 37B shows that lines 674 and 680 extend to a rectifier 684 which derives a haversine waveform at lines 682 and 686. Rectifier 684 may be provided as a type D25×360 marketed by Schindengen America, Inc. of Westlake Village, Calif. Small filter capacitors C5 and C6 extend between these lines. The full wave rectified A.C. voltage is applied across the latter capacitors to the input of the earlier-described power factor correction boost converter represented generally at 462 and comprised of transistors Q1 and Q2 which perform in conjunction with principal components including inductor L3 and diodes D4 and D5 under the switching control of a controller driven driver represented at block 687. In this regard, note that control line 688 extends from output A of the driver 686 to the gate of transistor Q1 to effect switching control thereof in conjunction with peripheral components including resistors R3 and R4, diode D6, capacitor C7 and bead . In similar fashion output B of driver 686 carries out switching control at the gate of transistor via line 690 in conjunction with resistors R5 and R6, diode D7, capacitor C8 and bead B2. Device 687 is controlled by a DRV_PFC signal at input line 692, receives primary circuit low voltage input, +12V_PRI at line 694 and is configured in conjunction with capacitors C9–C11 and resistor R7. Device 686 may be provided, for example, as a type MI424 BiCMOS/DMOS buffer/driver/ MOSFET driver marketed by Micrel, Inc. of San Jose, Calif. The earlier described pre-regulated 380 volts across lines 682 and 686 is applied across very large holdup capacitors C12 and C13 which function to protect the system against vagaries such as transient sags and surges induced at the line input. In effect, the capacitors provide energy storage to "ride through" such anomalies.

The figure also reveals an A.C. current sense signal (AC_I) at line 916 extending from line 682 which is associated with parallel resistors and. That signal is employed in conjunction with power factor control (FIG. 44B) in association with a corresponding A. C. voltage sense signal, (AC_V) at line 686 extending from line 922 and a +380V signal at line 830. The circuitry thus far described represents the earlier-discussed primary circuit which subsequently extends to a secondary circuit upon passing the primary transformer function 496.

Looking to FIG. 39, an over-temperature switch, which is mounted upon a heat sink within the console 64 is represented at 696. Where an over-temperature condition exists, then the low logic true signal, TEMP is generated at line 697.

Referring to FIG. 40, the regulator for developing the important motor voltage input is shown at 698. Device 698 may be provided, for example, as a type LM2941 Low Dropout Adjustable Regulator marketed by National Semiconductor Corp. of Santa Clara, Calif. The device functions in connection with a +12V input at line 700 and is configured in conjunction with capacitors C14–C16 and resistors R10 and R11 to provide a motor voltage output, V_MOTOR at line 702.

Figure 41:
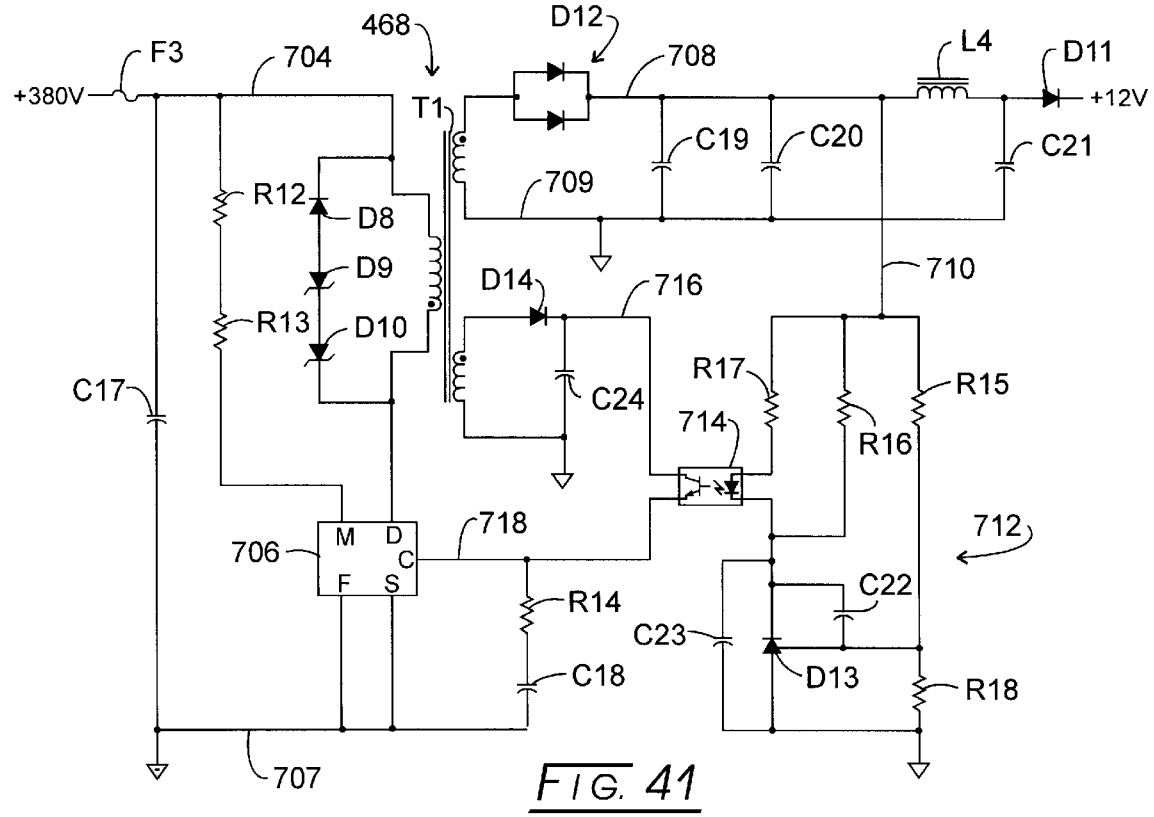
FIG. 41 is an electrical schematic diagram of one low voltage power supply shown in block diagrammatic form in FIG. 34.

As discussed above in connection with FIG. 34, the present control system includes two low voltage power supplies as described in connection with blocks 468 and 470. These redundant power supplies provide logically ORed outputs. FIG. 41 reveals one of these identical circuits which is represented in general at 468 in consonance with the discussion at FIG. 34. Circuit 468 taps the +380V high voltage output at line 704 incorporating fuse and which is directed to one end of the primary side of a transformer T1. The opposite end of the primary side is coupled to primary circuit ground ultimately provided from line 706. Switched control input to the input side of transformer T1 is carried out by a control device or controller 706 which is configured in conjunction with capacitors C17 and C18, resistors R12–R14 and diodes D8–D10. Switching control 706 is referred to as a "smart power switch" which incorporates regulating circuitries including a power transistor along with PWM control circuitry and the like. The device may be provided as a type TOP234Y Integrated Off-Line Switcher marketed by Power Integrations, Inc., of Sunnyvale, Calif. Transformer T1 provides galvanic isolation and its secondary is tapped at lines 708 and 709 to present a +12V low power supply to ORing diode D11. That output is rectified by diode pair D12 and filtered by inductor and capacitors C9–C21.

Feedback control to the switching controller 706 is derived at the secondary side of transformer T1 at line 710 which extends to a secondary side input network represented generally at 712 and comprised of resistors C15–C18, capacitors C22 and C23 and diode D13. Network 712 provides a voltage proportional signal to the input diode of an opto-isolator 714. The output of opto-isolator 714 returns a feedback signal representing the voltage level at line 708 to the primary circuit side of the power supply by modulating an input from the connection with a second portion of the secondary side of transformer incorporating line 716, diode 4 and capacitor 4. This signal is modulated at the opto-isolator 714 and directed via line 718 to the control input of controller 706.

Figure 42:
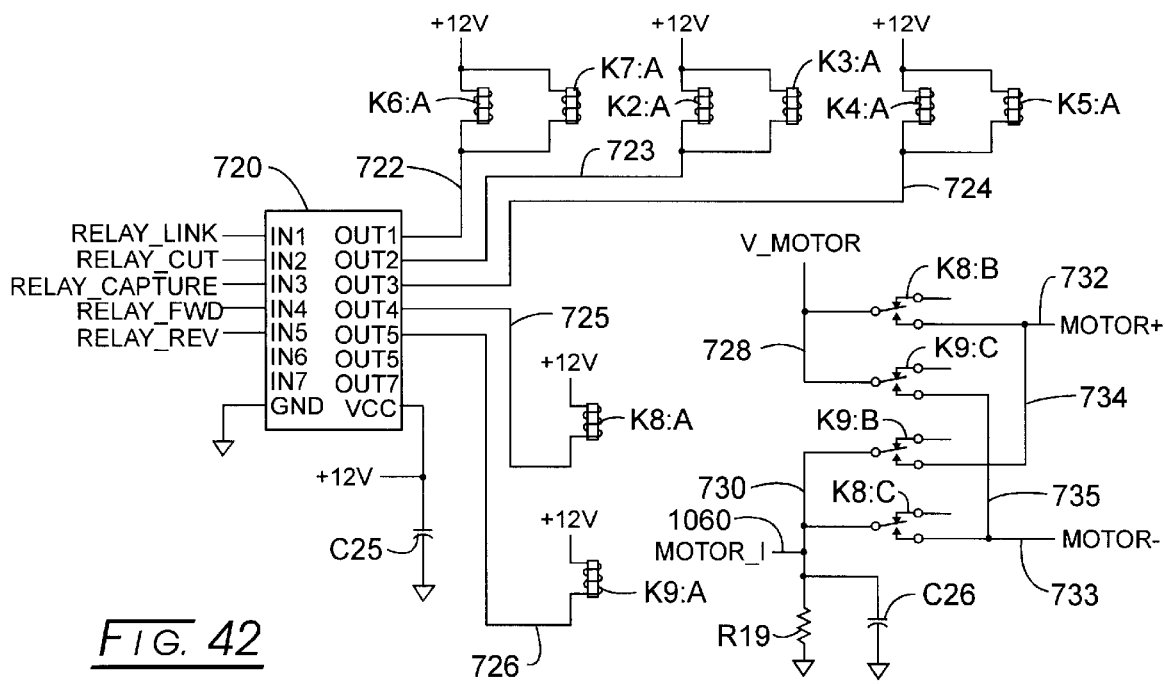
FIG. 42 is an electrical schematic diagram of a motor drive shown in block schematic form in FIG. 34 and further showing the solenoid components of relays employed with the system of the invention.

A variety of relays are employed for the purpose of motor activation, safety and control over the dual electrosurgical cutting sequences and the like. Referring to FIG. 42, a relay controller 720 is illustrated in conjunction with a sequence of five relay input control signals at its I—I input terminals. Device 720 may be provided as a type ULN2004 High-Voltage, High Current Darlington Array marketed by Micro Systems, Inc. of Worcester, Mass. The device 720 is configured with +12V input and capacitor C25 and functions to provide drive outputs to the solenoid components of a sequence of relays. In this regard, relay solenoid components K6:A and K7:A are connected with terminal OUT1 and line 722, thence to +12V. Solenoid components K2:A and K3:A are coupled between output terminal OUT2 by line 723 and thence to +12V. Relay solenoid components K4:A and K5:A are coupled with output terminal OUT3 by line 724 and thence to +12V. Relay solenoid K8:A is coupled to output terminal OUT9 via line 725 and thence to +12V and relay solenoid :A is coupled with terminal OUT5 of device 720 via line 726 and thence to +12V. The latter two solenoid actuators function to selectively actuate or drive respective dual relay contacts :B, :C and :C, :B to provide directional control to motor 170a. The inputs to the contacts K8:B and K9:C are coupled with the earlier described V_MOTOR input at line 728 and the corresponding inputs of contacts K9:B and K8:C are coupled with line 730. Line 730 is seen to be coupled to secondary circuit ground in conjunction with resistor 9 and filter capacitor 6. A positive motor drive output, MOTOR+ is provided at line 732 and a negative or opposite polarity motor drive output MOTOR_, is seen provided at line 733. Note that line 734 couples the MOTOR+signal with one side of relay contacts :B and that line 735 couples line 733 with one side of relay contacts :C.

Thus, energization of relay K8:A provides a forward motor drive, while energization of relay K9:A provides a reverse motor drive. Motor current is monitored at lines 1060 and 730 to provide a signal, "MOTOR_I", used to evaluate the instantaneous motor current draw or load characteristic.

Figure 43A:
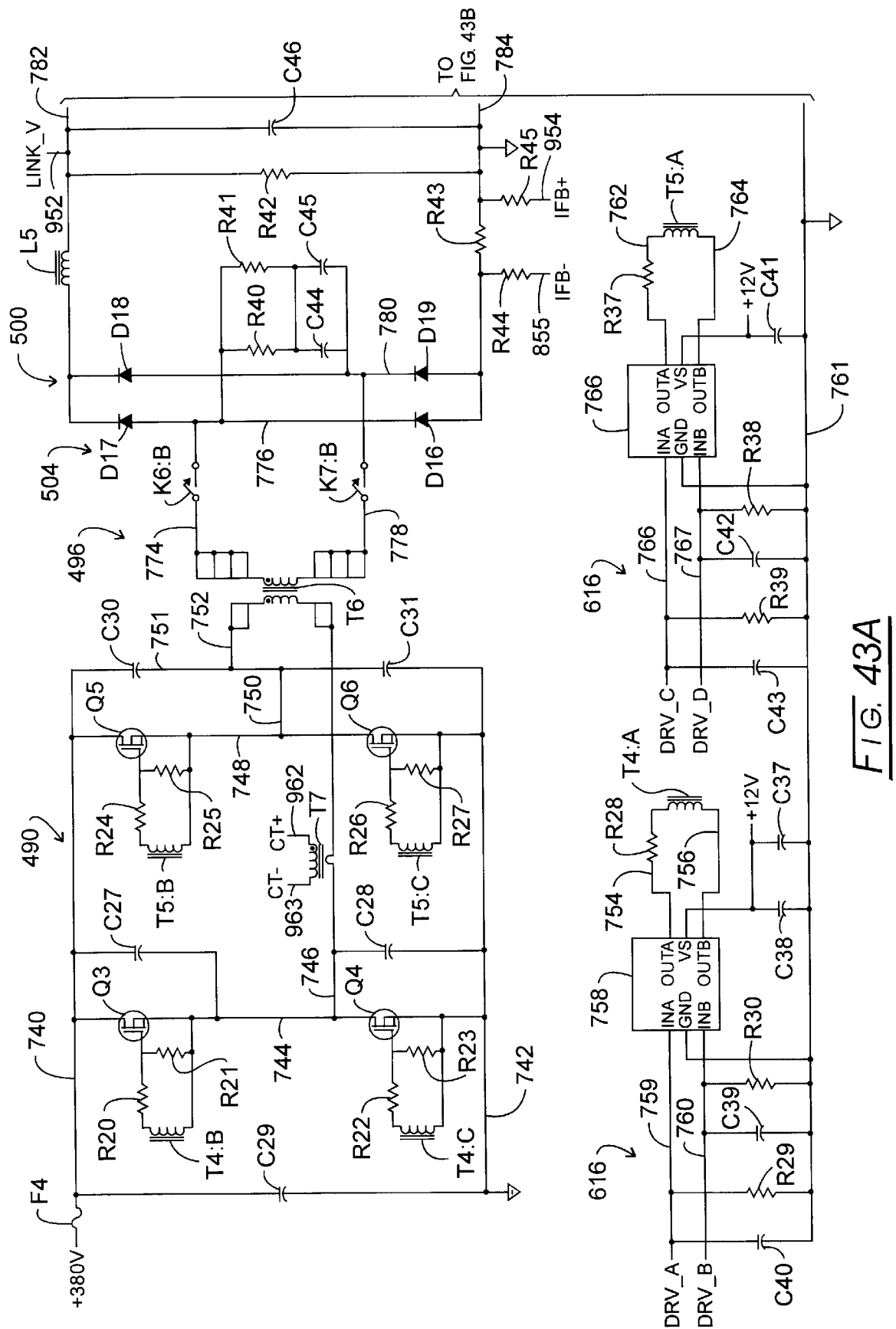
FIGS. 43A and 43B combine as labeled thereon to provide an electrical circuit diagram of a 100 KHz inverter, an isolation transformer, a rectifier, an LC filter; relay disconnects, an RF inverter, a high voltage transformer and a high voltage output stage shown in block diagrammatic fashion in FIG. 34.
Figures 43B, 43C:
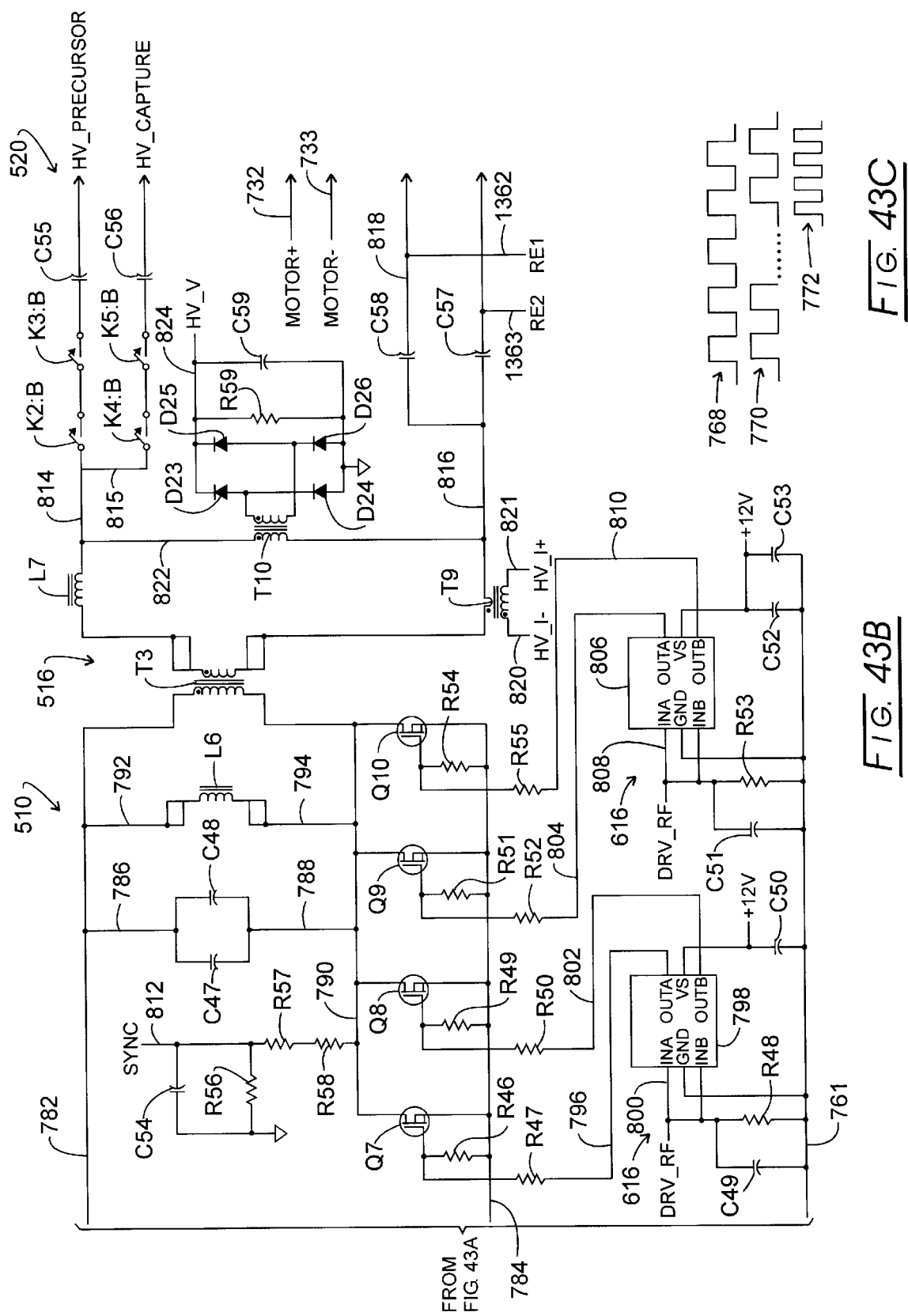
FIG. 43C is a schematic pulse diagram illustrating the operation of the resonant transition phase shift converter shown in 43A.
Figure 46:
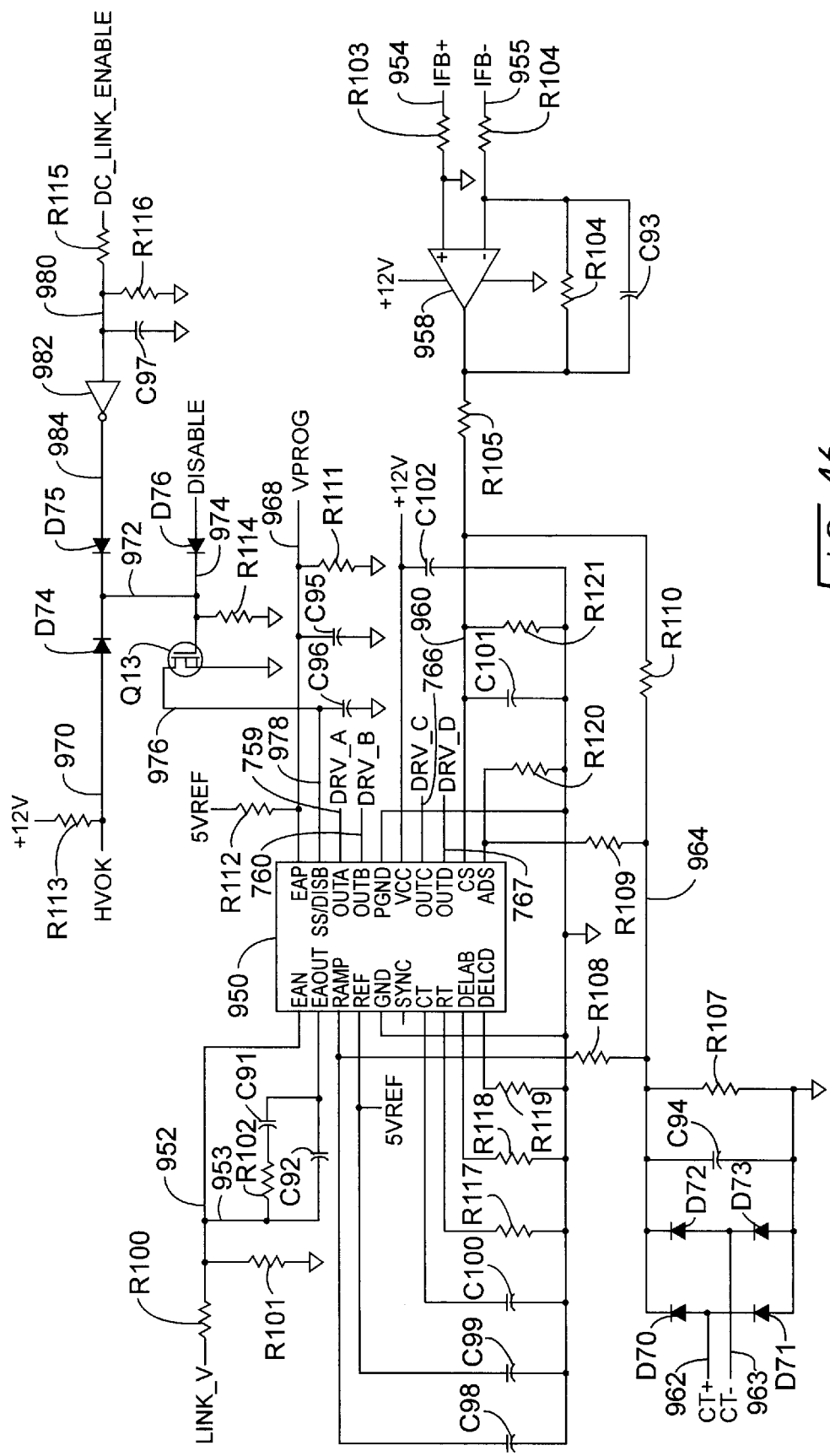
FIG. 46 is an electrical schematic diagram of a control circuit for providing phase shift resonant transition control.

FIGS. 43A and 43B should be considered in accordance with the labeling thereon. Referring to FIG. 43A, a more detailed illustration of the 100 KHz link inverter described at block 490 in connection with FIG. 34 is revealed. The inverter is represented in general with that same numeration. Inverter 490 is implemented in a unique manner for electrosurgical applications, inasmuch as it is a "resonant transition phase shift inverter" which evokes what may be termed "soft" switching, driving the primary side of main isolation transformer, earlier described at block 496 in FIG. 34. The transformer is additionally identified with that earlier numeration. Inverter 490 is formed with MOSFET transistors Q3–Q6. Of these transistors, transistors Q3 and Q4 are switched in complementary fashion as are transistors Q5 and Q6. Because these switching transistors perform in the primary circuit domain in conjunction with 380V extant at line 740 containing fuse f4 and primary circuit ground as present at line 742, it is necessary to provide for a primary to secondary circuit isolation between the control input to the inverter 490 and the switching components of it. Accordingly, the switching function is implemented with pulse transformers. In the figure, transistors Q3 and Q4 are seen to be coupled within line 744. Transistor Q3 is configured in conjunction with resistors R20 and R21 and capacitor C27. Correspondingly, complimentary transistor Q4 is implemented with resistors R22 and R23 and capacitor C28. A capacitor C29 is coupled between lines 740 and 742. Coupled to the gate of transistor is the secondary side of a pulse transformer T4:B and similarly coupled to the gate of transistor Q4 is the secondary side, T4:C of the same pulse transformer. A node is established between transistors Q3 and Q4 at line 746 which extends, in turn, to one end of the primary side of isolation transformer T6. Transformer T6 was described at bock 496 in connection with FIG. 34, and is represented in general by that same number in the instant figure. The pulsed output at line 746 is monitored for control purposes by a current transformer T7 to provide control output signals CT− (line 963) and CT+ (line 962). Those signals are employed in conjunction with the phase shift resonant controller which controls inverter 490 (FIG. 46).

Transistor Q5 is configured in conjunction with resistors R24 and R25 and capacitor C30. Similarly, transistor Q6 is configured with resistors R26 and R27 and capacitor C31. Transistors Q5 and Q6 are connected in series within line 748, and the node between them is tapped at lines 750–752 which are coupled to another end of the primary side of isolation transformer T6. Complementary transistors Q5 and Q6 are switched by inputs into transformer secondary sides T5:B and T5:C respectively. Transistors Q3–Q6 may be provided as type IRF460 Repetitive Avalanche and d/v/dt Rated HEXFET® transistors marketed by International Rectifier, Inc. of El Segundo, Calif.

Now looking to the primary side controlling inputs to these three-winding transformers, the primary side, T4:A of the transformer is shown coupled through line 754 incorporating resistor R28, and line 756 to the output terminals of a driver component 758. Device 758 may be provided, for example, as a type MIC424. Performing in conjunction with a +12V input and configured with capacitors C37–C40 and resistors R29 and R30, connected with ground line 761, the device responds to inputs DRV_A and DRV_B derived from the drive circuit board as described earlier in connection with arrow 616 and shown here being coupled to device 758 via respective lines 759 and 760. Those inputs are derived by the controller for inverter 490 (FIG. 46).

The corresponding switching to transistors and is derived from the primary side of three-winding transformer T5 at T5:A. That primary side is coupled via line 762, incorporating resistor R37, and line 764 to the output terminals of a driver component 766 which also may be provided as a type MIC4424. Device 766 performs in conjunction with +12V and is configured with capacitors C41–C43 and resistors 8 and 9 to respond to control inputs DRV_C and DRV_D derived from the noted arrow 616 and provided at respective lines 766 and 767 to carry out complimentary switching of the transistors Q5 and Q6. Those inputs also are derived by the controller for inverter 490 (FIG. 46).

Looking momentarily to FIG. 43C, a schematic representation of the squarewave generated for example at, the switching node between transistors Q5 and Q6 is represented in general at 768. The corresponding squarewave generated at the switching node intermediate transistors and is represented schematically at 770. When these squarewaves are in phase, there is no voltage difference between them and thus no voltage is impressed across the isolation transformer T6. However, the voltage output of the isolation transformer T6 is controlled by modulating the phase between the squarewave arrays 768 and 770 to evolve a resultant squarewave, for example, as symbolically represented at the right of the resultant wave 772.

Returning to FIG. 43A, as this inverter switching is carried out, the secondary side output of transformer T6 is directed to each half of a full wave bridge rectifier described at block 500 in connection with FIG. 34. In what are referred to as "resonant transitions", the capacitors C30 and C31 as well as capacitors C27 and C28 combine with the leakage inductance of transformer T6 to create soft switching resonant transitions on the two switch nodes. Thus, transistor pairs and and and switch in a very "soft" manner with low stress and with high efficiency.

The secondary side of isolation transformer is coupled via line 774, incorporating relay contacts T6:B to line 776. Correspondingly, the opposite end of the secondary side of transformer is coupled via line 778, incorporating relay contacts K7:B, to line 780. Relay contacts K6:B and K7:B are selectively actuated from the relay solenoids described respectively at K6:A and K7:A in FIG. 42. The relays correspond with block 504 described in connection with FIG. 34. Line 776, incorporating diodes 6 and D17 and line 780 incorporating diodes D18 and D19 comprise the earlier-described full wave rectifier 500 which is implemented in combination with resistors R40 and R41 and capacitors C44 and C45 to derive the d.c. link voltage across lines 782 and 784.

Filtering of the rectified d.c. link voltage further is provided by inductor L5 and capacitor C46. Additionally, a resistor R42 is coupled between output lines 782 and 784 of this rectifying and filtering function. Capacitor C46 carries the D.C. link voltage monitored at line 952 as a "LINK_V" signal which is used for a high gain controller feedback and other control purposes. Resistors R43 at line 784, R44 at line 955 and R45 at line 954 are employed to derive the current-proportional monitor signals IFB– and IFB+ employed, inter alia, by the noted inverter 490 controller (FIG. 46).

The capability for amplitude modulation of the system RF output may be utilized at the commencement of any given electrosurgical cutting procedure carried out either by the pursing cables or by the precursor electrodes to provide a "boost" in voltage for a short boost interval to accommodate any cutting start or restart. Under such conditions, the electrodes, whether precursors or pursing cables may be resting upon tissue and encountering an impedance which may be too low to initiate a necessary cutting arc. In this regard, the cutting of tissue occurs when high temperatures derived from an arc form a vapor between the cutting electrode and adjacent confronting tissue. Without evoking that arc at the commencement of any cutting action, the electrode may be passing current into the tissue to create a deleterious necrosing rather than desired cutting activity. Accordingly, a modulation of the link voltage is provided for a three-eights second boost interval at start up with a boost amounting to the value of the square root of two times the normal link voltage. Thus, the electrodes may operate in either a normal cutting mode or a boost mode. Inasmuch as power is proportional to the square of the voltage, such an arrangement boosts the power by a factor of two during the boost interval. As noted above, this boost control as well as the necessarily precise control over the link voltage is carried out advantageously with the phase shifting control feature for the network 490. In that regard, the LINK_V signal as at lines 782 and 952 is fed back to the noted phase shift resonant controller (FIG. 46).

The link voltage which, as noted, is applied across capacitor C46, is applied to the RF inverter described earlier at block 510 in connection with FIG. 34 and represented by the same general numeration in FIG. 43B. RF inverter 510 is configured as a resonant tank circuit comprised of capacitors C47 and C48 along with an inductor L6. In this regard, note that the capacitors C47 and C48 are positioned within lines 786 and 788 between lines 782 and 790. Similarly, inductor L6 is coupled by lines 792 and 794 between lines 782 and 790. To excite or induce oscillation in the tank circuit, four MOSFET transistors Q7–Q10 are selectively gated to couple line 790 with D.C. link voltage line 784. The gate of transistor is configured with resistors R46 and R47 and line 796 which extends to one output, OUTA, of a driver or buffer 798. The driver 798 is configured with capacitors C49 and C50, resistor R48 and +12V and responds to a DRV_RF signal at its input line 800 to carry out gating. The device 798 may be provided as a type MIC4424. The second output, OUTB, of device 798 is coupled via line 802 with the gate of transistor Q8. That coupling is configured in conjunction with resistors R49 and R50.

In similar fashion, the gate of transistor Q9 is configured with line 804 and resistors R51 and R52. Line 804 extends to the OUTA output terminal of a driver or buffer 806. Driver 806 is configured with capacitors C51–C53, resistor 3 and +12V and receives a control input, DRV_RF at its input line 808. Device 806 also may be of the noted type MIC4424. The second output terminal, OUTB, of device 806 is coupled via line 810 with the gate of transistor Q10 which is configured in conjunction with resistors R54 and R55. A SYNC signal is generated from line 790 at line 812 which is configured in conjunction with resistors R56–R58 and capacitor C54.

The stable frequency sinewave generated by RF inverter 510 is applied to the primary side of a step-up transformer T3 described earlier at block 516 in FIG. 34 and identified generally by that same numeration in the instant figure. A stepped-up output from transformer T3 is provided at lines 814 and 815. An inductor, at active electrode line 814 provides a smoothing of the sinewave output. The output at line 814 is directed through relay contacts K2:B and K3:B and coupling capacitor C55 to derive the cutting output, HV_PRECURSOR which is directed to the precursor electrodes. Correspondingly, active electrode line 815, extending from line 814, carries relay contacts K4:B and K5:B and extends in combination with coupling capacitor 6 to provide the electrosurgical cutting output, HV_CAPTURE which is supplied to the pursing cables 300–304. Relay contacts K2:B–K5:B are controlled from the solenoid components described above in connection with FIG. 42 and function as components of output stage 520 (FIG. 34). Return line 816 is coupled with the corresponding two pads or surfaces of the return electrode. In this regard, the line is connected with coupling capacitor 7 and is coupled with PCSM circuit 528 at line 1363 to provide an R signal. Line 816 is coupled to line 818 and coupling capacitor 8 to provide a second return which is coupled with PCSM circuit 528 at line 1362 to provide the signal R. A small monitoring current transformer T9 is coupled with line 816 to develop the high voltage current monitoring signals HV_I– and HV_I+ at respective lines 820 and 821.

Similarly, a voltage monitoring transformer 0 is connected within line 822 between lines 814 and 816. The secondary of transistor 0 is configured in conjunction with rectifier-defining diodes D23–D26, resistor R59 and capacitor C59 to provide a voltage monitoring signal, HV_V at line 824. A specially treated version of that signal provides an outer loop slow or low gain program input to the control of link inverter 490.

Figure 44B:
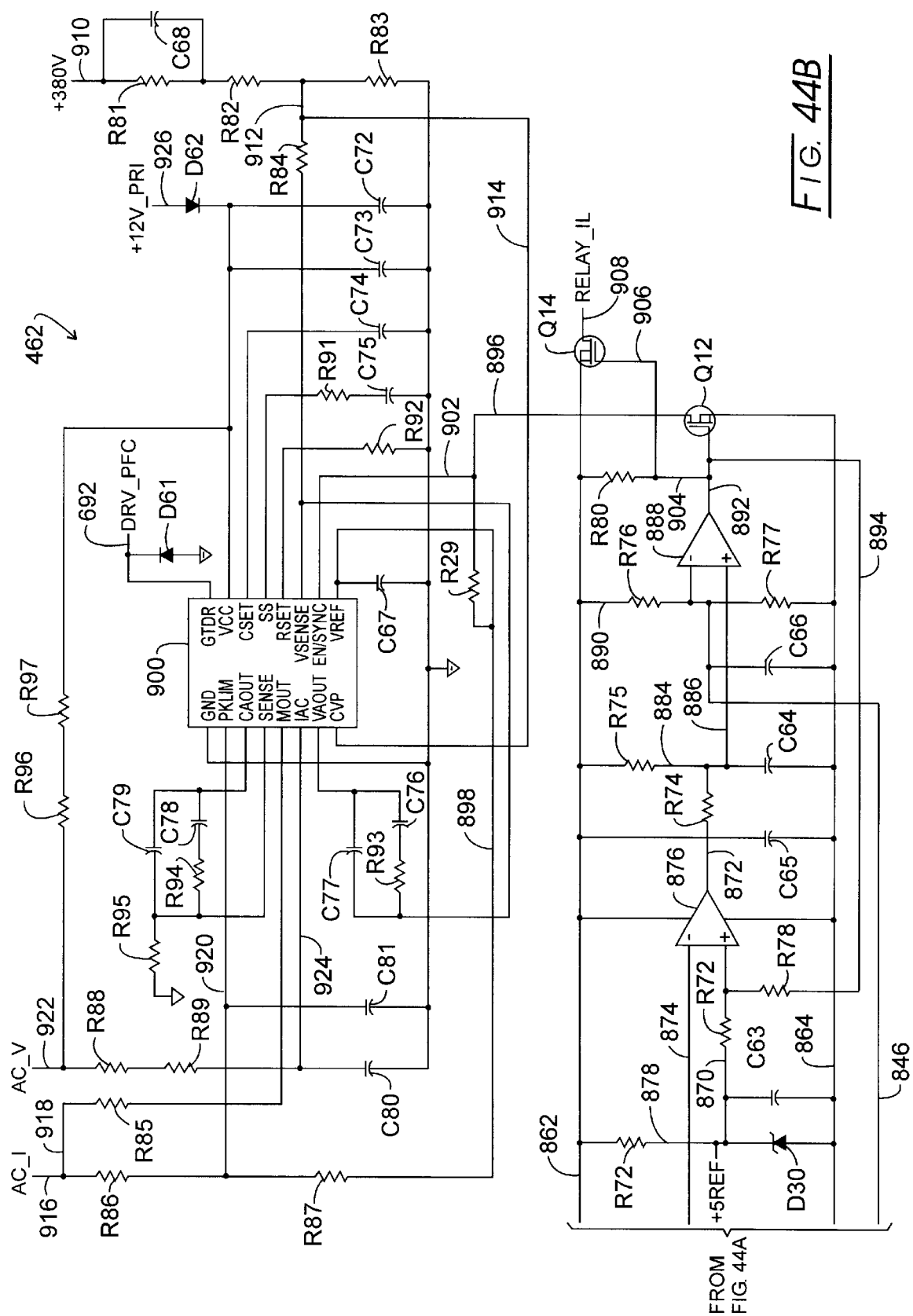

FIGS. 44A and 44B should be considered together in the manner labeled thereon. These figures are concerned with components mounted at the drive board 622 (FIG. 36B) which carries, inter alia, monitoring and control functions for the PFC boost converter 462 which has been discussed in connection with FIGS. 34 and 37B.

Looking initially to FIG. 44A, the pre-regulated 380 volt interim voltage level as present at capacitors C12 and C13 and described in connection with FIG. 37B in conjunction with lines 686 and 830 provides a monitoring input, +380V represented at line 830. The level of this interim voltage is divided by resistor grouping R60–R62, filtered at capacitor R60 and delivered via line 832 to one input of a comparator 834. The reference input to comparator 834 is derived from +5REF at line 836 which incorporates level adjusting resistors R63 and R64 and provides the reference input at line 837. When the 380V input at line 830 is of proper amplitude, comparator 834 provides an output at line 838 incorporating resistor R65 which is submitted to an R-C timing network represented generally at 840 and comprised of resistor R66 and capacitor C61 within line 842. The time constant selected for network 840 accommodates for any line vagaries or the like. Accordingly, the slightly delayed signal then is introduced via line 844 to one input of a buffer 846, the opposite input to which is provided from line 848. The output of buffer 846 at line 850 extends to line 852 which is coupled through resistor R67 to +12V primary power input at line 862. Line 852, is coupled via line 858 to the gate of transistor Q11. Transistor Q11 is connected within line 860, incorporating resistor R68, between line 862 carrying +12_ PRI and primary ground at line 864. Transistor Q1 is turned off in response to a logic true low at line 850 to, in turn, energize the diode of an opto-isolator 866 via lines 868 and 870 from +12V primary power supply (+12V_PRI). The resultant output from the opto-isolator 866 provides a low logic true high voltage ok signal, HVOK, for enabling employment by controller circuitry at the lower voltage secondary side. See FIG. 46 in the latter regard.

The 380V d.c. output itself is not enabled until assurance is made that the A. C. input as described at line 450 in connection with FIG. 34, is at a proper level. The sensing of this value was provided from line 682 as described in connection with FIG. 37A. That AC_SENSE is monitored as seen at line 872 which incorporates resistors R69 and R70 and capacitor C62 and then is connected to line 864 and tapped at line 874. A resistor R71 is incorporated between lines 874 and 864.

Looking to FIG. 44B, line 874 is seen to extend to one input of a comparator 876. The opposite input to comparator 876 is +5REF which is derived at line 878 intermediate resistor R72 and diode D30. The reference (+5REF) at line 878 is tapped at line 880 incorporating resistor R73 and coupled through filtering capacitor C63 to line 864. Line 874, carrying the adjusted AC_SENSE signal, extends to the opposite input of comparator 876, and in the presence of an appropriate voltage level, an output is provided by comparator 876 at line 882. Line 882 incorporates resistor R74 and extends to line 884 wherein the output is subjected to the time constant established by resistor R75 and capacitor C64. The output from that R-C network then is directed via line 886 to one input of a comparator-buffer 888. The opposite input to buffer 888 is derived from line 848 extending to line 890, in turn, incorporating resistors R76 and R77. Filter capacitors are shown at C65 and C66 and the low logic true output of comparator 888 at line 892 is seen to be directed to the gate of transistor Q12. Transistor Q12 normally is held on from line 894 incorporating resistor R78. The source of transistor Q12 is connected with line 864 and its drain is coupled with line 896 incorporating resistor R79. Line 896 is coupled, in turn, to line 898 which is filtered by capacitor C67 and extends to the VREF terminal of the controller 900 for the PFC boost converter 462. Note that line 896 further is coupled via line 902 to the enabling input terminal EN/SYNC of device 900. Thus transistor Q12 turns off in the presence of an AC_SENSE signal of proper amplitude to enable controller 900 by application of a voltage from line 898, resistor R79 and line 902. Device 900 may be provided as a type LT1248 power factor controller marketed by Linear Technology Corp. of Milpitas, Calif.

Line 892 additionally is seen to be coupled via line 904 and resistor R80 to line 862 which extends, in turn, to the source of transistor 4. The gate of transistor Q14 is coupled to line 904 by line 906. Accordingly, the low true signal at line 892 functions additionally to turn on transistor Q14 providing a solenoid energizing true signal at line 908. In this regard, the signal at line 908 provides a RELAY_IL signal which, in turn, functions to energize the relay solenoid K1:A described in conjunction with FIG. 38. That relay closes the contacts K1:B to shunt thermistor 670 (FIG. 37A) which had been active to avoid in-rush currents.

Controller 900 functions to derive the control input, DRV_PFC applied to line 692 of driver device 686 described in connection with FIG. 37B. Line 692 is protected by diode D61. Device 900 performs in conjunction with a sensing of the 380V level output; the sensing of A. C. current, AC_I; and A. C. voltage, AC_V. 380V monitoring is represented at line 910 which incorporates resistors R81–R83 and capacitor C68. The adjusted voltage signal level then is introduced via line 912 incorporating resistor R84 to the voltage sense terminal (VSENSE) of controller 900. This signal level at line 912 also is extended via line 914 to the CVP terminal of device 900. The A. C. current level signal, AC_I, is provided from line 916 and is derived from line 682 as described in conjunction with FIG. 37B. This signal at line 916 is seen to extend via line 918 and resistor R85 to the MOUT terminal of controller 900. Line 916 also incorporates a resistor R86 and extends to line 920 which, in turn, extends to the PKLIM terminal of controller 900. Line 898 is seen to extend with resistor R87 to line 920.

The A. C. voltage signal, AC_V, is provided from line 922 and was derived at line 686 of FIG. 37B. Line 922 is seen to incorporate resistors R88 and R89 and extends to line 924 which, in turn, is coupled with the IAC terminal of controller 900. Controller 900 performs in conjunction with the primary circuit power supply, +12V_PRI as shown introduced from line 926 incorporating diode D62. The device further is configured in conjunction with capacitors C72–C81 and resistors R91–C97.

As noted earlier herein the power factor correction developed in association with controller 900 not only permits the electrosurgical generator to be used universally with diverse worldwide utility line inputs, but also derives a preregulated interim voltage output which permits an optimization of the link inverter stage carrying out the constant voltage-based control permitting generation of a sustained cutting arc in the presence of an active electrode exhibiting a dynamic surface area or geometry.

Looking to FIG. 45, the low voltage primary circuit power floating bias supply is depicted. The 380V d.c. level(FIG. 37B) is tapped as represented at line 930 incorporating fuse and filtered by capacitor 5. Line 930 extends to line 932 incorporating diodes 3 and 4 and extending to the D (Drain) terminal of a regulator 934 which may be provided as a type TO221P Three-terminal/Off-line PWM Switch marketed by Power Integration, Inc. of Sunnyvale, Calif. Component 934 is referred to as a "smart power device", combining a power transistor and a PWM control circuit. Its source terminals are seen coupled to ground in conjunction with line 933. Line 932 is connected across the primary side of a step down transformer T12 and asserts a chopped input thereto under the control of device 934. The secondary side of transformer T12 is connected at line 936 and diode D65 to line 938 incorporating rectifying diodes D66 and D67 and coupled via resistor R98 to the C (control) input of device 934. This serves as a feedback to device 934. The primary circuit power supply, +12V_PRI is then presented through resistor R99. Filtering capacitors are provided as represented at C86–C88.

Also located upon the drive board 622 is the resonant transition control integrated circuit which develops the DRV_A through DRV_D control signals which are submitted to the inverter 490 as described in conjunction with FIG. 43A. Referring to FIG. 46, this controller is shown at 950 extending from which the noted drive signals are identified in conjunction with respective lines 759, 760, 766 and 767 as are repeated from FIG. 43A. The value of link voltage, LINK_V is submitted to the EAN and EAOUT terminals of device 950 from respective lines 952 and 953 which are configured in combination with resistors R100–R102 and capacitors C91 and C92. Line 952 reappears in conjunction with derivation of the LINK_V signal in FIG. 43A. This link voltage input at resistor R100 represents an inner relatively fast or high gain control feedback loop to the link voltage controller 950, which performs, inter alia, in conjunction with an outer feedback loop program control which is comparatively slow or of a low-gain nature. Link voltage current related signals IFB- and IFB+are applied respectively from lines 954 and 955 incorporating resistors R103 and R104 to the inputs of a type LP1215 amplifier 958 which is configured in conjunction with resistors R105 and R106 and capacitor C93. The signals are derived with the noted lines in FIG. 43A. The output of amplifier 958 is provided via line 960 to the CS terminal of device 950.

Inverter 490 current signals, CT+ and CT–, are submitted via respective lines 962 and 963 to rectifying diode pairs D70, D71 and D72, D73 configured within a network including capacitor C94 and resistor R107. Derivation of these signals is described in conjunction with FIG. 43A. From this network, corresponding signals are submitted via line 964 and resistor R108 to the RAMP terminal of device 950. Similarly, the signal is submitted via resistor R109 to the ADS terminal and through resistor R110 to line 960 and the CS terminal of device 950. The system elected link voltage as well as its resultant control in deriving a constant system output voltage is determined by a signal identified as "VPROG" (FIG. 47A) which is submitted via line 968 to the EAP terminal of device 950. Line 968 is configured in conjunction with resistor R111 and capacitor C95 and is coupled through pull-up resistor R112 to 5 VREF, the latter reference having been described in conjunction with FIG. 44B. As noted above, an outer feedback control loop, ultimately responsive to the level of system output voltage is combined with a high gain inner loop. This arrangement permits a constant voltage-based control accommodating the otherwise unstable oscillative tendencies posed by the negative dynamic impedance of the required cutting arc, as well as the impedance variation exhibited by the cables when operating in a capture mode. Accordingly the outer feedback loop signal, VPROG applied at line 968 is programmed to device 950 in a very slow manner by selecting a relatively high capacitance value for capacitor C95, for example, 4.7 micro-farads, evolving a time constant of about 35 milliseconds. This achieves a stable, constant voltage control over the RF inverter 510 output.

Device 950 also is selectively enabled or disabled in response to three signal inputs. One of those signal inputs is the earlier-described logic low true HVOK signal generated from interim voltage responsive opto-isolator 866 described in conjunction with FIG. 44A. This active low signal, HVOK, is seen introduced via line 970 which is coupled to +12V through pull-up resistor R113. Line 970 extends through steering diode D74 and lines 972 and 974 to the gate of a MOSFET transistor Q13. Line 974 is coupled through resistor R114 to ground and transistor Q13 is seen coupled between ground and lines 976 and 978 to the soft start/disable terminal of device 950. Line 976 extends to ground through capacitor C96. Accordingly, when the signal at line 970 is at a logic high value, representing an inadequate interim voltage level, then transistor Q13 is turned on to bring line 978 to a logic low condition. This disables device 950 until such time as a logic true low condition occurs at line 970, whereupon transistor Q13 turns off to remove the low signal at line 978 and permit the internal circuitry of device 950 to effect its enablement.

As the practitioner actuates the energize/position switch 55 on instrument 12 or the footswitch 86a, a high voltage output is called for to energize the precursor electrodes. Before that condition occurs, the d. c. link voltage must be created. The PLD based control system (FIG. 62A, line 1237) thus provides a logic high true DC_LINK_ENABLE input as shown at line 980 incorporating resistor R115 and configured in conjunction with filter resistor R116 and filter capacitor C97. Line 980 extends to an inverter buffer 982 having an output at line 984 extending through steering diode D75 to line 972. Thus lines 984, 972 and 974 are maintained at a logic high level to turn on transistor Q13 and effect disablement of device 950 until line 980 assumes a high logic level upon enabling command, DC_LINK_ ENABLE from the PLD-based control. Accordingly in the absence of an appropriate link enable signal, or an HVOK signal, device 950 will not provide a link control. Device 982 may be provided as a type CD40106B CMOS Schmitt trigger marketed by Texas Instruments, Inc. of Dallas, Tex. Use of such a component takes advantage of its filtering histeresis characteristic.

A detected d.c. link over-voltage fault condition will derive a logic high true "DISABLE" signal (see FIG. 59) which is presented at line 974 through steering diode D76. Accordingly, if such a fault arises in the absence of a BOOST_MASK signal (FIG. 47A), the system will be shut down. It is at this location through diode D76 that such shut down activity takes place by turning on transistor Q6. Device 950 is seen to be further configured in conjunction with capacitors C98–C102 and resistors R117–R121 and may be provided as a type UCC3895 BiCMOS Advanced Phase Shift PWM Controller marketed by Unitrode Corp. of Merrimack, N.H.

Figures 47A, 47B, 47C:
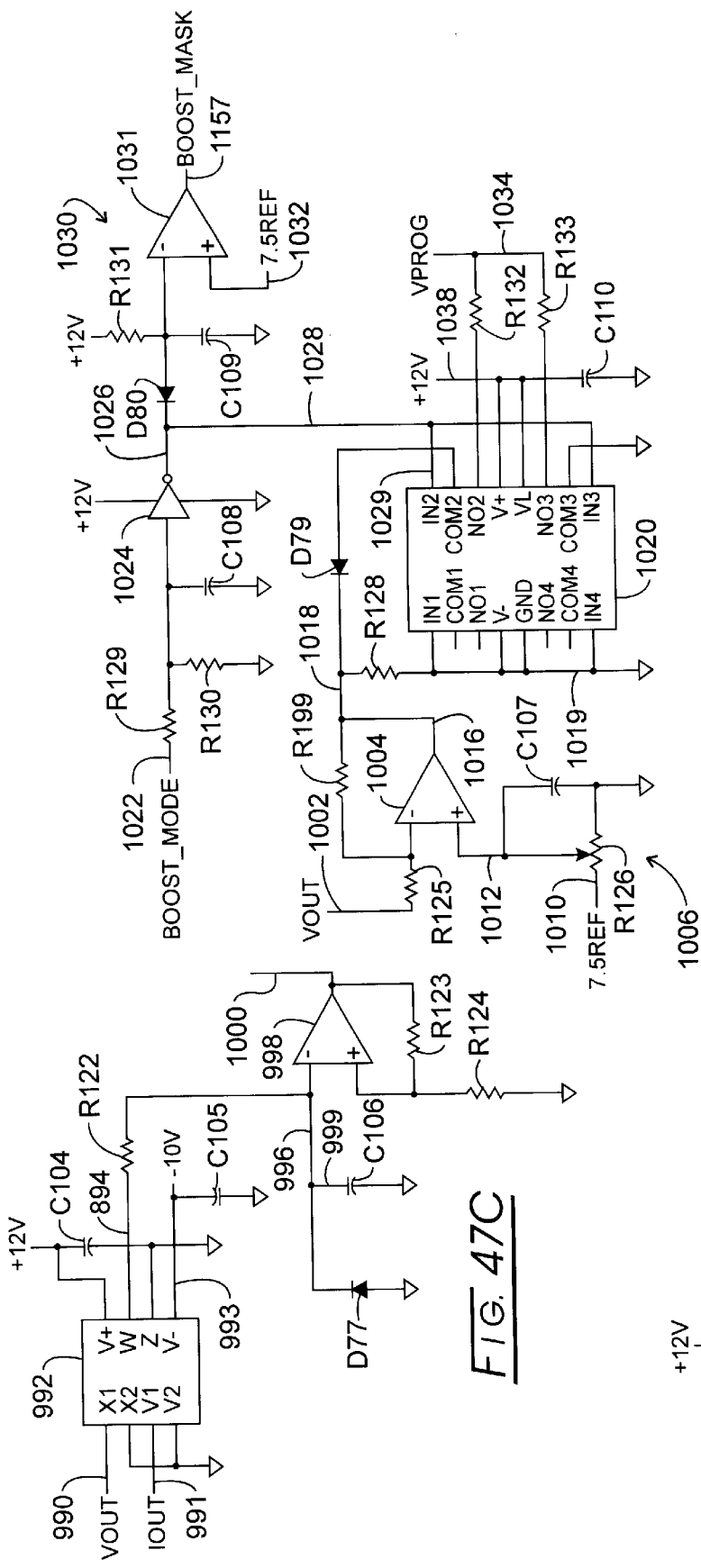
FIG. 47A is an electrical schematic diagram of a control circuit for adjusting d.c. link voltage.
FIG. 47B is an electrical schematic diagram of a reference voltage deriving circuit.
FIG. 47C is an electrical schematic diagram of a multiplier circuit for deriving an output power monitoring signal.

Referring to FIG. 47A, the control system output voltage outer loop monitoring circuit feature carried at the drive board is illustrated. The high voltage output monitoring signal described in FIG. 43B as HV_V at line 824 is filtered as described in conjunction with FIG. 56 to provide the signal, VOUT which is introduced to line 1002. Line 1002 incorporates input resistor R125 and extends to one input of an error amplifier 1004. The reference input to device 1004 is derived from a potentiometer represented generally at 1006 incorporating a resistor component R126 and a capacitor C107. Resistor component R126 is coupled with a 7.5V reference input.

Looking momentarily to FIG. 47B, the derivation of that reference is illustrated. In the figure, line 1008 incorporating resistor R127 and diode D78 is tapped to provide the 7.5REF signal at line 1010 which reappears in FIG. 47A. A wiper arm extended input to device 1004 is represented at line 1012. The output of comparator 1004 at line 1016 represents an output voltage error signal which is directed to lines 1018, 1019 and input resistor R128 to the IN1, V-, GND, and IN4 terminals of an analog switching device 1020. Analog switch 1020 is provided as a type MAX4665 CMOS analog switch, marketed by Maxim Integrated Products of Sunnyvale, Calif. Line 1018 extends from input line 1002 to the COM2 terminal of analog switch 1020 and incorporates resistor R199 along with blocking diode D79. This arrangement assures a unidirectional input to device 1020. Switch 1020 additionally responds to a logic high true "BOOST_MODE" signal generated from the control board PLD (FIG. 61, line 1240) and shown presented at line 1022. It may be recalled that the boost mode provides for increasing the output voltage and thus the power output of the precursor electrode and the pursing cables for about three-eighths second at any start-up or restart. Line 1022 is configured in conjunction with resistors R129 and R130 and capacitor C108 and extends to the input of a buffer inverter 1024. Device 1024 may be provided as a type CD40106B Schmitt trigger (supra). Accordingly, the logic high true signal at line 1022 is inverted to a logic low at line 1026 and is directed via lines 1028 and 1029 to the IN2 and IN3 terminals of device 1020 to create a boost mode of performance.

Because the control system includes a d.c. link overvoltage fault condition, it is necessary to simultaneously develop a "BOOST_MASK" signal to overcome a false fault condition during a boost mode. Accordingly, line 1026 is seen to incorporate a steering diode D80 which is positioned forwardly of an RC network shown generally at 1030 and comprised of resistor R131 and capacitor C109 extending between +12V and secondary ground. Network 1030 provides a normally high input to a comparator 1031 to establish a normally logic low at its output line 1157. The opposite input to device 1031 at line 1032 carries the 7.5REF signal described in connection with FIG. 47B. Comparator 1031 provides a logic or active high BOOST_MASK output at line 1157 upon the occurrence of a boost mode indicating logic low at line 1026. The BOOST_MASK active high output at line 1157 is present during the occurrence of the BOOST_MODE command. As a safety feature, however, following the termination of the BOOST_MODE command signal, the logic high BOOST_MAST condition at line 1157 will persist for about the time constant of RC network 1030. In this regard, upon the assumption of an active low condition at line 1026, capacitor C109 immediately discharges. At the termination of the boost mode, diode D80 is back-biased and capacitor C109 is gradually charged through resistor R131 to ultimately establish a voltage level causing boost mask comparator 1031 to revert its output to a logic low level removing the BOOST_MASK signal.

Device 1020 responds to the condition at lines 1028 and 1029 to provide a boost voltage value signal level through resistor R132 which derives the VPROG signal for a boost mode output at line 1034. In the boost mode, power is increased by a factor of two. Accordingly the link voltage may be increased by VPROG by the square root of two, power being proportional to the square of voltage. In general, the boost voltage level will be greater than the normal cutting voltage level by a factor within a range from about 1.2 to about 1.5. Alternately, the device 1020 provides a lower level, normal cut voltage value signal at line 1034 as is established by the resistance value of a resistor R133. Those resistors R132 and R133, in effect, form a voltage divider with pull-up resistor R112 described in FIG. 46. To assure a unidirectional input to device 1020, line 1018 is coupled to the COM2 terminal of switch 1020 and serves as a feedback line incorporating blocking diode D80 extending through resistor R149 to line 1000. Device 1020 further is configured with +12V source and a capacitor C110 at line 1038 and may be provided as a type MAX4465, 5-ohm, SPST, CMOS Analog Switched marketed by Maxim Integrated Products of Sunnyvale, Calif.

Referring to FIG. 47C a control system power derivation circuit feature carried by the drive board as illustrated. Overall power is determined by a monitoring of the output voltage and output current to derive signals VOUT and IOUT for presentation a respective lines 990 and 991 extending to a solid state multiplier 992. The derivation of the signals is described in conjunction with respective FIGS. 56 and 55. Device 992 may be provided, for example, as a type AB633JN Analog Multiplier marketed by Analog Devices, Inc., of Norwood, Mass. Multiplier 992 is configured in conjunction with +12V and −10V power supply inputs, as well as capacitors C104 and C105. Forming a component of a power derivation network, the product output of multiplier 992 at line 994 is sent to an integrating resistor R122. Line 994 further extends to lines 996 and 998, the latter line incorporating an integrating capacitor C106. Line 996 further extends to a diode D77 and to the input of an amplifier 998. With the arrangement shown, power is, in effect, computed in accordance with the conventional expression:

$$P = \frac{1}{T} \int vi\, dt$$

Thus, capacitor C106 carries a monitored power signal proportional to output power. That signal is fed to amplifier stage 998 which is configured with resistors R123 and R124 to double the amplitude of the signal. This provides a power value signal utilized by the system at line 1000 identified as "PWR_OUT" to monitor for an excessive output power condition. (See FIG. 57).

Figure 48:
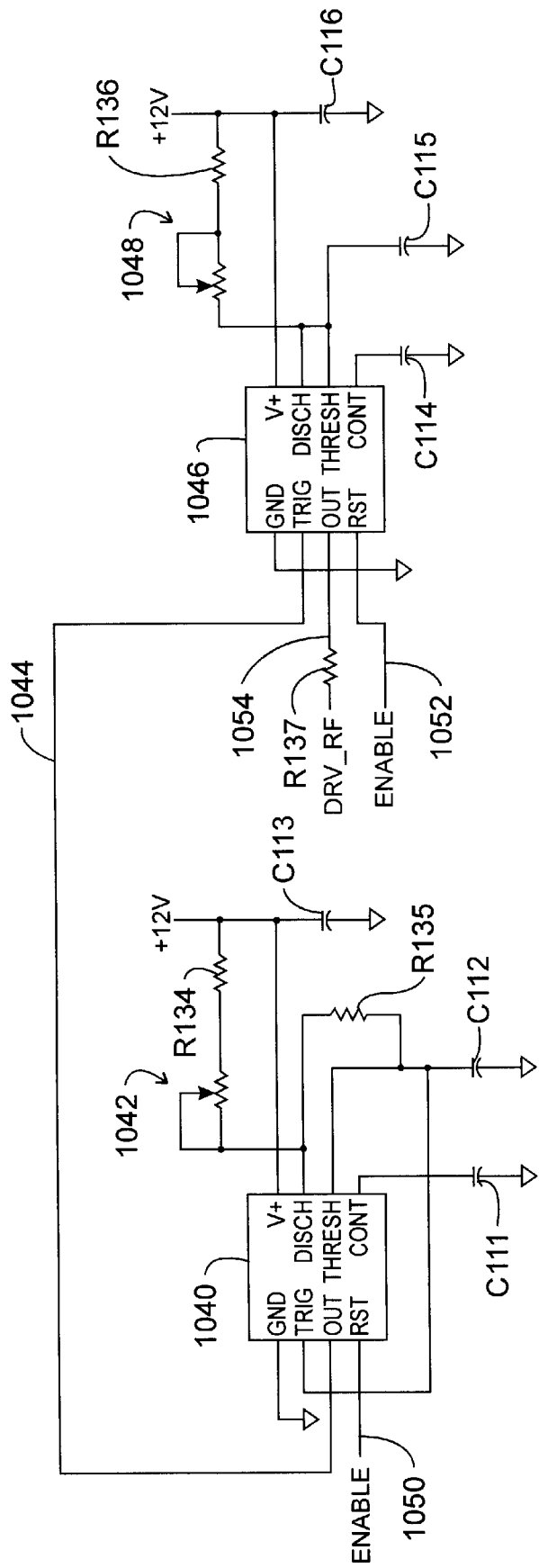
FIG. 48 is an electrical schematic diagram of a control circuit utilized with an RF inverter.

Referring to FIG. 48, the circuitry providing the control input, DRV_RF applied to devices 798 and 806 in FIG. 43B for the RF resonant inverter 510 is illustrated. In the figure, the basic frequency is derived with an oscillator integrated circuit 1040 which may be provided as a type LMC555 CMOS Timer marketed by National Semiconductor Corp. of Santa Clara, Calif., which is configured in conjunction with capacitors C111–C113 and resistors R134 and R145. Frequency adjustment may be provided by the manufacturer in conjunction with a potentiometer represented at 1042. The frequency output of device 1040 is presented along line 1044 to the trigger input of another type LMC555 device 1046 which establishes pulse width. Device 1046 is configured in conjunction with capacitors C114–C116 and resistor R136. Pulse width is adjusted by the manufacturer at a potentiometer represented at 1048. Devices 1040 and 1046 are simultaneously enabled both by PLD and start-up reset derived ENABLE inputs respectively provided at lines 1050 and 1052. In this regard, while enablement is provided on the occasion of a sequential signal ultimately provided from the PLD, the RF inverter is not permitted to be enabled during initial system startup. Accordingly, as a safety feature, the logic or active high ENABLE signal is not provided until after the interval of Power-On Reset (PWR_ON_RST, FIG. 54). The final control signal, DRV_RF is provided from device 1046 at line 1054 which incorporates a resistor R137.

Figure 49:
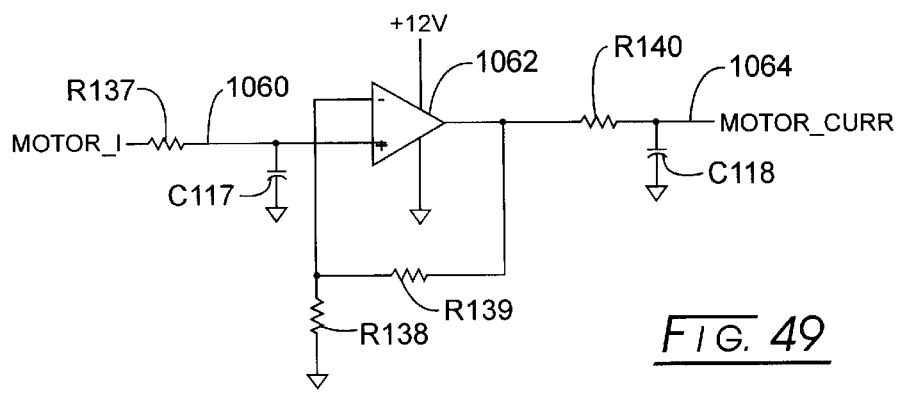
FIG. 49 is an electrical schematic diagram of a circuit for amplifying motor current.

FIGS. 49 through 53 illustrate circuitry associated with the logic used in conjunction with the energization of the motor 170*a* of motor assembly 170. In this regard, motor current, identified as "MOTOR_I" is monitored to carry out this logic. That monitored current is generally too low to be useful and its derivation is described in connection with FIG. 42. Thus, it is amplified initially to develop an enhanced signal identified as "MOTOR_CURR". FIG. 49 shows the amplification of these signals. In this regard, the initial current signal is introduced through resistor R137 and line 1060 to an amplifier 1062. Amplifier 1062 is configured in conjunction with resistors R138–R140 and capacitors C117 and C118 and provides an enhanced MOTOR_CURR signal at output line 1064.

FIGS. 50 through 53 provide varying threshold analyses of the motor current for use by the PLD logic device of the system. FIG. 50 shows the initial threshold test which is to determine, at the outset of motor energization, whether the motor is indeed working. For this purpose, a small amount of free movement of the yoke 184 is permitted prior to contact being made with the ears as at 134 and 136 (FIG. 6) of the drive member 324. During this very short test interval (about 0.5 second), the motor current is very low but discernable, for example, exhibiting at least about a 10 milliamp threshold value. If the motor is not on at a time when it should be on, then a system fault will be at hand with appropriate shut-down and visual cueing. FIG. 50 shows that the MOTOR_CURR signal is introduced at line 1066 to one input of a comparator 1068. The reference input to comparator 1068 is the earlier described 7.5REF disclosed in connection with FIG. 47B. That reference voltage is adjusted by resistors R141–R143 and introduced via line 1070 to device 1068. The output of device 1068 is provided at line 1072 which is coupled to +12V source through a pull-up resistor R144. Where the properly performing motor current level has been detected, a "MOTOR_ON" signal is generated by turning off transistor Q16.

Looking to FIG. 51, the MOTOR_CURR signal is introduced to comparator 1074 from along line 1076. Comparator 1074 is configured with the 7.5REF reference signal and resistors R145–R147 to react to a threshold provided at line 1075 representing, for instance, about 23 milliamps of motor current draw. As the yoke 184 engages the ears 134 and 136 (FIG. 6) the motor will commence doing more involved work and typically will exhibit a current draw of about 45 milliamps. This condition then is witnessed at comparator 1074 and where the established threshold for this motor condition is exceeded, then comparator 1074 reacts at its output line 1078 to turn off transistor Q17. Thus, a "MOTOR_ENGAGED" signal is generated for the logic of the control system. As before, line 1078 is coupled with +12V through pull-up resistor R148. The networks of FIGS. 50 and 51 perform in concert. A determination by the network of FIG. 50 during the initial 0.5 second test interval that motor current is above a low threshold, for example, of 5 milliamps, results in the MOTOR_ON signal being generated. However, during this same test interval, should the motor current exceed the threshold of the network of FIG. 51 to result in a MOTOR_ENGAGED signal, then this initial test fails, resulting in a fault condition. (See FIG. 70D, block 1560). Following passage of the initial one-half second test, the network of FIG. 51 will detect whether or not its threshold, for example, of 23 milliamps has been met. That indicates appropriate engagement of the yoke 184 with ears 134 and 136. If during forward movement of drive member 324, the threshold of the network of FIG. 51 is not sustained, a fault condition results with a system halt and visual cueing.

Referring to FIG. 52, as a tissue capture is completed, for example, as illustrated in connection with FIG. 29, the motor will enter a forward stall condition and the current will rapidly spike to about 130 milliamps. Looking to FIG. 52, the MOTOR_CURR signal again is introduced to a comparator 1080 via line 1082. Comparator 1080 is configured with 7.5REF and resistors R149–R151 to react to a threshold at line 1083 to, in turn, provide an output at output line 1084 when forward stall current levels are present. As before, line 1084 is coupled through pull-up resistor R152 to +12V source and is coupled to the gate of transistor Q18. Accordingly, a "MOTOR_STALL" signal is generated by the turning off of transistor Q18.

Upon detecting the forward motor stall, the logic of the system reverses the drive polarity to the motor 170*a* and the transfer assembly 180 releases from its abutting engagement with drive member 324, ears 134 and 136, whereupon it is driven back to its "home" position as described in connection with FIG. 5. (See FIG. 42). The resultant reverse stall current is of lower amplitude than the forward stall current and is detected. Looking to FIG. 53, the MOTOR_CURR signal is introduced at line 1086 to a comparator 1088. The reference level for comparator 1088 is set for the detection of a reverse stall current level and is provided at line 1089, from 7.5REF in conjunction with resistors R153–R155. Upon detection of a reverse stall condition, output line 1090, which is coupled to transfer Q19 as well as through pull-up resistor R156 to +12V source, assumes a logic low level and transistor Q19 is turned off to establish a "MOTOR_REV_STALL" condition or signal. Comparators 1068, 1074, 1080 and 1088 may be provided, for example, as type LM339 Low Power, Low Offset Voltage Comparators, marketed by National Semiconductor Corp. (Supra).

Looking to FIG. 54, circuitry is represented which provides "ENABLE" and "RESET" signals upon the occurrence of respective RF_INV_ENABLE and PWR_ON_RST signals. The latter reset signal is developed from the control system PLD. (See FIG. 61A). In the figure, the former logic high true input signal is introduced through resistor R157 at line 1092 to the input of a Schmitt trigger implemented buffer 1094, the logic low inverted output of which at line 1096 extends through ORing diode D82 to the input of a second inverter 1098 to provide an active or logic high "ENABLE" signal at output line 1100. Filtering resistor R158 and filtering capacitor C119 are coupled to line 1092, and the hysteresis characteristic of device 1094 also provides filtering. The logic or active low power on reset (PWR_ON_RST) signal is introduced through resistor R159 and line 1102 to the input of a Schmitt trigger implemented buffer 1104, the logic low output of which is provided at line 1106 which is directed to the input of an inverter 1108. The logic high output of buffer 1108 provides a "RESET" signal at line 1110 and also negates the ENABLE signal at line 1100 by a wired ORing established via line 1111, ORing diode D83 and line 1112. Line 1112 is coupled through resistor R160 to ground. Filtering resistor R161 and filtering capacitor C120 are coupled between line 1102 and ground. As noted earlier, as a safety feature, the RF inverter operation is blocked during system startup occurring during the power on reset interval. This is achieved, inter alia, by the above-noted ORing arrangement derived with diodes D82 and D83, which functions to remove the ENABLE signal during this initial interval. Devices 1094, 1098, 1104 and 1108 may be provided as type CD40106B CMOS Schmitt triggers (Supra).

Figure 55:
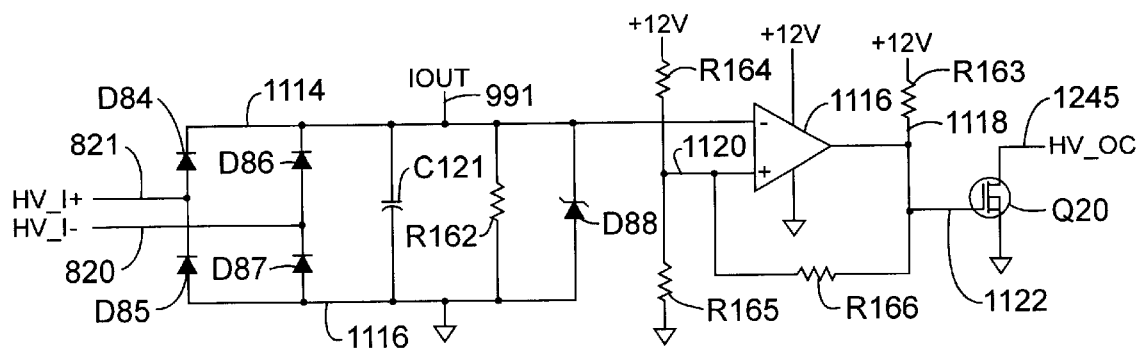
FIG. 55 is an electrical schematic diagram of a circuit deriving an over-current condition.

Referring to FIG. 55, comparator circuitry monitoring for a high voltage over-current condition is revealed. In the figure, the current signals HV_I+ and HV_I− as were developed at the high voltage output stage 520 as described in connection with FIG. 43B are rectified. In this regard, positive current is introduced to intermediate diode pair D84 and D85 from line 821 and the negative current signals are introduced to diode pair D86 and D87 from line 820. These rectifying diode pairs are located between lines 1114 and 1116. The signal "IOUT" is developed from line 1114 and is represented at line 991 (See FIG. 47C). Capacitor C121 and resistor R162 provide a filtering function, while diode D88 functions as a clamp. Line 1114 extends to one input of a comparator 1116 having an output at line 1118 coupled through pull-up resistor R163 to +12V source. Comparator 1116 is configured for establishing a high voltage over-current threshold reference input at line 1120 in conjunction with +12V source and resistors R164–R166. Output line 1118 extends via line 1122 to the gate of transistor Q20. Accordingly, a low true output at the comparator 1116 generates a corresponding over-current condition, "HV_OC" at line 1245 by turning off transistor Q20. (See FIG. 61A where that line reappears).

Figure 56:
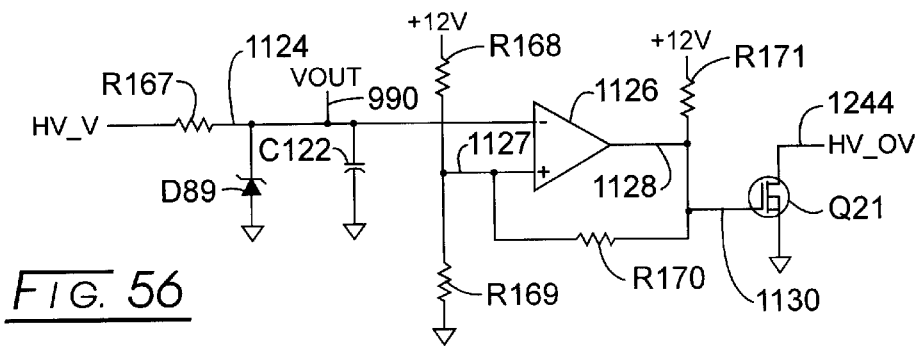
FIG. 56 is an electrical schematic diagram of a circuit for monitoring an over-voltage condition.

Looking to FIG. 56, comparator circuitry is illustrated which determines the presence of an over-voltage condition at the generator output. The HV_V signal, the derivation of which was described in connection with FIG. 43B, line 824, is introduced to line 1124 and resistor R167 to be asserted at one input of a comparator 1126. Line 1124 is coupled with a filter capacitor C122 and clamping diode D89. The over-voltage reference input to device 1126 is provided at line 1127 and is derived from +12V source in conjunction with resistors R168–R170 and the low true logic output of device 1126 is provided at line 1128 which is coupled through pull-up resistor R171 to +12V source. Output line 1128 is connected through line 1130 to the gate of transistor Q21. Accordingly, a low true output at comparator 1126 turns off transistor Q21 to create an over-voltage condition "HV_OV" at line 1244 which reappears in FIG. 61A. Devices 1116 and 1126 may be provided as type LM339 comparators (supra).

Figure 57:
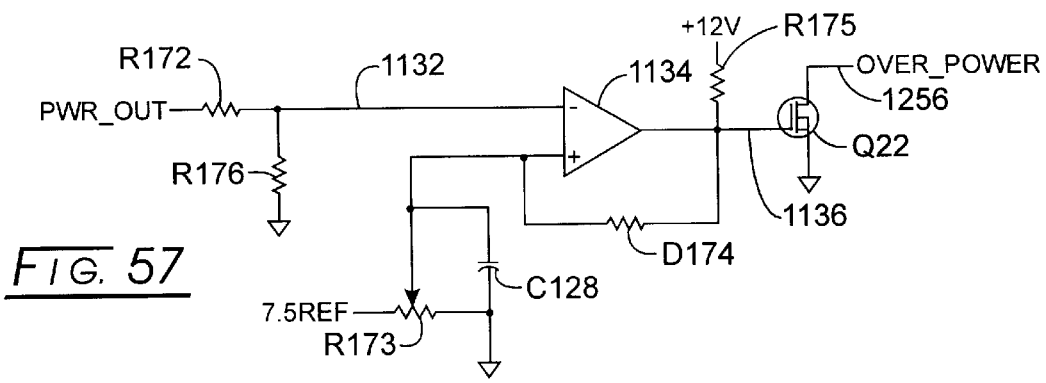
FIG. 57 is an electrical schematic diagram of a circuit for monitoring power level.

Referring to FIG. 57, a comparator circuit is illustrated which determines the presence of an over-power condition at the generator output. This monitoring is carried out in conjunction with the PVWR_OUT signal, the derivation of which was described in connection with FIG. 47C. That signal is introduced through resistor R172 and line 1132 to one input of a comparator 1134. A reference input to comparator 1134 is derived in conjunction with a potentiometer network incorporating resistors R173 and R174, capacitor C128 and the reference, 7.5 REF, the derivation of which was described in connection with FIG. 47B. The output of device 1134 at line 1136 is coupled through pull-up resistor R175 to +12V source and to the gate of transistor Q22. Accordingly, a low true output of device 1134 turns off transistor Q22 to derive an "OVER_POWER" condition at line 1256 which reappears in FIG. 61A. A filter resistor R176 is connected between line 1132 and ground. Comparators 1116 and 1126 may be provided as type LM339 devices, while comparator 1134 may be provided as a type LT1215 device.

Figure 58:
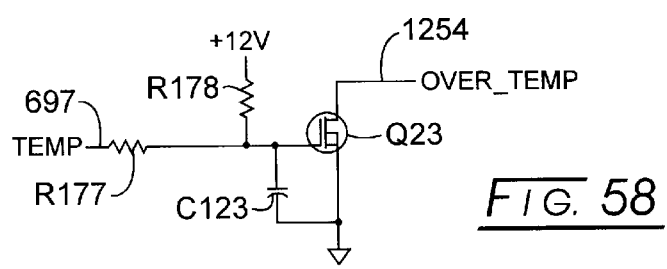
FIG. 58 is an electrical schematic diagram of a circuit monitoring for over-temperature conditions.

Referring to FIG. 58, an over-temperature circuit is portrayed. The temperature signal, TEMP having a low true condition when monitored temperature is excessive, has been described in connection with FIG. 39. Line 697 from the temperature responsive device, described in that figure, incorporating a resistor R177, is coupled through pull-up resistor R178 to +12V source and extends to the gate of transistor Q23. A filter capacitor C123 is coupled between lines 697 and ground. With the arrangement shown, a low true "OVER_TEMP" signal is derived at line 1254 which reappears in FIG. 61A in the presence of an excessive hardware temperature.

The d. c. link voltage has been described in connection with FIG. 43A as being monitored at line 952. That monitoring signal has been identified as "LINK_V". The control system determines whether this voltage is either above or below a window of acceptable operation. Of course, such a window may reduce to a point value.

Figure 59:
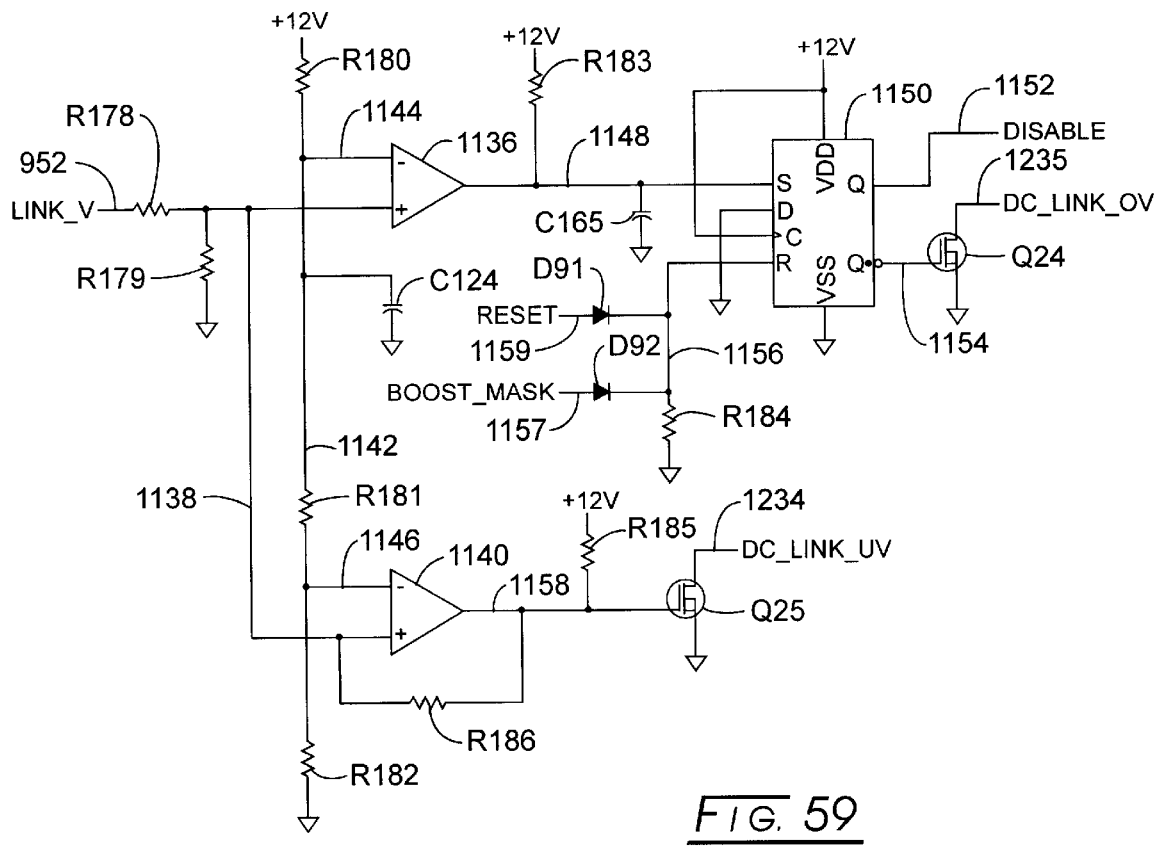
FIG. 59 is an electrical schematic diagram of a circuit for monitoring the level of d.c. link voltage.

Referring to FIG. 59, the LINK_V input is seen introduced with line 952 and resistor 178 to one input of a link over-voltage comparator 1136. A filter resistor R179 is connected between line 952 and ground. Additionally connected to line 952 is line 1138 which extends to the input of a link under-voltage comparator 1140. The reference inputs for both comparators 1136 and 1140 are derived from +12V source at line 1142. In this regard, +12V source is introduced to line 1142 through resistor R180 and that reference value then is directed to device 1136 through line 1144. Line 1142 additionally incorporates resistors R181 and R182 to establish a d. c. link under-voltage threshold reference input to comparator 1140 at line 1146. Line 1142 is filtered by a capacitor C124.

The output of comparator 1136 at line 1148 is coupled through pull-up resistor R183 to +12V source; is coupled with filter capacitor C124; and extends to the S (set) terminal of an RS flip-flop 1150 configured latch. Device 1150 may be provided as a type 4013B CMOS Dual "D" type Flip-Flop marketed by Texas Instruments, Inc. of Dallas, Tex. If the level of monitored link voltage at line 952 exceeds the threshold established at line 1144, output line 1148 assumes a logic high condition to cause latch 1150 to assume a set state. As a consequence, its Q output at line 1152 changes to a logic high level to create the DISABLE signal turning on MOSFET transistor Q13 (FIG. 46) to disable the link voltage controller 950. A complimentary low true output occurs at the Q -terminal at line 1154. Line 1154 is coupled to the gate of MOSFET transistor Q24, the drain and source terminals of which are coupled respectively with line 1198 and ground. This turns off transistor Q24 to derive the link over-voltage signal, "DC_LINK_OV", which is transmitted to and further developed at the control PLD.

As discussed in connection with FIG. 47A, during an enhanced link voltage-based boost mode, a logic high true BOOST_MASK signal is developed at line 1157. Line 1157 reappears in the instant figure extending through ORing diode D92 to line 1156 incorporating resistor R184 and extending to the reset (R) terminal of latch 1150. Accordingly, during the boost mode, latch 1150 is held in a reset state wherein its Q terminal at line 1152 is held at a logic low to block any DISABLE signal and its Q terminal at line 1154 is held at a logic high level turning on transistor Q24. Thus the DC_LINK_OV signal is blocked for the duration of the boost mode.

As another feature, during the interval of power-up reset, the system holds latch 1150 in a reset state to assure the over-voltage-based signals as above discussed will not appear at lines 1152 and 1154. Accordingly, the active high level RESET signal developed as described in connection with FIG. 54 at line 1159 is transmitted through ORing diode D91 to line 1156 and the reset terminal, R of latch 1150. It may be recalled from FIG. 54 that the presence of a RESET signal negates an ENABLE signal to disable the RF inverter 490 function. Line 1156 is seen to extend from the reset, R terminal through resistor R184 to ground.

Looking to d.c. link under-voltage comparator 1140, the output of this device is provided at line 1158. Line 1158 is coupled with pull-up resistor R185 to +12V source and through resistor R186 to input line 1138. Output line 1158 extends to the gate of MOSFET transistor Q25. Accordingly, in the presence of an under-voltage at the d. c. link, then the output of comparator 1140 at line 1150 assumes a low logic true condition to turn transistor Q25 off and a d. c. link under-voltage signal, "DC_LINK_UV" is generated for conveyance to the PLD at the control board. Device 1136 and 1140 may be provided as type LM339 comparators (Supra).

Figure 60:
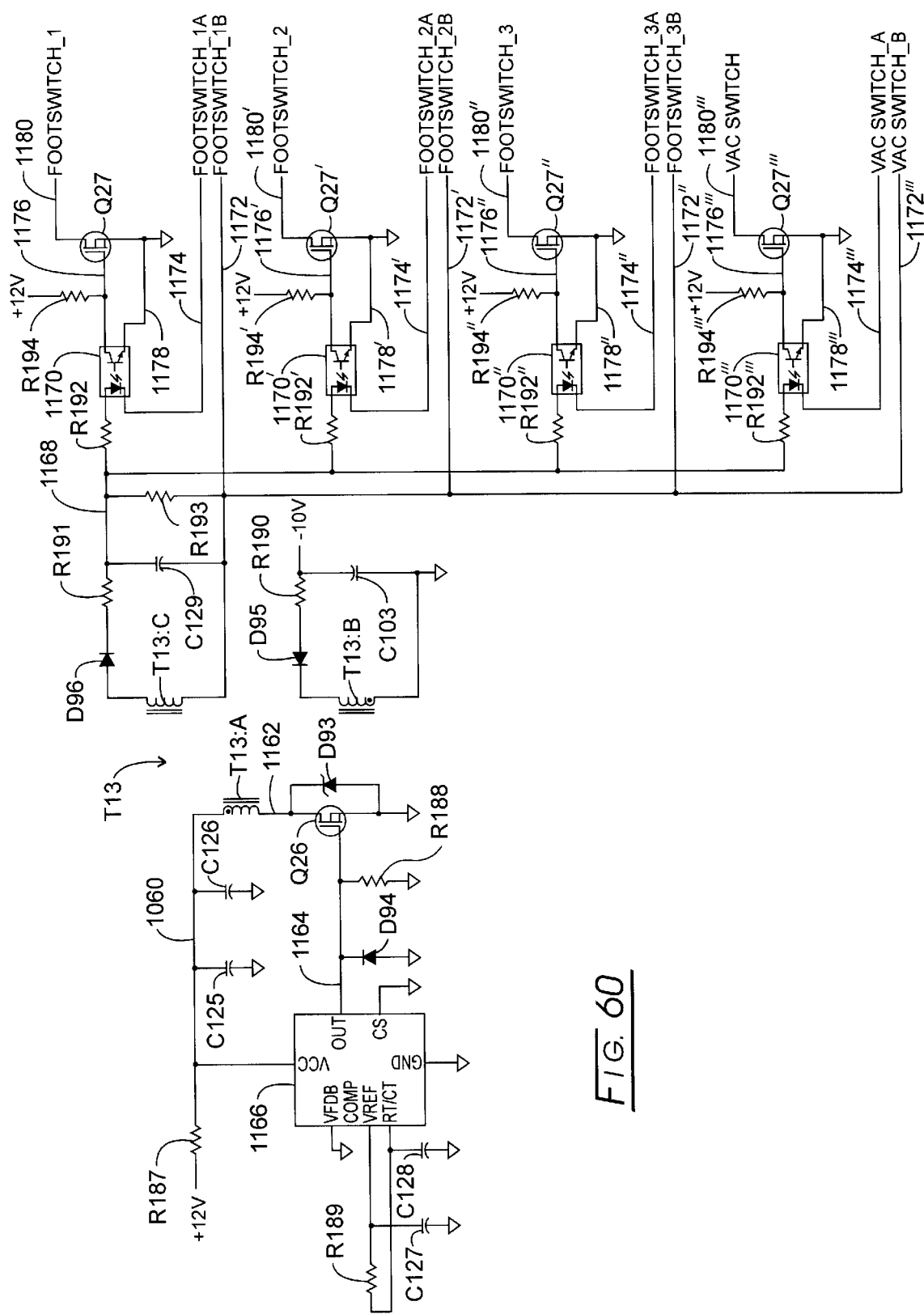
FIG. 60 is an electrical schematic diagram showing a circuit deriving footswitch and vacuum switch actuation inputs.

Referring to FIG. 60, a power converter and isolation circuit employing a network for response to actuation of the footswitch 86 and vacuum switch 51 (FIG. 1) is portrayed. This circuit is designed to accommodate footswitch and vacuum switch devices which do not have built-in electrical isolation characteristics. Thus, an opto-isolator feature is provided. In the figure, +12V source is applied through resistor R187 and line 1160 to the primary side, T13:A of an isolation transformer T13. Line 1160 is filtered with capacitors C125 and C126. The opposite side of transformer primary T13:A at line 1162 is coupled with the drain terminal of transistor Q26. A blocking diode D93 extends across the drain and source terminals of transistor Q26. The gate of transistor Q26 is coupled by line 1164 to the OUT terminal of power converter 1166. Line 1164 is coupled with filter resistor R188 and clamping diode D94. Provided, for example, as a type UC3845 device marketed by Unitrode Corp. of Merrimack, N.H., converter 1166 is configured with resistor R189 and capacitors C127 and C128 and functions to chop the input to primary transformer side T13:A by selectively turning transistor Q26 on and off. One secondary of transformer T13 shown at T13:B derives a −10V output and is shown performing in conjunction with rectifying diode D95, resistor R190 and filter capacitor C153. The −10V source is employed with multiplier 992 (FIG. 47C) at line 993.

A next secondary side of transformer T13 is shown at T13:C, providing for electrical isolation of footswitch 86 and vacuum switch 51. The input lead pair from each of the footswitches 86a–86c as well as the vacuum switch 51 are opto-isolated and connected with secondary side T13:C. One side of secondary T13:C is coupled at line 1168 incorporating rectifying diode D96 and resistor R191. The opposite side of secondary T13:C is coupled to line 1172. Capacitor C129 and resistor R193 extend between lines 1168 and 1172 and, in effect, a node utilized by four identical isolation networks is developed across resistor R193. The first of these networks, for example, associated with footswitch 86a incorporates line 1168 and resistor R192 which extends to the anode input of opto-isolator 1170. The cathode input of opto-isolator 1170 is coupled with line 1174 which extends to one side of footswitch 86a and is labeled "FOOTSWITCH_1A". Line 1172 extends to the opposite side of switch 86a and is labeled "FOOTSWITCH_1B". The low voltage output side of opto-isolator 1170 is connected at line 1176 to the gate of transistor Q27 and the opposite output thereof is coupled via line 1178 to its source terminal and to secondary circuit ground. Line 1176 is coupled through pull-up resistor R192 to +12V source and, accordingly, with the actuation of footswitch 86a, the signal "FOOTSWITCH_1" is produced in low logic true fashion at line 1180. This network, incorporating resistors R192 and R194 opto-isolator 1170, and transistor Q27 is repeated and connected across resistor R193 for the remaining footswitches 86b and 86c as well as for vacuum switch 51. Accordingly, the same network identifying numberation is used to describe these networks, but in primed fashion. In this regard, the footswitch 86b network is identified in single primed fashion in combination with the switch labels "FOOTSWITCH_2A" and "FOOTSWITCH_2B" providing the low logic true output signal "FOOTSWITCH_2". Footswitch 86c is identified in double primed fashion in combination with the switch labels FOOTSWITCH_3". Similarly the vacuum switch 51 network is identified in triple primed fashion in combination with the switch labels "VACSWITCH_A" and "VACSWITCH_B", providing the low logic true output signal, "VACSWITCH".

Figure 61A:
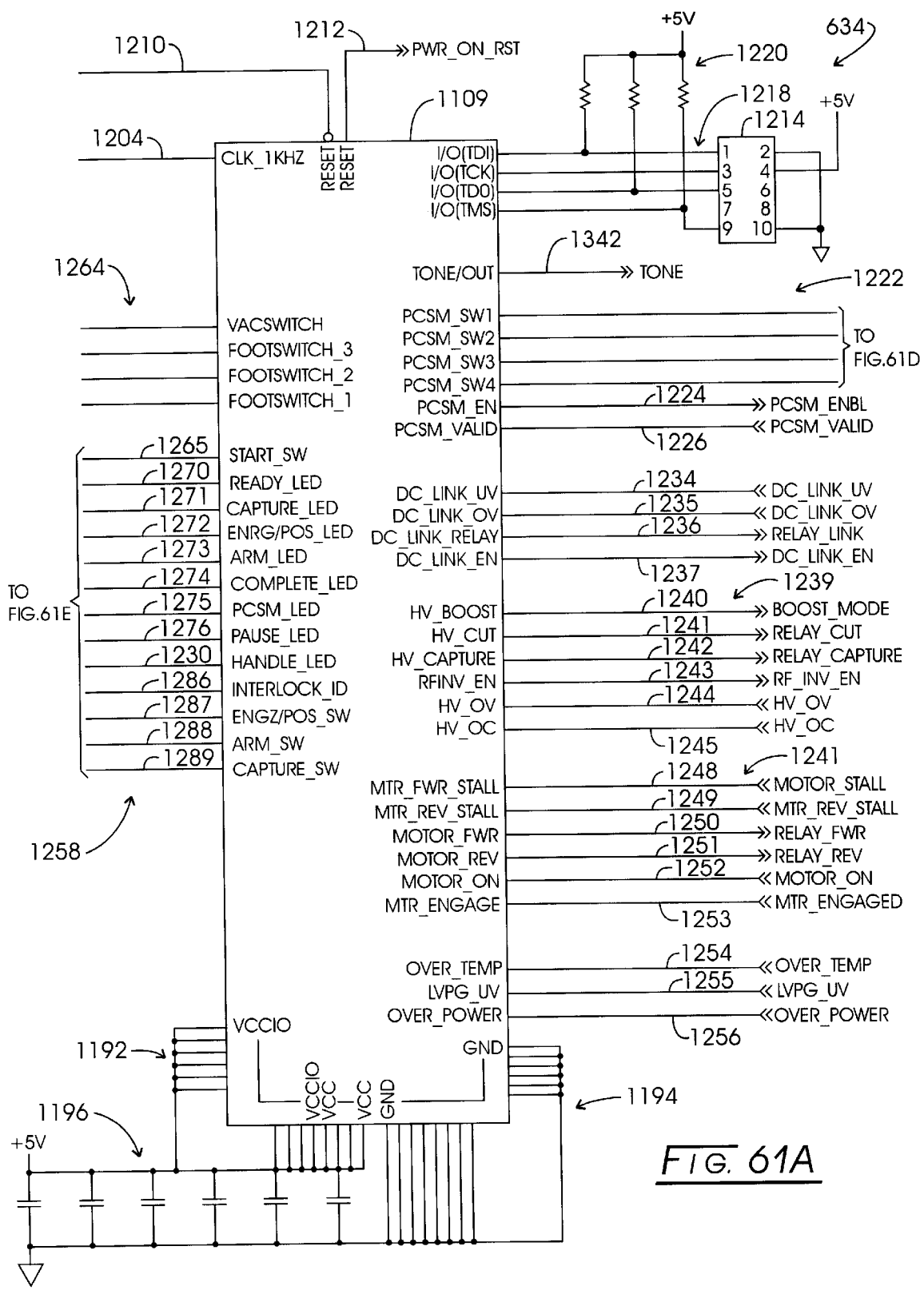

As described in connection with FIG. 36A, the control board component 624 of the controller is characterized principally in the incorporation of a programmable logic device (PLD) which generally is a hardware programmable compilation of logic gates. This gate compilation responds in a sequential logic to develop a series of states effecting a control for the system at hand. This device, may be, for example, a type EPM7192SQC160–15 Programmable Logic Device marketed by Altera, Inc. of San Jose, Calif. The device is represented at 1190 in FIG. 61A. Board 624 also incorporates filtering and logic-supporting pull-up functions. In general, where transistors have been described as being turned off, the relevant lines typically are pulled to a logic high at the control board. FIG. 61A should be considered in conjunction with FIGS. 61B–61E in the manner labeled thereon to reveal those connections of features drawn so as to connect in uninterrupted fashion with this logic center. In FIG. 61A, a regulated +5V and associated ground are shown introduced from respective line arrays 1192 and 1194 to corresponding terminals of device 1190. The +5V inputs are shown filtered by a six capacitor array 1196.

Looking additionally to FIG. 61 B, a clock network is represented generally at 1198. Network 1198 includes a crystal oscillator device 1200 which may be provided, for example, as a type 74302 marketed by M-Tron Industries of Yankton, S.D., which responds to an_RESET input applied at line 1202. Configured in conjunction with inductor L10 and capacitors C130–C132, the network 1198 provides a 1 KHz input at line 1204 to PLD 1190.

Looking to FIG. 61C, a reset network is shown generally at 1206 which functions to hold the system low for a specified amount of time to assure a power supply stabilization. It may be recalled that, during this reset interval, as a safety feature, the RF inverter 490 function is not enabled (FIG. 5A). Network 1206 performs at the time of system power on or at such time as the regulated 5V power supply for the instant circuit diminishes to a certain extent. The network is centered about reset device 1208 which may, for example, be a type DS1233DZ-5 marketed by Dallas Semiconductor, Inc. of Dallas, Tex., and which is configured in conjunction with capacitors C133 and C134 as well as resistor R201. A_RESET output is provided at line 1202 which is described in connection with FIG. 61B as being introduced to oscillator device 1200. The same signal is directed via line 1210 to the _RESET terminal of PLD 1190. PLD 1190 also provides the logic high true PWR_ON_ RST signal at line 1212 as described in conjunction with FIG. 54.

Returning to FIG. 61A, an externally accessible jumper or connector is shown at 1214 which provides a four line array input to I/O ports of PLD 1190 as shown in general at 1218. Three of those four lines of the array 1218 are pulled up to +5V through a pull-up resistor array shown generally at 1220.

Extending from PLD 1190 is a four line array shown generally at 1222 which provides an output for controlling four relays of the PCSM circuit 528 (FIG. 34). Below array 1222 is a line 1224 providing a PCSM circuit enablement signal, PCSM_ENBL. Below line 1224 is an input line 1226 carrying a PCSM circuit valid input signal, PCSM_ VALID. The PCSM circuit is discussed in detail in connection with FIGS. 66A–66C and 68A–68B.

Looking momentarily to FIG. 61D, the four line array 1222 reappears extending to input terminals of a buffer circuit 1228. Additionally extending to the input of device 1228 is an LED activation signal from PLD 1190 identified as "LED_DRVIN" and provided at line 1230. The corresponding buffered outputs are shown at five line array 1232, the upper four lines of which are directed to relays of the PCSM circuit and the fifth of which provides the signal "_LED_DRVOUT".

Returning to FIG. 61A, the d. c. link monitoring features as described in conjunction with FIG. 59 as being inputted to PLD 1190 are shown at input lines 1234 and 1235. Corresponding link relay 504 activation (FIG. 42) link enablement (FIG. 46) are provided at output lines 1236 and 1237. Below that grouping is an array 1239 of input and output lines to PLD 1190 concerned with the high voltage output function including the boost mode signal, BOOST_ MODE, at line 1240, earlier described at line 1022 (FIG. 47A), the high voltage precursor electrode cut signal, RELAY_CUT (FIG. 42) as represented at line 1241, the high voltage capture cutting signal, RELAY_CAPTURE (FIG. 42) represented at line 1242, the RF inverter 510 enablement signal, RF_INV_EN at line 1243, introduced at line 1092 in FIG. 54, the high voltage over-voltage input HV_OV (FIG. 56) at line 1244 and the high voltage over-current input HV_OC (FIG. 55) represented at line 1245.

Below line array 1239 is another array 1247 of inputs and outputs to PLD 1190. At this array 1247, input lines 1248 and 1249 are concerned respectively with motor forward (MOTOR_STALL) and reverse (MTR_REV_STALL) stall. Output lines 1250 and 1251 are concerned with motor forward (RELAY_FWD) and motor reverse (RELAY_ REV) drives. Input at lines 1252 and 1253 respectively carry the signal; MOTOR_ON, monitoring initial motor energization with turning and a monitoring condition, MTR_ ENGAGED, active when the yoke 184 has engaged the drive member 324. These motor functions as identified in connection with lines 1248, 1249, 1252 and 1253 have been discussed in connection with FIGS. 50–53, while lines 1250 and 1251 reappear in FIG. 42.

The over-temperature, OVER_TEMP (FIG. 58) input to PLD 1190 is shown at line 1254; while a low voltage power supply under-voltage condition, signal, LVRS-UN (FIG. 63) is inputted at line 1255 and the over-power condition signal, OVER_POWER as described in connection with FIG. 57 is inputted to PLD 1190 as represented at line 1256.

Looking to the opposite side of PLD 1190, a thirteen line array is represented generally at 1258. Of the lines within array 1258, certain of them carry signals responding to external switching and an interlock test, as well as providing outputs for selectively illuminating light emitting diodes (LEDs) both at the front panel of console 64 and at the instrument 12 housing 14.

Above the line array 1258 a line array 1264 is shown with labeling corresponding with the opto-isolated input signals from footswitches 86 and vacuum switch 51. These input signals were discussed above in connection with FIG. 60.

Figure 61E:
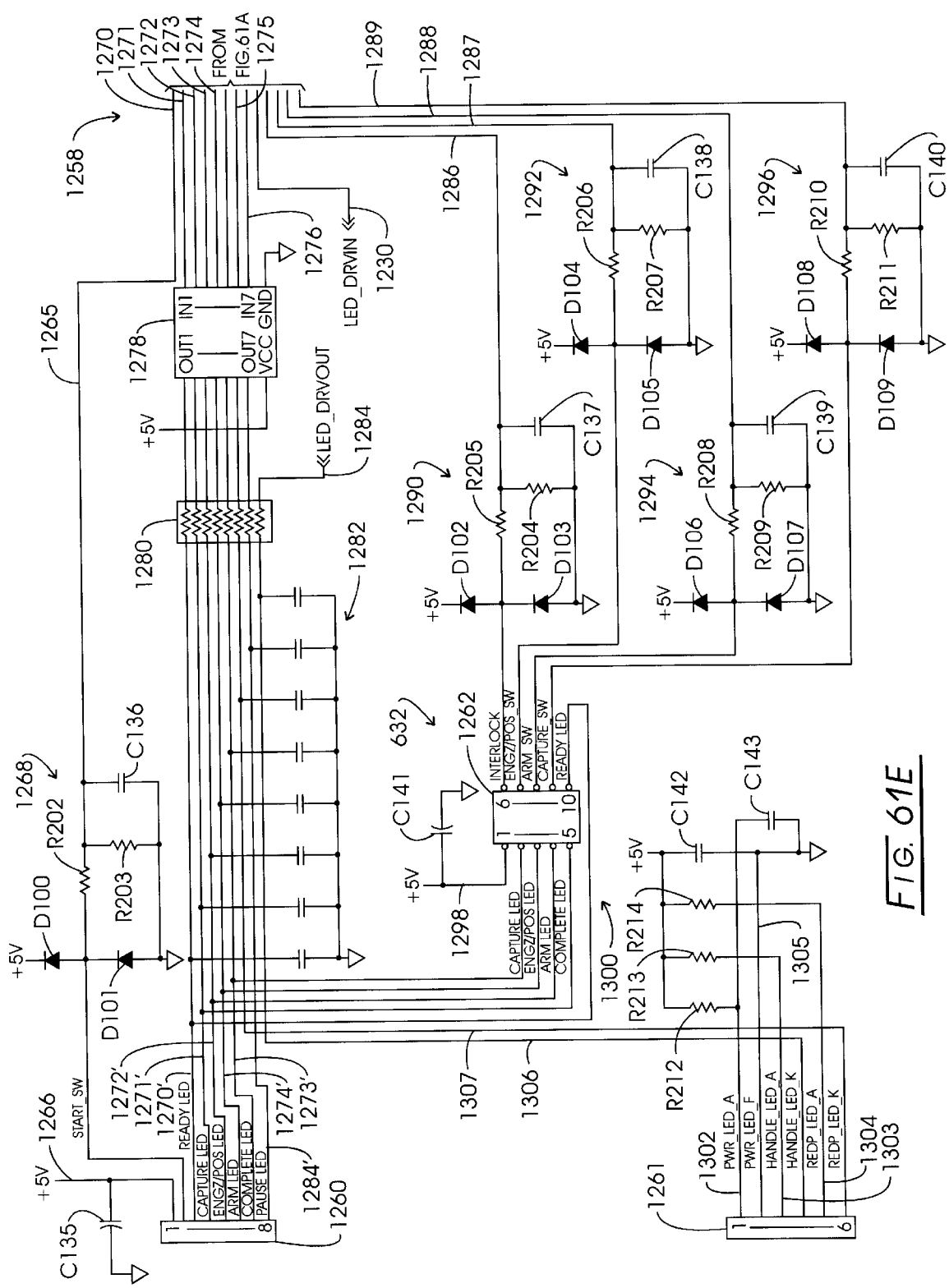

Referring additionally to FIG. 61E, line array 1258 reappears and the inputs and outputs represented thereby may be seen to extend through intermediate signal treatment features to three connectors 1260–1262. Connector 1260 is coupled with a printed circuit board 642 (FIG. 36A) located at the upper portion of the front panel of console 64; connector 1261 is coupled with a lower panel assembly serving the lower portion of the front panel of console 64; and connector 1262 is operationally associated with connector 66 (FIG. 1) performing in conjunction with the housing assembly 14 of instrument 12.

Line 1265 which carries a start switch signal identified as "START_SW" as initially derived by the actuation of switch 92 on console 64 (FIG. 1) is uppermost in array 1258. This is the only console-mounted switch having an input to PLD 1190. The switch must be actuated in order for any procedure to commence, the switch signal being utilized for an initial setup of the motor driven components of the device and to commence the PCSM return electrode test. The start/reset signal provided by this switch is derived in conjunction with the regulated +5V voltage associated with PLD 1190 as represented at line 1266 and filter capacitor C135. Line 1265 also is implemented with a protective network represented generally at 1268 comprised of clamping diodes D100 and D101, resistors R202 and R203 and capacitor C136. Thus configured, the diodes of network 1268 provide clamps limiting the signal at line 1265 to values between +5V and ground and an R-C filter is incorporated. The protective arrangement assures appropriate signaling without interference.

Output lines 1270–1274 provide outputs effecting the energization of the four LED illuminators at the top portion of the front panel of console 64. Looking additionally to FIG. 1, the READY_LED signal at line 1270 effects the illumination of LED illuminator 94; the CAPTURE_LED signal at line 1271 effects the illumination of illuminator LED 100; the ENGZ/POS LED signal at line 1272 effects the illumination of illuminator LED 96; the ARM_LED signal at line 1273 effects the illumination of illumination LED 98; line 1274, carrying a COMPLETE_LED signal, effects the illumination of illuminator LED 102; and the PAUSE_LED signal at line 1276 effects the illumination of illuminator LED 104. These signals are buffered at buffer 1278 and filtered by connection with six resistors within a resistor array 1280 performing in connection with a filter associated six capacitors of a capacitor array 1282. These buffered and filtered lines 1270–1275 are identified in primed fashion extending to the console upper front panel connector 1260. These LED energizing signals also are directed to the housing assembly LED arrays as at 60.

Pause LED 104 is illuminated under the control of PLD 1190 at such time as the practitioner releases footswitch 86 during a capture mode of operation wherein the pursing cables are electrosurgically excited. Such excitation of the pursing cables is terminated as well as energization of motor assembly 170 during a pause interval and their re-energization can occur only following actuation of the arm/disarm switch 54 on housing assembly 14, re-engagement of footswitch 86, and actuation of capture switch 56.

The handle interlock check LED 80 on console 64 is illuminated in response to the presence of the signal, HANDLE_LED at a terminal, of PLD coupled to line 1230. That signal is buffered as earlier discussed in connection with FIG. 61D, at buffer 1228 to provide an _LED_ DRVOUT buffered signal at line 1284 which reappears in FIG. 61E being introduced to one resistor of the array 1280 in operative association with a capacitor of array 1282 for filtered output at line 1306 which extends to console 64 front panel connector 1261.

Lines 1286–1289 of the line array 1258 extending from PLD 1190 carry interlock data and switching signals from the instrument 12 housing assembly 14. In this regard the above-noted interlock signal, INTERLOCK_ID, is one providing for the passage of current through a coding resistor mounted within the housing assembly 14 to assure proper interconnection with connector 67 (FIG. 1). To protect interlock line 1286, a protective network, represented generally at 1290, is provided with it. Configured identically as network 1268, network 1290 is implemented with clamping diodes D102 and D103, resistors R204 and R205 and capacitor C137.

Line 1287 carries the signal representing an actuation of the energize/position switch 54 mounted upon housing assembly 14. That signal, identified as "ENGZ/POS_SW", is submitted from connector 1262 through a protective network represented in general at 1292 to PLD 1190. Network 1292 is identical to network 1268 and comprises clamping diodes D104 and D105, resistors R206 and R207 and capacitor C138. Next below line 1287 is line 1288 carrying the output signal, "ARM_SW" of the arm switch 54 mounted upon housing assembly 14. This signal extends through a protective network identified generally at 1294 which is identical to network 1268 and comprises clamping diodes D106 and D107, resistors R208 and R209 and capacitor C139. Line 1289 carries the output of the capture switch 56 at housing assembly 14 which is identified as "CAPTURE_SW" and extends through protective network 1296 which is structured identically as network 1268. In this regard, network 1296 is comprised of clamping diodes D108 and D109, resistors R210 and R211 and capacitor C140.

Additionally submitted to the housing assembly 14 via connector 1262 is +5V regulated power supply at line 1298, which is filtered by capacitor C141, and LED energization signals provided at the earlier-described five lead array 1300. From the bottommost lead looking upwardly, the array 1300 includes a line input to the ready LED emanating from line 1270; a line input to the capture LED emanating from line 1271; a line input to the energize/position LED emanating from line 1272; a line input to the arm LED emanating from line 1273; and a line input to the capture complete LED emanating from line 1274. The inputs to connector 1262 correspond with the inputs described earlier in connection with FIG. 36A at arrow 632.

Connector 1261 extends to the harness components described in connection with FIG. 36A at line pairs 636, 638 and 640. Those line pairs are components of a harness extending to respective LEDs 84, 80 and 78 in the lower portion of the front panel of console 64 as illustrated in FIG. 1. Input leads to power LED 84, connector LED 80, and PCSM fault LED 78 are configured with +5V and respective resistors R212–R214 as shown at respective lines 1302–1304. The power LED return line is shown as configured with capacitor C142 extending to ground and its input line extends through resistor R212 to +5V and is filtered by capacitor R143. The handle (housing assembly 14) connector return is shown at the above noted line 1306 which is under the control of PLD 1190 providing a low true condition at that line to effect illumination of LED 80. Correspondingly, the dispersive electrode 68 return (PCSM) fault LED 78 is illuminated in flashing fashion by imposition of a low true pulsing condition at line 1307 under the control of PLD 1190. That line is activated from PLD 1190 at line 1275 (PSCM_LED), the signal being treated at buffer 1278 and a resistor at 1280 in association with a capacitor at array 1282.

Figure 62:
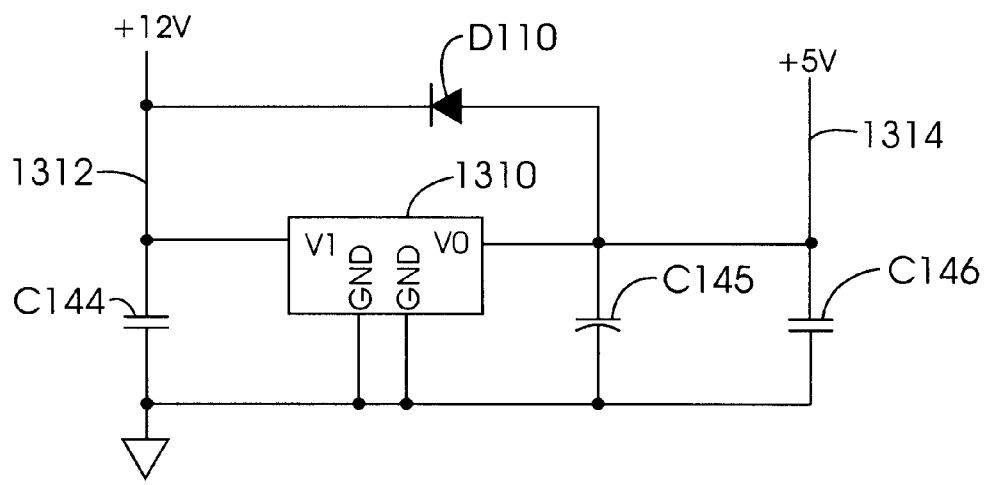
FIG. 62 is an electrical schematic diagram of a power supply.

The +5V regulated power supply discussed in connection with FIGS. 61A–61E is derived at the control board 624 by the circuit illustrated in FIG. 62. Looking to that figure, a type LM2940CT-5.0 regulator marketed by National Semiconductor, Inc. of Sunnyvale, Calif., is shown at 1310 coupled to a +12V input at line 1312 and configured with capacitors C144–C146 and diode D10 to provide the noted regulated +5V supply at line 1314. The +12V input is derived at control board 624 as discussed in connection with FIG. 67.

Figure 63:
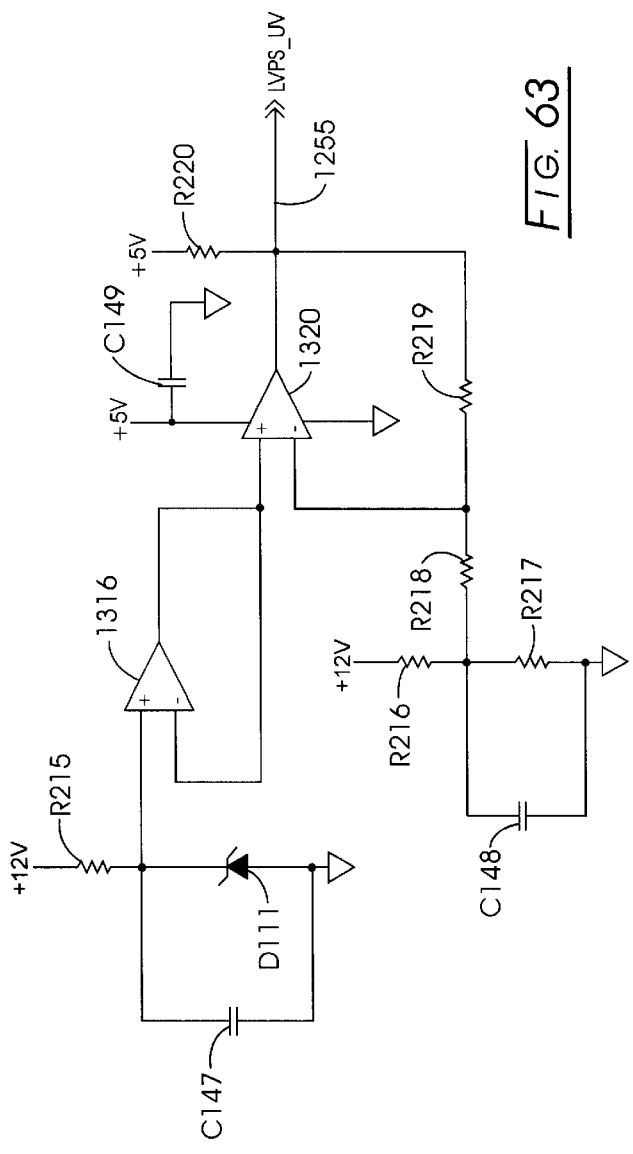
FIG. 63 is an electrical schematic diagram of a circuit for monitoring a low voltage power supply.

Referring to FIG. 63, a network for determining the presence of a low voltage power supply under-voltage condition as presented to PLD 1190 at line 1255 is represented. Looking to the figure, the above-noted +12V power supply is treated and reduced by a network including resistor R215, capacitor C147, diode D111 and passive operational amplifier 1316 having a feedback configured output at line 1318 directed to one input of a comparator 1320. Comparator 1380 may be a type LM358D marketed by National Semiconductor, Inc. of Sunnyvale, Calif. The reference input to comparator 1320 is derived at a divider network coupled to the noted +12V supply and configured with resistors R216–R219 and capacitor C148 to provide a reference input at line 1322. Device 1320 is configured with +5V input and capacitor C149 to provide a low logic true output at line 1255 in the event of an under-voltage condition. Note in this regard that line 1255 is coupled through pull-up resistor R220 to +5V supply.

Figure 64:
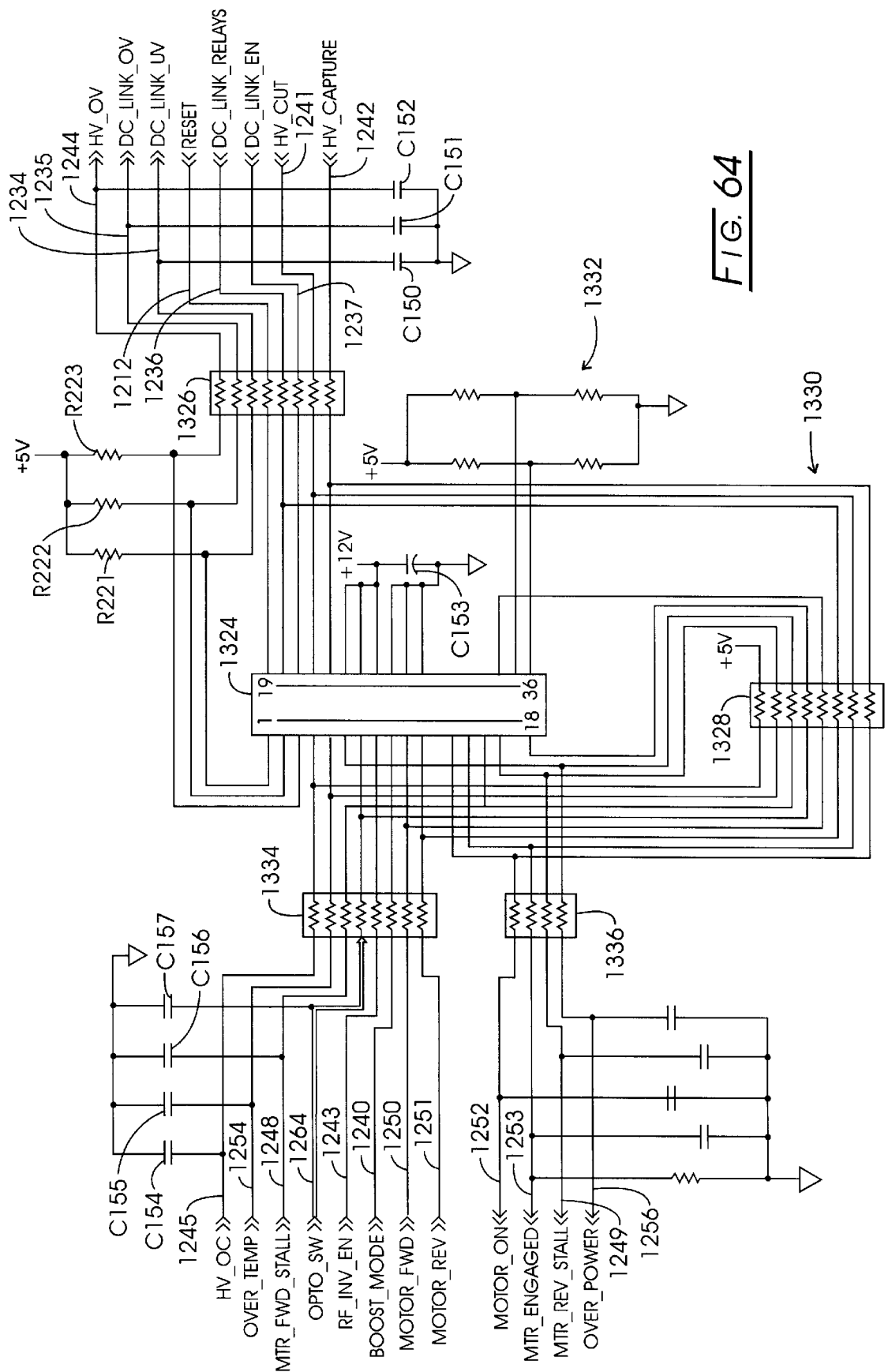
FIG. 64 is an electrical circuit diagram illustrating the treatment of programmable logic device (PLD) signal inputs and outputs.

Referring to FIG. 64, a filtering network is revealed which provides an RC filtering of the inputs and outputs associated with PLD 1190 and provides those filtered signals along with power supply inputs to a connector 1324 providing connection from the control board 624 to the power board 614 as represented in general at arrow 626 in FIG. 36A. In the figure, the high voltage over-voltage signal, the d. c. link voltage over-voltage signal and the d. c. link voltage under-voltage signal at respective lines 1244, 1235 and 1234 are received from connector 1324 and coupled via respective pull-up resistors R221–R223 to +5V source. Additionally, the signals so received are filtered by the discrete resistors of multi-resistor component 1326 and respective filter capacitors C15–C152. Line 1212, carrying the reset output; line 1236, carrying the d. c. link relays output; line 1237, carrying the d. c. link enable signal; line 1241 carrying the high voltage precursor energization command signal; and line 1242 carrying the high voltage capture command signal are each treated by discrete resistors within multi-resistor component 1326. Lines 1237, 1241 and 1242 additionally are coupled to +5V source through a pull-up resistor within multi-resistor component 1328 as provided by three line array 1330. Divided voltages are provided from resistor array 1332 to the connector 1324 and +12V source and ground inputs are submitted to the connector from opposite sides of capacitor C153.

The high voltage over-current signal at line 1245; the over-temperature signal at line 1254; the motor forward stall signal at line 1248; and the footswitch and vacuum switch actuation signals represented in general at arrow 1264 and labeled "OPTO_SW" are filtered by discrete resistors within multi-resistor component 1334 and respective capacitors C154–C157. Of this line grouping, lines 1245, 1254 and the footswitch and vacuum switch lines represented in general at 1264 are coupled through discrete pull-up resistors within component 1328 to +5V source.

The RF inverter enable command; boost mode command; motor forward command; and motor reverse command are treated by discrete resistors within multi-resistor component 1334. Of this grouping, lines 1250 and 1251 are coupled to +5V source through pull-up resistors within multi-resistor component 1328.

The motor on input; motor engaged input; motor reverse stall; and the overpower input at respective lines 1252, 1253, 1249 and 1256 are treated by discrete resistors within a multi-resistor component 1336 and filtered by respective capacitors C200, C201, C202 and C203. A filter resistor R231 is coupled with line 1253. Of these lines, lines 1252 and 1253 additionally are coupled to +5V source through discrete pull-up resistors within multi-resistor component 1328.

Figure 65:
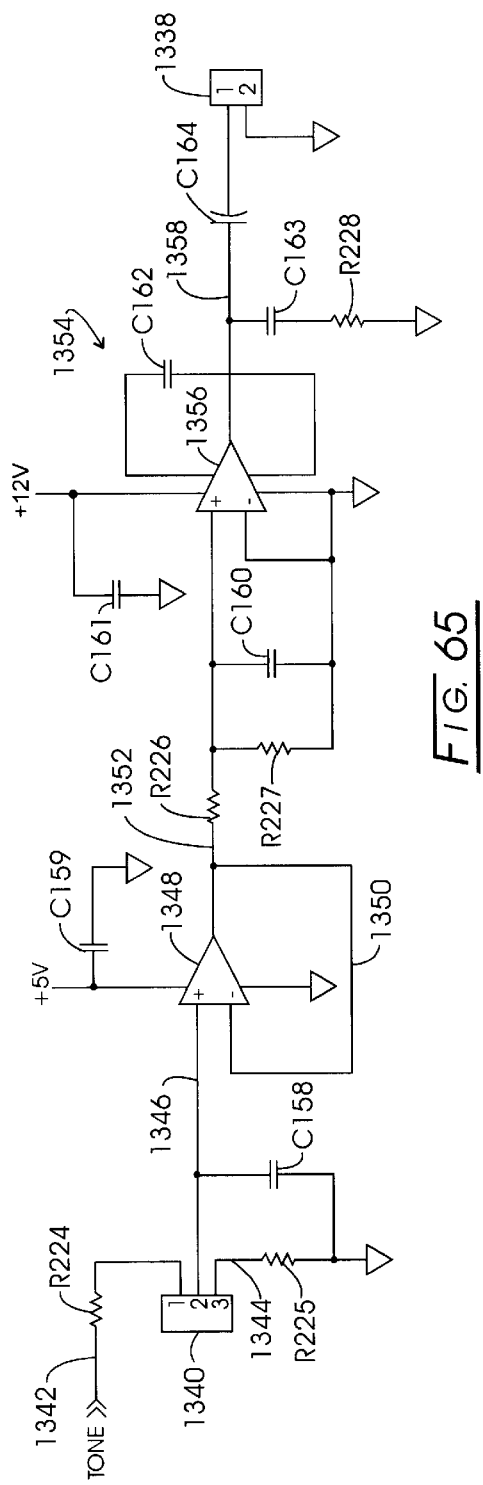
FIG. 65 is an electrical circuit diagram of an audio control.

Referring to FIG. 65, the circuit driving speaker 646 and adjusting its volume with a potentiometer represented generally at 438 in FIG. 36A is revealed. The latter figure reveals a line pair 648 extending to speaker 646. That line pair is coupled with a connector shown in the instant figure at 1338. Correspondingly, the three line array 650 extending from potentiometer 438 is coupled to a connector shown in FIG. 65 at 1340.

The PLD derived tone signal line 1342 reappears in the instant figure, is asserted via resistor R224 to potentiometer 438 in combination with a ground provided in conjunction with line 1344 and resistor R225. A volume input, filtered at capacitor C158, is then provided at line 1346. Line 1346 is directed to an amplification stage including operational amplifier 1348 configured with +5V regulated power supply, capacitor C159 and feedback line 1350. An output is provided at line 1352 incorporating resistor R226 and extending to an oscillator network represented generally at 1354 including a type LM386N-1 amplifier component 1356 configured with resistors R227 and R228, capacitors C160–C164 and +12V power supply to provide a tone output at line 1358. That tone output is provided whenever electrosurgical cutting is taking place either by the precursor electrodes or the pursing cables. Additionally, the tone is pulsed in the event of a failure occurring in the PCSM testing of dispersive return electrode 68. Amplifiers as at 1356 are marketed by Analog Devices, Inc. of Norwood, Mass.

Figure 66A:
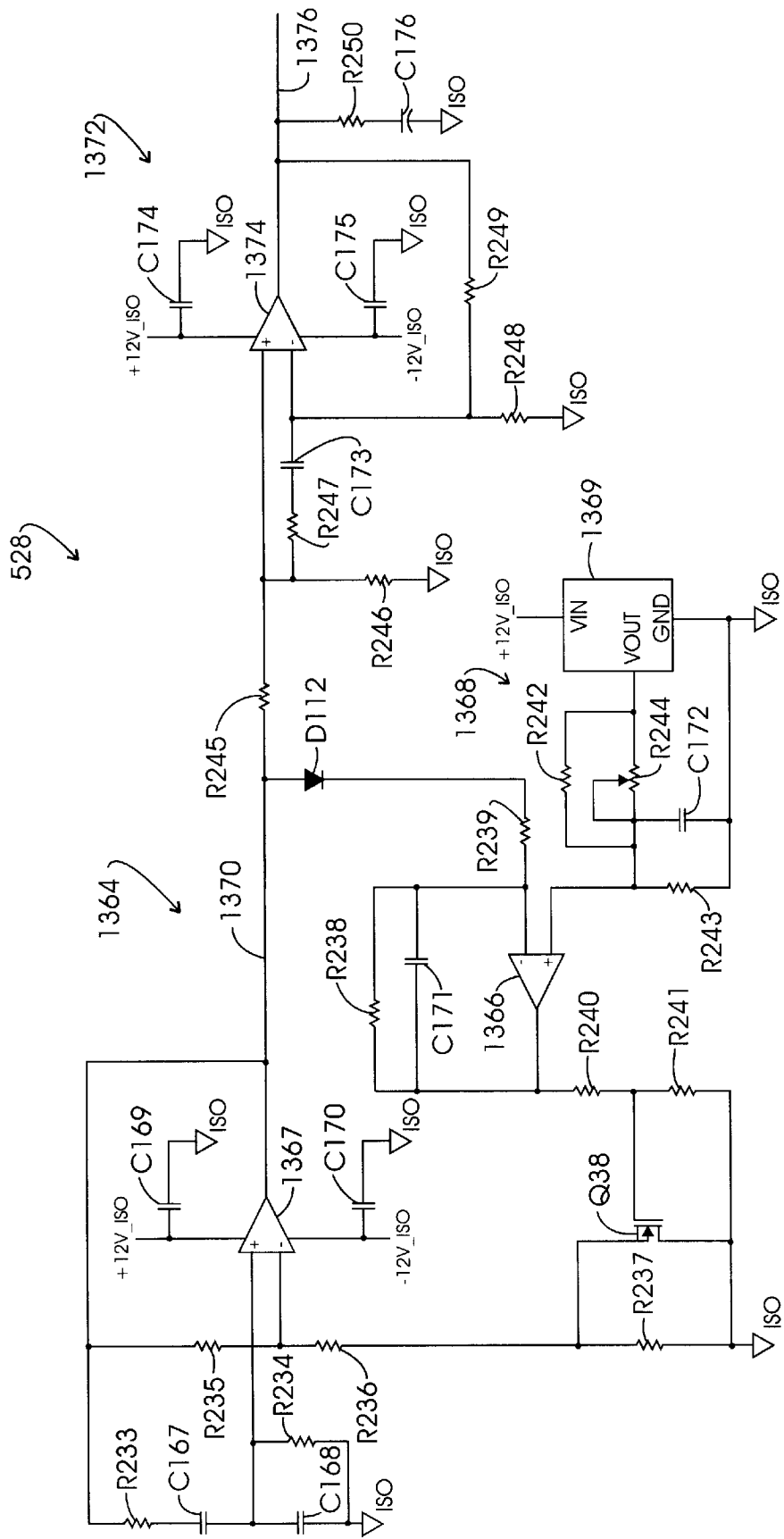
FIGS. 66A–66C combine as labeled thereon to describe frequency generation and test switching components of a patient circuit safety monitor (PCSM) circuit.
Figure 66B:
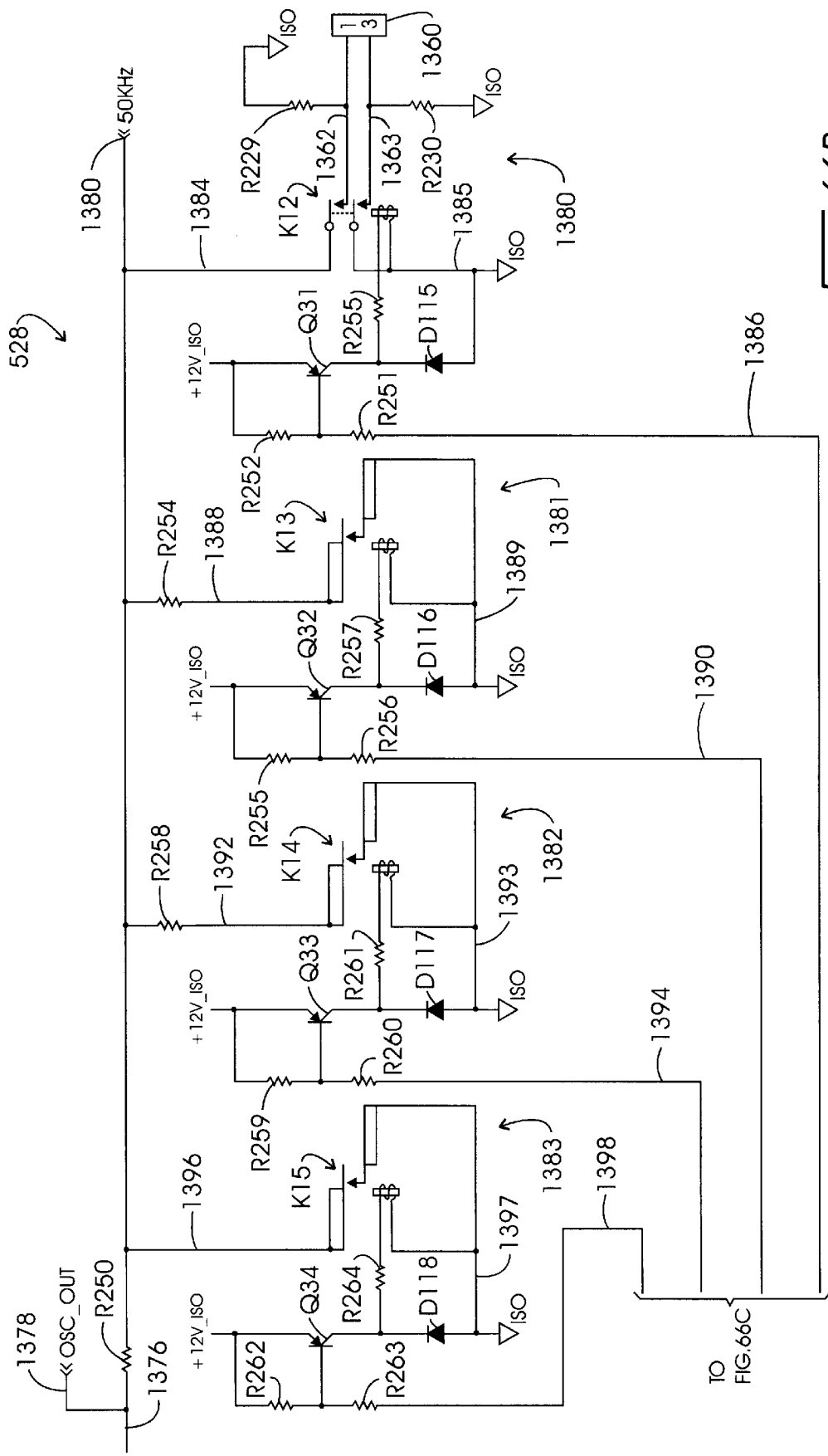
Figure 66C:
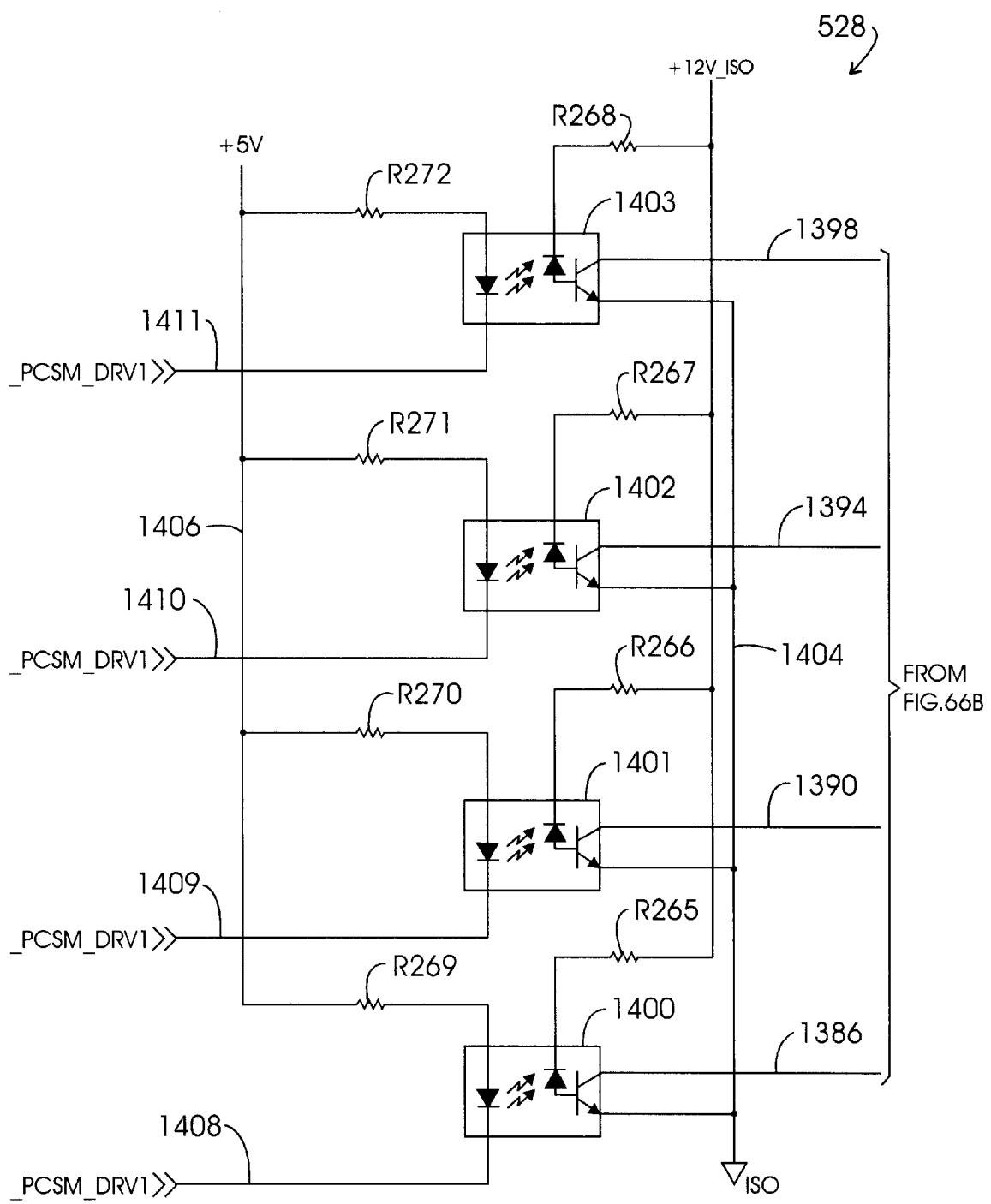

FIGS. 66A–66C should be considered together in the manner labeled thereon. These figures illustrate the test signal generation and switching involved in self testing and fault testing with respect to the dispersive return electrode 68. The circuit shown is a component of the PCSM circuit described in conjunction with block 528 in FIG. 34. This PCSM test is carried out at the very commencement of a procedure and failure of the test will prohibit the procedure from being carried out along with the development of pulsed warning signals of both an aural and visible variety in conjunction with speaker 646 and LED 78. Looking to FIG. 66B, a connector 1360 is provided which, as illustrated in connection with FIG. 36A couples to line pair 628 and 629 which extend to power circuit board 614 and, in turn, from that power circuit board extend via line pair 654 to the return electrode connection as represented at block 652. Connection RE1 is represented in FIGS. 66B at line 1362 which is coupled through resistor R229 to ground. Connection RE2 is represented at line 1363 which is connected through resistor R230 to ground. The circuits represented by RE1 and RE2 in general extend from electrode pads 70 and 72 to return to the high voltage output stage 520 but are tapped for the instant testing purposes. PCSM circuit 528 functions to impress about a 50 KHz low voltage signal across pads 70 and 72 to verify that dispersive return electrode 68 is properly connected to the patient. In general, the testing evaluates with respect to a resistance tolerance, for example, between about 20 and about 80 ohms. A resistance representation less than the former indicates a shorting condition and a resistance above the latter represents a nonconnection. Those resistance values may be varied in accordance with the desires of the designer.

Looking to FIG. 66A, the oscillator network deriving the above-noted 50 KHz frequency is represented in general at 1364. Network 1364 is comprised of operational amplifier 1367 configured in conjunction with resistors R233–R237; capacitors C167–C170; complementary amplifier 1366 configured with resistors R238–R241, capacitor C171 and the potentiometer frequency adjusting network 1368; a power supply input 1369; transistor Q30 and diode D112. Potentiometer 1368; is configured in conjunction with capacitor C172 and resistor components R242–R244. Input device 1369 may be provided as a type REF–02C/AD marketed by Analog Devices, Inc. of Norwood Mass. The 50 KHz output developed by network 1364 is provided at line 1370 and is directed through input resistor R245 to an amplification stage represented generally at 1372 functioning to adjust the 50 KHz signal to about 7V, RMS or 12V peak-to-peak. The stage 1372 is implemented with an operational amplifier 1374 configured with resistors R246–R249 and capacitors C173–C175. The treated 50 KHz output is provided at line 1376 which is filtered at resistor R250 and capacitor C176. Looking again to FIG. 66B, line 1376 is seen to be tapped at line 1378 to provide an "OSC_OUT" signal. Following the tap at line 1378, line 1376 incorporates a resistor R250 having a value of about 50 ohms and extends to an oppositely disposed tap identified at 1380, labeled "50 KHz". Extending between taps 1378 and 1380 is a sequence of four relay implemented networks represented in general at 1380–1383.

Looking to network 1380, relay K12 is seen to be connected between lines 1384 and 1385. It is actuated by PLD 1190 by a signal ultimately developed at line 1386 incorporating resistors R251 and R252 and extending to the gate of pnp transistor Q31. Transistor Q31 is configured with diode D115 and resistor R253 to energize the solenoid component of relay K12 in response to a signal impressed from line 1386. This functions to couple the 50 KHz signal at line 1376 and ground to respective lines 1362 and 1363 to carry out the PCSM test. This test occurs upon practitioner actuation of start/reset switch 92 (FIG. 1).

Looking to relay network 1381, relay K13 is connected between lines 1388 and 1389, the latter extending to ground and the former incorporating a 200 ohm resistor R254. Relay K13 is closed in response to an actuation signal imposed ultimately from PLD 1190 at line 1390. Line 1390 incorporates resistors R255 and R256 and is connected to the gate of pnp transistor Q32. Transistor Q32 is configured with diode D116 and resistor R257 to effect the energization of the solenoid component of relay K13, closing it and connecting a 50 KHz signal at line 1376 through resistor R254 to ground to provide a high resistance self test. Looking to relay network 1382, relay K14 is seen to be connected with the 50 KHz signal at line 1376 by line 1392 and with ground via line 1393. Line 1392 incorporates a 49.9 ohm resistor R258. The solenoid component of relay K14 is energized to close the relay in response to a signal from PLD 1190 ultimately presented at line 1394. Line 1394 incorporates resistors R259 and R260 and extends to the gate of pnp transistor Q33. Transistor Q33 is configured in conjunction with diode D117 and resistor R261 to energize the solenoid component of relay K14 when turned on in response to the signal at line 1394. This diverts the 50 KHz signal across the 49.9 ohm resistance at resistor R258 from line 1376 to ground.

Looking to relay network 1383, relay K15 is seen to be coupled between line 1396 connected to line 1376 and line 1397 coupled to ground. The solenoid component of relay K15 is energized upon the occurrence of a signal ultimately derived from PLD 1190 and asserted at line 1398. Line 1398 incorporates resistors R262 and R263 and is coupled to the gate of pnp transistor Q34. Transistor Q34 is configured with diode D118 and resistor R264 to energize the solenoid component of relay K15 upon being turned on from line 1398. This couples line 1376 to ground through lines 1396 and 1397, providing a self test representing a short circuit.

Referring to FIG. 66C, actuation lines 1386, 1390, 1394 and 1398 are seen to be coupled to the collector output stages of respective opto-couplers 1400–1403. The emitter components of the outputs of couplers 1401–1403 are coupled to ground via line 1404 and each coupler is coupled with +12V source through respective resistors R265–R268. The anode inputs to opto-couplers 1400–1403 are coupled through respective resistors R269–R272 to +5V source at line 1406, while the cathode side inputs thereof are coupled with respective input lines 1408–1411. Returning momentarily to FIG. 61D the latter line grouping is represented at line array 1232 as providing the buffered outputs of the lines of line array 1222 extending from PLD 1190. Thus, the return electrode 68 test, as well as the PCSM self-test are carried out under the command of PLD 1190. It may be noted that relay KI5 of network 1383 is energized to short the signal at line1376 during those intervals wherein the tests asserted from networks 1380–1383 are not being carried out, even though relay K12 will be open.

Figures 67, 68B:
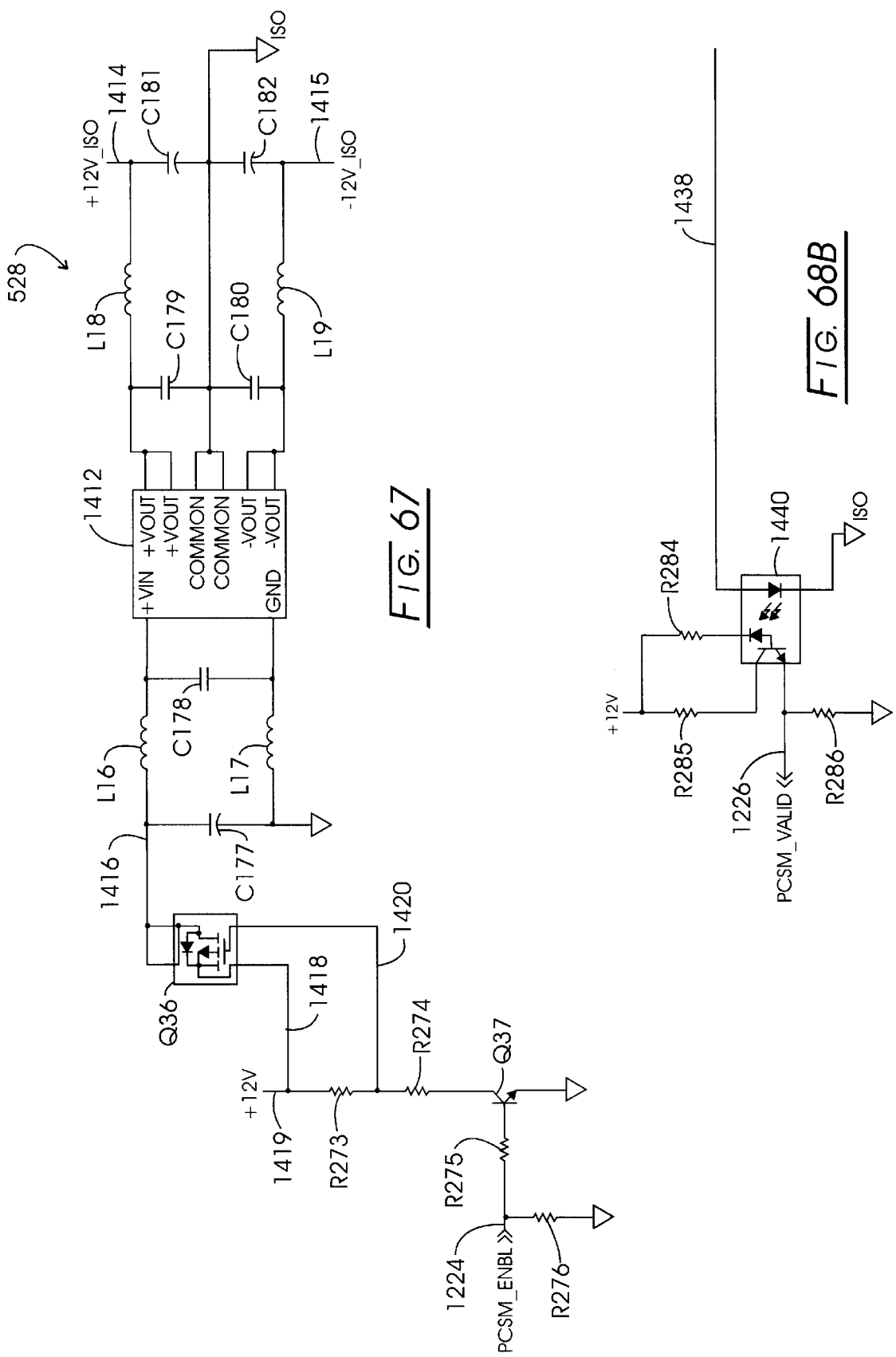
FIG. 67 is an electrical schematic diagram of a power supply.
FIGS. 68A and 68B combine as labeled thereon to illustrate a circuit for carrying out a window based analysis of a return electrode test.

Referring to FIG. 67, an isolated power supply utilized to generate the noted +12V is illustrated. This power supply is configured about a supply component 1412, provided as a type NMS1212 device marketed by Newport Components, Inc. by Milton Keynes, GB. In effect, device 1412 converts +12V to +12V and −12V. It is configured with inductors L16–L19 and capacitors C177–C182 to provide an isolated +12V at output 1414 and an isolated −12V at output 1415. Device 1412 is provided a +12V input at line 1416 from power transistor Q36, the source of which is coupled to +12V from lines 1418 and 1419 and the gate terminal of which is coupled with line 1420 to line 1419. Line 1419 incorporates resistors R273 and R274 and is coupled with the collection of NPN transistor Q37, the emitter of which is connected to ground. Transistor Q37 is gated on to enable the power supply 1412 by a PCSM_ENBL signal asserted from PLD 1190 at line 1224 through base resistor R275. Line 1224 is coupled through resistor R276 to ground and is seen extending from PLD 1190 in FIG. 61A.

Figure 68A:
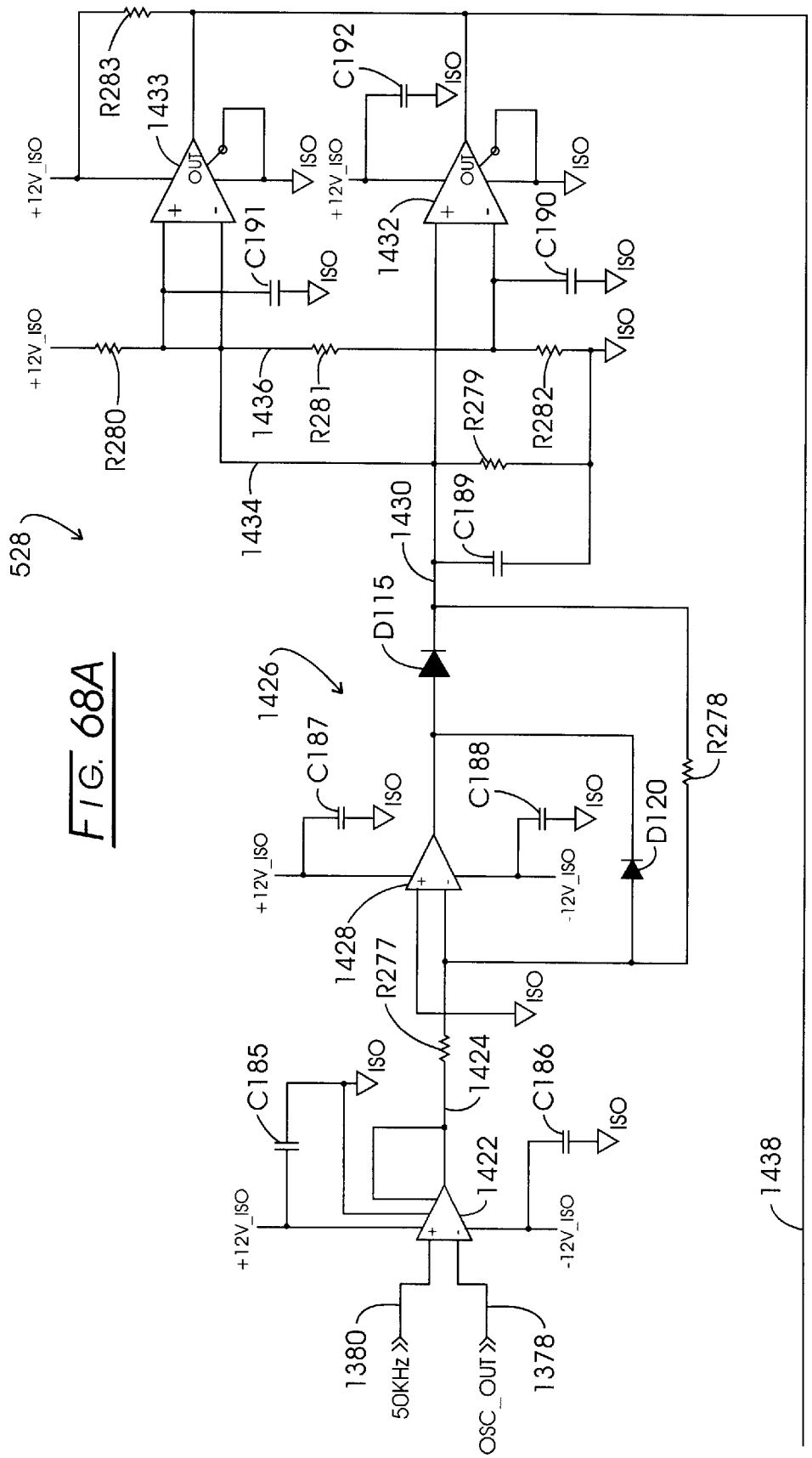

Referring to FIGS. 68A and 68B, which should be considered in the orientations as labeled thereon, a window defining detection or comparison circuit is illustrated which evaluates the actual PCSM test from network 1380 (FIG. 66B) as well as the self test of networks 1381–1383. In general, the ohmic window representing a valid dispersive electrode 68 connection will reside between about 20 and 80 ohms. Referring to FIG. 68A, the taps 1378 and 1380 as described in connection with FIG. 66B are shown to extend to the inputs of a differential amplifier 1422. Amplifier 1422 may, for example, be a type AMP02FS device marketed by Analog Devices, Inc. of Norwood, Mass., and is implemented with +12V and −12V and capacitors C185 and C186. Thus configured, device 1422 responds to the floating signal at resistor R250 (FIG. 66B) and provides a single ended signal to ground at output line 1424. This A. C. signal at line 1424 then is submitted through input resistor R277 to a precision rectifier represented in general at 1426. The rectifier 1426 provides rectification without diode drop phenomena and is seen to comprise operational amplifier 1428 configured with resistor R278, diodes D119 and D120 and capacitors C187 and C188. The d. c. signal at output line 1430 then is proportional to the current in the return electrode or to the test evaluations from networks 1381–1383 and is impressed across capacitor C189. A resistor R279 extends between line 1430 and ground and functions for the selective discharge of capacitor C189.

The d. c. signal at line 1430 is directed to the positive input of a comparator 1432 and via line 1434 to the negative input of a corresponding comparator 1433. Reference inputs to these comparators 1432 and 1433 are provided from line 1436 and +12V which incorporates reference defining resistors R280–R282. The reference inputs are seen to be connected additionally with filtering capacitors C190 and C191, while the +12V input to comparator 1432 is filtered at capacitor 0192. Capacitors 1432 and 1433 may be provided as type LM319M devices marketed by National Semiconductor, Inc. of Sunnyvale, Calif.

When the current represented at line 1430 corresponds with a resistance falling within a window defined between a lower threshold of for example 20 ohms and an upper limit of for example, 80 ohms, then a positive voltage signal will be impressed from resistor R283 at line 1438. Looking to FIG. 68B, line 1438 is seen to extend to the anode of the input side of an opto-coupler 1440. The collector component of the output of opto-coupler 1440 is coupled with +12V through resistors R284 and R285, while the emitter output thereof is provided at line 1226 which is coupled through resistor R286 to ground. Line 1226 serves to apply the signal thereat representing a valid test, "PCSM_VALID" to PLD 1190 as shown in FIG. 61A.

Figure 69:
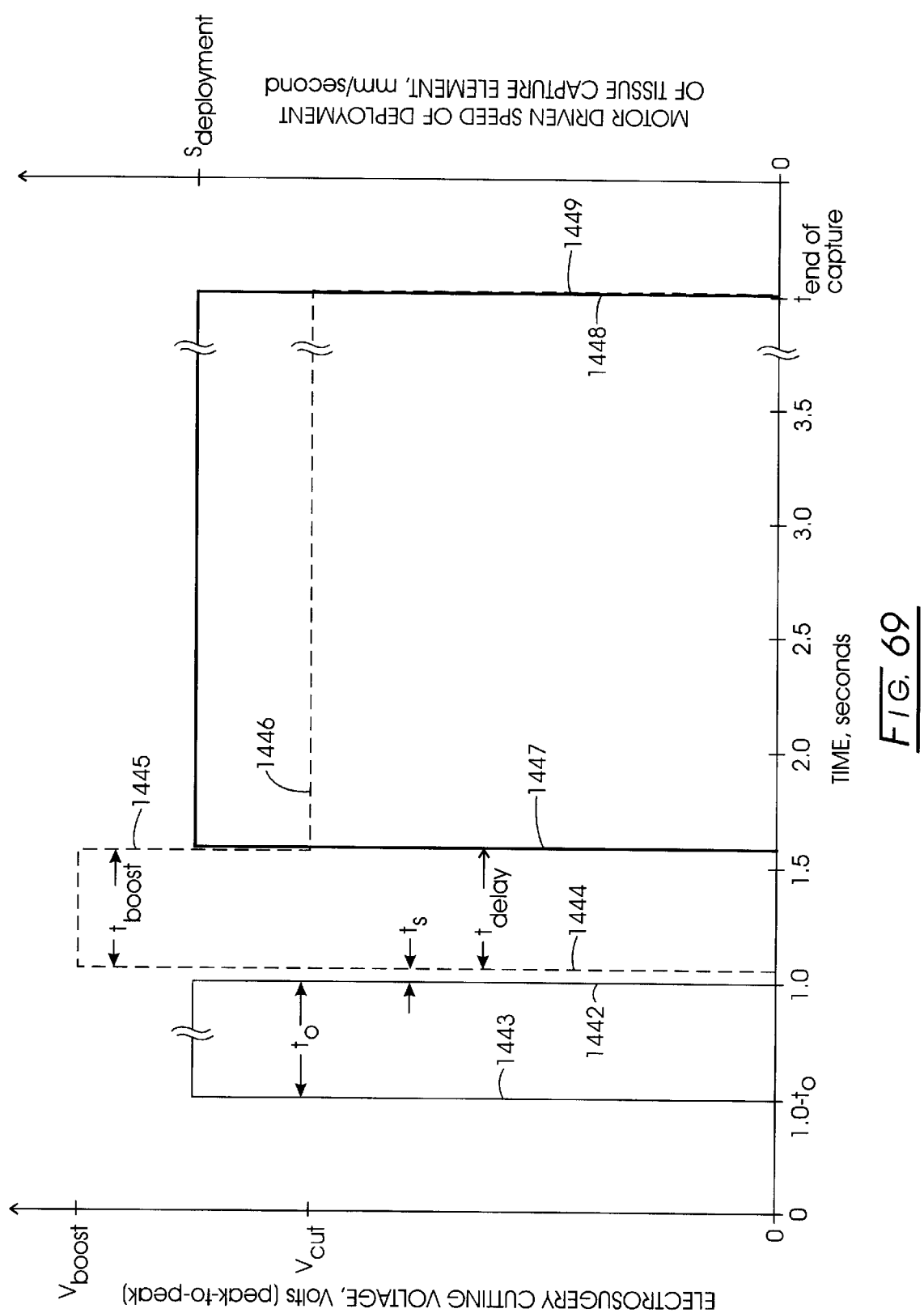
FIG. 69 is a schematically portrayed timing chart relating time with cutting voltages and motor operation.

Referring to FIG. 69, a schematically portrayed timing diagram is provided which describes the control over motor assembly 170 in terms of time and the corresponding application of boost and normal cutting voltages at the pursing cables 300–304 during the operation of the capture component. The diagram utilizes an arbitrarily established one second point-in-time at line 1442. Extending backwardly in time from line 1442, a time increment represented as $t_0$, is line 1443 representing the instant-in-time when the practitioner will have actuated the start tissue capture switch 56 on instrument housing assembly 14 or footswitch 86c (FIG. 1) by holding one or the other in a continuously depressed condition. Arm/disarm switch 54 or footswitch 86b will have been actuated momentarily earlier. Accordingly, at the time represented at line 1443, motor assembly 170 is energized. Transition component 176 will be rotating and the yoke 184 of the transfer assembly 180 will be moving forwardly but will not have touched drive member ears 134 and 136. It is during a test interval of one-half second within this interval, $t_o$, that the test described in connection with FIG. 50 is carried out to assure that the motor assembly and transition component are working properly, i.e., not binding or experiencing anomalies. In general, the motor current draw status should be one wherein the motor is not drawing more than 23 milliamps. At the time represented at line 1442, the control as described in connection with FIG. 51, determines that the yoke 184 has engaged ears 134 and 136. At this point-in-time, the motor assembly 170 is de-energized, and following a switching delay, $t_s$, electrosurgical cutting current at a boost voltage level is applied to the pursing cables 300–304. The commencement of application of this electrosurgical boost current is represented at dashed line 1444 the height of which indicates the level of boost voltage. Boost current is applied during the period, $t_{boost}$, for an interval of 100 to 1000 ms and preferably for an interval from about 250 ms to 750 ms. The boost voltage, $V_{boost}$ is selected within a range extending from about 1100 volts, peak-to peak to about 2000 volts, peak-to-peak, and, preferably is within a range extending from about 1100 volts, peak-to-peak to about 1300 volts, peak-to-peak. At the termination of the boost interval as represented at dashed line 1445, the electrosurgical energy is dropped to a normal cutting voltage level, $V_{cut}$, as represented at dashed line 1446. The cut voltage, $V_{cut}$ is selected within a range extending from about 700 volts, peak-to-peak to about 1200 volts, peak-to-peak, and, preferably, within a range extending from about 800 volts, peak-to-peak to about 1000 volts, peak-to-peak. Just following the alteration of voltage level to, $V_{cut}$, at a time interval represented as tdelay, and as indicated by solid line 1447, the motor assembly 170 again is energized for an interval of time required to complete the capture of the tissue specimen, an interval which will vary depending upon the maximum diametric extent defined by the outwardly extending leafs. In general, where that diameter is about 10 mm, $t_{end\ of\ capture}$ will occur at about 5 to 6 seconds. By contrast, a maximum diametric extent of about 20 mm will involve about 10–12 seconds of time to $t_{end\ of\ capture}$. During the interval of driving the capture component the load characteristic or current draw of motor assembly 170 is monitored as described in connection with FIG. 51. Where that load current falls below a predetermined threshold, a fault condition obtains with a flashing of all LEDs. A termination of motor forward drive is determined by the forward stall detection as described in connection with FIG. 52 and is indicated by the solid line 1448. Line 1448 also coincides with the termination of electrosurgical cutting current as represented by coincident dashed line 1449. In general, the rate of speed of deployment of the capture component leafs may range from about one mm per second to 5 mm per second and preferably will be in a range of about 2.5 mm per second to 4 mm per second. This movement rate is exhibited at transfer assembly 186 and engaged drive member 324.

Control over the cutting energy supplied from the electrosurgical generator function to the pursing cables 300–304 is predicated inter alia, upon both a conventional design approach wherein the power developed must be effective to cut while not being of an extent causing excessive damage to tissue adjacent the cut, the instrument or the recovered tissue specimen. With system 10, however, additional criteria arise. The active electrode, when manifested as the tissue encountering portions of cables 300–304, is changing in surface area extent during the procedure. It initially commences to be excited under boost voltage having a geometry somewhat resembling a point source. Then it increases in peripheral extent resembling a gradually expanding line source, whereupon it then returns to assume a geometry again approaching a point source. Thus the system 10 calls for an increasing power output during the initial expansion, with surface area increase, followed by a decreasing power output characteristic as contracting pursing encapsulation occurs. Additionally, at the commencement of the procedure, the active electrode assembly whether precursor electrodes or pursing cables, is embedded in tissue and boost voltage is called for during a boost interval adequate to cause the commencement of an arc extending between the cutting portions of cables 300–304 and the tissue being cut. In effect, it is this arc and not the cables that create the cut. The active cable portions as well as the precursor electrodes merely slide within a vapor developed from the adjacent tissue cell layers.

Conventional electrosurgical generators are designed to perform in conjunction with an active electrode of fixed configuration or geometry such as a blade or rod. Development of a necessary cutting arc is achieved by the technique or experience of the surgeon who causes initial arc formation or creation by moving the active electrode toward the targeted tissue until the arc forms, for example, at about one millimeter. Looking to FIGS. 70A and 70B, this technique is portrayed. A patient is depicted at 1450 whose back is abuttingly engaged with a large dispersive electrode 1451 which provides a return to an electrosurgical generator 1452. Generator 1452 feeds cutting energy to an active electrode 1453 of fixed geometry.

Figure 70B:
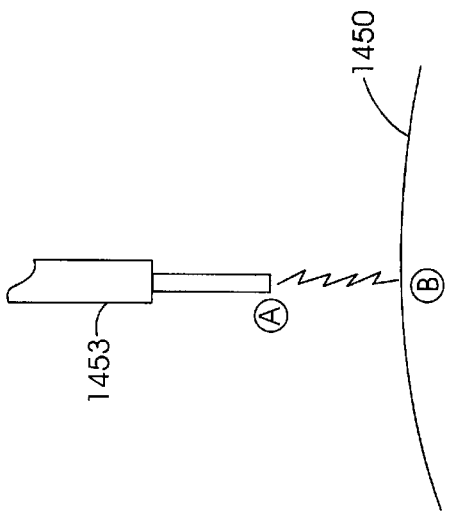
FIG. 70B is a schematic representation of a portion of the illustration of FIG. 70A.
Figure 71:
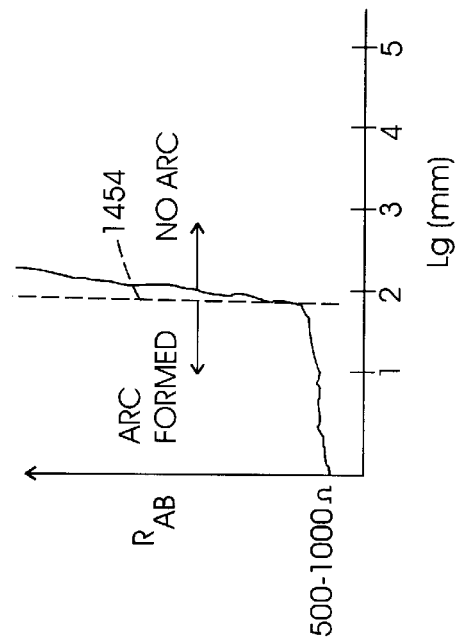
FIG. 71 is a schematic chart demonstrating the formation of an arc with a conventional electrosurgical active electrode of fixed geometry.
Figure 70A:
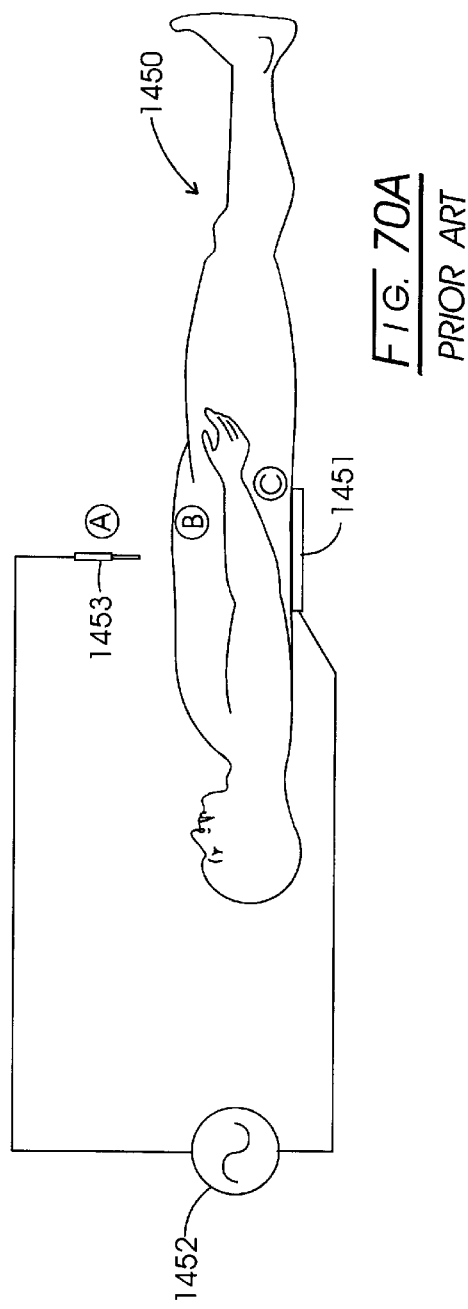
FIG. 70A is a schematic representation of a patient and an electrosurgical system provided to demonstrate tissue impedance and total impedance.

To achieve arc commencement, the electrosurgical generator output must confront an impedance of adequate range, for example, 1300 to 1500 ohms. This impedance is resistant in nature and comprises the resistance, $R_{tissue}$, exhibited by the body of the patient 1450, as represented by the distance from B to C, the value ranging from about 300 ohms to 500 ohms, in combination with the impedance or resistance developed by the active electrode spacing from tissue. FIG. 70B illustrates, in enlarged fashion, that spacing, $L_g$, as the distance from A to B. Looking to FIG. 71, this resistance, $R_{AB}$ is plotted at dashed line 1454 with respect to variations in the distance, $L_g$. Note that at values of $L_g$, greater than about 2 millimeters, the resistance $R_{AB}$ approaches infinity and no arc is developed. However, as the active electrode of fixed configuration approaches a distance, $L_g$ of value of about one millimeter, a resistance of about 500 ohms to 1000 ohms is witnessed which, when combined with the resistance, $R_{tissue}$ (B to C) permits an arc to be formed. With the proper resistance, $R_{total}$, represented from A to C, the cutting arc will be sustained in accordance with the generalized expression: $R_{total} = R_{tissue}$ and $R_{arc}$. With the above arrangement, conventional electrosurgical generators are operated in conjunction with a fixed output power and a variable applied voltage. The output power levels thus are maintained within a safe range, for example, from about 80 watts to about 100 watts.

The equivalent of the arc formation otherwise created by electrode spacing carried out with the technique of the surgeon is achieved with system 10 even though the active electrode initially is embedded in tissue with no initial spacing available. Application of the short term ($t_{boost}$) boost voltage ($V_{boost}$) causes a vaporization of the tissue solid structure adjacent the initially exposed and tissue embedded active portions of cables 300–304. This evokes the equivalent of an initial spacing to achieve requisite impedance for arc commencement. The interval of application of the boost voltage may be of a fixed duration, for example, about 500 milliseconds or less (about 250 milliseconds to about 375 milliseconds currently being preferred) or may be defined by the creation of the arc following the application of this boost voltage. The impedance change, $R_{total}$, at the formation of the arc represents a quite abrupt alteration and results in a correspondingly abrupt drop in output current flow. Accordingly, the formation of the arc is readily detected to carry out boost voltage application termination.

Figure 72:
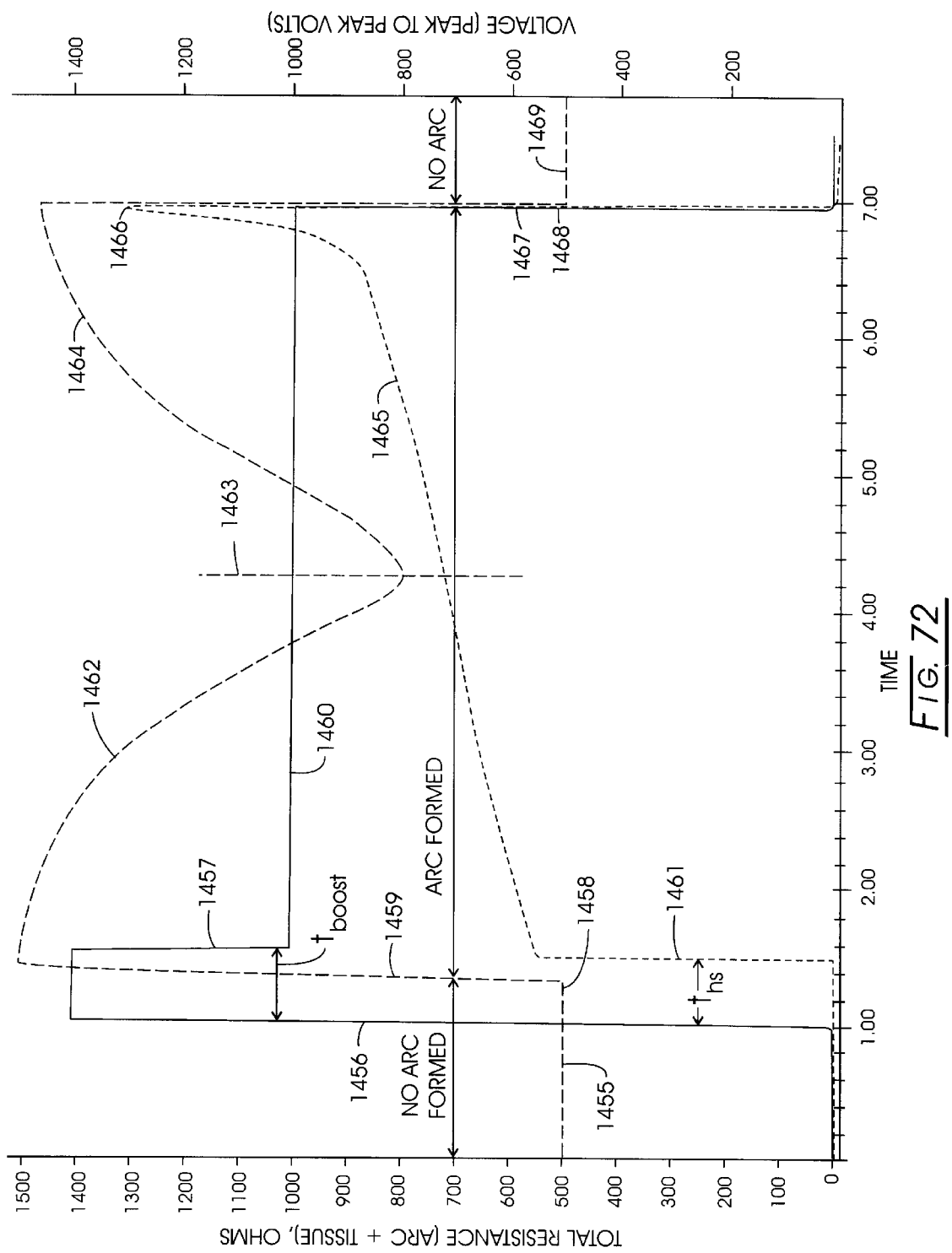
FIG. 72 is a graph relating time with applied voltage and total resistance for an electrosurgical system according to the invention.
Figure 74A:
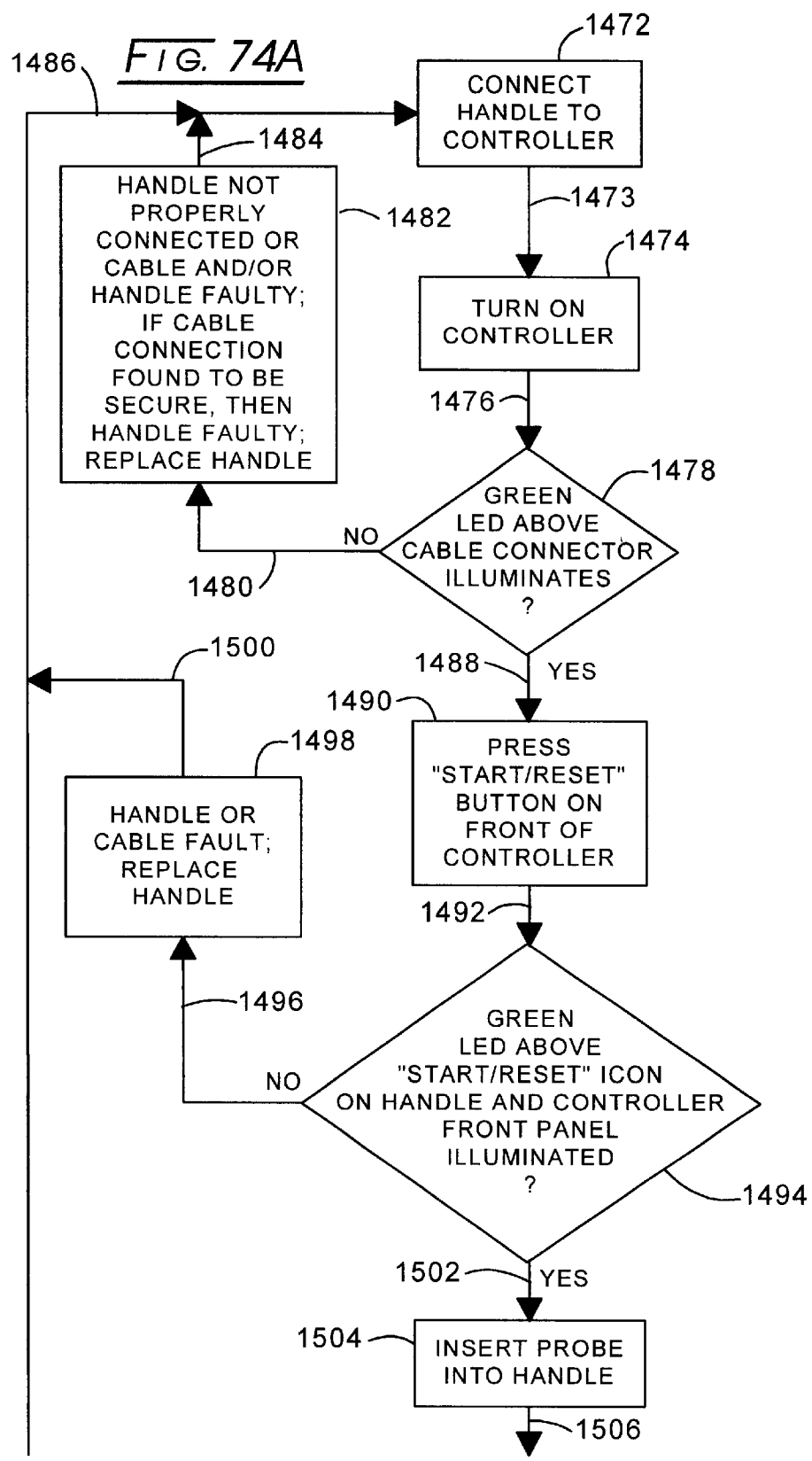
Figure 74B:
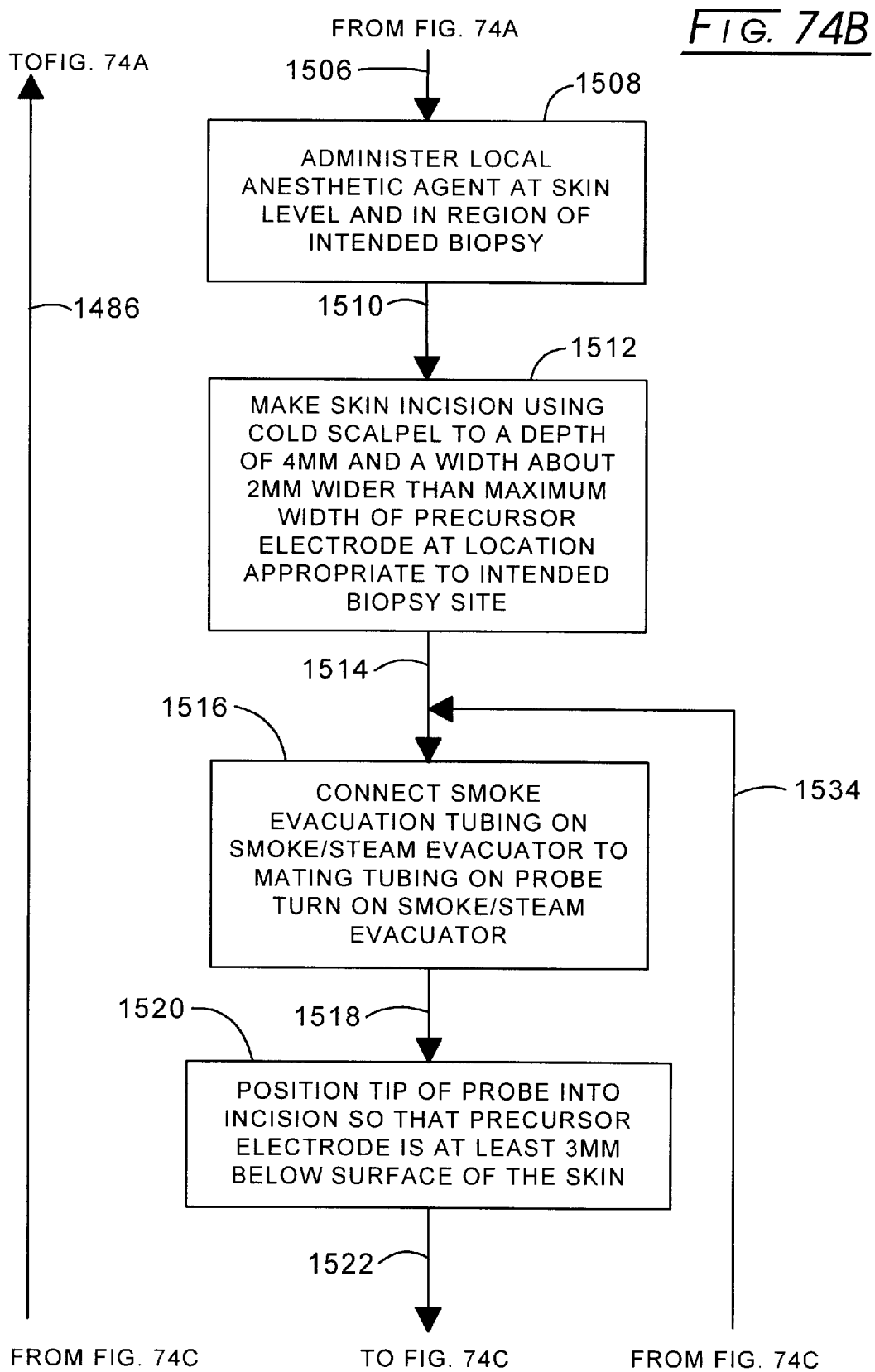
Figure 74C:
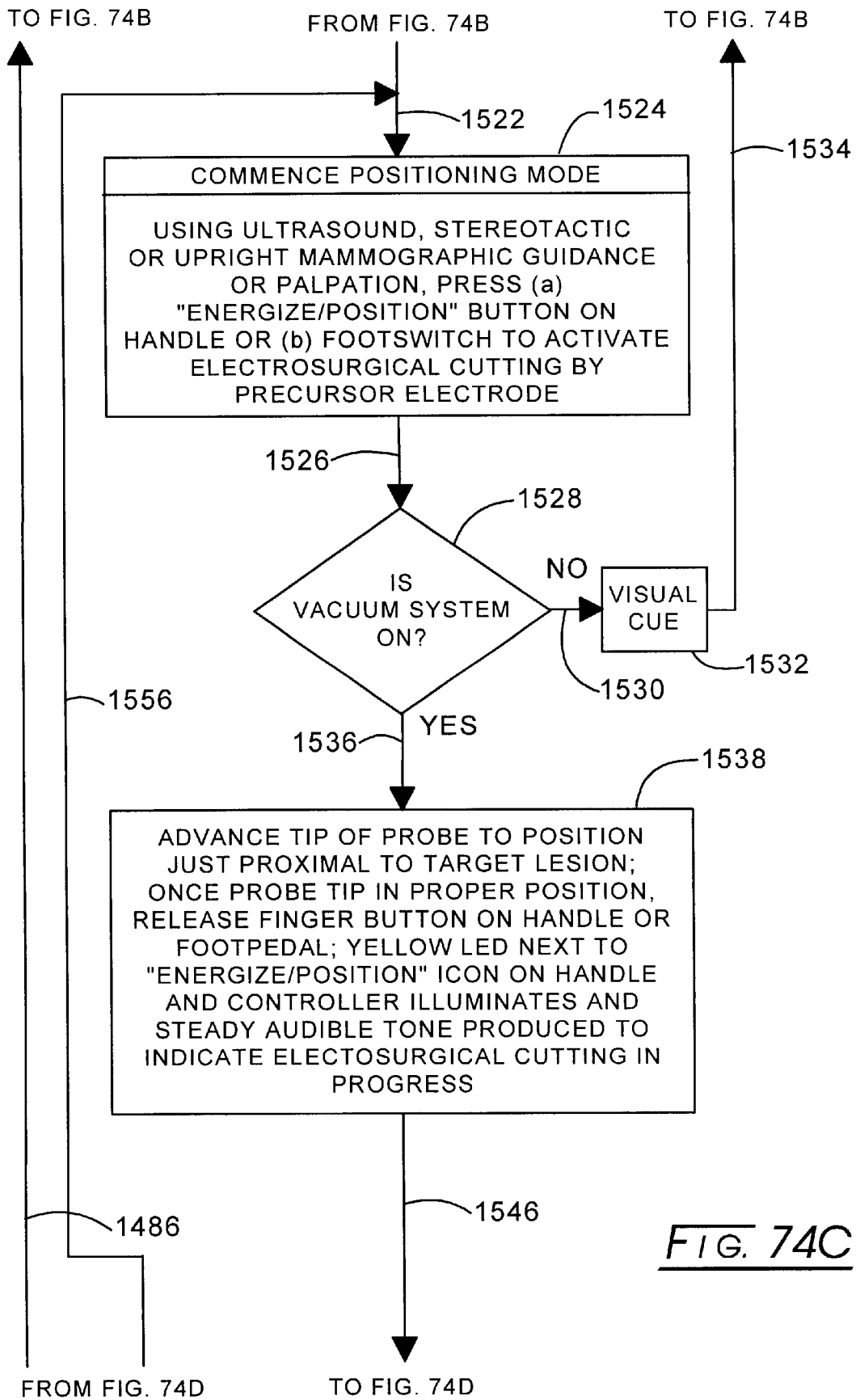
Figure 74E:
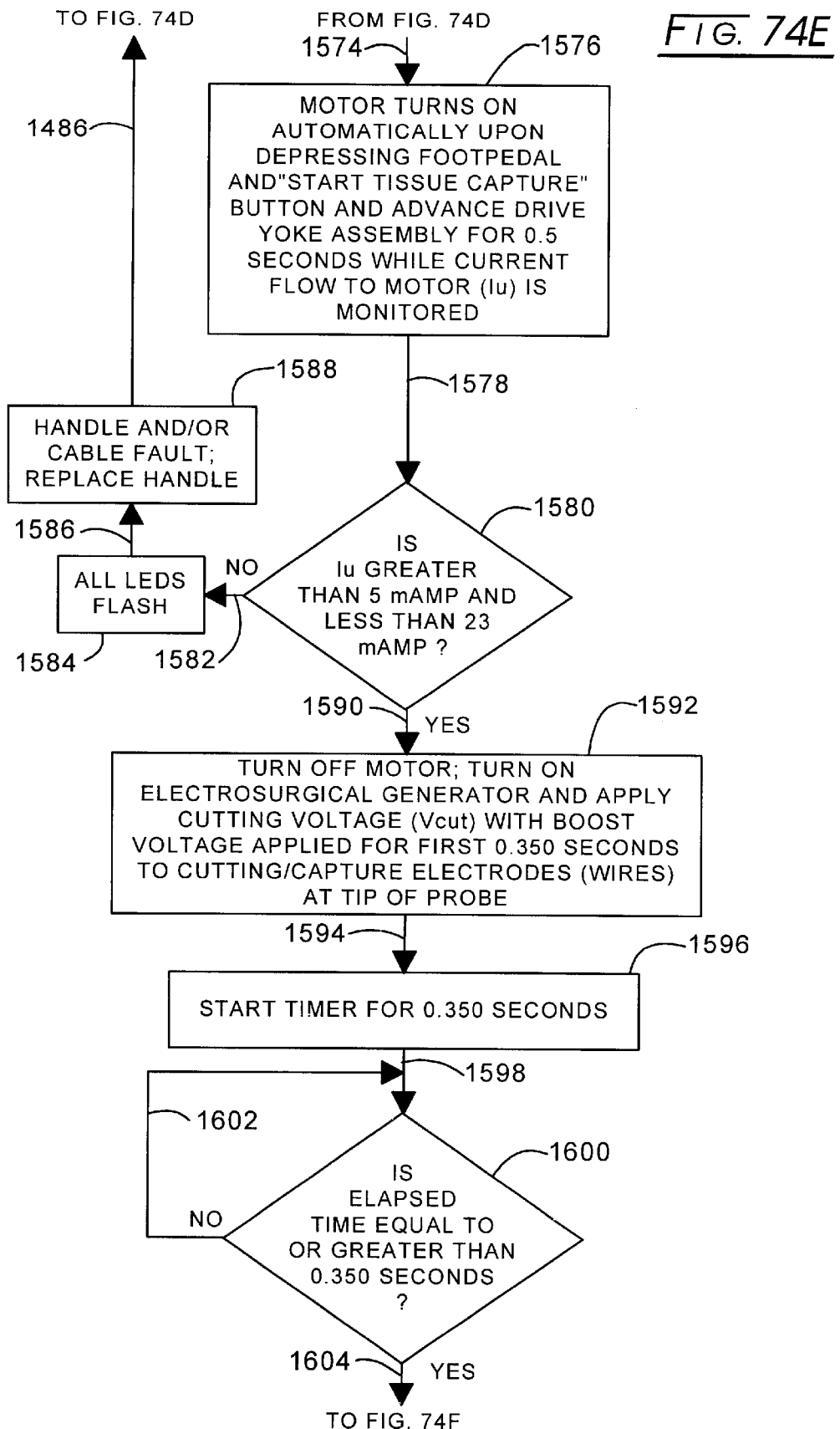
Figure 74F:
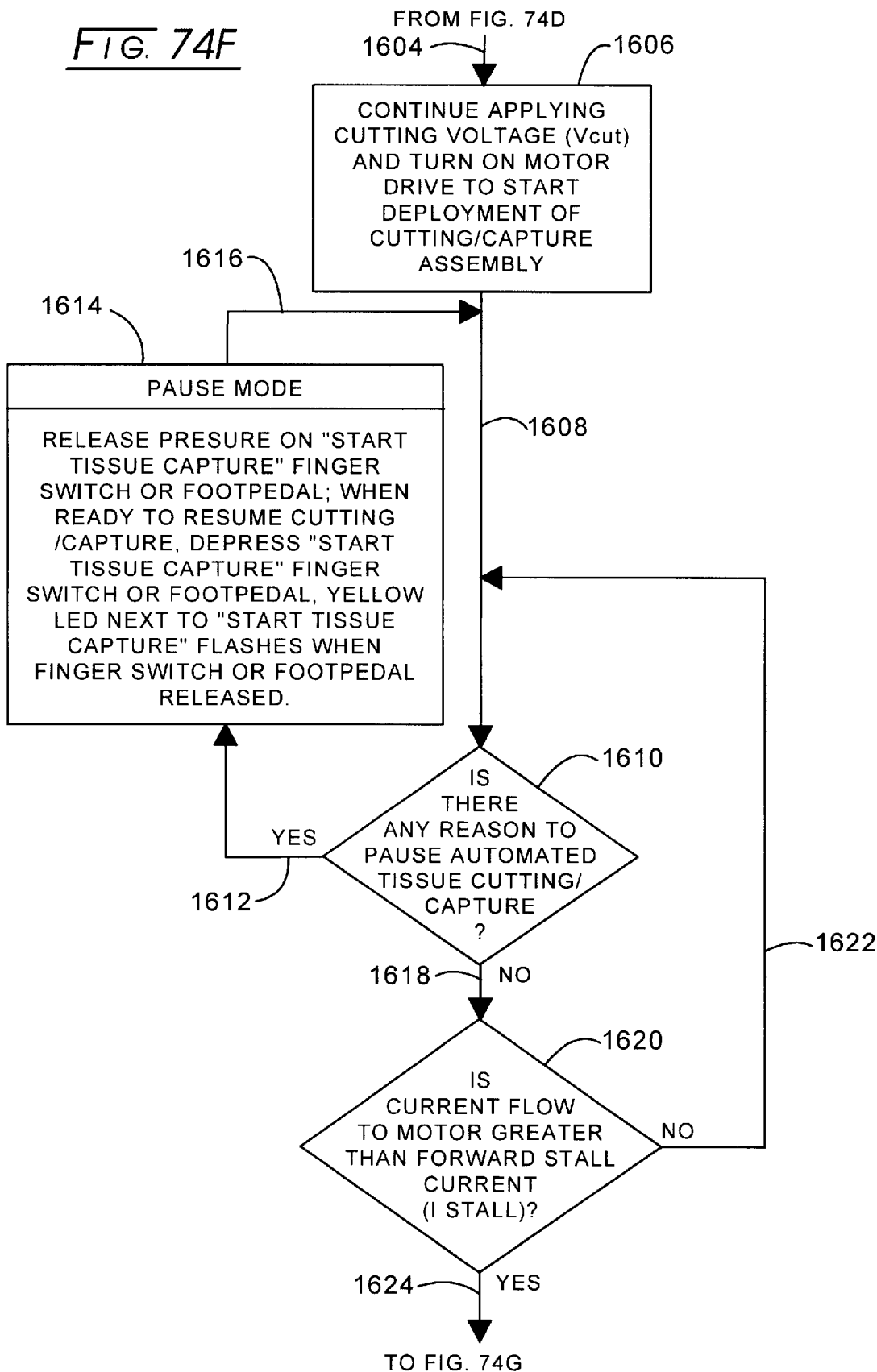

Referring to FIG. 72, the performance of system 10 in connection with an experiment carried out using slab bacon and a capture maximum diametric extent of 10 millimeters is portrayed. In the figure, total resistance in terms of ohms as computed is plotted with respect to time. Additionally, applied, peak-to-peak voltage is plotted with respect to that time. Further, the current witnessed at d.c. motor 170a (as seen in FIG. 4) is set forth. At the commencement of the procedure, prior to the application of boost voltage the total resistance was equal to the tissue resistance, $R_{tissue}$ as earlier described in connection with the distance B–C in FIG. 70A. That 500 ohm level is represented at dashed line segment 1455. Boost voltage was applied to the cable electrodes to commence the boost interval at a boost voltage of 1400 volts peak-to-peak. That boost voltage was imposed for an interval, $T_{boost}$ of 500 milliseconds, whereupon the applied voltage abruptly dropped as represented at solid line segment 1457. During the boost interval, following about 200 milliseconds, as represented at dashed line segment 1458 and vertical dashed line segment 1459 an arc was formed and total resistance abruptly elevated to about 1500 ohms at a point in time near the termination of the fixed boost interval, as represented at line segment 1457 the applied voltage was dropped to a normal cutting voltage level represented at horizontal solid line segment 1460. This applied normal cutting voltage is seen to have been at a level of 1000 volts peak-to-peak. Essentially simultaneously, as represented at vertical dashed line segment 1461 motor 170a was energized following a head start interval from the application of boost voltage identified as $t_{hs}$. With the energization of the motor assembly 170, the leafs commenced to be extended as the cables 300–304 began to be played out toward a peripheral extent of maximum diameter. As this occurred, the length and consequent surface area of the cables engaged in active cutting of tissue expanded and the corresponding total resistance commenced to drop as represented by the dashed curve segment 1462. When the maximum peripheral extent of the leaf tip portions and active cable cutting length reached a maximum value, as represented at vertical dashed line 1463 resistance reached a lowest value and applied current reached a maximum value with concomitant power increase.

As the time interval of the procedure continued beyond the time represented at vertical dashed line 1463, the active surface area of cables 300–304 employed in cutting tissue reduced as pursing ensued and the effective cable length engaged in tissue cutting reduced as total resistance again increased as represented by the curved dashed line segment 1464. During this interval, the d.c. motor current which commenced at line segment 1460 gradually increased as represented at dashed line segment 1465 until motor stall threshold was reached as represented at the current level 1466. Motor drive and normal cutting voltage were terminated abruptly as represented at respective dashed line segments 1467 and 1468. Following the procedure the total resistance returned to the value of the tissue resistance, $R_{tissue}$ as represented at horizontal dashed line segment 1469.

Figure 73:
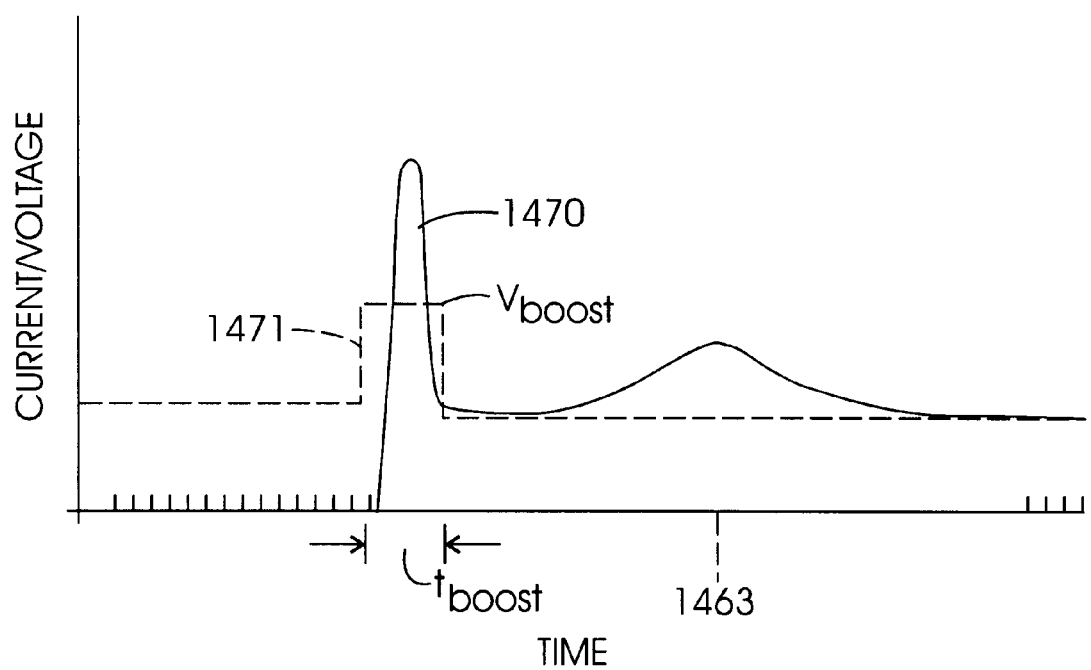
FIG. 73 is a graph showing an application of boost voltage and resultant current.

Referring additionally to FIG. 73 (adjacent FIG. 62), a plot of peak current output occurring during the interval represented by the procedure carried out in connection with FIG. 72 is revealed. In the figure, at the commencement of the procedure, a very abrupt current rise for a very short interval of about 200 milliseconds is revealed followed by an abrupt drop. As the total resistance dropped at the time represented at vertical dashed line 1463, current rose again to a peak and thereafter diminished to about the same level it assumed following the formation of an arc at the termination of the initial current spike. It is during that current spike that the effective initial spacing is carried out by vaporization of tissue cells. The plot of FIG. 73 also may be considered to correspond with power dissipation during the procedure.

Returning to FIG. 72, and recalling that with system 10, power applied from the electrosurgical generator is varied in accordance with the application of boost voltage and with the changing of the cable electrode geometry for the example at hand, power dissipation may be evaluated. The commencement of the application of boost voltage is represented at line 1456, a tissue resistance of 500 ohms was encountered. Accordingly, until the arc was formed, under an applied boost voltage of 1400 volts peak-to-peak, a power dissipation (computed as based upon RMS voltage) of about 500 watts occurred. However that power was produced in a highly constricted region for the very short interval occurring until the arc was formed as represented at dashed line 1459, for example, an interval of about 200 milliseconds. As soon as the arc was formed, as represented at dashed line 1459, the impedance represented by the arc was added to the 500 ohms tissue impedance and the power dissipation dropped to about 167 watts which, although slightly higher, remained only until the removal of boost voltage as represented at vertical line 1457. Normal cutting voltage at 1000 volts peak-to-peak then ensued with a power dissipation of about 85 watts. However, now the expansion of the active electrode commenced, power again rose as the total resistance dropped to about 800 ohms as the cable length enlarged and the maximum peripheral extent of the leading edge of the capture component was reached as represented by the dashed locator line 1463. Accordingly, the power will have elevated from about 85 watts to about 159 watts. However, the 159 watt power value is one associated with a relatively widely disbursed line source electrode at its maximum linear extent. As pursing activity then ensued, that linear extent diminishes toward a point value and power dissipation also diminishes to again approach 85 watts at the termination of capture.

As is apparent from the forgoing, it is possible to apply electrosurgical energy at the boost voltage level (e.g., 1100 volts, peak-to-peak) continuously throughout the procedure. In effect, the boost interval, $t_{boost}$ is extended to encompass the entire time of the procedure whether positioning with precursor electrodes or capturing with pursing cables. However, the consequence of so expanding the boost interval is the potential generation of excessive power during the biopsy procedure which results in greater depth of thermal injury to the biopsy specimen and surrounding healthy tissue.

Unlike conventional electrosurgical cutting systems, the instant generator sustains the essential cutting arc by employing a constant voltage output. Conventional feedback loop approaches for developing such control typically will evoke a non-stable oscillatory output unsuitable for electrosurgical cutting. Such instability is in consequence of the negative dynamic impedance characteristic of an arc. By employing the above-discussed inner and outer feedback loop in conjunction with control to the D. C. link inverter 490, stable, constant voltage-based control is achieved.

FIGS. 74A–74G combine as labeled thereon to provide a flow chart describing the operation of the instant system. In the discourse to follow, the term "handle" refers to instrument 12; the term "precursor electrode" refers to the electrode assembly as at 228; and the term "controller" refers to console 64. Cueing icons representing given switch functions, test results or operational modes are provided, where appropriate adjacent switches and elsewhere on instrument 12 and console 64. Looking to FIG. 74A, the procedure starts as represented at block 1472 and line 1473 providing for the connection of connector 66 of cable 62 to console connector 67. Next, as represented at block 1474 and line 1476 controller 64 is turned on by actuating front panel switch 82. As this occurs, a handle interlock test is carried out as described in conjunction with line 286 of FIG. 61 E. In this regard, an interlock current is caused to pass through a 10 kohm coding resistor present in the instrument 12 housing assembly 14. If the test for this interlock connection is passed, then the green LED 80, above the console cable connector 67 will be illuminated represented by the query posed at block 1478 where LED 80 is not energized, then the procedure reverts as indicated at line 1480 and block 1482, the practitioner being pre-instructed to check for a proper handle (housing assembly 14) connection and if that connection is proper, then the instrument 12 is replaced. For either of these improper conditions, the procedure loops to commencement block 1470 as represented at lines 1484 and 1486. Where the query posed at block 1478 indicates that proper handle (housing assembly 14) connection is present and the green LED 80 is illuminated, then the procedure continues as represented at line 1488 and block 1490. Turning on switch 82 also causes the carrying out of the self test features of PCSM system 528 as described in conjunction with networks 1381–1383 in connection with FIGS. 66A–66B and 68A–68B.

Block 1490 calls for an actuation of the console mounted start/reset switch 92. This causes the motor assembly 170 to be energized in a reverse sense to cause the rotation of translation component 176 and the driving of transfer assembly 180 rearwardly until the nut 182 engages bulkhead surface 248. As described in conjunction with FIG. 53, this derives a MOTOR_REV_STALL signal, whereupon the motor assembly 170 is energized in a forward sense for 0.125 second to relax the thus caused axial load. This dual energization procedure is monitored. As represented at line 1492 and block 1494, a determination is made as to whether the green LED below the start/reset icon on the housing assembly 14 as well as the corresponding green LED 94 at console 64 is illuminated. Where those LEDs are not illuminated, the activity described at block 1490 failed and the procedure reverts as represented at line 1496 and block 1498, the practitioner having been pre-instructed that a faulty cable or "handle" is at hand and the procedure reverts to starting block 1470 as represented at lines 1500 and 1486.

Actuation of switch 92 also causes the carrying out of the test for proper connection of dispersive return electrode 68 by the PCSM system 528 as discussed in conjunction with network 1380 in connection with FIGS. 66A–66B and 68A–68B. A failure to pass this test results in the flashing of red LED 78, generation of a pulsing sound output, and the procedure is halted.

Where the query posed at block 1494 results in an affirmative determination with the illumination of the noted green LEDs, then, as represented at line 1502 and block 1504, the practitioner inserts the disposable probe component 108 (FIG. 2) into the housing 15. Proper insertion is assured inasmuch as disposable component 108 cannot be inserted within the housing 15 to create housing assembly 14 unless the indexing pin 116 is aligned for slidable insertion within the slot 118. (See FIG. 4). Additionally, color codes on the disposable components as well as on the housing 15 are provided to assure proper registry. For example, one such color code is shown at 252 in FIG. 8. Thus guides in the handle(ears 134 and 136) along with the noted indexing on the probe with a color coded inserion point assure proper insertion and that electrical contacts on the probe body register with malting contacts in the handle. The particular disposable component 108 selected for the procedure will, as described in connection with FIGS. 14, 28, 29 and 31, 32 be prefabricated with a position for cable stop 322 selected with respect to the maximum effective diametric extent of expansion and forward extension of the capture component leafs. Practitioner selection is made with respect to the predetermined size of the tissue volume desired to be removed. In general, the pursing cable and leafs will extend through healthy tissue surrounding a targeted lesion. This will avoid seeding complications and the like upon removal of the biological specimen. The program then continues as represented at line 1506 and block 1508 providing for the administration of a local anesthetic at the skin level in the region of the intended biopsy. This step is performed several minutes before a skin incision is made to commence probe positioning. For example, this step should be performed at least 5 minutes before the start of the biopsy procedure to assure perfusion of the target site with the antesthetic agent. This allows avoids entrapped bolous of anesthetic fluid along the path of biopsy. Skin incision and the administration of a local antesthic agent can optionally be performed at prior to any of the revious steps. Following the administration of the anesthetic agent, as represented at line 1510 and block 1512 a cold scalpel is employed to make a skin incision to a depth of about 4 mm and a length approximately 2 mm wider than the maximum width of the precursor electrode. Then, as represented at line 1514 and block 1516 switch 46 of the smoke/steam evacuator assembly 44 is turned on or footswitch 48 is actuated (FIG. 1). Next, as represented at line 1518 and block 1520 the tip 32 of the delivery cannula 22 of the instrument 12 is positioned within the incision made in conjunction with block 1512 at a location wherein the precursor electrodes are at least about 3 mm below the surface of the skin.

The procedure then commences a positioning mode as represented at line 1522 and block 1524. During this mode, the practitioner, using ultrasound, stereotactic, upright mammography guidance or palpation, presses the energize/position switch button 55 on the housing assembly 14 or actuates footswitch 86a to cause the application of electrosurgical current to the precursor electrodes at the tip 32. At this juncture in the procedure, the control assembly carries out an interlock form of test to assure that the vacuum system turned on at block 1516 is indeed on and working.

This test provides an assurance that steam will not migrate along the outer surface at delivery cannula 22. Accordingly, as represented at line 1526 and block 1528 a query is made as to whether the vacuum system is on. In general, this test is carried out in conjunction with a vacuum sensor 51 combined with component 44 (FIG. 1). Where no vacuum is sensed, as represented at line 1530 and block 1532, the system turns on all cueing LEDs and the procedure dwells as represented by line 1534, until the vacuum system is activated. Where the vacuum system is in proper order and activated, then as represented at line 1536 and block 1538, the practitioner advances the tip 32 of the probe to a position just proximal to the target lesion. Yellow LED outputs adjacent switch 55 will be illuminated as well as yellow LED 96 at console 64. Additionally, a steady audible tone is produced from loudspeaker 646 (FIG. 36A). As discussed in connection with FIG. 28, the distance between the tip 32 of the probe and the center of the target lesion (Ls) depends upon the diameter of the intended tissue volume capture and the maximum diametric extent of the probe (Dc). It may be recalled that the maximum effective diametric extent is reached as the pursing cables draw cable terminator component 296 into engagement with the cable stop 322 (see FIG. 28). In general, the distance Ls will equal about 0.6*Dc. Dimensions of the intended biopsy specimen, i.e., diameter and the length, are determined by probe design at the time of manufacture.

The procedure then continues as represented at line 1546 and block 1548. At this juncture of the procedure, the practitioner must be assured that tip 32 of the delivery cannula 22 is in proper position and orientation for carrying out a specimen capture. Accordingly, as represented at line 1550 and block 1552, a determination is made as to whether the probe tip 32 is in a correct position. If it is not, then as represented at lines 1554 and 1556, the procedure reverts to line 1522 and the positioning mode represented at block 1524.

Where the delivery cannula tip 32 is in proper confronting adjacency with the involved tissue volume, then as represented at line 1558 and block 1560, an arm capture mode is entered as the practitioner momentarily presses the arm/disarm switch at footswitch 86b or the button 54 on the housing assembly 14. As this occurs, the green LED outputs positioned adjacent switch 54 on the handle are illuminated as well as green LED 98 on console 64. Actuation of button switch 54 or footswitch 86b is a prerequisite step before starting tissue capture, disabling the energize/position switch button 55 and footswitch 86a. Should the practitioner wish to return to the positioning mode of block 1524 following the actuation of switch 54, as represented at line 1562 and block 1564, upon making a determination that tip 32 is not in proper position, but the arm capture mode is at hand, then as represented at line 1566 and block 1568, the practitioner presses the arm/disarm footswitch 86b or handle button 54 again. Then, as represented at lines 1556 and 1522, the positioning mode is reentered and both the footswitch 86a and energize/position switch button 55 again are active.

If the delivery cannula tip 32 is in a correct position for entering the capture mode from the arm capture mode, then as represented at line 1570 and block 1572 the capture mode may be entered. This entry into the capture mode starts a three stage automated sequence. As a stage one, the motor assembly 170 is test energized for about one half second as described at to in connection with FIG. 69. This motor drive system integrity test assures that the motor drive assembly is performing properly before allowing the tissue cutting/capture sequence to commerce. The yoke 184 will not have engaged the ears 134 and 136 of drive member 324 for this initial one half second by virtue of the above-discussed spacing design. The control system monitors motor current for at least that one half second. Where the proper low current levels are detected during that one half second (FIG. 50) this capture mode test then is satisfied. Motor assembly 170 will be de-energized upon detection of its current condition representing engagement of the yoke 184 with ears 134 and 136 as discussed in connection with FIG. 51. Thus, the test measures current flow to the motor while it advances the drive yolk from its "home" position to initial contact with the drive ears or the disposable probe, but without starting deployment of the cutting/capture electrode assembly. As a stage two, while the motor is de-energized at this juncture, the interval $t_{boost}$ occurs with the application of boost level voltage electrosurgical cutting current to the pursing cables. This initiation of the electrosurgical cutting arc occurs typically within about 0.25 second. Following a three-eighths second boost interval, the normal cut voltage described at dashed line 1458 in FIG. 69 ensues. At stage three, as described in conjunction with line 1460 in FIG. 69, motor drive again is commenced to start tissue cutting and capture, an arrangement which continues until the pursing down of the cutting cable electrode is completed. During this interval of time, monitoring of motor load current continues (FIG. 51), and start tissue capture button 56 or footswitch 86c are continuously actuated or depressed to maintain the capture mode. With the depression of either the start capture footswitch 86c or the start capture switch or button 56, yellow LED outputs adjacent to switch 56 on instrument 12 are illuminated as well as LED 100 on console 64. The motor current demand continues to be sensed during tissue capture, and, when forward stall current exceeds a preset threshold, capture is complete.

The initial motor test run is represented at line 1574 and block 1576 and the current monitoring test carried out by the circuit of FIGS. 50 and 51 is represented at line 1578 and block 1580. Where the motor test carried out during the noted one half second test interval fails, then as represented at line 1582 and 1584, all LEDs on both the housing assembly 14 and the console 64 commence to flash and, as represented at line 1586 and block 1588 a handle and/or cable fault is at hand and the handle reusable housing 15 should be replaced. The procedure then follows the path represented at line 1486 to block 1470 calling for a restart of the entire procedure. Where the one half second motor test as represented at block 1580 shows proper performance and the yoke 184 has made contact with ears 134 and 136 of drive member 324 (FIG. 4) then the control system will have detected this motor engaged condition as described in conjunction with FIG. 51 and the motor is de-energized as represented at line 1450 in FIG. 69. Correspondingly, as discussed in connection with line 1454 in that figure, the electrosurgical generator function is turned on with boost voltage. Preferably that boost output is applied for three-eighths second as represented at line 1590 and block 1592. Commencement of timing of the 0.375 second interval is represented at line 1594 and block 1596. Determination of the 0.375 second interval is made as represented at line 1598, block 1600 and loop line 1602. At the termination of this 0.375 second interval, an affirmative determination is made as represented at line 1604 which is seen to lead to block 1606. At this point in the procedure, as described at dashed line 1458 and FIG. 69, normal cutting voltage is applied to the cables of the capture component and the motor assembly 170 is energized to start the deployment of the capture component, ears 134 and 136 being driven forwardly by yoke 184. This procedure normally continues with the earlier-noted motor current monitoring (FIG. 51) until capture is complete. However, should the motor current level fall below the motor engaged threshold established as described in connection with FIG. 51, then a fault condition is indicated and the procedure is halted. In this regard, loss of load related motor current levels is an indication of mechanical failure.

As represented at line 1608 and block 1610 the practitioner may encounter some reason for pausing this capture procedure. Accordingly, if an affirmative determination is made with respect to the query posed at block 1610, then as represented at line 1612 and block 1614 a pause mode is entered. This pause mode is entered by releasing the previously depressed footswitch 86*c* or handle button 56. The pause LED 104 on console 64 then is illuminated.

At such time as the practitioner is ready to resume the cutting capture procedure, either start capture switch button 56 or the footswitch 86*c* again is depressed returning to the capture mode. At the initial release of either of the capture switches to enter the pause mode, the yellow LED outputs adjacent the start capture switch 56 and LED 100 will have been illuminated in a flashing or intermittent fashion. Accordingly, following a reactivation from a pause mode, as represented at lines 1616, the capture mode is again underway as represented at line 1608. Where no pause mode is entered, then, as represented at line 1618 and block 1620 the system looks for the presence of a forward motor stall condition as described in connection with FIG. 52. As represented at the loop line 1622 extending to line 1608, the motor assembly 170 and pursing cables 300–304 continue to be energized until the forward stall is detected, such detection being represented at line 1624. Upon such detection of a forward stall condition, as represented at block 1626, a capture complete mode is entered, the capture of the target tissue or tissue volume being completed and the electrosurgical cutting voltage is terminated.

Motor assembly 170 then automatically reverses to return the yoke 184 to its home position. Additionally, green LED outputs positioned forwardly of switch 56 on housing 14 are illuminated as well as green LED 102 on console 64. Next, as represented at line 1628 and block 1630 a query is posed as to whether a reverse stall current threshold limit has been reached. Detection of this stall condition is described in connection with FIG. 53. Accordingly, as the motor is energized in reverse, the system awaits that stall condition as represented at loop line 1632. Upon an affirmative determination that the reverse stall condition is at hand, as represented at line 1634 and block 1636, the practitioner removes the delivery cannula 22 from the patient by appropriate manipulation of housing assembly 14. During this removal, some stretching of the tissue typically will be encountered with little or no disfigurement ensuing.

Next, as represented at line 1638 and block 1640 locking nut 24 is unscrewed and the vacuum equipment is disconnected, plug 41 being inserted into connector 40 (FIG. 1). Then, as represented at line 1642 and block 1644, as discussed in connection with FIG. 30, the practitioner retracts ears 134 and 136 to a position shown adjacent latches 336 and 338 to establish a specimen access orientation with the leafs. That containment orientation resembles a cup or basket (FIG. 30). Then, as represented at line 1646 and block 1648, the tissue specimen is placed in a container with appropriate solution for transport and storage in preparation for examination by a pathologist. As represented at line 1650 and block 1652 the specimen is transported to a pathology laboratory.

An optional arrangement is represented at line 1654 and block 1656. The latter block provides for placing a radio-opaque and/or echogenic marker in the tissue at the site of the biopsy and verifying the position thereof using radiography or ultrasonography. Then, as represented at line 1658 and block 1660 the skin incision is closed using appropriate conventional closure techniques.

Since certain changes may be made in the above method, system and apparatus without departing from the scope of the invention herein involved, it is intended that all matter contained in the above description or shown in the accompanying drawings shall be interpreted as illustrative and not in a limiting sense.

What is claimed is:

1. Apparatus for retrieving a tissue volume of given peripheral extent, comprising:
    a delivery cannula having an outer surface surmounting an interior channel and extending from a proximal end portion along a longitudinal axis to a forward region having a distal end positionable in confronting adjacency with said tissue volume;
    a capture component positioned within said delivery cannula interior channel at said forward region, having a forward portion extending to a forwardly disposed pursing cable assembly energizable to define an electrosurgical cutting leading edge portion, and including at least one tensionable cable extending from said pursing cable assembly into said inner channel, said leading edge of said forward portion being extendable from said delivery cannula laterally outwardly and forwardly toward an outer peripheral dimension having a predetermined diametric extent effective to provide a circumspective positioning about said tissue volume peripheral extent and subsequently extendable while being drawn in contraction toward said axis by stress at said pursing cable assembly to a capture orientation enveloping said tissue volume;
    a housing assembly having forward and rearward portions and coupled in supporting relationship with said delivery cannula at said proximal end portion;
    a drive assembly extending from driving engagement with said capture component to a driven engagement portion at said housing assembly and drivably movable along said axis from a start orientation to a capture position corresponding with said capture orientation; and
    an actuator and control assembly drivably engageable with said drive assembly to effect said movement thereof, responsive to control said drive assembly movement in correspondence with said stress exhibited by said cable and including a terminal assembly for effecting said energization of said pursing cable assembly.

2. The apparatus of claim 1 in which said actuator and control assembly comprises a cable terminator component coupled with said cable and a cable stop member engageable therewith, said cable terminator component being drivably movable by said cable along said axis in correspondence with said drive assembly movement, from an initial position into engagement with said cable stop member to define said capture component forward portion leading edge peripheral dimension of predetermined diametric extent and to effect said subsequent contraction thereof by said pursing cable assembly.

3. The apparatus of claim 1 comprising a drive stop assembly engageable with said drive assembly driven engagement portion and positioned to limit said movement along said axis beyond said capture position.

4. The apparatus of claim 1 including a precursor electrosurgical electrode assembly supported forwardly from said delivery cannula distal end and having a tissue encountering and severing portion generally extending normally to said longitudinal axis and configured to facilitate the said positioning of said distal end in said confronting adjacency with said tissue volume.

5. The apparatus of claim 4 including an arc isolating and electrically insulative member mounted at said delivery cannula distal end rearwardly of said precursor electrosurgical electrode assembly tissue encountering and severing portion.

6. The apparatus of claim 4 in which said tissue encountering and severing portion has an effective length less than but corresponding with said capture component predetermined diametric extent.

7. The apparatus of claim 4 in which said precursor electrosurgical electrode assembly tissue encountering and severing portion is configured as four discrete severing portions arranged generally in quadrature about said longitudinal axis.

8. The apparatus of claim 1 further comprising:
an elongate support member extending within said delivery cannula along said longitudinal axis from said forward region into said housing assembly and secured thereto adjacent said rearward portion, and
said drive assembly is positioned over said support member and includes a drive member located within said housing assembly, and engageable with said actuator and control assembly to move from said start orientation along a capture region to a said capture position and including a positioning component configured for slidable engagement with portions of said housing assembly.

9. The apparatus of claim 8 comprising a drive stop assembly abuttably engageable with said drive member and positioned to limit said movement along said axis beyond said capture position.

10. The apparatus of claim 8 in which said drive assembly comprises a latch assembly mounted within said housing assembly within said capture region and engageable with said drive member to limit a movement thereof along said longitudinal axis toward said rearward portion to a return position located forwardly from said start orientation.

11. The apparatus of claim 8 in which said drive assembly drive member positioning component extends outwardly from said housing assembly portions to an extent wherein it is abuttably engageable in driven relationship with said actuator and control assembly.

12. The apparatus of claim 11 in which said positioning component is configured for hand grasping to carry out movement of said drive member from a said capture position toward said start orientation.

13. The apparatus of claim 8 in which said actuator and control assembly comprises:
a cable terminator component mounted for movement upon said support member and coupled with said cable;
a cable stop member fixed to said support member at a predetermined stop position and abuttably engageable with said cable terminator component; and
said cable terminator component being drivably moveable by said cable from an initial position along said axis into engagement with said cable stop member at said stop position to define said capture component forward portion leading edge peripheral dimension of predetermined diametric extent.

14. The apparatus of claim 13 comprising a drive stop assembly abuttably engageable with said drive member and positioned to limit said movement along said axis beyond said capture position.

15. The apparatus of claim 13 in which:
said actuator and control assembly terminal assembly includes an electrical contact assembly mounted within said housing assembly and coupled in electrical communication with said capture component cable.

16. The apparatus of claim 15 in which:
said delivery cannula, said capture component, said support member, said drive assembly, said cable terminator component, said cable stop member and said electrical contact assembly are combined in operational association with a support housing configured for operative association with a housing component of said housing assembly to provide a discrete removable component of said apparatus.

17. The apparatus of claim 1 in which:
said capture component forward portion comprises:
a plurality of discrete cage defining leafs, each having a tip portion and a width and thickness between sides which are generally parallel with said longitudinal axis,
a guidance assembly fixed to said delivery cannula at said forward region and configured to effect deployment of said leafs into tissue at a predetermined angle of attack, and
said leaf thickness is of an extent effecting formation of a generally curvilinear cage periphery when said capture component forward portion is subsequently extended while being drawn in contraction toward said axis.

18. The apparatus of claim 17 in which:
each said leaf is formed of metal; and
each said leaf includes an electrically insulative coating having a thickness in a range of about 0.00025 inch to about 0.005 inch.

19. The apparatus of claim 17 in which:
each said leaf is formed of metal; and
each said leaf includes an electrically insulative coating having a thickness in a range of about 0.0005 inch to about 0.0025 inch.

20. The apparatus of claim 17 in which:
said leaf width is of an extent effective to provide extensional cage defining stable movement of said leafs through said guidance assembly along said plane extending through said longitudinal axis.

21. The apparatus of claim 17 in which:
said tip portions of said leafs incorporate apertures dimensioned to receive said flexible pursing cable assembly in slideable relationship;
said pursing cable assembly is comprised of a number of discrete cables, each passing through a predetermined number of said apertures and having a forward end fixed to the tip portion of a said leaf; and
the said number of discrete cables is selected with respect to the number of said leafs to derive the shape of said curvilinear cage periphery.

22. The apparatus of claim 21 in which each said leaf having a said aperture through which a said discrete cable initially extends includes a cable guide fixed to said leaf and into which said discrete cable extends.

23. The apparatus of claim 22 in which said cable guide comprises a flexible polymeric tube.

24. The apparatus of claim 22 in which said capture component comprises five said leafs and five said discrete cables.

25. The apparatus of claim 1 in which said delivery cannula includes an evacuation channel connectable with a vacuum source and extending from said proximal end portion to at least one suction port at said forward region, and including an outwardly extending continuous steam migration block surrounding said cannula adjacent said port.

26. Apparatus for retrieving a tissue volume of given peripheral extent, comprising:

a delivery cannula having an outer surface surmounting an interior channel and extending from a proximal end portion along a longitudinal axis to a forward region having a distal end positionable in confronting adjacency with said tissue volume;

a capture component positioned within said delivery cannula interior channel, having a forward portion extending to a forwardly disposed electrically conducting electrosurgical cutting leading edge portion and being extendible toward an outer peripheral dimension effective for the circumscriptive engagement of said tissue volume peripheral extent when moved along said longitudinal axis to egress from said delivery cannula:

a housing assembly having forward and rearward portions and coupled in supporting relationship with said delivery cannula at said proximal end portion;

a drive assembly including a drive component extending from driving engagement with said capture component within said delivery cannula interior channel into said housing and having a drive member with a driven surface fixed to said drive component in driving relationship, said drive member being movable along said axis from a start orientation to a capture position;

an actuator assembly within said housing including an elongate rotational translation component located in generally parallel relationship with said drive assembly, fixed for rotation at said housing forward portion and extending rearwardly therefrom to a self-aligning coupling assembly having a forward driving connection portion coupled therewith and an rearward driven connection portion, a motor assembly having a rotational drive output coupled in driving relationship with said coupling assembly rearward driven connection portion, said motor assembly being mounted in self-aligning confinement within said housing assembly, having nonrotational freedom of movement extending from said coupling assembly and being actuable to drive said translation component from said coupling assembly;

a transfer assembly mounted in driven relationship with said rotational translation component having a home position in association therewith and having an engaging portion engagable in driving relationship with said drive member driven surface to effect movement of said drive member along said axis when said motor assembly is actuated; and a terminal assembly responsive to an applied control input for effecting the application of electrosurgical cutting current to said capture component leading edge portion.

27. The apparatus of claim 26 in which said transfer assembly engaging portion is configured for freely abutting contact with said drive assembly drive member driven surface.

28. The apparatus of claim 26 in which:

said transfer assembly is movable by said translation component from a home position toward said housing forward portion when said motor assembly is actuated, said movement being carried out until said drive member arrives at a capture completing location along said longitudinal axis effecting a forward stall condition of said motor assembly.

29. The apparatus of claim 28 in which:

said motor assembly is responsive to reverse its rotational drive output in the presence of said forward stall condition to effect the return of said transfer assembly to said home position by said translation component.

30. The apparatus of claim 29 further comprising a drive stop assembly engageable with said drive member at a location forwardly beyond said capture position to limit said movement along said axis.

31. The apparatus of claim 29 in which:

said motor assembly is responsive to terminate its rotational drive output in the presence of a reverse stall condition.

32. The apparatus of claim 26 in which said coupling assembly of said actuator assembly comprises:

a coupling chamber within said housing;

a coupler extending through said coupling chamber and connected between said rotational translation component and said motor assembly rotational drive output; and a fluid seal surmounting said coupler within said coupling chamber.

33. The apparatus of claim 26 in which said coupling assembly comprises a torsionally rigid and axially flexible coupler connected between said rotational translation component and said motor assembly rotational drive output.

34. The apparatus of claim 33 in which said coupler is configured as a bellows.

35. The apparatus of claim 33 in which said coupler is a U-joint coupling.

36. The apparatus of claim 26 in which said coupler is an elastomeric tube.

37. The apparatus of claim 33 in which said rotational translation component is configured with helical threads and is rotatably coupled in stress transfer relationship with said housing forward portion through a thrust bearing.

38. The apparatus of claim 26 in which:

said delivery cannula, said capture component, said drive assembly and an electrical contact assembly component of said terminal assembly coupled electrically with said capture component leading edge portion are combined in operational association with a support housing configured for operative association with a housing component of said housing assembly to provide a discrete removable component of said apparatus; and said housing incorporates a receiving region extending rearwardly from said housing forward portion and configured for receiving said support housing in an operational association wherein, when said support housing is installed at said receiving region, said electrical contact assembly is in electrical communication with said terminal assembly, and said transfer assembly is at said home position and oriented for engagement with said drive member driven surface.

39. The apparatus of claim 38 in which:

said drive assembly includes an elongate support member extending within said delivery cannula interior channel along said longitudinal axis into said support housing;

said drive component and said drive member are mounted for movement along said support member; and said drive member driven surface extends outwardly from said support housing and is configured for manual grasping and movement toward said start orientation from said capture position.

40. The apparatus of claim 39 in which said drive assembly includes a latch assembly mounted within said support housing forwardly from said drive member start orientation to limit rearward movement thereof.

41. A system for carrying out a procedure for retrieving a tissue volume, comprising:

a delivery cannula having an outer surface surmounting an interior channel and extending from a proximal end portion along a longitudinal axis to a forward region having a distal end positionable in confronting adjacency with said tissue volume;

a capture component positioned within said delivery cannula interior channel at said forward region having a containment structure extending to a forwardly disposed pursing cable assembly energizable to define an electrosurgical cutting leading edge, said containment structure being extensible from said forward region at an angle of attack with respect to said axis to define an outer periphery having a dimension effective for the circumscriptive engagement of said tissue volume and subsequently extendable while said leading edge is drawn in contraction toward said axis by a pursing stress applied to said pursing cable assembly;

a housing assembly coupled in supporting relationship with said delivery cannula at said proximal end portion;

a drive assembly including a drive component extending from driving engagement with said containment structure within said delivery cannula into said housing and having a drive member with a driven surface fixed to said drive component in driving relationship, said drive member being movable along said axis from a start orientation to a capture position a translation component within said housing located in generally parallel relationship with said drive assembly, responsive to a rotational drive input to provide a translation drive output;

a transfer assembly within said housing, coupled in driven relationship with said translation drive output, having a home position, having an engaging portion engagable in driving relationship with said drive member driven surface to effect movement of said drive member along said axis;

a motor within said housing for providing said rotational drive input to said translation component, having load current characteristics, responsive to a forward input to provide a forward said rotational drive input and to a reverse input to provide a rearward said rotational drive input;

an electrosurgical generator having an output connectable with said capture component pursing cable assembly and responsive to an energize input to provide electrosurgical cutting energy having a voltage level at said output; and a control assembly connected with said motor and said electrosurgical generator, responsive to a capture input to provide said energize input to said electrosurgical generator and effect application of said electrosurgical cutting energy to said pursing cable assembly and to provide said forward input to said motor, responsive to terminate said forward input when a said motor load characteristic corresponds with the presence of said drive member at said capture position.

42. The system of claim 41 in which:

said control assembly is responsive to provide said reverse input to said motor when said motor load characteristic corresponds with the presence of said drive member at said capture position.

43. The system of claim 42 in which said control assembly is responsive to terminate said reverse input when said motor load characteristic corresponds with said transfer assembly reaching said home position.

44. The system of claim 43 in which said transfer assembly engaging portion is engageable in freely abuttable driving relationship with said drive member driven surface and releases from said engagement in the presence of said reverse input to said motor when said motor load characteristic corresponds with the presence of said drive member at said capture position.

45. The system of claim 41 in which said control assembly is responsive to a start procedure input occurring prior to said capture input to provide said reverse input to said motor and subsequently is responsive to terminate said reverse input when said motor load characteristic corresponds with the presence of said transfer assembly at said home position.

46. The system of claim 45 in which said control assembly is responsive at the said termination of said reverse input when said motor load characteristic corresponds with the presence of said transfer assembly at said home position to provide said forward input to said motor for an interval effective to reduce stress at said motor and said transition component.

47. The system of claim 41 further comprising:

a drive stop assembly engageable with said drive member at a location forwardly beyond said capture position to terminate said movement along said axis; and said control assembly is responsive to a forward stall said motor load characteristic when said drive member engages said drive stop assembly to terminate said forward input to said motor.

48. The system of claim 41 in which:

said transfer assembly engaging portion is spaced from said drive member driven surface a preliminary drive distance when said drive member is at said start orientation and said transfer assembly is at said home position; and said control assembly is responsive to said capture input to provide a test said forward input to said motor for a predetermined test interval occurring prior to said provision of said energize input to said electrosurgical generator is responsive to halt said procedure when said motor load characteristic exceeds a predetermined low load threshold value.

49. The system of claim 48 in which said control assembly is responsive to a said load characteristic corresponding with a driving engagement of said transfer assembly engaging portion with said drive member driven surface to terminate the test said forward input to said motor.

50. The system of claim 41 in which:

said electrosurgical generator is responsive to a boost said energize input to provide said electrosurgical cutting energy at an arc initiating boost said voltage level effective to initiate an arc when said electrosurgical cutting leading edge is in contact with tissue; and said control assembly is responsive to said capture input to provide said energize input to said electrosurgical generator as a boost energize input for a boost interval.

51. The system of claim 41 comprising:

a precursor electrosurgical electrode assembly having a precursor input, supported forwardly from said delivery cannula distal end and having a tissue encountering and severing portion generally extending normally to said longitudinal axis and energizable with said cutting energy to facilitate the positioning of said distal end in confronting adjacency with said tissue volume;

said electrosurgical generator is responsive to a boost said energize input to provide said electrosurgical cutting energy at an arc initiating boost voltage level effective to initiate an arc when said tissue encountering and severing portion is in contact with tissue; and said control assembly is responsive to a position input to provide said energize input to said electrosurgical generator and effect application of said electrosurgical energy to said precursor input at said boost voltage level for a boost interval.

52. The system of claim 41 in which:

said electrosurgical generator is responsive to a cut said energize input to provide said electrosurgical cuffing energy at a cut said voltage level and is responsive to a boost said energize input to provide said electrosurgical cutting energy at a boost said voltage level greater than said cut voltage level; and said control assembly is responsive to said capture input to provide said energize input to said electrosurgical generator as a boost energize input for a boost start-up interval and to provide said energize input as a cut energize input at the termination of said boost interval.

53. The system of claim 52 comprising:

a precursor electrosurgical electrode assembly having a precursor input, supported forwardly from said delivery cannula distal end and having a tissue encountering and severing portion generally extending normally to said longitudinal axis and energizable with said cutting energy to facilitate the positioning of said distal end in confronting adjacency with said tissue volume; and said control assembly is responsive to a position input to provide said energize input to said electrosurgical generator and effect application of said electrosurgical cutting energy to said precursor input as a boost energize input for a boost interval and to provide said energize input as a cut energize input at the termination of said boost interval.

54. The system of claim 41 including:

a precursor electrosurgical electrode assembly having a precursor input, supported forwardly from said delivery cannula distal end and having a tissue encountering and severing portion extending normally to said longitudinal axis and outwardly from said outer surface a distance selected in correspondence with said capture component outer periphery and located for circuit completing contacting engagement with said capture component pursing cable assembly when said containment structure is extended from said forward region of said delivery cannula; and said control assembly is responsive to a position input to provide said energize input to said electrosurgical generator and to connect said electrosurgical cutting energy to said precursor input, is responsive to the removal of said position input to disconnect said electrosurgical cutting energy from said precursor input to enable the application of electrosurgical cutting energy thereto from said capture component pursing cable assembly.

55. The system of claim 41 in which said control assembly includes a manually actuable tissue capture switch and a footswitch actuable between off and on conditions, said control assembly being responsive to actuation of said tissue capture switch or said footswitch to said on condition to derive said capture input.

56. The system of claim 55 in which said control assembly tissue capture switch is mounted upon said housing.

57. The system of claim 55 in which said control assembly is responsive to an actuation of said tissue capture switch or said footswitch to said off condition in the presence of said capture input to terminate said capture input and enter a pause mode.

58. The system of claim 57 in which said control assembly includes a pause indicator component energizable to provide a perceptible output in the presence of said pause mode.

59. The system of claim 41 in which said control assembly includes a tissue capture switch actuable between off and on conditions, and an arm switch actuable between off and on conditions, said control assembly being responsive to actuation of said arm switch to said on condition to derive an arm capture mode, and being responsive to said actuation of said tissue capture switch to said on condition to derive said capture input in the presence of said arm capture mode.

60. The system of claim 59 in which said control assembly includes an arm capture output indicator component energizable to provide a perceptible output in the presence of said arm capture mode.

61. The system of claim 59 in which:

said capture component containment structure leading edge is drawn in said contraction toward said axis by a said pursing stress applied to said pursing cable assembly effective to derive a capture complete status terminating said contraction; and said control assembly includes a capture complete indicator component energizable to provide a perceptible output in the presence of said capture complete status.

62. The system of claim 59 in which said control assembly is responsive to an actuation of said tissue capture switch to said off condition to terminate said capture input and enter a pause mode.

63. The system of claim 62 in which said control assembly is responsive to an actuation of said tissue capture switch to said on condition when in said pause mode to derive said capture input.

64. The system of claim 59 in which said tissue capture switch and said arm switch are mounted upon said housing.

65. The system of claim 59 including:

a precursor electrosurgical electrode assembly having a precursor input, supported forwardly from said delivery cannula distal end, having a tissue encountering and severing portion extending normally to said longitudinal axis and configured to facilitate the positioning of said distal end in said confronting adjacency with said tissue volume; and said control assembly includes a position switch manually actuable to provide a position input, said control assembly being responsive to said position input in the absence of said arm capture mode to provide said energize input to said electrosurgical generator and to connect said electrosurgical cutting energy to said precursor input.

66. The system of claim 59 including:

a precursor electrosurgical electrode assembly having a precursor input, supported forwardly from said delivery cannula distal end, having a tissue encountering and severing portion extending normally to said longitudinal axis and configured to facilitate the positioning of said distal end in said confronting adjacency with said tissue volume; and said control assembly includes a position switch as a footswitch actuable in the absence of said arm capture mode to provide said energize input to said electrosurgical generator and to connect said electrosurgical cutting energy to said precursor input.

67. The system of claim 65 in which said tissue capture switch, said arm switch and said position switch are mounted upon said housing.

68. The system of claim 65 in which said tissue capture switch, said arm switch and said position switch are configured as footswitches.

69. The system of claims 67 or 68 in which said position switch is located intermediate said tissue capture switch and said arm switch.

70. The system of claim 41 in which said control assembly is responsive to provide said forward input to said motor when said transfer assembly engaging portion is drivably engaged with said drive member and effecting its said movement along said axis in the presence of a said motor load characteristic exceeding a predetermined motor engaged threshold value.

71. The system of claim 41 in which said control assembly is responsive to halt said procedure when said transfer assembly engaging portion is drivably engaged with said drive member and effecting its said movement along said axis in the absence of a said motor load characteristic exceeding a predetermined motor engaged threshold value.

72. The system of claim 41 in which said control assembly is responsive to provide a said forward input to said motor providing said rotational drive input to said translation component effecting said movement of said drive member along said axis by said transfer assembly at a rate of from about one millimeter per second to ten millimeters per second.

73. The system of claim 41 in which said control assembly is responsive to provide said forward input to said motor providing said rotational drive input to said translation component effecting said movement of said drive member along said axis by said transfer assembly at a rate of from about two and one-half millimeters per second to four millimeters per second.

74. The system of claim 41 comprising:
   a vacuum generating assembly having a vacuum port and actuable to generate a vacuum at said vacuum port effective for the collection of electrosurgically caused smoke and steam;
   said delivery cannula includes an evacuation channel having an evacuation input at said proximal end portion and extending to at least one suction port at said forward region;
   a vacuum conduit coupling said vacuum port with said evacuation input in vacuum deriving association;
   a vacuum responsive switch responsive to the presence of a vacuum condition generated at said vacuum port for providing a vacuum signal; and
   said control assembly is responsive in the presence of said vacuum signal to said capture input.

75. A system for retrieving a tissue volume, comprising:
   a delivery cannula having an outer surface surmounting an interior channel and extending from a proximal end portion along a longitudinal axis to a forward region, having a distal end positionable in confronting adjacency with said tissue volume;
   a capture component positioned within said delivery cannula interior channel, having a forward portion extending to a forwardly disposed electrically conducting electrosurgical cutting leading edge portion extendable outwardly from said delivery cannula forward portion to establish an outer peripheral dimension selected for the circumscriptive engagement of said tissue volume and subsequently extendable while being drawn in contraction toward said longitudinal axis to a capture orientation;
   a deployment assembly extending within said interior channel, drivably coupled with said capture component and controllable to effect said extension of said capture component and including an input assembly for transmitting an electrical cutting energy input to said leading edge portion;
   an electrosurgical generator connectable with a power input, including:
   an input treatment network responsive to said power input to derive an interim voltage output of first value;
   a first inverter network responsive to said interim voltage and to a first inverter control input to derive a first alternating voltage output of second value less than said first value at a first inverter output;
   a first inverter control network coupled with said first inverter network and deriving said first inverter control input;
   a rectifier network responsive to said first alternating voltage output to derive a link output at a d.c. voltage level corresponding with said first alternating voltage output second value;
   a second inverter network having an input, and responsive to said link output to derive a second alternating voltage output at an electrosurgical frequency value and with voltage amplitudes established by said link output d.c. voltage level;
   a second inverter control network coupled with said second inverter network to effect derivation of said second alternating voltage output electrosurgical frequency;
   a high voltage transformer having a primary side responsive to said second alternating voltage output and a secondary side deriving said electrical cutting energy input at an electrosurgical voltage level and at said electrosurgical frequency; and
   an output stage coupled with said high voltage transformer secondary side and connectable in electrical communication with said input assembly of said deployment assembly.

76. The system of claim 75 in which said first inverter control network derives said first inverter control input to effect a resonant transition phase shift control of said first inverter.

77. The system of claim 75 in which said first inverter control network comprises:
   a voltage monitoring circuit responsive to said electrical cutting energy input to derive a program signal; and
   a controller network responsive to said program signal to derive said first inverter control input.

78. The system of claim 75 comprising:
   a high voltage monitor responsive to said electrical cutting energy input to derive a high voltage monitor signal; and
   said first inverter control network comprises:
   a comparator network responsive to a predetermined electrosurgical cutting voltage level and to said high voltage monitor signal to derive a program signal; and
   a controller network responsive to said program signal to derive said first inverter control input.

79. The system of claim 78 in which said controller network is configured derive said first inverter control input as a slowly applied said program signal.

80. The system of claim 79 in which said first inverter control network comprises:
a link voltage monitor responsive to said link output to provide a link voltage controlling feedback signal; and
said controller network is further responsive to said link voltage controlling feedback signal to derive said first inverter control input.

81. The system of claim 75 comprising:
a control assembly actuable to derive a boost voltage signal for a boost interval; and
said first inverter control network is responsive to said boost voltage signal to derive a said first inverter control input effecting derivation of said first alternating voltage output second value at a boost voltage value, and is responsive thereafter to derive said first inverter control input effecting derivation of said first alternating voltage output second value at a normal cut voltage value less than said boost voltage value.

82. The system of claim 81 in which said boost voltage valve is greater than said normal cut voltage value by a factor within a range from about 1.2 to about 1.5.

83. The system of claim 75 including an isolation transformer having a primary side coupled with said first alternating output and a secondary side providing said first alternating voltage output to said rectifier network.

84. The system of claim 75 in which said second inverter network comprises a resonant tank circuit.

85. The system of claim 81 in which said boost interval is about 100 to 1000 milliseconds.

86. The system of claim 81 in which said boost interval is about 250 to 750 milliseconds.

87. The system of claim 81 in which said boost voltage value effects derivation of a said select electrosurgical cutting voltage level of about 1000 volts peak-to-peak to about 2000 volts peak-to-peak.

88. The system of claim 81 in which in which said boost voltage value effects derivation of a said select electrosurgical cutting level of about 1100 volts, peak-to-peak to about 1300 volts, peak-to-peak.

89. The system of claim 87 in which said normal cut voltage value effects derivation of said select electrosurgical cutting voltage level of about 700 volts, peak-to-peak to about 1200 volts, peak-to-peak.

90. The system of claim 88 in which said normal cut voltage value effects derivation of said select electrosurgical cutting voltage level of about 800 volts, peak-too-peak to about 1000 volts, peak-to-peak.

91. The system of claim 75 in which said input treatment network comprises:
a boost converter network responsive to a converter control input to derive said interim voltage of first value; and
a converter control network responsive to said power input and to said interim voltage first value to derive a said converter control input effective to provide power factor correction.

92. The system of claim 75 comprising:
a relay switch connected between said rectifier network and said second inverter network input and responsive to a relay control input to convey or terminate conveyance of said link output to said second inverter network; and
a control assembly responsive to a fault condition to derive a said relay control input terminating conveyance of said link output to said second inverter network input.

93. The system of claim 92 in which:
said first inverter control network comprises a power monitoring circuit responsive to said electrical cutting energy input to derive a power signal corresponding with the level of power exhibited by said electrical cutting energy input; and
said control assembly is responsive to derive a said relay control input terminating said conveyance of said link output when said power signal exceeds a power threshold level.

94. The system of claim 92 comprising:
a high voltage monitor responsive to said electrical cutting energy input to derive a high voltage monitor signal; and said control assembly is responsive to derive a said relay control input terminating said conveyance of said link output when said high voltage monitor signal exceeds a high voltage threshold level.

95. The system of claim 92 comprising:
a high voltage current monitor responsive to said electrical cufting energy input to derive a high voltage current monitor signal; and
said control assembly is responsive to derive a said relay control input terminating said conveyance of said link output when said high voltage current monitor signal exceeds a current threshold level.

96. The system of claim 92 comprising:
a link voltage monitor responsive to said rectifier network link output to derive a link monitor signal corresponding with said link output d.c. voltage level; and
said control assembly is responsive to derive a said relay control input terminating said conveyance of said link output when said link monitor signal corresponds with a said link output d.c. voltage level which exceeds a link over-voltage threshold level.

97. The system of claim 96 in which said control assembly is responsive to derive said relay control input terminating said conveyance of said link output when said link monitor signal corresponds with a said link output d.c. voltage level which is below a predetermined under-voltage threshold level.

98. Apparatus for retrieving a tissue volume, comprising:
a delivery cannula having an outer surface surmounting an interior channel and extending from a proximal end portion along a longitudinal axis to a forward region having a distal end positionable in confronting adjacency with said tissue volume;
a capture component positioned within said delivery cannula at said forward region, having a forward portion comprising a plurality of leafs having widths and thicknesses effective for lateral stability and flexure, each leaf having a length extending from a base portion to said forward portion and having a tip portion, each said tip portion having a pursing eyelet, a retainer groove extending along the length of each said leaf, a cable guide fixed to each said leaf at said retainer groove, the base portions of said leafs being interconnected to define a tube structure base supporting forwardly extending discrete said leafs at said forward portion, a pursing cable assembly comprised of a plurality of discrete electrically conductive cables each slideably extending through a said cable guide and an associated said pursing eyelet and from said pursing eyelet extending to and connected to the tip portion of a next adjacent said leaf, a guidance assembly fixed to said delivery cannula at said forward region and configured to effect deployment of said leafs mutually outwardly from said longitudinal axis;

a housing assembly coupled in supporting relationship with said delivery cannula at said proximal end portion;

a drive assembly including a drive rod connected with said capture component tube structure base within said delivery cannula interior channel and extending into said housing assembly, said drive rod being drivably movable along said axis to effect extension of said leaf forward portions and associated said cables mutually outwardly from said guidance assembly to establish a periphery of predetermined effective diametric extent defined by said tip portions, thereafter said drive assembly controlling movement of said cables while said drive rod is moved along said axis to effect a mutually inward flexure of said leaf tip portions to a capture orientation for enveloping said tissue volume; and an actuator and control assembly drivably engagable with said drive assembly to effect movement of said drive rod and to effect electrosurgical cutting energization of said cables.

99. The apparatus of claim 98 in which each said leaf is coated with a vitreous material.

100. The apparatus of claim 98 in which each said leaf is coated with an electrically insulative material.

101. The apparatus of claim 98 in which each said leaf is coated with an electrically insulative polymeric material.

102. The apparatus of claim 98E in which each said cable guide is a flexible metal tube coated with an electrically insulative material.

103. The apparatus of claim 98 in which each said leaf is coated with a vapor-phase-polymerized conformal coating.

104. The apparatus of claim 98 in which each said cable guide is fixed to each said leaf with a vapor-phase-polymerized conformal coating.

105. The apparatus of claim 98 in which each said cable guide is an electrically insulative guide tube fixed to each said leaf with a vapor-phase-polymerized conformal coating.

106. The apparatus of claim 105 in which said conformal coating is poly-para-xylene.

107. The apparatus of claim 105 in which said conformal coating has a thickness of from about 0.0002 inch to about 0.003 inch.

108. The apparatus of claim 105 in which said conformal coating has a thickness of from about 0.00075 inch to about 0.00125 inch.

109. The apparatus of claim 105 in which each said guide tube is formed of a polyamide.

110. The apparatus of claim 98 in which each said leaf tip portion is bent generally normally to the widthwise extent of the leaf.

111. The apparatus of claim 98 in which said leafs are formed of stainless steel having a said thickness of about 0.003 inch.

112. The apparatus of claim 98 in which said leafs are formed of stainless steel and have a said width of about 0.080 inch.

113. The apparatus of claim 98 in which each one of said discrete cables is formed of a multi-strand braided stainless steel.

114. The apparatus of claim 98 in which each one of said discrete cables has a diameter within a range from about 0.002 inch to about 0.020 inch.

115. The apparatus of claim 113 in which each one of said discrete cables has a diameter of about 0.005 inch.

116. The apparatus of claim 98 in which:

said capture component tube structure base exhibits a polygonal cross-section with mutually inwardly facing surfaces; and said drive assembly drive rod extends within said tube structure and is attached thereto.

117. In a system for retrieving a tissue volume wherein a re-usable component is provided having a re-usable housing connected in electrical communication with an electrosurgical generator and control assembly and having a receiving region for receiving a replaceable component extending about a longitudinal region axis rearwardly from a forward portion, a motor assembly within said re-usable housing coupled in driving association with a translation component, a transfer assembly within said re-usable housing coupled in driven relationship with said translation component and having a transfer yoke with oppositely disposed drive surfaces movable forwardly and rearwardly in parallel with said region axis in adjacency with said receiving region from and to a home position, and an input terminal assembly within said re-usable housing at a location adjacent said receiving region connectable in said electrical communication with said electrosurgical generator, an improved replaceable component, comprising;

a support housing dimensioned for removable operative association with said re-usable housing when at an operative position within said receiving region, said support housing having rearward and forward portions and disposed about said longitudinal region axis when positioned within said receiving region;

a delivery cannula having an outer surface surmounting an interior channel and extending from a proximal end portion fixed to said support housing forward portion along a longitudinal cannula axis to a forward region having a distal end positionable in confronting adjacency with said tissue volume;

a capture component positioned within said delivery cannula interior channel at said forward region, having a forward portion extending to a forwardly disposed pursing cable assembly energizable to define an electrosurgical cutting leading edge portion, and including at least two tensionable cables extending from said pursing cable assembly into said inner channel, said leading edge of said expansible forward portion being extendable from said delivery cannula laterally outwardly and forwardly toward an outer peripheral dimension having a predetermined diametric extent effective to provide a circumspective positioning about said tissue volume and subsequently extendable while being drawn in contraction toward said cannula axis by stress at said pursing cable assembly to a capture orientation enveloping said tissue volume;

a drive assembly including a drive rod connected in driving relationship with said capture component and extending to driven connection with a drive member within said support housing and movable therein from a start position along said cannula axis, said drive member having oppositely disposed ears extending outwardly from said support housing, each having a driven surface abuttably engageable with said transfer yoke drive surfaces when said support housing is at said operative position;

an elongate support member mounted within said support housing and extending along said cannula axis to said rearward region and slidably supporting said drive member;

a cable stop member fixed to said support member at a stop position deriving said capture component forward portion outer peripheral dimension;

a cable terminator component mounted for movement upon said support member, coupled with and drivably movable by said cables from an initial position into engagement with said cable stop member at said stop position; and an electrical contact assembly mounted upon said housing electrically coupled with said cables and engaged with said reusable housing contained input terminal assembly when said support housing is at said operative position.

118. The system of claim 117 in which:

said support housing is configured with oppositely disposed elongate drive slots at said forward portion; and said drive member oppositely disposed ears slidably extend through said drive slots.

119. The system of claim 117 in which:

said support housing is configured with oppositely disposed stabilizer slots at said rearward portion; and said cable terminator component is configured with oppositely disposed tabs extending within and slidable along said stabilizer slots.

120. The system of claim 117 including:

a precursor electrosurgical electrode assembly supported forwardly from said delivery cannula distal end and having a tissue encountering and severing portion generally extending normally to said cannula axis and configured to facilitate the said positioning of said distal end in said confronting adjacency with said tissue volume; and an electrical connector coupling said electrode with said electrical contact assembly.

121. The system of claim 117 including a latch assembly mounted within said support housing forwardly from said drive member start position to limit rearward movement thereof.

122. The system of claim 117 in which said capture component comprises:

a plurality of discrete cage defining leafs, each having a tip portion and a width and thickness between sides which are generally parallel with said cannula axis;

a guidance assembly fixed to said delivery cannula at said forward region and configured to effect deployment of said leafs into tissue at a predetermined angle of attack; and said leaf thickness is of an extent effecting formation of a generally curvilinear cage periphery when said capture component forward portion is subsequently extended while being drawn in contraction toward said cannula axis.

123. The apparatus of claim 122 in which:

said leaf width is of an extent effective to provide extensional cage defining stable movement of said leafs through said guidance assembly along said plane extending through said longitudinal axis.

124. The apparatus of claim 122 in which:

said tip portions of said leafs incorporate apertures dimensioned to receive said flexible pursing cable assembly in slideable relationship;

said pursing cable assembly is comprised of a number of discrete cables, each passing through a predetermined number of said apertures and having a forward end fixed to the tip portion of a said leaf; and the said number of discrete cables is selected with respect to the number of said leafs to derive the shape of said curvilinear cage periphery.

125. The apparatus of claim 124 in which each said leaf having a said aperture through which a said discrete cable initially extends includes a flexible guide tube fixed to said leaf and into which said discrete cable extends.

126. The apparatus of claim 125 in which said capture component comprises five said leafs and five said discrete cables.

127. The method for isolating and retrieving a tissue volume of given peripheral extent within adjacent tissue of a patient comprising the steps of:

(a) providing an electrosurgical generator controllable to derive an electrosurgical cutting output at a cutting voltage level;

(b) providing a tissue retrieval instrument having a delivery cannula with an internal channel and extending from a proximal end portion along a longitudinal axis to a forward region having a tip, said instrument having a capture component positioned within said delivery cannula internal channel having a forward portion extending to a forwardly disposed pursing cable assembly energizable to define an electrosurgical cutting leading edge, said capture component being actuable to cause said leading edge to extend from said delivery cannula laterally outwardly and forwardly toward a maximum peripheral extent selected to correspond with said given peripheral extent and subsequently extendable while being drawn toward said axis to a capture orientation, a controllable motor assembly, a translation assembly, a transfer assembly and a drive assembly configured for actuating said capture component, said instrument further including a precursor electrode assembly mounted at said delivery cannula tip and energizable for electrosurgical cutting from said electrosurgical generator;

(c) providing a control assembly, electrically coupled with said electrosurgical generator and said instrument, having a position switch, an arm switch and a capture switch, each said switch having an on condition and an off condition;

(d) electrosurgically exciting said precursor electrode by actuating said position switch to said on condition causing said control assembly to assume a position mode;

(e) positioning said delivery cannula within said adjacent tissue in a manner wherein said tip is in confronting adjacency with said tissue volume;

(f) causing said control assembly to enter an arm capture mode terminating said excitation of said precursor electrode, terminating said position mode and disabling said position switch, by actuating said arm switch to said on condition;

(g) causing said control assembly to enter a capture mode effecting the electrosurgical excitation of said pursing cable assembly and controlling said motor to commence actuation of said capture component by applying forward drive to said translation assembly and effecting forward movement of said translation assembly in engagement with said drive assembly to actuate said capture component to effect an isolation and envelopment of said tissue volume, by actuating said capture switch to said on condition;

(h) detecting the reaching of said capture orientation by said capture component with said control assembly to provide a capture complete mode terminating said capture mode, controlling said motor to terminate said actuation of said capture component and terminating said electrosurgical excitation of said pursing cable assembly; and (i) removing said delivery cannula with the capture component retained isolated tissue volume from said adjacent tissue.

128. The method of claim 127 in which:
subsequent to said step (f) for causing said control assembly to enter an arm capture mode, carrying out the steps of:
(f1) causing said control assembly to re-enter said position mode from said arm capture mode by actuating said arm switch to said on condition;
(f2) then reiterating said step (e); and
(f3) then reiterating said step (f) to cause said control assembly to re-enter said arm capture mode.

129. The method of claim 127 in which:
said step (g) for causing said control assembly to enter a capture mode includes the step of:
(g1) causing said control assembly to enter into and maintain said capture mode by actuating said capture switch to said on condition and maintaining said on condition continuously.

130. The method of claim 129 in which:
said step (g) for causing said control assembly to enter a capture mode includes the step of:
(g2) subsequent to said step (g1) for actuating said capture switch into said on condition, actuating said capture switch into said off condition to cause said control assembly to enter a pause mode controlling said motor to terminate said actuation of said capture component and controlling said electrosurgical generator to effect termination of electrosurgical excitation of said pursing cable assembly.

131. The method of claim 130 in which said step (c) provides said position switch, said arm switch and said capture switch as footswitches.

132. The method of claim 130 in which:
said step (g) for causing said control assembly to enter a capture mode includes the steps of:
(g3) subsequent to said step (g2) for causing said control assembly to enter a pause mode, re-entering said arm capture mode by actuating said arm switch; and
(g4) then re-entering said capture mode by actuating said capture switch into said on condition.

133. The method of claim 132 in which said step (g4) is carried out by initially effecting the electrosurgical excitation of said pursing cable assembly for a predetermined interval and then controlling said motor to recommence actuation of said capture component in conjunction with continued electrosurgical excitation of said pursing cable assembly.

134. The method of claim 132 in which said step (g4) includes the steps of:
(g4a) controlling said electrosurgical generator with said control assembly to provide said electrosurgical cutting output at a boost cutting voltage level for a boost interval; and
(g4b) then controlling said electrosurgical generator with said control assembly to provide said electrosurgical cutting output at a normal cutting voltage level less than said boost cutting voltage level.

135. The method of claim 134 in which said step (g4) is carried out by initially effecting the said electrosurgical excitation of said pursing cable assembly for said boost interval and then controlling said motor assembly to re-commence actuation of said capture component in conjunction with electrosurgical excitation of said pursing cable assembly at said normal cutting voltage level.

136. The method of claim 127 in which said step (d) includes the steps of:
(d1) controlling said electrosurgical generator with said control assembly to provide said electrosurgical cuffing output at a boost cutting voltage level for a boost interval; and
(d2) then controlling said electrosurgical generator with said control assembly to provide said electrosurgical cutting output at a normal cutting voltage level less than said boost cutting voltage level.

137. The method of claim 136 in which:
said step (dl) provides said electrosurgical cutting output at a said boost cutting voltage level which is greater than said normal cutting voltage level by a factor within a range of about 1.2 to about 1.5.

138. The method of claim 136 in which:
said step (d1) provides said electrosurgical cutting output at said boost cutting voltage level for a boost interval of between about 100 milliseconds to about 1000 milliseconds.

139. The method of claim 136 in which:
said step (d1) provides said electrosurgical cutting output at said boost cutting voltage level for a boost interval of between about 250 milliseconds to about 750 milliseconds.

140. The method of claim 136 in which said step (g) is carried out by controlling said motor to commence actuation of said capture component following said boost interval.

141. The method of claim 127 in which said step (g) includes the steps of:
(g5) controlling said electrosurgical generator with said control assembly to provide said electrosurgical cutting output at a boost cutting voltage level for a boost interval; and
(g6) then controlling said electrosurgical generator with said control assembly to provide said electrosurgical cutting output at a normal cutting voltage level less than said boost cutting voltage level.

142. The method of claim 141 in which:
said step (g6) provides said electrosurgical cutting output at a said boost cutting voltage level which is greater than said normal cutting voltage level by a factor within a range from about 1.2 to 1.5.

143. The method of claim 141 in which:
said step (g5) provides said electrosurgical cutting output at said boost cutting voltage level for a boost interval of between about 100 milliseconds to about 1000 milliseconds.

144. The method of claim 141 in which:
said step (g5) provides said electrosurgical cutting output at said boost cutting voltage level for a boost interval of between about 250 milliseconds to about 750 milliseconds.

145. The method of claim 127 in which said step (g) is carried out by initially effecting the electrosurgical excitation of said pursing cable assembly for a predetermined interval and then controlling said motor to commence actuation of said capture component in conjunction with continued electrosurgical excitation of said pursing cable assembly.

146. The method of claim 136 in which:
said step (d) provides said electrosurgical cutting output at a said boost cutting voltage level of from about 1000 volts, peak-to-peak to about 2000 volts, peak-to-peak.

147. The method of claim 136 in which:
said step (d) provides said electrosurgical cutting output at a said boost cutting voltage level of from about 1100 volts, peak-to-peak to about 1300 volts, peak-to-peak.

148. The method of claim 127 in which said step (e) is carried out by locating said delivery cannula tip a distance, $L_s$, from the center of said tissue volume in general correspondence with the expression:

$$L_s = 0.6\, Dc$$

where, Dc, corresponds with said given peripheral extent.

149. The method for isolating and retrieving a tissue volume of given peripheral extent within adjacent tissue of a patient, comprising the steps of:
- (a) providing an electrosurgical generator controllable to derive an electrosurgical cutting output at a cutting voltage level;
- (b) providing a tissue retrieval instrument having a delivery cannula with an internal channel and extending from a proximal end portion along a cannula axis to a forward region having a tip, said instrument having a capture component positioned within said delivery cannula internal channel, said capture component having a forward portion extending to a forwardly disposed pursing cable assembly energizable to define an electrosurgical cutting leading edge, said capture component being actuable to cause said leading edge to extend from said delivery cannula laterally outwardly and forwardly toward a maximum peripheral extent selected to correspond with said given peripheral extent and subsequently extendable while being drawn toward said cannula axis to a capture orientation, an energization controlled motor exhibiting a load characteristic, a translation assembly coupled in driven relationship with said motor, a transfer assembly having a drive surface and movable to and from a home position, and a drive assembly coupled in driven relationship with said capture component for effecting the actuation thereof and having a driven surface abuttably engagable with said transfer assembly drive surface and when being at an initial position spaced a test distance from said transfer assembly drive surface when said transfer assembly is at said home position
- (c) providing a control assembly, electrically coupled with said electrosurgical generator and said instrument, having a fault condition output, having an arm switch, and a capture switch;
- (d) positioning said delivery cannula within said adjacent tissue in a manner wherein said tip is in confronting adjacency with said tissue volume;
- (e) actuating said arm switch to cause said control assembly to enter an arm capture mode;
- (f) actuating said capture switch in the presence of said arm capture mode to cause said control assembly to enter a capture mode and to control said motor to effect test movement of said translation assembly along said test distance for a test interval;
- (g) monitoring said motor load characteristic with said control assembly during said test interval, deriving a said fault condition and terminating said capture mode when said load characteristic exceeds a test threshold level;
- (h) terminating said test movement following said test interval in the continued presence of said capture mode;
- (i) then controlling said electrosurgical generator with said control assembly to effect the electrosurgical excitation of said pursing cable assembly in the presence of said capture mode for an initial interval; controlling said motor with said control assembly while continuing said electrosurgical excitation of said pursing cable assembly in the presence of said capture mode to effect actuation of said capture component by a drive engagement of said transfer assembly drive surface with said drive assembly driven surface to effect isolating envelopment of said tissue volume;
- (k) detecting the presence of said capture component capture orientation with said control assembly to enter a capture complete mode wherein said electrosurgical generator is controlled to terminate said electrosurgical excitation of said pursing cable assembly; and
- (l) removing said delivery cannula, with the capture component enveloped isolated tissue volume, from said adjacent tissue.

150. The method of claim 149 in which:
said step (i) for effecting the electrosurgical excitation of said pursing cable assembly for said initial interval provides a said cutting voltage level by said electrosurgical generator at a boost voltage level; and
said step (l) for effecting the continuing electrosurgical excitation of said pursing cable assembly, provides a said cutting voltage level by said electrosurgical generator at a normal cut voltage level less than said boost voltage level.

151. The method of claim 150 in which said step (i) effects provision of said cutting voltage level at a said boost voltage level from about 1000 volts, peak-to-peak to about 2000 volts, peak-to-peak.

152. The method of claim 150 in which said step (i) effects provision of said cutting voltage level at a said boost voltage level from about 1100 volts, peak-to-peak to about 1300 volts, peak-to-peak.

153. The method of claim 149 in which said step (j) for controlling said motor in the presence of said capture mode includes the step:
- (j1) monitoring said motor load characteristic with said control assembly during said drive engagement of said transfer assembly drive surface with said drive assembly driven surface, and deriving a said fault condition and terminating said capture mode when said load characteristic falls below a motor engaged threshold level.

154. The method of claim 149 in which said step (k) carries out said detecting of said capture orientation by a determination of the presence of a said load characteristic representing a forward stall of said motor.

155. The method of claim 149 in which said step (k) for detecting the presence of said capture component capture orientation includes the step of:
- (k1) reversing said motor with said control assembly in response to said detection to effect movement of said transfer assembly toward said home position and out of said drive engagement with said drive assembly driven surface.

156. The method of claim 155 in which said step (k) for detecting the presence of said capture component capture orientation includes the step of:
- (k2) detecting the acquiring of said home position by said transfer assembly with said control assembly and effecting termination of energization of said motor in response to said detection of said acquisition.

157. The method of claim 156 in which said step (k2) carries out said detecting of said acquiring of said home position by the determination of the presence of a said load characteristic representing a reverse stall of said motor.

158. The method of claim 149 in which:

said step (c) provides said control assembly with a start switch; and including the steps of:

(m) actuating said start switch prior to said step (e) to carry out reverse energization control of said motor to effect any available movement of said transfer assembly toward said home position; and (n) then detecting the presence of said transfer assembly at said home position with said control assembly and effecting termination of energization of said motor.

159. The method of claim 149 in which:

said step (j) for effecting actuation of said capture component includes the step of:

(j1) prior to said step (k) detecting the presence of said capture component capture orientation, actuating said capture switch into an off condition to cause said control assembly to enter a pause mode wherein said motor is controlled to terminate said actuation of said capture component and said electrosurgical generator is controlled to effect termination of electrosurgical excitation of said pursing cable assembly.

160. The method of claim 159 in which said step (j) for effecting actuation of said capture component includes the step of:

(j2) re-entering said capture mode by actuating said capture switch into an on condition.

161. The method of claim 160 in which said step (j2) includes the steps of:

(j2a) controlling said electrosurgical generator with said control assembly to provide said electrosurgical cutting output at a boost cutting level for a boost interval; and (j2b) then controlling said electrosurgical generator with said control assembly to provide said electrosurgical cutting output at a normal cutting voltage level less than said boost cutting level.

162. The method of claim 161 in which said step (j2) is carried out by initially effecting the said electrosurgical excitation of said pursing cable assembly for said boost interval and then controlling said motor to recommence actuation of said capture component in conjunction with electrosurgical excitation of said pursing cable assembly at said normal cutting voltage level.

163. The method of claim 155 including the step of:

(o) subsequent to said step (k1) for effecting movement of said transfer assembly toward said home position, opening said capture component leading edge to access said isolated and enveloped tissue volume by manually moving said drive assembly toward said initial position.

164. The method of claim 163 in which said step (b) provides a disposable component of said tissue retrieval instrument as comprising said delivery cannula, said capture component and said drive assembly.

165. The method of claim 149 in which said step (j) controls said motor to effect forward movement of said transfer assembly at a rate of from about one millimeter per second to about ten millimeters per second.

166. The method of claim 149 in which said step (j) controls said motor to effect forward movement of said transfer assembly at a rate of from about two and one-half millimeters per second to about four millimeters per second.

167. Apparatus for retrieving a tissue volume comprising:

a delivery cannula having an outer surface surmounting an interior channel and extending from a proximal end portion along a longitudinal axis to a forward region having a distal end positionable in confronting adjacency with said tissue volume;

a capture component positioned within said delivery cannula interior channel, having a forward portion extending to a forwardly disposed electrically conducting electrosurgical cutting leading edge portion and being extendable toward an outer peripheral dimension effective for the circumscriptive engagement of said tissue volume and contractible thereafter toward said axis to envelope said tissue volume when moved along said longitudinal axis to egress from said delivery cannula;

a hand grippable housing having left and right side portions extending outwardly from a medial plane with a housing forward portion coupled in supporting relationship with said delivery cannula at said proximal end portion;

a deployment assembly extending within said interior channel from said housing, drivably coupled with said capture component and energizable to effect said movement of said capture component along said longitudinal axis;

a first switch positioned adjacent said medial plane at said housing forward portion and manually actuable to energize said deployment assembly;

a right grip connector fixed to said housing right side portion adjacent said forward portion and said first switch;

a left grip connector fixed to said housing left side portion adjacent said forward portion and said first switch; and a manually graspable stabilizer grip removably connectable with said right grip connector or said left grip connector.

168. The apparatus of claim 167 in which:

said right grip connector and said left grip connector extend in generally parallel relationship with said longitudinal axis; and said stabilizer grip is adjustably connectable with said right grip connector and said left grip connector in parallel with said axis to adjust the distance from said grip to said first switch.

169. The apparatus of claim 167 in which said grip is configured as an annulus.

170. The apparatus of claim 167 in which:

said right grip connector and said left grip connector are each configured as an elongate platform supported from a pier component fixed to said housing and spacing said platform outwardly therefrom; and said grip is configured having an elongate slot configured to slidably receive said platform.

* * * * *